US006821980B1

United States Patent
Guerry et al.

(10) Patent No.: US 6,821,980 B1
(45) Date of Patent: Nov. 23, 2004

(54) SUBSTITUTED 5-BENZYL-2,4-DIAMINOPYRIMIDINES

(75) Inventors: Philippe Guerry, Binningen (CH); Peter Mohr, Basel (CH); Marc Muller, St. Louis (FR); Werner Mueller, Augarten (CH); Philippe Pflieger, Schwoben (FR)

(73) Assignee: Basilea Pharmaceutica AG (CH)

( * ) Notice: Subject to any disclaimer, the term of this patent is extended or adjusted under 35 U.S.C. 154(b) by 74 days.

(21) Appl. No.: 10/129,461

(22) PCT Filed: Oct. 27, 2000

(86) PCT No.: PCT/CH00/00575

§ 371 (c)(1),
(2), (4) Date: Jul. 18, 2002

(87) PCT Pub. No.: WO01/32633

PCT Pub. Date: May 10, 2001

(30) Foreign Application Priority Data

Nov. 4, 1999 (CH) ................................. 2021/99

(51) Int. Cl.[7] ..................... A61K 31/505; A61K 31/506; C07D 239/48
(52) U.S. Cl. ....................... 514/275; 544/326; 544/327; 544/328
(58) Field of Search .......................... 514/275; 544/328, 544/326, 327

(56) References Cited

U.S. PATENT DOCUMENTS 4,515,948 A    5/1985   Kompis et al. ............. 544/325

FOREIGN PATENT DOCUMENTS

WO    WO 96/16046    5/1996

OTHER PUBLICATIONS

Baccanari et al, Biochemistry, 20, pp. 1710–1716 (1981).
Hartman et al., FEB, 242, pp. 157–160 (1988).
Locher et al., Can. J. Infect. Dis., 6, Suppl. C, p. 469C (1995).
Burdeska et al., FEBS, 266, pp. 159–162 (1990).
Dale et al., J. Mol. Biol., 266, pp. 23–30 (1997).

*Primary Examiner*—Richard L. Raymond
(74) *Attorney, Agent, or Firm*—Gibbons, Del Deo, Dolan, Griffinger & Vecchione

(57) ABSTRACT

The invention relates to substituted 5-benzyl-2,4-diaminopyrimidines of general formula (A)

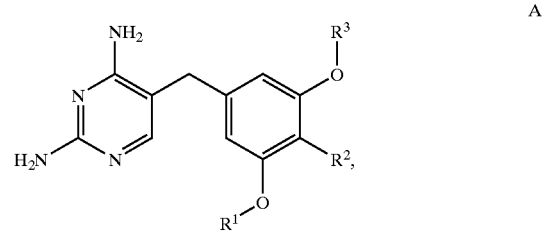

wherein $R^1$ is C2–C3 alkyl an $R^2$ is heterocyclyl, phenyl or naphthyl, bonded by one of its C-atoms and $R^3$ is C2–C6 alkyl, alkenyl, cycloalkyl, cycloalkylalkyl, heterocyclylalkyl, alkylsulfonyl, cycloalkylsulfonyl, cycloalkylalkylsulfamoyl, heterocyclysylfonyl, heterocyclylalkylsulfonyl or dialkylsulfamoyl; wherein alkyl, cycloalkyl and alyenyl can carry up to 6 carbon atoms alone or in compositions and can carry up to 6 ring members heterocyclically, alone, or in compositions and the groups $R^2$ and $R^3$ can be substituted; and to acid addition salts of compounds. The invention also relates to a method for producing the above 5-benzyl-2,4-diaminopyrimidines, to the intermediate. products that are produced, to corresponding medicaments and to the use of 5-benzyl-2,4-diaminopyrimidines as medicinal preparations. The products have antibiotic properties and are useful for combating or preventing infectious diseases.

28 Claims, No Drawings

SUBSTITUTED 5-BENZYL-2,4-DIAMINOPYRIMIDINES

This patent application is filed under 35 U.S.C. §371 of PCT/CH00/00575, filed Oct. 27, 2000.

BACKGROUND OF THE INVENTION

A Substituted 5-benzyl-2,4-diaminopyrimidines are used in combating or preventing infectious diseases, as described, for example, in EP-A 0 793 656.

SUMMARY OF THE INVENTION

The present invention provides substituted 5-benzyl-2,4-diaminopyrimidines of the formula

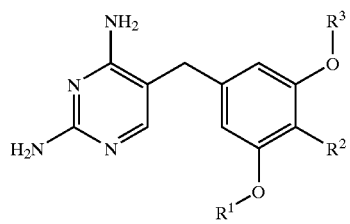

A in which $R^1$ is C2–C3 alkyl;

$R^2$ denotes phenyl, naphthyl or heterocyclyl bonded via one of its C atoms, wherein phenyl, naphthyl or heterocyclyl can be mono- or polysubstituted; and $R^3$ represents C2–C6 alkyl, C2–C6 alkenyl, cycloalkyl, cycloalkylalkyl, heterocyclylalkyl, alkylsulphonyl, phenylsulphonyl, cycloalkylsulphonyl, cycloalkylalkylsulphonyl, cycloalkylalkylsulphamoyl, heterocyclylsulphonyl, heterocyclylalkylsulphonyl or dialkylsulphamoyl, wherein these groups can be unsubstituted or substituted, and acid addition salts of these compounds.

The compounds of the present invention are useful as antibacterial agents.

The present invention also provides a pharmaceutical composition comprising a compound of formula A and a carrier.

The present invention also provides a pharmaceutical composition comprising a compound of formula A, a sulphonamide compound, and a carrier, wherein the ratio in parts by weight of the compound of formula A to sulphonamide is between 1:40 and 1:1.

In addition, the present invention provides a process for the preparation of a compound of formula A according to claim 1, comprising a) reacting a compound of the formula

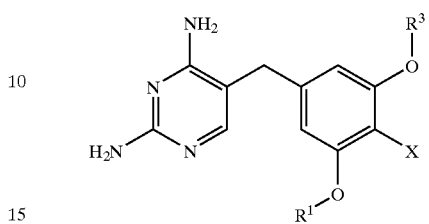

B with a compound of the formula:

$R^2Y$    C in which $R^1$, $R^2$ and $R^3$ have the meaning according to claim 1, wherein any phenolic hydroxyl groups and amino/alkylamino groups present are protected, one of the symbols X and Y represents a leaving group and the other represents a group which withdraws with this leaving group, protective groups present are split off and, optionally, aromatic substituents on $R^2/R^3$ are derivatized, or b) reacting a compound of the formula

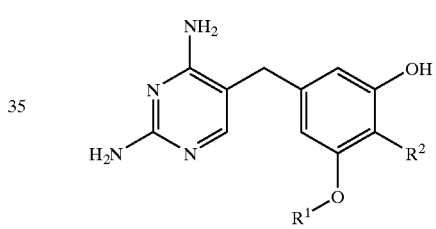

D with a compound of the formula $R^3Z$    E in the presence of a base, wherein any phenolic hydroxyl groups and amino/alkylamino groups present are protected and Z represents a leaving group, protective groups present are split off and, optionally, aromatic substituents on $R^2/R^3$ are derivatized, and optionally, either or both of the following steps:

to prepare compounds of the formula A wherein $R^2$ and/or $R^3$ has a sulphonyl group —$SO_2$—, a corresponding compound wherein $R^2$ and/or $R^3$ has a corresponding sulphanyl group —S— or sulphinyl group —SO—, is subjected to an oxidation, converting a compound of the formula A into a pharmaceutically acceptable acid addition salt

DETAILED DESCRIPTION OF THE INVENTION

The compounds of the present invention have valuable antibiotic properties. They can be used in combating or preventing infectious diseases. They show in particular a pronounced antibacterial action, including against multiresistant Gram-positive strains, such as *Streptococcus* pneumoniae, *Moraxella catarrhalis* and *Staphylococcus aureus* (including methicillin-resistant strains), and against opportunistic pathogens, such as e.g. *Pneumocystis carinii*. These compounds can also be administered in combination with known antibacterially active substances and then show synergistic effects. Typical combination partners are e.g. sulphonamides, which can be admixed to the compounds of the formula A or salts thereof in various ratios.

The present invention provides compounds of the formula A

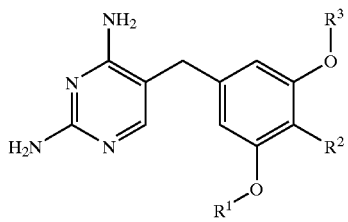

in which
$R^1$ is C2AC3 alkyl;
$R^2$ denotes phenyl, naphthyl or heterocyclyl bonded via one of its C atoms, wherein phenyl, naphthyl or heterocyclyl can be mono- or polysubstituted; and
$R^3$ represents C2–C6 alkyl, C2–C6 alkenyl, cycloalkyl, cycloalkylalkyl, heterocyclylalkyl, alkylsulphonyl, phenylsulphonyl, cycloalkylsulphonyl, cycloalkylalkylsulphonyl, cycloalkylalkylsulphamoyl, heterocyclylsulphonyl, heterocyclylalkylsulphonyl or dialkylsulphamoyl, wherein these groups can be unsubstituted or substituted
and pharmaceutically acceptable acid addition salts thereof.

The present invention also relates to the use of the compounds of formula A and acid addition salts thereof as therapeutic active compounds, and to medicaments based on these substances, optionally in combination with sulphonamides, and the preparation thereof; the use of these substances as medicines and for the preparation of active antibacterial medicaments; and the preparation of the compounds of the formula A and their pharmaceutically acceptable salts and intermediate products for the preparation thereof.

A sub-group of compounds of the formula A is that wherein heterocyclyl and phenyl groups $R^2$ are unsubstituted or mono- or polysubstituted by halogen, cyano, alkyl, alkoxy, hydroxyl, nitro, amino, alkylamino, dialkylamino, alkanoylamino, formyl, alkanoyloxy, cyanoalkyl, cyanoalkoxy, hydroxyalkyl, alkoxyalkyl, hydroxyalkoxy, hydroxyalkylamino, alkoxyalkoxy, carbamoylalkoxy, alkylaminoalkyl, dialkylaminoalkyl, halogenoalkylaminoalkyl, N-alkyl-N-halogenoalkyl-aminoalkyl, alkylsulphanyl (alkylthio), alkylsulphinyl, alkylsulphonyl, alkylsulphonyloxy, alkylsulphonylamino, $R^7$, $R^7$-alkyl, $R^7$-alkoxy, $R^7$-carbonylalkoxyalkyl or $R^7$-alkanoylamino or are also substituted by two adjacent substituents which together form a fused-on 5- or 6-membered heterocyclic ring; wherein $R^7$ represents optionally substituted heterocyclyl and alkyl, by itself or in combinations, can carry up to 6 carbon atoms.

A further sub-group of compounds of the formula A is that wherein $R^2$ represents naphthyl, which is unsubstituted or mono- or polysubstituted by hydroxyl.

A sub-group is furthermore represented by compounds of the formula A wherein the heterocyclyl groups $R^7$ are unsubstituted or substituted by halogen, alkyl, alkoxyalkyl, hydroxyalkyl, alkanoyl, alkanoylaminoalkyl or oxo; wherein alkyl, alkoxy and alkanoyl, by themselves or in combinations, can carry up to 6 carbon atoms.

A further sub-group of the compounds of the formula A is that wherein $R^3$ denotes C2–C6 alkyl, C2–C6 alkenyl, alkylsulphonyl or dialkylsulphamoyl and is unsubstituted or substituted by halogen, cyano, hydroxyl or alkoxy having up to 6 carbon atoms.

Yet another sub-group of the above compounds is that wherein $R^3$ denotes cycloalkyl, cycloalkylalkyl, heterocyclylalkyl, cycloalkylsulphonyl, cycloalkylalkylsulphonyl, heterocyclylsulphonyl, heterocyclylalkylsulphonyl, phenylsulphonyl or cycloalkylalkylsulphamoyl and these groups are unsubstituted or substituted by alkyl, alkoxy, hydroxyalkyl, alkoxyalkyl, cyano, cyanoalkyl or cyanoalkenyl; wherein alkyl, alkoxy and alkenyl, by themselves or in combinations, can carry up to 6 carbon atoms.

A more detailed explanation of the radicals defined above follows below. If a radical is composed of two or more of the radicals below (e.g. "cycloalkylalkyl" from "cycloalkyl" and "alkyl"; "halogenoalkylaminoalkyl" from "halogen", "alkyl" and "alkyl" etc.), the explanations below apply accordingly:

"Halogen" in the context of the present invention includes fluorine, chlorine, bromine and iodine; fluorine or chlorine are preferred.

"Alkyl" and "alkoxy" in the context of the present invention denote straight-chain or branched hydrocarbon groups having at most 6, preferably at most 4 carbon atoms, unless defined otherwise, such as e.g. methyl, ethyl, n-propyl, isopropyl, butyl, isobutyl, sec-butyl, tert-butyl and methoxy, ethoxy, n-propyloxy, isopropyloxy, butyloxy, isobutyloxy, sec-butyloxy, tert-butyloxy.

"Alkenyl" denotes an unsaturated hydrocarbon group and carries not more than 6, preferably up to 4 carbon atoms, such as e.g. vinyl, 2-propenyl, 2,4-butadienyl.

"Cycloalkyl" denotes a cyclic hydrocarbon having 3 to 6 carbon atoms, such as eg. in cyclopropyl, cyclobutyl, cyclopentyl and cyclohexyl.

"Alkanoyloxy" and "alkanoylamino" denote alkyl-COO— and alkyl-CONH— groups having at most 6, preferably up to 4 carbon atoms, wherein alkyl has the meaning explained above.

"Heterocyclyl" and "heterocyclic radical" in the context of the present invention denote unsaturated or saturated, unsubstituted or substituted 5- or 6-membered heterocyclic rings with at least one heteroatom from nitrogen, oxygen and sulphur. Examples of these are pyridyl, pyrazinyl, pyridazinyl, pyrimidyl, piperidyl, piperazinyl, piperimidyl, pyrrolidinyl, pyrazolyl, pyrazolidinyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl; thienyl, furyl, 3H-1,2,3-oxathiazolyl, 1,2,3-oxadiazolyl, 1,2, 5-oxadithiolyl, isoxazolyl, isothiazolyl, 4H-1,2,4-oxadiazinyl, 1,2,5-oxathiazinyl, 1,2,3,5-oxathiadiazinyl, oxazolidinyl, tetrahydrofuranyl, tetrahydrothienyl, morpholino, thiomorphino, pyranyl, tetrahydropyranyl, dioxanyl etc. Preferred heterocyclic radicals among these are: pyridyl, piperidyl, pyrrolidinyl, pyrazolidinyl, thiazolyl, thienyl, furyl, oxazolidinyl, tetrahydrofuranyl, morpholinyl, thiomorpholinyl and tetrahydropyranyl. These heterocyclic radicals can be unsubstituted or substituted by halogen, hydroxyl, alkyl, alkoxy, hydroxyalkyl, alkoxyalkyl, cyano, cyanoalkyl or cyanoalkenyl.

Two adjacent substituents on a phenyl ring or heterocyclic radical can together form a fused-on, 5- or 6-membered heterocyclic radical, examples of such rings are 1H-indolyl, 1H-indazolyl, 3,4-dihydro-2H-benzo[1,4]oxazinyl, benzo[1,3]dioxolyl, 2,3-dihydro-benzo[1,4]dioxinyl, quinolinyl or 1,2,3,4-tetrahydroquinolinyl.

The compounds of the formula A form pharmaceutically acceptable acid addition salts with organic and inorganic acids. Examples of acid addition salts of compounds of the formula A are salts with mineral acids, for example hydrogen halide acids, such as hydrochloric acid, hydrobromic acid and hydrogen iodide, sulphuric acid, nitric acid, phosphoric acid and the like, salts with organic sulphonic acids, for example with alkyl-and arylsulphonic acids, such as methanesulphonic acid, p-toluenesulphonic acid, benzenesulphonic acid and the like, and salts with organic carboxylic acids, for example with acetic acid, tartaric acid, maleic acid, citric acid, benzoic acid, salicylic acid, ascorbic acid and the like.

Preferred sub-groups of the 5-benzyl-2,4-diaminopyrimidines of the formula A according to the invention with particularly valuable antibiotic properties are the following sub-groups A1, A2 and A3:

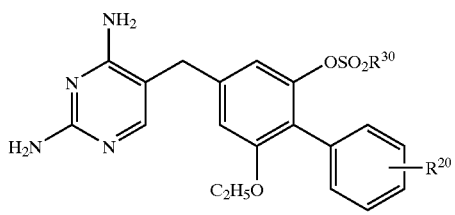

A1 in which
R$^{20}$ represents C1–C6 alkyl, C1–C6 alkoxy, amino, C1–C6 alkylamino, fluorine or chlorine and
R$^{30}$ C1–C6 alkyl, C3–C6 cycloalkyl; di-(C1–C6 alkyl)amino, N-(C3–C6 cycloalkyl)-N-(C1–C6 alkyl)amino or a 5- or 6-membered, saturated N-heterocyclic radical linked on the nitrogen,
and acid addition salts of these compounds.

R$^{20}$ is preferably methyl, methoxy, amino, methylamino or fluorine; R$^{30}$ is preferably isopropyl, sec-butyl, cyclobutyl, dimethylamino, N-cyclopropyl-N-methylamino or morpholino.

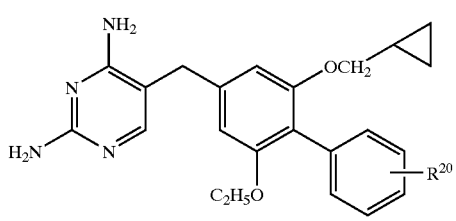

A2 in which R20 denotes C1–C6 alkyl, C1–C6 alkoxy, amino, C1–C6 alkylamino, fluorine or chlorine,
and acid addition salts of these compounds.

R$^{20}$ is preferably methyl, methoxy, amino, methylamino or fluorine.

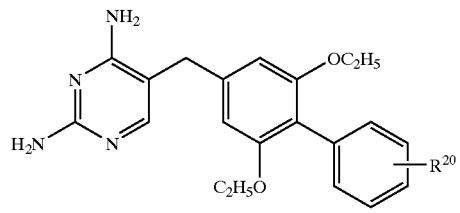

A3 in which R$^{20}$ denotes C1–C6 alkyl, C1–C6 alkoxy, amino, C1–C6 alkylamino, fluorine or chlorine,
and acid addition salts of these compounds.

R$^{20}$ is preferably methyl, methoxy, amino, methylamino or fluorine.

Preferred compounds with particularly valuable antibiotic properties are:
butane-2-sulphonic acid 4'-amino-4-(2,4-diamino-pyrimidin-5-ylmethyl)-6-ethoxy-biphenyl-2-yl ester,
cyclobutane-sulphonic acid 4'-amino-4-(2,4-diamino-pyrimidin-5-ylmethyl)-6-ethoxy-3'-methyl-biphenyl-2-yl ester,
morpholino-4-sulphonic acid 4-(2,4-diamino-pyrimidin-5-ylmethyl)-6-ethoxy-4'-methylamino-biphenyl-2-yl ester,
dimethyl-sulphamic acid 3'-amino-4-(2,4-diamino-pyrimidin-5-ylmethyl)-6-ethoxy-4'-methyl-biphenyl-2-yl ester,
propane-2-sulphonic acid 4'-amino-4-(2,4-diamino-pyrimidin-5-ylmethyl)-6-ethoxy-biphenyl-2-yl ester,
butane-2-sulphonic acid 3'-amino-4-(2,4-diamino-pyrimidin-5-ylmethyl)-6-ethoxy-biphenyl-2-yl ester,
N-cyclopropyl-N-methyl-sulphamic acid 4'-amino-4-(2,4-diamino-pyrimidin-5-ylmethyl)-6-ethoxy-biphenyl-2-yl ester,
propane-2-sulphonic acid 3'-amino-4-(2,4-diamino-pyrimidin-5-ylmethyl)-6-ethoxy-biphenyl-2-yl ester,
propane-2-sulphonic acid 4'-amino-4-(2,4-diamino-pyrimidin-5-ylmethyl)-6-ethoxy-3'-methyl-biphenyl-2-yl ester,
5-(3'-amino-6-cyclopropylmethoxy-2-ethoxy-biphenyl-4-ylmethyl)-pyrimidine-2,4-diamine,
5-(3'-amino-2,6-diethoxy-biphenyl-4-ylmethyl)-pyrimidine-2,4-diamine and acid addition salts of these compounds.

The compounds of the formula A and their pharmaceutically acceptable salts can be prepared according to the invention by a procedure in which a) a compounds [sic] of the general formula

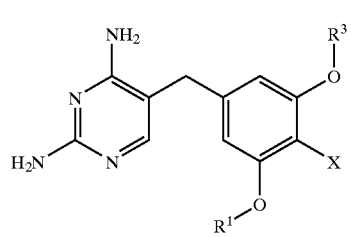

B is reacted with a compound of the general formula

R$^2$Y

C in which R$^1$, R$^2$ and R$^3$ have the above meaning, wherein phenolic hydroxyl groups and amino/alkylamino groups optionally present therein are protected, one of the symbols X and Y represents a leaving group and the other represents a group which withdraws with this leaving group, protective groups present are split off and, if desired, aromatic substituents on R²/R³ are derivatized, or that b) a compound of the general formula

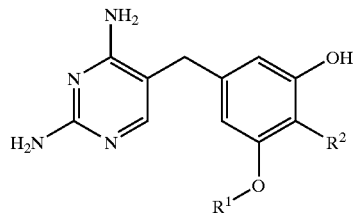

D is reacted with a compound of the general formula

R³Z          E in the presence of a base, in which R¹, R² and R³ have the above meaning, wherein phenolic hydroxyl groups and amino/alkylamino groups optionally present therein are protected, and Z represents a leaving group, protective groups present are split off and, if desired, aromatic substituents on R²/R³ are derivatized, or that c) for the preparation of compounds of the formula A wherein R² and/or R³ contains a sulphonyl group —SO₂— a corresponding compound wherein R² and/or R³ contains a corresponding sulphanyl group —S— or sulphinyl group —SO— is subjected to an oxidation, or that d) a compound of the formula A is converted into a pharmaceutically acceptable acid addition salt.

In the reaction of the compounds of the formulae B and C according to process variant a) of the process according to the invention, withdrawing groups are understood as meaning leaving groups X and Y which react with one another and thus, with the formation of a withdrawing by-product, both "withdraw". Many possibilities in this respect are open to the expert; the following embodiments may be mentioned as examples:

X denotes, for example, bromine, iodine, methylsulphonyloxy, trifluoromethylsulphonyloxy, phenylsulphonyloxy, p-tosylsulphonyloxy; and Y is (OH)₂B—.

This reaction with an aryl/heterocyclylboron acid C, also known as "Suzuki coupling", is preferably carried out in an inert organic solvent, such as e.g. dioxane, tetrahydrofuran, dimethylformamide or dimethoxyethane, at a temperature of between about 20° C. and the boiling point of the reaction mixture. A base, such as an alkali metal carbonate, e.g. potassium carbonate, is preferably added, as well as a catalyst, preferably a palladium complex, such as tetrakis-triphenylphosphine-palladium.

One variant of Suzuki coupling comprises in situ generation of the reagent R²—B(OH)₂, by reacting the compound of the formula B with protected tetrahydroxydiboron (e.g. bis(pinacolato)diboron) and a compound of the formula R²Y¹, wherein Y¹ . . . [sic] a withdrawing group, such as bromine, iodine, methylsulphonyloxy, trifluoromethylsulphonyloxy, phenylsulphonyloxy or p-tosylsulphonyloxy. The reaction conditions are otherwise the same.

An aryl/heterocyclyl-metal compound where Y=Sn (lower-alkyl)₃, e.g. —Sn(CH₃)₃ or —Sn(n-butyl)₃ ("Stille reaction"); —MgHal ("Grignard coupling"); or —ZnHal where Hal=bromine or iodine, can be employed in the above reaction as the reaction partner of the formula C. In this reaction, no base is used, but preferably the catalyst described above. It may also be advantageous to add an inert salt, in particular lithium chloride.

The abovementioned reaction can also be carried out with the substituents X and Y exchanged, e.g. where X=—Sn(CH₃)₃, —MgHal or —ZnHal and Y=bromine, iodine, methylsulphonyloxy, trifluoromethylsulphonyloxy, phenylsulphonyloxy, p-tosylsulphonyloxy. The reaction conditions are substantially the same.

The compound of the formula E employed in process variant b) of the process according to the invention contains a leaving group Z; this preferably represents chlorine, bromine, iodine, methylsulphonyloxy, trifluoromethylsulphonyloxy, phenylsulphonyloxy or p-tosylsulphonyloxy, preferably chlorine or bromine. The base used in the reaction of compounds D and E is preferably an alkali metal lower alkoxide, in particular potassium tert-butoxide, but can also be an alkali metal carbonate or hydride, e.g. sodium or potassium carbonate, sodium or potassium hydride. The reaction is preferably carried out in an inert organic solvent, such as e.g. dimethylformamide, dimethylacetamide, tetrahydrofuran or dioxane or a mixture of these solvents, at a temperature of between about −80° C. and +150° C., preferably 0–80° C. Phenolic hydroxyl groups present in the reaction participants of process variants a) and b) are preferably protected by benzyl substitution at a precursor stage. This is carried out by treatment with the corresponding benzyl halide. The splitting off to give the hydroxyl end product is carried out catalytically over palladium-on-charcoal, e.g. in ethanol/acetic acid at room temperature. Further possibilities [sic] for protection of phenolic hydroxyl groups is methoxymethyl substitution. The introduction is carried out by reaction with a methoxymethyl halide, e.g. with the chloride, and splitting off is carried out e.g. with hydrogen chloride in tetrahydrofuran at about 0° C. to 60° C.

The phenolic hydroxyl groups can also be protected using silyl groups, e.g. trimethylsilyl, t-butyldimethylsilyl. These are advantageously introduced by treatment with the corresponding silyl chloride. The splitting off can be carried out by the action of a fluoride, preferably an alkali metal fluoride or tetrabutylammonium fluoride, in an organic solvent, e.g. dimethylformamide or acetonitrile, at about 0° C. to 50° C.

The phenolic hydroxyl groups can also be protected by lower alkanoyl groups, e.g. acetyl. These are introduced e.g. by treatment with a lower alkanoyl halide or anhydride, e.g. the chloride, in the presence of a base, such as sodium hydroxide, DBU (1,5-diazabicyclo[4.3.0]non-5-ene) or diisopropylethylamine. The splitting off is carried out under mild alkaline conditions (pH about 7–8), e.g. with sodium hydroxide or carbonate, at about 0° C. to 50° C.

Amino groups or alkylamino groups present in the reaction participants of process variants a) and b) are expediently protected by trifluoroacetyl, tert-butoxycarbonyl or benzyloxycarbonyl. Introduction of the protective groups is carried out with the corresponding anhydride or halide in a base, such as pyridine, in an inert solvent, such as methylene chloride, at about −20° C. to room temperature. The protective groups are often split off spontaneously during the coupling or also by treatment with dilute aqueous sodium hydroxide solution and ethanol at about room temperature up to the boiling point of the reaction mixture.

Aromatic substituents on $R^2/R^3$ can be further derivatized. Examples of this are:

1) —$NO_2$→—$NH_2$
This reduction is advantageously carried out by catalytic hydrogenation with palladium-on-charcoal, a lower alkanecarboxylic acid and a lower alkanol, e.g. acetic acid/methanol, at about 20° C. up to the boiling point of the reaction mixture (cf example 2).

2) —CHO→—$CH_2$—R, wherein R represents alkylamino, halogenoalkylamino, dialkylamino or N-heterocyclyl.
This reductive coupling is carried out e.g. by reaction of the aldehyde with the corresponding amine and an alkali metal borohydride or alkali metal cyanoborohydride, e.g. the sodium compound, in a lower alkanol, such as methanol, at about 0° C. to room temperature (cf. example 4v).

3) alkylamino→dialkylamino
A methyl group is introduced by reductive alkylation with formaldehyde in the same manner as for 2 above. Other lower alkylaldehydes lead to the corresponding result (cf. examples 4ac and 4ad).

4)

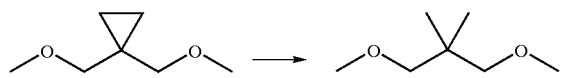

This cyclopropyl group is opened by catalytic reduction with platinum dioxide in a lower alkanecarboxylic acid/a lower alkanol, e.g. acetic acid/methanol, at about 20 to 100° C. (cf. example 8a).

5)

The conversion is carried out by oxidation of the hydroxyl group to aldehyde with e.g. manganese dioxide, followed by Wittig synthesis with triphenylphosphoranylideneacetonitrile in methylene chloride and/or dimethylformamide at about 20° C. up to the boiling point of the reaction mixture (cf. example 8d).

6)

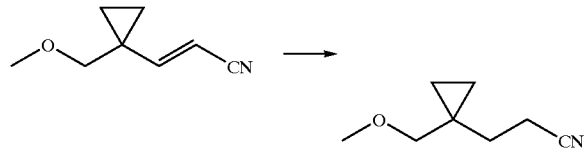

This reduction is carried out with an alkali metal borohydride or alkali metal cyanoborohydride, e.g. the sodium compound, in a lower alkanol, such as isopropanol, at about −20° C. up to the boiling point of the reaction mixture (cf. examples 9c, 47 and 48).

7) Substitution of aromatic amino and phenolic hydroxyl, e.g. $NH_2$→$NHSO_2$alkyl; OH→$OSO_2$alkyl; OH→carbamoylalkoxy; OH→cyanoalkoxy; OH→alkanoyloxy; OH→alkoxyalkoxy; OH→hydroxyalkoxy; OH→heterocyclylalkoxy.

These reactions are carried out with the corresponding halide, e.g. the chloride, bromide or iodide, with the azide or with the acid anhydride in an inert organic solvent, such as methylene chloride, chloroform, dimethylformamide, dimethylacetamide, tetrahydrofuran or dioxane, at about −50° C. to about 80° C. For the formation of hydroxyalkoxy, the reaction is carried out with a protected hydroxyalkyl derivative, e.g. with a tetrahydropyranyloxyalkyl chloride, trimethylsilyloxyalkyl iodide or t-butyl-dimethylsilyloxyalkyl iodide, and the protective group is then split off under acid conditions, e.g. with mineral acid, e.g. methanolic hydrochloric acid, at room temperature. (Cf. examples 44, 45, 46, 50, 55, 56, 58, 59 and 61).

8) Saturation of aromatics, e.g.

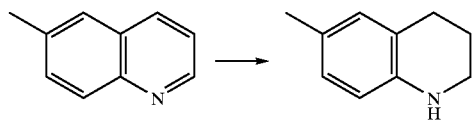

This reaction is carried out with an alkali metal borohydride, e.g. the sodium compound. During this, the quinoline group is converted into the 1,2,3,4-tetrahydroquinoline group in the presence of a nickel(II) chloride catalyst at room temperature.

To prepare end products with a sulphonyl group —$SO_2$— according to the above process variant c), the corresponding sulphanyl or sulphinyl compound can be prepared and then oxidized. For example, an alkylsulphanyl substituent on $R^2$ (alkylthio) is converted into the corresponding alkylsulphonyl compound by oxidation in an inert organic solvent, such as methylene chloride, with $H_2O_2$ or with m-chloroperbenzoic acid and trifluoroacetic acid, followed by treatment with thiosulphate ($Na_2S_2O_3$) at 0° C. to room temperature.

The preparation of the acid addition salts of the compounds of the formula A according to variant d) can be carried out in a manner known per se, e.g. by addition of an organic or inorganic acid. The temperature of the salt formation is not critical. It is in general room temperature, but can also be slightly above or below, for example in the range from 0° C. to +50° C.

The following reaction equations 1 and 2 illustrate the preparation of the end products:

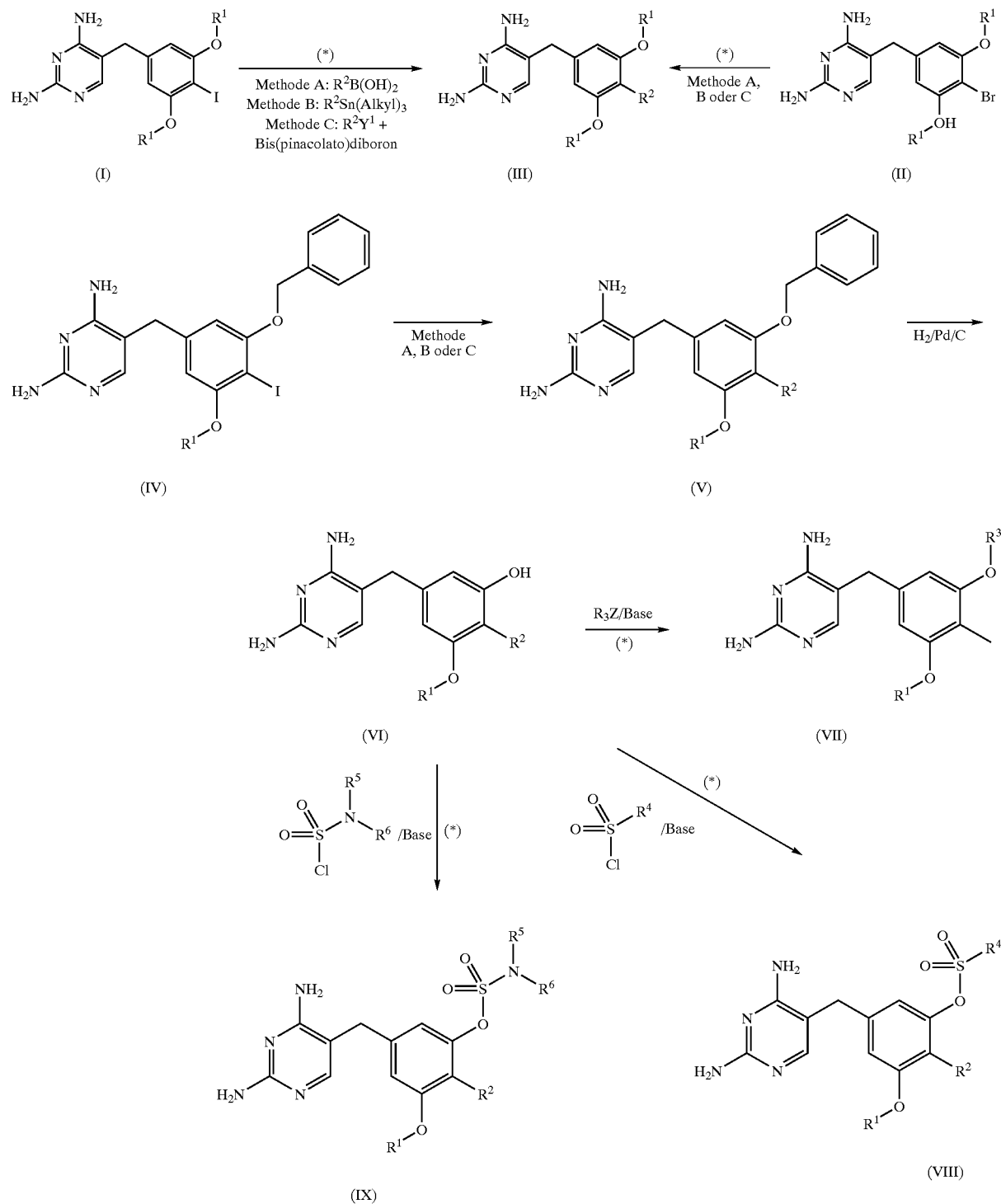

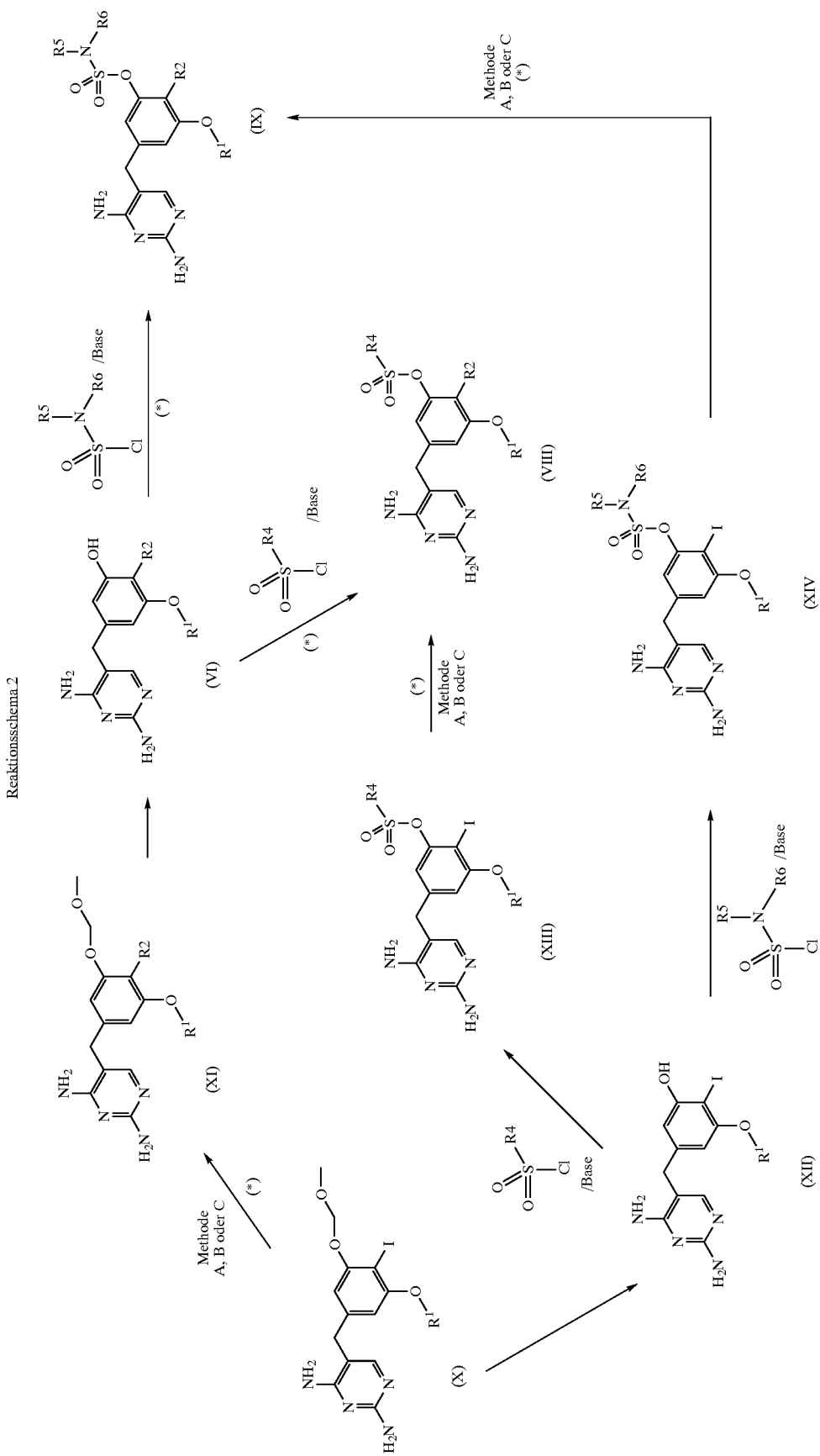

In the reaction equations 1 and 2, the symbols denote as follows:

$Y^1$: a leaving group, e.g. bromine, iodine, methylsulphonyloxy, trifluoromethylsulphonyloxy, phenylsulphonyloxy or p-tosylsulphonyloxy;

$R^4$: C1–C6 alkyl, C3–C6 cycloalkyl; C3–C6 cycloalkylalkyl or heterocyclyl-C1–C6 alkyl;

$R^5$, $R^6$: C1–C6 alkyl or, with the adjacent nitrogen atom, a saturated, 5- or 6-membered N-heterocyclic radical.

$R^1$, $R^2$ and $R^3$ have the above meaning.

I→III; II→III; IV→V; X→XI; XIII→VIII; XIV→IX

The starting compound II where $R^1$=ethyl is known (Proc. Meet., 1980, 177–189), the starting compounds I, IV and X are analogues thereof which can be prepared according to example 1, 6 and 25. The reaction conditions are the same as are stated above for process alternative a).

V→VI

The benzyl protective group in compounds V is split off catalytically with hydrogen and palladium-on-charcoal in a lower alkanol, such as ethanol, and a lower alkanecarboxylic acid, such as concentrated acetic acid, at about 0–50° C., preferably at room temperature.

X→XII; XI→VI

The methoxymethyl protective group in compounds X is split off by acid hydrolysis in aqueous mineral acid, e.g. aqueous hydrochloric acid, at room temperature up to the boiling point of the reaction mixture.

VI→VII; VI→IX; VI→VIII; XII→XIII

These condensation reactions are carried out in the same manner as described above for process alternative b).

As already mentioned, the compounds of the formula A and their pharmaceutically acceptable salts have valuable antibacterial properties. They are active against a large number of pathogenic microorganisms, such as e.g. *Staphylococcus aureus, Streptococcus pneumoniae* including resistant strains, and owe their action to inhibition of bacterial dihydrofolate reductase (DHFR).

The inhibition of this enzyme has been taken as a measure of the antibacterial action. It is determined by the method of BaCanari and Joyner (Biochemistry 20, 1710 (1981)); cf. also P.G. Hartman et al., FEB 242, 157–160 (1988).

The $IC_5$ values (concentration at which the enzyme is inhibited to the extent of 50%) are determined by means of a graph.

The following tables 1 and 2 contain the inhibitory concentrations determined in the above test for representative representatives of the compound class defined by the formula A. The following are stated:

Column 1: MIC SP1/1; µg/ml (*Streptococcus pneumoniae* 1/1, trimethoprim- and penicillin-resistant, serotype 6; clinical isolate, stored at −80° C.).

Lit.: H. Locher et al., Can. J. Infect. Dis. 6: Suppl. C, p 469C.

Column 2: MIC Sa101; µg/ml (*Staphylococcus aureus* 101, MRSA*)- and trimethoprim-resistant; clinical isolate, stored at 0° C.).

*) MRSA=Methicillin-Resistant *Staphylococcus Aureus*

Lit.: A. Burdeska et al., FEBS 266: 159–162, 1999; G. Dale et al., J. Mol. Biol. 266: 23–30, 1997.

Column 3: DHFR SP1/1; µM)—the $IC_{50}$ values in µM against the purified DHFR of the above strain Sp1/1 of *StreptocoCus pneumoniae*.

Column 4: DHFR Sa1; µM—the $IC_{50}$ values in µM against the purified DHFR of strain 157/4696 (highly trimethoprim-resistant; clinical isolate) of *Staphylococcus aureus*.

Lit.: A. Burdeska et al., FEBS 266: 159–162, 1999; G. Dale et al., J. Mol. Biol. 266: 23–30,1997.

TABLE 1

Activity of the preferred compounds

| Example no. | MIC Sp1/1 µg/ml | MIC Sa101 µg/ml | DHFR Sp1/1 µM | DHFR Sa1 µM |
|---|---|---|---|---|
| 35e | 0.5 | 1 | 0.0046 | 0.062 |
| 40c | 0.5 | 1 | 0.019 | 0.037 |
| 26c | 0.5 | 1 | 0.0032 | 0.056 |
| 31a | 1 | 1 | 0.0019 | 0.11 |
| 35a | 0.5 | 2 | 0.0037 | 0.11 |
| 18 | 1 | 2 | 0.0056 | 0.039 |
| 14g | 1 | 1 | 0.0037 | 0.03 |
| 22e | 1 | 2 | 0.013 | 0.15 |
| 14c | 1 | 1 | 0.02 | 0.061 |
| 33e | 1 | 1 | 0.019 | 0.2 |
| 7a | 1 | 8 | 0.0021 | 0.51 |
| 2a | 4 | 8 | 0.03 | 0.75 |
| Trimethoprim | >32 | 32 | 3.1 | 19 |
| Epiroprim | 4 | 16 | 0.19 | 2 |

TABLE 2

| Example | MIC Sp1/1 µg/ml | MIC Sa101 µg/ml | DHFR Sp1/1 µM | DHFR Sa1 µM |
|---|---|---|---|---|
| 02-aa | 4 | 8 | 0.06 | 2.5 |
| 02-ab | 2 | 4 | 0.038 | 0.88 |
| 02-ac | 2 | 8 | 0.065 | 0.65 |
| 02-ad | 4 | 8 | 0.085 | 2 |
| 02-ae | 8 | 4 | 0.15 | 1.6 |
| 02-af | 8 | 8 | 0.085 | 1.8 |
| 02-ag | 8 | 8 | 0.13 | 2.2 |
| 02-d | 1 | 8 | 0.035 | 1.4 |
| 02-e | 2 | 4 | 0.022 | 1 |
| 02-f | 4 | 4 | 0.028 | 1.7 |
| 02-g | 2 | 8 | 0.012 | 0.65 |
| 02-h | 4 | 8 | 0.038 | 1.2 |
| 02-i | 2 | 8 | 0.1 | 1.6 |
| 02-j | 4 | 8 | 0.072 | 1.7 |
| 02-l | 4 | 8 | 0.16 | 8 |
| 02-m | 4 | 8 | 0.058 | 0.7 |
| 02-n | 4 | 8 | 0.11 | 1.4 |
| 02-o | 4 | 4 | 0.1 | 2.2 |
| 02-p | 4 | 8 | 0.1 | 2.2 |
| 02-q | 8 | 4 | 0.079 | 1.1 |
| 02-r | 4 | 4 | 0.07 | 2.5 |
| 02-s | 8 | 4 | 0.083 | 2.2 |
| 02-t | 4 | 8 | 0.081 | 1.1 |
| 02-u | 4 | 8 | 0.18 | 4 |
| 02-v | 4 | 8 | 0.11 | 10 |
| 02-w | 4 | 8 | 0.28 | 2.2 |
| 02-x | 2 | 8 | 0.075 | 2.33 |
| 02-y | 4 | 8 | 0.15 | 0.8 |
| 02-z | 8 | 8 | 0.06 | 1.6 |
| 03-a | 2 | 8 | 0.031 | 1.8 |
| 03-b | 2 | 8 | 0.019 | 1.6 |
| 03-c | 2 | 8 | 0.011 | 2 |
| 03-d | 8 | 8 | 0.34 | 6 |
| 03-e | 4 | 8 | 0.08 | 2.1 |
| 04-a | 4 | 8 | 0.082 | 2.7 |
| 04-aa | 8 | 8 | 0.33 | 1.8 |
| 04-ab | 4 | 8 | 0.12 | 1.4 |
| 04-ac | 4 | 8 | 0.059 | 0.45 |
| 04-ad | 4 | 8 | 0.17 | 2.7 |
| 04-ae | 8 | 8 | 0.019 | 1.4 |
| 04-ag | 8 | 8 | 0.35 | 1.8 |
| 04-aa | 8 | 8 | 0.18 | 1.8 |
| 04-b | 2 | 8 | 0.036 | 1.7 |
| 04-c | 4 | 8 | 0.04 | 0.7 |
| 04-d | 4 | 8 | 0.065 | 2.1 |
| 04-e | 4 | 8 | 0.03 | 1.8 |
| 04-f | 2 | 4 | 0.055 | 1.5 |
| 04-g | 4 | 8 | 0.04 | 1.1 |
| 04-h | 2 | 4 | 0.042 | 1 |

TABLE 2-continued

| Example | MIC Sp1/1 μg/ml | MIC Sa101 μg/ml | DHFR Sp1/1 μM | DHFR Sa1 μM |
|---|---|---|---|---|
| 04-i | 4 | 8 | 0.043 | 1.2 |
| 04-j | 4 | 8 | 0.048 | 0.85 |
| 04-k | 4 | 8 | 0.095 | 10 |
| 04-l | 4 | 8 | 0.082 | 1.9 |
| 04-m | 8 | 8 | 0.072 | 1.8 |
| 04-n | 2 | 8 | 0.068 | 1.4 |
| 04-o | 8 | 8 | 0.06 | 1.3 |
| 04-p | 2 | 8 | | |
| 04-q | 4 | 8 | 0.069 | 1.9 |
| 04-r | 4 | 8 | 0.085 | 3.2 |
| 04-s | 4 | 8 | 0.061 | 1.9 |
| 04-t | 2 | 8 | 0.031 | 1.2 |
| 04-u | 4 | 8 | 0.065 | 1.9 |
| 04-v | 4 | 8 | 0.15 | 1.3 |
| 04-w | 8 | 8 | 0.082 | 1.2 |
| 04-x | 8 | 8 | 0.08 | 7.9 |
| 04-y | 8 | 8 | 0.092 | 0.89 |
| 04-z | 4 | 8 | 0.058 | 3.8 |
| 05-a | 2 | 8 | 0.046 | 6.1 |
| 05-b | 4 | 16 | 0.04 | 1.5 |
| 05-c | 4 | 8 | 0.03 | 2.6 |
| 05-d | 2 | 4 | 0.07 | 3.1 |
| 07-b | 2 | 8 | 0.036 | 0.95 |
| 07-c | 4 | 8 | 0.048 | 2.2 |
| 07-d | 1 | 4 | 0.0082 | 0.68 |
| 07-e | 1 | 4 | 0.028 | 0.64 |
| 07-f | 2 | 8 | 0.055 | 0.75 |
| 07-g | 8 | 8 | 0.03 | 0.65 |
| 07-h | 2 | 8 | 0.027 | 2.2 |
| 07-i | 4 | 4 | 0.028 | 0.9 |
| 07-j | 1 | 8 | 0.029 | 1.3 |
| 08-a | 2 | 8 | 0.018 | 1.7 |
| 08-b | 2 | 8 | 0.038 | 0.95 |
| 08-c | 4 | 8 | 0.024 | 1.6 |
| 08-d | 4 | 8 | 0.016 | 0.62 |
| 08-e | 1 | 8 | 0.0056 | 0.95 |
| 08-f | 4 | 8 | 0.049 | 0.95 |
| 08-g | 4 | 8 | 0.052 | 1.3 |
| 08-h | 2 | 4 | 0.011 | 1.2 |
| 08-i | 4 | 2 | 0.04 | 1 |
| 08-j | 2 | 2 | 0.026 | 1.6 |
| 08-k | 2 | 4 | 0.043 | 2.1 |
| 08-l | 8 | 4 | 0.058 | 2.2 |
| 08-m | 4 | 8 | 0.065 | 0.86 |
| 08-n | 2 | 4 | 0.015 | 1.2 |
| 08-o | 2 | 4 | 0.051 | 1.4 |
| 08-p | 4 | 8 | 0.02 | 0.8 |
| 08-q | 8 | 8 | 0.028 | 1.4 |
| 08-r | 8 | 8 | 0.037 | 1.2 |
| 08-s | 2 | 4 | 0.031 | 3.7 |
| 08-t | 2 | 8 | 0.025 | 2.4 |
| 08-u | 4 | 8 | 0.15 | 1.8 |
| 08-v | 2 | 8 | 0.082 | 1.5 |
| 08-w | 4 | 8 | 0.021 | 0.92 |
| 08-x | 4 | 8 | 0.025 | 1.4 |
| 08-y | 4 | 8 | 0.095 | 2.7 |
| 09-a | 4 | 8 | 0.09 | 3.1 |
| 09-b | 2 | 8 | | 1.9 |
| 09-c | 1 | 4 | 0.016 | 0.9 |
| 09-d | 2 | 4 | 0.03 | 1.5 |
| 09-e | 4 | 4 | 0.045 | 1 |
| 09-f | 8 | 8 | 0.14 | 1.9 |
| 09-g | 4 | 4 | 0.05 | 1.6 |
| 10-a | 8 | 8 | 0.034 | 1.4 |
| 10-b | 2 | 8 | 0.04 | 2.4 |
| 10-c | 4 | 8 | 0.011 | 5 |
| 10-d | 8 | 4 | 0.042 | 1.7 |
| 10-e | 8 | 8 | 0.05 | 1.8 |
| 10-f | 8 | 8 | 0.085 | 1.8 |
| 11-a | 1 | 8 | 0.018 | 1.8 |
| 11-b | 1 | 8 | 0.0098 | 0.9 |
| 12- | 2 | 8 | 0.014 | 1.8 |
| 13- | 2 | 8 | 0.016 | 1.4 |
| 14-a | 4 | 8 | 0.023 | 0.35 |
| 14-b | 2 | 2 | 0.019 | 0.14 |
| 14-d | 1 | 2 | 0.016 | 0.082 |
| 14-e | 1 | 8 | 0.012 | 0.41 |
| 14-f | 1 | 4 | 0.0018 | 0.32 |
| 14-h | 0.5 | 2 | 0.0048 | 0.32 |
| 14-i | 0.5 | 8 | 0.0054 | 0.22 |
| 15-a | 4 | 8 | 0.032 | 0.55 |
| 15-b | 2 | 4 | 0.023 | 0.18 |
| 15-c | 1 | 1 | 0.012 | 0.064 |
| 15-d | 1 | 2 | 0.018 | 0.062 |
| 15-e | 1 | 8 | 0.012 | 0.094 |
| 15-f | 0.5 | 4 | 0.0067 | 0.38 |
| 15-g | 0.5 | 2 | 0.025 | 0.039 |
| 15-h | 0.25 | 4 | 0.0041 | 0.92 |
| 15-i | 4 | 2 | 0.022 | 0.081 |
| 15-j | 1 | 8 | 0.0017 | 0.55 |
| 16-a | 2 | 4 | 0.021 | 0.31 |
| 16-b | 2 | 2 | 0.039 | 0.1 |
| 16-c | 2 | 2 | 0.018 | 0.26 |
| 17-a | 2 | 4 | 0.038 | 0.6 |
| 17-b | 2 | 4 | 0.038 | 0.37 |
| 17-c | 2 | 2 | 0.033 | 0.18 |
| 17-d | 1 | 4 | 0.014 | 0.15 |
| 19-a | 1 | 1 | 0.0062 | 0.085 |
| 19-b | 0.5 | 1 | 0.0024 | 0.13 |
| 19-c | 1 | 2 | 0.019 | 0.066 |
| 19-d | 2 | 2 | 0.0083 | 0.055 |
| 19-e | 1 | 2 | 0.0039 | 0.038 |
| 19-f | 1 | 1 | 0.0062 | 0.082 |
| 19-g | 1 | 1 | 0.0068 | 0.056 |
| 19-h | 1 | 2 | 0.00055 | 0.16 |
| 20-a | 1 | 2 | 0.0075 | 0.15 |
| 20-b | 0.5 | 1 | 0.0018 | 0.14 |
| 20-c | 1 | 4 | 0.0081 | 0.18 |
| 20-d | 1 | 8 | 0.0058 | 0.095 |
| 20-e | 2 | 2 | 0.014 | 0.16 |
| 20-f | 1 | 1 | 0.0098 | 0.14 |
| 20-g | 1 | 2 | 0.0072 | 0.16 |
| 20-h | 1 | 2 | 0.0092 | 0.35 |
| 21- | 2 | 2 | 0.052 | 0.13 |
| 22-a | 1 | 2 | 0.0031 | 0.048 |
| 22-b | 1 | 1 | 0.0023 | 0.038 |
| 22-c | 1 | 1 | 0.0033 | 0.14 |
| 22-d | 1 | 2 | 0.0061 | 0.045 |
| 22-f | 1 | 2 | 0.014 | 0.15 |
| 23- | 1 | 8 | 0.008 | 2.6 |
| 24- | 1 | 4 | 0.016 | 0.19 |
| 26-a | 1 | 1 | 0.0021 | 0.13 |
| 26-b | 1 | 1 | 0.0019 | 0.17 |
| 26-d | 1 | 1 | 0.0051 | 0.14 |
| 26-e | 1 | 1 | 0.0023 | 0.13 |
| 26-f | 1 | 2 | 0.0088 | 0.23 |
| 27-a | 1 | 2 | 0.022 | 0.22 |
| 27-b | 1 | 2 | 0.014 | 0.19 |
| 27-c | 1 | 1 | 0.0026 | 0.18 |
| 28-a | 1 | 2 | 0.0058 | 0.32 |
| 28-b | 1 | 2 | 0.0068 | 0.32 |
| 28-c | 1 | 2 | 0.018 | 0.24 |
| 29-a | 2 | 1 | 0.0063 | 0.22 |
| 29-b | 2 | 2 | 0.014 | 0.095 |
| 29-c | 2 | 2 | 0.0052 | 0.17 |
| 30-a | 2 | 2 | 0.0045 | 0.088 |
| 30-b | 2 | 2 | 0.014 | 0.037 |
| 30-c | 2 | 2 | 0.016 | 0.14 |
| 31-b | 1 | 2 | 0.0044 | 0.13 |
| 32-a | 1 | 4 | 0.0046 | 0.12 |
| 32-b | 1 | 4 | 0.0042 | 0.16 |
| 32-c | 1 | 4 | 0.0061 | 0.13 |
| 32-d | 1 | 2 | 0.0059 | 0.14 |
| 32-e | 1 | 4 | 0.0068 | 0.28 |
| 32-f | 1 | 4 | 0.03 | 0.42 |
| 32-g | 4 | 8 | 0.075 | 0.068 |
| 33-a | 1 | 1 | 0.012 | 0.065 |
| 33-b | 1 | 2 | 0.014 | 0.26 |
| 33-c | 2 | 2 | 0.014 | 0.1 |
| 33-d | 2 | 2 | 0.0091 | 0.039 |
| 33-f | 8 | 2 | 0.089 | 0.042 |
| 33-g | 8 | 4 | 0.076 | 0.98 |

TABLE 2-continued

| Example | MIC Sp1/1 μg/ml | MIC Sa101 μg/ml | DHFR Sp1/1 μM | DHFR Sa1 μM |
|---|---|---|---|---|
| 34-a | 1 | 2 | 0.0092 | 0.27 |
| 34-b | 1 | 2 | 0.011 | 0.21 |
| 34-c | 2 | 4 | 0.0034 | 0.19 |
| 34-d | 1 | 2 | 0.0024 | 0.14 |
| 34-e | 4 | 4 | 0.015 | 0.14 |
| 34-f | 1 | 2 | 0.0095 | 0.097 |
| 35-b | 0.5 | 2 | 0.009 | 0.13 |
| 35-c | 1 | 2 | 0.0046 | 0.043 |
| 35-d | 1 | 2 | 0.0043 | 0.095 |
| 35-f | 0.5 | 4 | 0.0085 | 0.12 |
| 36-a | 0.25 | 2 | 0.0033 | 0.032 |
| 36-b | 0.5 | 8 | 0.0058 | 0.23 |
| 36-c | 0.5 | 2 | 0.0048 | 0.24 |
| 36-d | 0.5 | 2 | 0.00068 | 0.066 |
| 36-e | 0.5 | 4 | 0.0021 | 0.25 |
| 37-a | 0.25 | 4 | 0.0045 | 0.55 |
| 37-b | 0.25 | 4 | 0.0017 | 0.26 |
| 37-c | 0.5 | 4 | 0.0018 | 0.58 |
| 37-d | 0.25 | 8 | 0.0015 | 0.29 |
| 38-a | 1 | 2 | 0.0052 | 0.16 |
| 38-b | 1 | 2 | 0.0065 | 0.22 |
| 38-c | 0.5 | 2 | 0.0058 | 0.19 |
| 38-d | 1 | 4 | 0.0032 | 0.24 |
| 39-a | 1 | 4 | 0.0042 | 0.39 |
| 39-b | 0.5 | 4 | 0.0049 | 0.25 |
| 39-c | 1 | 8 | 0.014 | 1 |
| 39-d | 2 | 8 | 0.0026 | 0.41 |
| 40-a | 1 | 2 | 0.0065 | 0.052 |
| 40-b | 1 | 2 | 0.027 | 0.31 |
| 40-d | 2 | 2 | 0.017 | 0.13 |
| 40-e | 2 | 2 | 0.079 | 0.16 |
| 41-a | 0.5 | 2 | 0.0003 | 0.055 |
| 41-b | 0.5 | 4 | 0.0062 | 0.25 |
| 41-c | 0.5 | 4 | 0.0042 | 0.043 |
| 42-a | 2 | 8 | 0.0057 | 0.25 |
| 42-b | 2 | 8 | 0.0076 | 0.51 |
| 42-c | 1 | 8 | 0.0063 | 0.3 |
| 43-a | 4 | 2 | 0.0067 | 0.32 |
| 43-b | 1 | 1 | 0.0098 | 0.26 |
| 43-c | 2 | 2 | 0.024 | 0.16 |
| 43-d | 1 | 1 | 0.042 | 0.18 |
| 44- | 2 | 8 | 0.018 | 0.68 |
| 45- | 4 | 8 | 0.13 | 2.4 |
| 46- | 2 | 8 | 0.055 | 0.75 |
| 47- | 2 | 8 | 0.01 | 1.2 |
| 48- | 2 | 4 | 0.03 | 0.75 |
| 49- | 8 | 4 | 0.046 | 0.82 |
| 50- | 4 | 8 | 0.032 | 10 |
| 51- | 2 | 8 | 0.043 | 8.5 |
| 52- | 1 | 8 | 0.02 | 5.8 |
| 53- | 4 | 8 | 0.028 | 1.8 |
| 54- | 2 | 8 | 0.019 | 3.1 |
| 55- | 4 | 8 | 0.048 | 1.7 |
| 56- | 2 | 8 | 0.032 | 0.8 |
| 57- | 4 | 8 | 0.03 | 3.6 |
| 58- | 2 | 2 | 0.032 | 0.055 |
| 59- | 2 | 8 | 0.018 | 1.8 |
| 60- | 8 | 4 | 0.088 | 0.28 |
| 61-a | 0.5 | 2 | 0.0018 | 0.55 |
| 61-b | 1 | 2 | 0.011 | 0.21 |
| 62- | 2 | 2 | 0.0079 | 0.33 |
| 63- | 1 | 4 | 0.0018 | 0.38 |
| 64-a | 4 | 8 | 0.052 | 1.5 |
| 64-b | 2 | 2 | 0.027 | 0.3 |
| 65- | 2 | 2 | 0.024 | 0.16 |
| 66- | 4 | 2 | 0.052 | 0.17 |
| Trimethoprim | >32 | 32 | 3.1 | 19 |
| Epiroprim | 4 | 16 | 0.19 | 2 |

The products according to the invention can be used as medicines, e.g. in the form of pharmaceutical preparations for enteral or parenteral administration. The products according to the invention can be administered, for example, perorally, e.g. in the form of tablets, lacquered tablets, coated tablets, hard and soft gelatine capsules, solutions, emulsions or suspensions, rectally, e.g. in the form of suppositories, or parenterally, e.g. in the form of injection solutions.

The pharmaceutical preparations can be prepared in a manner familiar to any expert by bringing the substances according to the invention into a pharmaceutical administration form, optionally in combination with other therapeutically valuable substances, together with suitable non-toxic, inert, therapeutically tolerated solid or liquid carrier materials and optionally the conventional pharmaceutical auxiliaries.

Both inorganic and organic carrier materials are suitable as such carrier materials. Thus, for example, lactose, maize starch or derivatives thereof, talc, stearic acid or salts thereof can be used as carrier materials for tablets, lacquered tablets, coated tablets and hard gelatine capsules. Suitable carriers for soft gelatine capsules are, for example, vegetable oils, waxes, fats and semi-solid and liquid polyols (depending on the nature of the active compound, however, no carriers are necessary for soft gelatine capsules). Suitable carrier materials for the preparation of solutions and syrups are, for example, water, polyols, sucrose, inverted sugar and glucose. Suitable carrier materials for injection solutions are, for example, water, alcohols, polyols, glycerol and vegetable oils. Suitable carrier materials for suppositories are, for example, naturally occurring or hydrogenated oils, waxes, fats and semi-liquid or liquid polyols.

Possible pharmaceutical auxiliaries are the conventional preservatives, solubilizing agents, stabilizing agents, wetting agents, emulsifying agents, sweeteners, colorants, flavouring agents, salts for modifying the osmotic pressure, buffers, coating agents and antioxidants.

For parenteral administration, the compounds of the formula I [sic] or their salts are preferably provided as a lyophilisate or dry powder for dilution with conventional carriers, such as water or isotonic saline solution.

As already mentioned, the compounds of the formula I [sic] and their salts are antibacterially active. They inhibit bacterial dihydrofolate reductase and potentiate the antibacterial action of sulphonamides, such as e.g. sulphisoxazole, sulphadimethoxine, sulphamethoxazoles 4-sulphanilamido-5,6-dimethoxy-pyrimidine, 2-sulphanilamido-4,5-dimethyl-pyrimidine or sulphaquinoxaline, sulphadiazine, sulphamonomethoxine, 2-sulphanilamido-4,5-dimethyl-isoxazole and other inhibitors for enzymes which participate in folic acid biosynthesis, such as e.g. pteridine derivatives.

Oral, rectal and parenteral administration are possible for such combinations of one or more of the compounds A according to the invention in human medicine. The ratio of compound of the formula A to sulphonamide can vary within a wide range; it is e.g. between 1:40 (parts by weight) and 1:1 (parts by weight); preferred ratios are 1:10 to 1:2.

Thus e.g. a tablet can comprise 80 mg of a compound of the formula A according to the invention and 400 mg sulphamethoxazole, a tablet for children can comprise 20 mg of a compound of the formula A according to the invention and 100 mg sulphamethoxazole; syrup can comprise (per 5 ml) 40 mg of compound of the formula A and 200 mg sulphamethoxazole.

A daily dose of about 0.2 g to about 2 g of a compound of the formula A according to the invention is possible for adults.

The compounds of the formula A are distinguished by a high antibacterial activity and a pronounced synergistic effect in combination with sulphonamides and a good tolerability.

The following examples illustrate the invention. The temperatures are stated in degrees Celsius.

EXAMPLE 1

Preparation of compound (I) wherein $R^1$ is ethyl (key intermediate product—equation 1):

5-(3,5-Diethoxy-4-iodo-benzyl)-pyrimidine-2,4-diamine

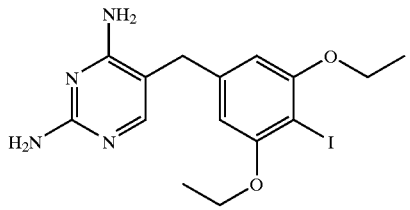

This compound can be obtained by the following reaction sequence (stages a)-g)): Stage a) 3,5-Dihydroxy-4-iodo-benzoic acid:

3,5 Dihydroxybenzoic acid (500 g; 3.24 mol) is dissolved in methanol (2,000 ml), while stirring and gassing with argon. After cooling to 1° C., a solution of N-iodosuccinimide (730 g; 3.24 mol) in methanol (2,000 ml) is added dropwise at 1–60° C. in the course of 90 minutes. After one hour the reaction solution is poured on to ice-water (1,500 ml) and a 5% sodium thiosulphate solution in water (500 ml) is added until decolourization has occurred. The mixture is extracted with tert-butyl methyl ether (4,050 ml). The organic phase is then washed twice with saturated aqueous sodium chloride solution (2,000 ml) and the aqueous phases are re-extracted with tert-butyl methyl ether (2×3,240 ml). The combined organic phases are dried with sodium sulphate (160 g), filtered and concentrated. The residue is crystallized from water. Yield: 816 g (90%) as pale beige crystals. M.p. 245–248° C.

MS: 280 (M)

Stage b) 3,5-Dihydroxy-4-iodo-benzoic acid methyl ester:

3,5-Dihydroxy-4-iodo-benzoic acid (810 g; 2.89 mol) is dissolved in methanol (3,800 ml), while stirring and gassing with argon, sulphuric acid (57.5 ml) is cautiously added and the mixture is heated to 60° C. After 3 hours at this temperature, sulphuric acid (12 ml) is added again and stirring is continued for 45 minutes. After removal of the heating bath water (5,000 ml) is cautiously added and the mixture is cooled to 0° C. The crystals which have precipitated out are then filtered off with suction, washed with ice-water (2×500 ml) and dried under a high vacuum. Yield: 772 g (90%) as white crystals.

M.p. 222–223° C. MS: 294 (M); 263 (M-OCH$_3$)

Stage c) 3,5-Diethoxy-4-iodo-benzoic acid methyl ester:

3,5-Dihydroxy-4-iodo-benzoic acid methyl ester (283 g; 1.30 mol) is dissolved in acetone (6, 170 ml), and potassium carbonate (362 g; 2.62 mol) and diethyl sulphate (402 g; 2.61 mol) are added. The mixture is then stirred under reflux for 3 hours (after 2.5 hours it is diluted with acetone (1,000 ml). After 3 hours, diethyl sulphate (20.4 g; 0.13 mol) is added again. After a total of 5.5 hours, the reaction mixture is filtered hot. The gelatinous residue is washed with acetone (40° C., 2×1,000 ml and 1,500 ml). The combined acetone phases are concentrated to 1,000 ml and the concentrate is left to stand overnight at 0° C. The crystals which have precipitated out are filtered off with suction, washed with acetone (−20° C., 250 ml) and dried (high vacuum). Yield: 437 g (96%) as white crystals.

MS: 350 (M)

Stage d) (3,5-Diethoxy-4-iodo-phenyl)-methanol:

3,5-Diethoxy-4-iodo-benzoic acid methyl ester (403 g; 1.15 mol) is dissolved in tetrahydrofuran (2,300 ml) at 35° C. and the solution is then cooled to +8° C. Di-isobutylaluminium hydride 1.2 M in toluene (2,400 ml; 2.85 mol) is added dropwise in the course of 190 minutes, while cooling to between 9 and 11° C. with an ice bath. After 30 minutes at +10° C. the reaction mixture is poured on to ice (2,820 g), and aqueous 3 N hydrochloric acid (4,030 ml) is added with vigorous stirring. Toluene (2,820 ml) is then added and the mixture is stirred vigorously. After separating off, the organic phase is washed successively with 0.3 N aqueous hydrochloric acid (4,030 ml) and aqueous sodium chloride solution (¼ saturated, 4,030 ml). The aqueous phases are re-extracted with toluene (2,015 ml). The combined organic phases are then dried over sodium sulphate (400 g), filtered with suction and concentrated.

Yield: 396 g of a white solid mass, which is employed in the next stage without further purification. MS; 322 (M)

Stage e) 3,5-Diethoxy-4-iodo-benzaldehyde:

(3,5-Dihydroxy-4-iodo-phenyl)-methanol (393 g; maximum 1.15 mol) is dissolved in methylene chloride (3,930 ml), while stirring and gassing with argon, and manganese dioxide (593 g; 6.9 mol) is added. After 15 hours under reflux, the warm solution is filtered over a 2.5 pressure filter and the residue is rinsed with methylene chloride (1,000 ml; 35° C.). The combined organic phases are concentrated and the residue is heated with n-hexane (1,650 ml) for 2 hours under reflux conditions, the mixture is cooled to 0° C. and filtered with suction and the residue is dried under a high vacuum.

Yield: 324 g of pale-yellowish crystals (88% over 2 stages). MS: 320 (M)

Stage f) 2-(3,5-Diethoxy-4-iodo-benzyl)-3-phenylamino-acrylonitrile

Potassium tert-butylate (120.7 g; 1.07 mol) is dissolved hot in tert-butanol (790 ml) under argon, while stirring. The solution is then cooled to 40° C. and added dropwise in the course of 25 minutes to a solution comprising 3,5-diethoxy-4-iodo-benzaldehyde (286 g; 0.893 mol) and 3-anilinopropionitrile (158 g; 1.08 mol) in dimethylsulphoxide (490 ml) at 38–40° C. (20 minutes). The reaction mixture is than heated at 58–60° C. for 2 hours. After this period of time, 980 ml of solvent are distilled off. The warm solution is diluted with water (1,650 ml), cooled to room temperature and filtered and the residue is washed with water (2×1,000 ml) and dried. The pale yellow, crystalline mass (369.5 g) is stirred with diisopropyl ether (2,200 ml) at 50° C. and filtered off, washed with diisopropyl ether (2×500 ml) and dried under a high vacuum.

Yield: 323 g of pale-beige crystals (67%) MS (ISP): 449.2 (M+H)$^+$; 466.1 (M+NH$_4$)$^+$; 471.0 (M+Na)$^+$ Stage g) 5-(3,5-Diethoxy-4-iodo-benzyl)-pyrimidine-2,4-diamine Guanidine-HCl (192.1 g; 2.01 mol) is dissolved in ethanol (2,420 ml), and potassium tert-butylate 245.6 g; 2.19 mol) is added. The temperature of the reaction mixture is kept below 38° C. for one hour by gentle cooling. 2-(3,5-Diethoxy-4-iodo-benzyl)-3-phenylamino-acrylonitrile (270 g; 0.60 mol) is then added and the reaction mixture is heated at 67–69° C. for 20 hours. The warm reaction solution is then diluted with water (1,000 ml), cooled to 3° C. and filtered. The crystals are washed successively with ethanol (2×500 ml, −20° C.), water (2×500 ml), ethanol (500 ml, −20° C.) and n-pentane (500 ml) and dried under a high vacuum.

Yield: 228 g of pale beige crystals (92%) MS (ISP): 415.1 (M+H)$^+$

EXAMPLE 2

Preparation of Compounds of the Formula III, Equation 1, by Method A (Suzuki Coupling with $R^2$—B(OH)$_2$)

(2a) 5-(3'-Amino-2,6-diethoxy-biphenyl-4-ylmethyl)-pyrimidine-2,4-diamine

Tetrakis-triphenylphosphine-palladium (555 mg; 0.48 mmol) is suspended in dimethoxyethane (7 ml) while gassing with argon, and 5-(3,5-diethoxy-4-iodo-benzyl)-pyrimidine-2,4-diamine (example 1) (4.14 g; 10 mmol) in dimethoxyethane (60 ml) is added. After stirring for 15 minutes at room temperature, 3-amino-phenylboron acid monnohydrate (2.37 g; 15 mmol) in ethanol (17 ml) is added, the mixture is stirred at room temperature for a further 10 minutes, aqueous 2 M sodium carbonate solution (44 ml) is added and the mixture is then boiled under reflux for 4 hours. The reaction mixture is concentrated and the residue is stirred with water and filtered off with suction. The filter cake is stirred with MeOH (230 ml) and filtered off with suction. The filtrate is concentrated and the residue is chromatographed over silica gel (225 g) with methylene chloride/methanol/ammonia (19/1/0.05, later 90/10/1). The pure fractions are combined and concentrated and the residue is dried under a high vacuum.

Yield 3.2 g (85%) 5-(3'-amino-2,6-diethoxy-biphenyl-4-ylmethyl)-pyrimidine-2,4-diamine as a colourless powder. MS (ISP): 380.3 (M+H)$^{30}$ NMR $^1$H: (250 MHz, δ, TMS, DMSO): 1.13 (t; J=6.9; 6H); 3.57 (s; 2H); 3.87 (q; J=6.9; 4H); 4.86 (s; 2H); 5.71 (s; 2H); 6.12 (s; 2H); 6.3–6.4 (m; 3H); 6.56 (s; 2H); 6.9 (m; 1H); 7.56 (s; 1H).

The following are prepared analogously:

(2b) 5-(2,6-diethoxy-biphenyl-4-ylmethyl)-pyrimidine-2,4-diamine

Starting from 5-(3,5-diethoxy-4-iodo-benzyl)-pyrimidine-2,4-diamine (example 1) (414 mg; 1 mmol) and phenylboron acid (488 mg; 4 mmol), 264 mg (72%) 5-(2,6-diethoxy-biphenyl-4-ylmethyl)-pyrimidine-2,4-diamine are obtained as a colourless powder.

M.p.: 187–188° C. MS (ISP): 365.2 (M+H)$^+$

(2c) 5-(3,5-Diethoxy-4-naphthalen-2-yl-benzyl)-pyrimidine-2,4-diamine

Starting from 5-(3,5-diethoxy-4-iodo-benzyl)-pyrimidine-2,4-diamine (example 1) (414 mg; 1 mmol) and naphthalen-2-yl-boron acid (690 mg; 4 mmol), 327 mg (79%) 5-(2,6-diethoxy-biphenyl-4-ylmethyl)-pyrimidine-2,4-diamine [sic] are obtained as a colourless powder.

M.p.: 189–191° C. MS (ISP): 365.2 (M+H)$^{30}$

(2d) 5-(3,5-Diethoxy-4-(1H-indol-5-yl)-benzyl)-pyrimidine-2,4-diamine

Starting from 5-(3,5-diethoxy-4-iodo-benzyl)-pyrimidine-2,4-diamine (example 1) (207 mg; 0.5 mmol) and 5-(1H-indolyl)-boron acid (161 mg; 1 mmol), 103 mg (51%) 5-(3,5-diethoxy-4-(1H-indol-5-yl)-benzyl)-pyrimidine-2,4-diamine are obtained as a colourless powder.

M.p.: 103–105° C. MS (ISP): 404.4 (M+H)$^+$

(2e) 5-[3,5-Diethoxy-4-(1H-indol-6-yl)-benzl]-pyrimidine-2,4-diamine

Starting from 5-(3,5-diethoxy-4-iodo-benzyl)-pyrimidine-2,4-diamine (example 1) (207 mg; 0.5 mmol) and 6-(1H-indolyl)-boron acid (161 mg; 1 mmol), 120 mg (60%) 5-(3,5-diethoxy-4-(1H-indol-6-yl)-benzyl)-pyrimidine-2,4-diamine are obtained as a colourless powder.

M.p.: 176–178° C. MS (ISP): 404.4 (M+H)$^+$

(2f) 6-[4-(2,4-Diamino-pyrimidin-5-ylmethyl)-2,6-diethoxy-phenyl]-naphthalen-2-ol Starting from 5-(3,5-diethoxy-4-iodo-benzyl)-pyrimidine-2,4-diamine (example 1) (828 mg; 2.0 mmol) and 6-hydroxy-2-naphthalene-boron acid (2.42 g; 8.0 mmol), 732 mg (85%) 6-(4-(2,4-diamino-pyrimidin-5-yllmethyl)-2,6-diethoxy-phenyll-naphthalen-2-ol are obtained as a beige powder.

M.p.: 250–251° C. MS (ISP): 431.3 (M+H)$^+$

(2g) 5-[3,5-Diethoxy-4-(1H-indazol-5-yl)-benzyl]-pyrimidine-2,4-diamine

Starting from 5-(3,5-diethoxy-4-iodo-benzyl)-pyrimidine-2,4-diamine (example 1) (230 mg; 0.55 mmol) and 5-(1H-indazole)-boron acid (89 mg; 0.55 mmol), 57 mg (26%) 5-(3,5-diethoxy-4-(1H-indazol-5-yl)-benzyl)-pyrimidine-2,4-diamine are obtained as a colourless powder.

M.p.: 174° C. MS (ISP): 405.3 (M+H)$^+$

The 5-(1H-indazole)-boron acid employed in example 2g) is prepared from 5-bromoindazole as follows:

5-Bromoindazole (638 mg; 3.24 mmol) is initially introduced into diethyl ether (10 ml), and a 1.6 M n-butyllithium solution in n-hexane (4.05 ml; 6.48 mmol) is added at –20° C. (cooling bath) in the course of 15 minutes. The cooling bath is removed, the reaction mixture is subsequently stirred for one hour at room temperature and then diluted with diethyl ether (10 ml), and stirring is continued for 90 minutes at room temperature and 15 minutes at 30° C. The reaction mixture is then poured at –70° C. on to a solution comprising trimethyl borate (0.36 ml; 3.24 mmol) in diethyl ether (5 ml). The reaction mixture is allowed to warm to room temperature and is subsequently stirred for 3 hours at room temperature. Diethyl ether (20 ml) is then added to the reaction mixture and stirring is continued for 12 hours at room temperature. Thereafter, the reaction mixture is poured on to aqueous 1 N hydrochloric acid and extracted with diethyl ether and the extract is dried over magnesium sulphate, filtered with suction and concentrated. The residue is chromatographed over silica gel (100 g) with methylene chloride/methanol (97.5/2.5 to 90/10).

Yield: 100 mg (19%) 5-(1H-indazole)-boron acid as a beige powder. MS (ISN): 161.3(M–H)$^-$

(2h) 5-[4-(3,4-Dihydro-2H-benzo[1.4]oxazin-6-yl)-3,5-diethoxy-benzyl]-pyrimidine-2,4-diamine Starting from 5-(3,5-diethoxy-4-iodo-benzyl)-pyrimidine-2,4-diamine (example 1) (414 mg; 1 mmol) and 2H-1,4-benzoxazine-3,4-dihydro-6-boron acid (179 mg; 1 mmol), 251 mg (60%) 5-[4-(3,4-dihydro-2H-benzo[1,4]oxazin-6-yl)-3,5-diethoxy-benzyl]-pyrimidine-2,4-diamine are obtained as brown crystals.

MS (ISP): 422.3 (M+H)$^+$

The 2H-1,4-benzoxazine-3,4-dihydro-6-boron acid employed in example (2h) is prepared from 2H-3,4-dihydro-6-bromo-1,4-benzoxazine as follows:

2H-3,4-Dihydro-6-bromo-1,4-benzoxazine (600 mg; 2.8 mmol) is dissolved in absolute tetrahydrofuran (30 ml), and sodium hydride (202 mg; 55%; 4.2 mmol) is added at 0° C. After stirring for one hour at this temperature, tert-butyldimethyl-chlorosilane (465 mg; 3.08 mmol) is added and stirring of the entire mixture is continued for half an hour at room temperature. The reaction mixture is then cooled to −78° C., tert-butyllithium (5.61 ml of a 1.5 M solution; 5.6 mmol) is added and stirring is continued for a quarter of an hour at −78° C. (cooling bath). Trimethoxy-borate (0.625 ml; 5.6 mmol) is then added and the cooling bath is removed. As soon as the reaction mixture has reached room temperature, aqueous hydrochloric acid (10 ml of a 2 M solution; 20 mmol) is added and stirring of the entire mixture is continued for one hour at room temperature. The reaction mixture is then poured on to ice-water and extracted twice with ethyl acetate. The combined organic phases are dried over sodium sulphate and filtered with suction and the solvent is evaporated off. The residue is recrystallized from a 1/1 n-hexane/ethyl acetate mixture.

Yield: 163 mg (32%) 2H-1,4-benzoxazine-3,4-dihydro-6-boron acid as a brown powder. NMR (1H, 250 MHz in DMSO): ppm: 3.1 (broad singlet, 2H); 4.0 (broad singlet, 2H); 5.47 (broad singlet, 1H); 6.47 (d, 1H); 6.85 (d, 1H); 6.93 (s, 1H)

(2i) 5-(2,6-Diethoxy-4'-methanesulphonyl-biphenyl-4-ylmethyl)-pyrimidine-2,4-diamine 5-(2,6-Diethoxy-4'-methylsulphanyl-biphenyl-4-ylmethyl)-pyrimidine-2,4-diamine (616 mg; 1.5 mmol) is suspended in methylene chloride (12 ml), and trifluoroacetic acid (0.276 ml; 3.6 mmol) is added. After cooling to 0° C., m-chloroperbenzoic acid (456 mg; 2.25 mmol) is added. After 40 minutes a 10% aqueous Na$_2$S$_2$O$_3$ solution (15 ml) is added and the mixture is stirred at room temperature for 15 minutes. It is then extracted with methylene chloride (60 ml) and the extract is washed with an aqueous saturated sodium bicarbonate solution, dried over magnesium sulphate, filtered with suction and concentrated. The crude product is chromatographed over silica gel (100 g) with methylene chloride/methanol/NH$_4$OH (conc.) (19/1/0.05).

Yield: 172 mg (26%) 5-(2,6-diethoxy-4'-methanesulphonyl-biphenyl-4-ylmethyl)-pyrimidine-2,4-diamine as a colourless powder.

MS: 442 (M)

The above starting compound 5-(2,6-diethoxy-4'-methylsulphanyl-biphenyl-4-ylmethyl)-pyrimidine-2,4-diamine is prepared analogously to example (2a):

Starting from 5-(3,5-diethoxy-4-iodo-benzyl)-pyrimidine-2,4-diamine (example 1) (1.243 g; 3.0 mmol) and 4-(methylthio)-phenylboron acid (0.780 g; 4.64 mmol), 1.09 g (89%) 5-(2,6-diethoxy-4'-methylsulphanyl-biphenyl-4-ylmethyl)-pyrimidine-2,4-diamine are obtained as a beige powder after crystallization from diethyl ether.

MS: 410 (M)

(2j) (RS)-5-(2,6-Diethoxy-4'-methanesulphinyl-biphenyl-4-ylmetyl)-pyrimidine-2,4-diamine Prepared the same way as example (2i) (by-product of the reaction). Starting from 5-(2,6-diethoxy-4'-methylsulphanyl-biphenyl-4-ylmethyl)-pyrimidine-2,4-diamine (616 mg; 1.5 mmol), 444 mg (67%) (RS)-5-(2,6-diethoxy-4'-methanesulphinyl-biphenyl-4-ylmethyl)-pyrimidine-2,4-diamine are obtained as a colourless powder.

MS: 426 (M); 411 (M-CH$_3$)

(2k) 5-(3,5-Diethoxy-4-thiophen-3-yl-benzyl)-pyrimidine-2,4-diamine

Starting from 5-(3,5-diethoxy-4-iodo-benzyl)-pyrimidine-2,4-diamine (example 1) (414 mg, 1.0 mmol) and 3-thiophene-boric acid (191 mg; 1.5 mmol), 146 mg (40%) 5-(3,5-diethoxy-4-thiophen-3-yl-benzyl)-pyrimidine-2,4-diamine are obtained as a beige powder after recrystallization from methanol.

MS (ISP): 371.2 (M+H)$^+$ (2l) 5-(2,6-Diethoxy-3',4'-dimethoxy-biphenyl-4-ylmethy)-pyrimidine-2,4-diamine Starting from 5-(3,5-diethoxy-4-iodo-benzyl)-pyrimidine-2,4-diamine (example 1) (414 mg; 1.0 mmol) and 3,4-dimethoxy-phenyl-boric acid (363 mg; 2.0 mmol), 328 mg (77%) 5-(3,5-diethoxy-4-thiophen-3-yl-benzyl)-pyrimidine-2,4-diamine [sic] are obtained as a yellowish powder after recrystallization from methanol.

MS (ISP): 425.3 (M+H)$^+$ (2m) 5-(3,5-Diethoxy-4-thiophen-2-yl-benzyl)-pyrimidine-2,4-diamine Starting from 5-(3,5-diethoxy-4-iodo-benzyl)-pyrimidine-2,4-diamine (example 1) (207 mg; 0.5 mmol) and 2-thiophene-boron acid (108 mg; 0.96 mmol), 110 mg (59%) 5-(3,5-diethoxy-4-thiophen-2-yl-benzyl)-pyrimidine-2,4-diamine are obtained as a beige powder after crystallization from methanol.

M.p.: 202–203° C. MS (ISP): 371.1 (M+H)$^+$ (2n) 5-(2,6-Diethoxy-4'-methoxy-3'-metyl-biphenyl-4-ylmethyl)-pyrimidine-2,4-diamine Starting from 5-(3,5-diethoxy-4-iodo-benzyl)-pyrimidine-2,4-diamine (example 1) (207 mg; 0.5 mmol) and 4-methoxy-3-methyl-phenyl-boron acid (125 mg; 0.75 mmol), 172 mg (84%) 5-(2,6-diethoxy-4'-methoxy-3'-methyl-biphenyl-4-ylmethyl)-pyrimidine-2,4-diamine are obtained as a colourless powder.

MS (ISP): 409.3 (M+H)$^+$ (2o) 5-(3,5-Diethoxy-4-furan-2-yl-benzyl)-pyrimidine-2,4-diamine Starting from 5-(3,5-diethoxy-4-iodo-benzyl)-pyrimidine-2,4-diamine (example 1) (100 mg; 0,24 mmol) and 2-furan-boron acid (108 mg; 0.96 mmol), 54 mg (63%) 5-(3,5-diethoxy-4-furan-2-yl-benzyl)-pyrimidine-2,4-diamine are obtained as a beige powder after crystallization from methanol.

M.p.: 196–198° C.

(2p) 5-(3,5-Diethoxy-4-pyridin-3-yl-benzyl)-pyrimidine-2,4-diamine

Starting from 5-(3,5-diethoxy-4-iodo-benzyl)-pyrimidine-2,4-diamine (example 1) (300 mg, 0.72 mmol) 3-pyridine-boron acid (221 mg; 1.8 mmol) and tetrakis-triphenylphosphine-palladium (42 mg; 0.036 mmol) in dimethylformamide (15 ml), ethanol (3 ml) and a 2 M aqueous potassium phosphate solution (2 ml), 163 mg (62%) 5-(3,5-diethoxy-pyridin-3-yl-benzyl)-pyrimidine-2,4-diamine are obtained as a colourless powder after crystallization from methanol.

MS (ISP): 366.3 (M+H)$^+$ (2q) 5-(2,6-Diethoxy-4'-methyl-biphenyl-4-ylmethyl)-pyrimidine-2,4-diamine Starting from 5-(3,5-diethoxy-4-iodo-benzyl)-pyrimidine-2,4-diamine (example 1) (300 mg; 0.72 mmol) and 4-methyl-phenylboron acid (147 mg; 1.08 mmol), 193 mg (71%) 5-(2,6-diethoxy-4'-methylbiphenyl-4-ylmethyl)-pyrimidine-2,4-diamine are obtained as a colourless powder.

MS (ISP): 379.3 (M+H)$^+$. M.p. 182–185° C.

(2r) 5-(4-Benzo[1,3]dioxol-5-yl-3,5-diethoxy-benzyl)-pyrimidine-2,4-diamine

Starting from 5-(3,5-diethoxy-4-iodo-benzyl)-pyrimidine-2,4-diamine (example 1) (207 mg; 0.5 mmol) 1,3-benzodioxole-5-boron acid (166 mg; 1.0 mmol) and tetrakis-triphenylphosphine-palladium (28 mg; 0.024 mmol) in dimethylformamide (3 ml), ethanol (0.84 ml) and a 2 M aqueous potassium phosphate solution (2.2 ml), 129 mg (63%) 5-(4-benzo[1,3]dioxol-5-yl-3,5-diethoxy-benzyl)-pyrimidine-2,4-diamine are obtained as a colourless powder after crystallization from methanol.

MS (ISP): 409.3 (M+H)$^+$

(2s) 4'-(2,4-Diamino-pyrimidin-5-ylmethyl)-2',6'-diethoxy-3-methyl-biphenyl-4-ol Starting from 5-(3,5-diethoxy-4-iodo-benzyl)-pyrimidine-2,4-diamine (example 1) (207 mg; 0.5 mmol) 4-benzyloxy-3-methyl-phenylboron acid (242 mg; 4.64 mmol) and tetrakis-triphenylphosphine-palladium (28 mg; 0.024 mmol) in dimethylformamide (3 ml), ethanol (0.84 ml) and 2 M aqueous potassium phosphate solution (2.2 ml), 220 mg (91%) 5-(4'-benzyloxy-2,6-diethoxy-3'-methyl-biphenyl-4-ylmethyl)-pyrimidine-2,4-diamine are obtained as a colourless powder after stirring with 20 ml n-hexane/diethyl ether (3/1).

MS(ISP): 485.4 (M+H)$^+$ 5-(4'-Benzyloxy-2,6-diethoxy-3'-methyl-biphenyl-4-ylmethyl)-pyrimidine-2,4-diamine (214 mg; 0.44 mmol) is dissolved in methanol (20 ml) and in concentrated acetic acid (2 ml) and hydrogenated over 10% Pd/C (250 mg). The catalyst is filtered off with suction and rinsed with methanol, and the filtrate is evaporated. The residue is stirred with diethyl ether (25 ml), filtered-off with suction, washed with diethyl ether and dried under a high vacuum. The colourless powder (129 mg) is then suspended in water (2 ml), the pH is adjusted to 10 by means of addition of a concentrated aqueous ammonia solution, the mixture is stirred for 15 minutes at room temperature and filtered with suction and the residue is washed thoroughly with water and dried under a high vacuum. Yield: 111 mg (64%) 4'-(2,4-diamino-pyrimidin-5-ylmethyl)-2',6'-diethoxy-3-methyl-biphenyl-4-ol as a colourless powder.

MS (ISP): 395.2 (M+H)$^+$

The 4-benzyloxy-3-methyl-phenylboron acid employed is obtained in two stages (a–b) starting from 4-bromo-2-methyl-phenol:

Stage a) 4-Bromo-1-benzyloxy-2-methyl-benzene

4-Bromo-2-methyl-phenol (1.0 g; 5 mmol) is dissolved in dimethylformamide (25 ml; dried over a molecular sieve), and potassium tert-butylate (0.8 g; 7.0 mmol) is added. After the mixture has been stirred at room temperature for one hour, it is cooled to 0° C. with an ice bath, and a solution of benzyl chloride (0.7 ml; 6.0 mmol) in dimethylformamide (15 ml; dried over a molecular sieve) is added in the course of 45 minutes. Stirring is continued for one hour at 0° C. and two hours at room temperature. After this period of time, the solvent is evaporated off, water is added to the residue, the mixture is extracted with ethyl acetate and the extract is washed with water, dried over magnesium sulphate, filtered with suction and concentrated. The residue obtained is dried to constant weight under a high vacuum.

Yield: 1.5 g 4-bromo-1-benzyloxy-2-methyl-benzene as a beige powder, which is employed in the next step without purification.

MS: 276 (M)

Stage b) 4-Benzyloxy-3-methyl-phenylboron acid

4-Bromo-1-benzyloxy-2-methyl-benzene (6.9 g; 25 mmol) is dissolved in tetrahydrofuran (37.5 ml; dried over a molecular sieve) and the solution is cooled to –78° C. A 1.6 M n-butyllithium solution in n-hexane (17 ml; 27.5 mmol) is added dropwise in the course of 30 minutes such that the temperature does not rise above –70° C. After a further 10 minutes at this temperature, trimethyl borate (8.3 ml; 75 mmol) is added dropwise in the course of 25 minutes at below –70° C. The reaction mixture is allowed to warm slowly to room temperature overnight. It is then cooled to 0° C. and an aqueous 1 N hydrochloric acid solution is added dropwise. The reaction mixture is diluted with water and ethyl acetate, the phases are separated and the aqueous phase is re-extracted with ethyl acetate. The combined organic phases are washed successively with water and a saturated aqueous sodium chloride solution, dried over magnesium sulphate, filtered with suction and concentrated.

Yield: 3.95 g (65%) 4-benzyloxy-3-methyl-phenylboron acid as a white powder.

MS(ISN): 301.2 (M–H)$^-$

(2t) 4'-(2,4-Diamino-pyrimidin-5-ylmethyl)-2',6'-diethoxy-biphenyl-4-ol

Starting from 5-(3,5-diethoxy-4-iodo-benzyl)-pyrimidine-2,4-diamine (example 1) (11.677 g, 28.19 mmol) and 4-methoxymethoxy-phenylboron acid (7.934 g; 43.6 mmol), 10.07 g (84%) 5-(2,6-diethoxy-4'-methoxymethoxy-biphenyl-4-ylmethyl)-pyrimidine-2,4-diamine are obtained as a greyish powder analogously to example (2a) after crystallization from methanol.

MS(ISP): 425.5 (M+H)$^+$ 5-(2,6-Diethoxy-4'-methoxymethoxy-biphenyl-4-ylmethyl)-pyrimidine-2,4-diamine (10.06 g; 23.7 mmol) is dissolved in methanol (410 ml), and a 3 N hydrochloric acid solution in methanol (119.1 ml; 357.3 mmol) is added. The reaction mixture is stirred for 30 minutes at a temperature of 56° C. and concentrated. The grey residue is then stirred with water (400 ml), the pH is brought to 9 by addition of an aqueous saturated ammonia solution (approx. 8 ml) and the entire mixture is stirred for 15 minutes. The greyish suspension is filtered with suction and the residue is dried under a high vacuum. 8.85 g (98%) 4'-(2,4-diamino-pyrimidin-5-ylmethyl)-2',6'-diethoxy-biphenyl-4-ol are obtained as a greyish powder.

MS (ISP): 381.3 (M+H)$^+$

(2u) 4'-(2,4-Diamino-pyrimidin-5-ylmethyl)-2',6'-diethoxy-biphenyl-3-carbonitrile Starting from 5-(3,5-diethoxy-4-iodo-benzyl)-pyrimidine-2,4-diamine (example 1) (207 mg; 0.5 mmol), 3-cyanophenyl-boron acid (147 mg; 1.0 mmol) and tetrakis-triphenylphosphine-palladium (28 mg; 0.024 mmol) in dimethylformamide (3 ml), ethanol (0.84 ml) and a 2 M aqueous potassium phosphate solution (2.2 ml), 52 mg (27%) 4'-(2,4-diamino-pyrimidin-5-ylmethyl)-2',6'-diethoxy-biphenyl-3-carbonitrie are obtained as a beige powder after chromatography over silica gel (100 g) with methylene chloride/methanol/NH$_4$OH conc. (19/1/0/0.05) and successive crystallization from n-hexane/diethyl ether 3/1 (20 ml) and methanol (1 ml).

MS (ISP): 390.2 (M+H)+

(2v) 5-(4'-Dimethylamino-2,6-diethoxy-biphenyl-4-ylmethyl)-pyrimidine-2,4-diamine Starting from 5-(3,5-diethoxy-4-iodo-benzyl)-pyrimidine-2,4-diamine (example 1) (207 mg; 0.5 mmol) 4-dimethylamino-phenylboron acid (165 mg; 1.0 mmol) and tetrakis-triphenylphosphine-palladium (28 mg; 0.024 mmol) in dimethylformamide (3 ml), ethanol (0.84 ml) and a 2 M aqueous potassium phosphate solution (2.2 ml), 143 mg (70%) 5-(4'-dimethylamino-2,6-diethoxy-biphenyl-4-ylmethyl)-pyrimidine-2,4-diamine are obtained as a beige powder after crystallization from n-hexane/diethyl ether 3/1 (20 ml).

MS (ISP): 408.3 (M+H)+

(2w) 5-(2,6-Diethoxy-4'-morpholine-4-ylmethyl-biphenyl-4-ylmethyl)-pyrimidine-2,4-diamine Starting from 5-(3,5-diethoxy-4-iodo-benzyl)-pyrimidine-2,4-diamine (example 1) (300 mg; 0.72 mmol) and 4'-morpholin-4-ylmethyl-phenylboron acid (260 mg; 1.08 mmol), 185 mg (56%) 5-(2,6-diethoxy-4'-morpholin-4-ylmethyl-biphenyl-4-ylmethyl)-pyrimidine-2,4-diamine are obtained as a colourless powder.

MS (ISP): 464.3 (M+H)+. M.p. >250° C.

(2x) 5-[4-(2,3-Dihydro-benzo[1,4]dioxin-6-yl)-3,5-diethoxy-benzyl]-pyrimidine-2,4-diamine Starting from 5-(3,5-diethoxy-4-iodo-benzyl)-pyrimidine-2,4-diamine (example 1) (207 mg; 0.5 mmol), 3,4-ethylenedioxy-phenylboron acid (180 mg; 1.0 mmol) and tetrakis-triphenylphosphine-palladium (28 mg; 0.024 mmol) in dimethylformamide (3 ml), ethanol (0.84 ml) and a 2 M aqueous potassium phosphate solution (2.2 ml), [124 mg (59%)] 5-[4-(2,3-dihydro-benzo[1,4]dioxin-6-yl)-3,5-diethoxy-benzyl]-pyrimidine-2,4-diamine are obtained as a colourless powder after successive crystallization from n-hexane/diethyl 3/1 (20 ml) and methanol.

MS (ISP): 423.3 (M+H)+

(2y) %) [sic] 5-(3'-Dimethylamino-2,6-diethoxy-biphenyl-4-ylmethyl)-pyrimidine-2,4-diamine Starting from 5-(3,5-diethoxy-4-iodo-benzyl)-pyrimidine-2,4-diamine (example 1) (207 mg; 0.5 mmol) 3-dimethylamino-phenylboron acid (165 mg; 1.0 mmol) and tetrakis-triphenylphosphine-palladium (28 mg; 0.024 mmol) in dimethylformamide (3 ml), ethanol (0.84 ml) and a 2 M aqueous potassium phosphate solution (2.2 ml), 151 mg (74%) 5-(3'-dimethylamino-2,6-diethoxy-biphenyl-4-ylmethyl)-pyrimidine-2,4-diamine are obtained as a colourless powder after successive crystallization from n-hexane/diethyl ether 3/1 (20 ml) and methanol.

MS (ISP): 408.4 (M+H)+

(2z) 5-(2,6-Diethoxy-3'-nitro-biphenyl-4-ylmethyl)-pyrimidine-2,4-diamine

Starting from 5-(3,5-diethoxy-4-iodo-benzyl)-pyrimidine-2,4-diamine (example 1) (207 mg; 0.5 mmol) 3-nitro-phenylboron acid (167 mg; 1.0 mmol) and tetrakis-triphenylphosphine-palladium (28 mg; 0.024 mmol) in dimethylformamide (3 ml), ethanol (0.84 ml) and a 2 M aqueous potassium phosphate solution (2.2 ml), 146 mg (71 %) 5-(2,6-diethoxy-3'-nitro-biphenyl-4-ylmethyl)-pyrimidine-2,4-diamine are obtained as a colourless powder after successive crystallization from n-hexane/diethyl ether 3/1 (20 ml) and methylene chloride.

MS (ISP): 410.3 (M+H)+

(2aa) 5-(2,6-Diethoxy-4'-methoxy-3'-methoxymethyl-biphenyl-4-ylmethyl)-pyrimidine-2,4-diamine Starting from 5-(3,5-diethoxy-4-iodo-benzyl)-pyrimidine-2,4-diamine (example 1) (207 mg; 0.5 mmol), 4-methoxy-3-methoxymethyl-phenylboron acid (196 mg; 1.0 mmol) and tetrakis-triphenylphosphine-palladium (28 mg; 0.024 mmol) in dimethylformamide (3 ml), ethanol (0.84 ml) and a 2 M aqueous potassium phosphate solution (2.2 ml), 200 mg (91%) 5-(2,6-diethoxy-4'-methoxy-3'-methoxymethyl-biphenyl-4-ylmethyl)-pyrimidine-2,4-diamine are obtained as a colourless powder after successive crystallization from n-hexane/diethyl ether 3/1 (30 ml).

MS (ISP): 439.4 (M+H)+

The 4-methoxy-3-methoxymethyl-phenylboron acid employed is obtained in two stages (a–b) starting from 5-bromo-2-hydroxy-benzyl alcohol:

Stage a) 4-Bromo-1-methoxy-2-methoxymethyl-benzene

5-Bromo-2-hydroxy-benzyl alcohol (4.4 g; 20 mmol) is dissolved in tetrahydrofuran (200 ml; dried over a molecular sieve), a 60% sodium hydride suspension in oil (3.2 g; 80 mmol) is added and the mixture is stirred for one hour at room temperature. Methyl iodide (3.75 ml; 60 mmol) is then added and the reaction mixture is stirred for 22 hours at 60° C. After cooling to room temperature, the reaction mixture is diluted with water and extracted with ethyl acetate. The combined organic phases are washed successively with water and a saturated aqueous sodium chloride solution, dried over magnesium sulphate, filtered with suction and concentrated. The yellow oil obtained is chromatographed over silica gel (100 g) with n-hexane/ethyl acetate 4/1. 3.04 g (66%) 4-bromo-1-methoxy-2-methoxymethyl-benzene are obtained as a colourless oil.

MS: 232 (M)

Stage b) 4-Benzyloxy-3-methyl-phenylboron acid

Prepared analogously to 4-benzyloxy-3-methyl-phenylboron acid (described in example (2s) stage b)).

Starting from 4-bromo-1-methoxy-2-methoxymethyl-benzene (3.77 g; 16.3 mmol), 1.55 g (49%) 4-benzyloxy-3-methyl-phenylboron acid are obtained as a colourless powder.

MS(ISN): 195.3 (M–H)−

(2ab) [5-[4-(2,4-Diamino-pyrimidin-5-ylmethyl)-2,6-diethoxy-phenyl]-thiophen-2-yl]-methanol Starting from 5-(3,5-diethoxy-4-iodo-benzyl)-pyrimidine-2,4-diamine (example 1) (828 mg; 2.0 mmol) and (5-hydroxymethyl-thiophen-2-yl)-boron acid (632 mg; 4.0 mmol), 55 mg (7%) [5-[4-(2,4-diamino-pyrimidin-5-ylmethyl)-2,6-diethoxy-phenyl]-thiophen-2-yl]-methanol are obtained as a beige powder after crystallization from methanol.

M.p.: 225–228° C. MS (ISP): 401.3 (M+H)+

(5-Hydroxymethyl-thiophen-2-yl)-boron acid is prepared as follows, starting from 2-hydroxymethyl-thiophene:

2-Hydroxymethyl-thiophene (2.28 g; 20 mmol) is dissolved in tetrahydrofuran (40 ml, dried over a molecular sieve) and the solution is cooled to −78° C. while gassing with argon. A 1.6 M n-butyllithium solution in n-hexane (25 ml; 40 mmol) is slowly added dropwise. The reaction mixture is then allowed to warm to −30° C. and cooled again to −78° C., and a solution of trimethyl borate (6.69 ml; 60 mmol) in tetrahydrofuran (20 ml) is added dropwise in the course of 15 minutes at between −78 and −70° C. After stirring at −78° C. for 2 hours, the mixture is allowed to warm to room temperature and is poured on to water (50 ml), the pH is brought to 3 by addition of a 2 N aqueous hydrochloric acid solution (28 ml), the mixture is extracted with diethyl ether and the extract is washed with a saturated aqueous sodium chloride solution, dried with sodium sulphate, filtered with suction and concentrated.

Yield: 1.1 g (36%) (5-hydroxymethyl-thiophen-2-yl)-boron acid as a brown oil.

MS: 158 (M)

(2ac) 5-f3,5-Diethoxy-4-(5-morpholin-4-ylmethyl-thiophen-2-yl)-benzyl-pyrimidine-2,4-diamine Starting from 5-(3,5-diethoxy-4-iodo-benzyl)-pyrimidine-2,4-diamine (example 1) (1.24 g; 3.0 mmol) and (5-morpholin-4-ylmethyl-thiophen-2-yl)-boron acid (1.02 g; 4.5 mmol), 280 mg (20%) 5-[3,5-diethoxy-4-(5-morpholin-4-ylmethyl-thiophen-2-yl)-benzyl]-pyrimidine-2,4-diamine are obtained as a colourless powder after crystallization from methanol/methylene chloride (2/1).

M.p.: 213–214° C. MS (ISP): 470.2 (M+H)$^+$ (5-Morpholin-4-ylmethyl-thiophen-2-yl)-boron acid is prepared analogously to (5-hydroxymethyl-thiophen-2-yl)-boron acid (described in example (2ab)) starting from 4-thiophen-2-ylmethyl-morpholine (1.83 g; 10 mmol).

Yield: 900 mg (40%) (5-morpholin-4-ylmethyl-thiophen-2-yl)-boron acid as a beige powder. M.p.: 100° C. (decomposition) MS (ISN): 226.2 (M−H)$^+$ The 4-thiophen-2-ylmethyl-morpholine employed for this is prepared as follows, starting from 2-chloromethyl-thiophene. 2-Chloromethyl-thiophene (2.11 g; 16 mmol), morpholine (1.39 ml; 16 mmol) and sodium carbonate (anhydrous; 1.76 g; 16 mmol) are boiled under reflux in toluene (3.2 ml, dried over a molecular sieve) for 3 days. The reaction mixture is then cooled to room temperature, diluted with water and extracted with diethyl ether and the extract is washed twice with a saturated aqueous sodium chloride solution, dried over sodium sulphate, filtered with suction and concentrated.

Yield: 2.7 g (92%) 4-thiophen-2-ylmethyl-morpholine as a brown liquid. MS: 183 (M)

(2ad) 5-(2,6-Diethoxy4'-methyl-3'-nitro-biphenyl-4-ylmethyl)-pyrimidine-2,4-diamine Starting from 5-(3,5-diethoxy-4-iodo-benzyl)-pyrimidine-2,4-diamine (example 1) (828 mg; 2 mmol) and 3-nitro-4-methyl-phenylboron acid (724 mg; 4 mmol), tetrakis-triphenyl-phosphine-palladium (83.3 mg; 0.07 mmol) and aqueous 2 M potassium phosphate solution (5.5 ml; 11.0 mmol) in dimethylformamide, 800 mg (94%) 5-(2,6-diethoxy-4'-methyl-3'-nitro-biphenyl-4-ylmethyl)-pyrimidine-2,4-diamine are obtained as a beige powder analogously to example 2a.

MS (ISP): 424.2 (M+H)$^+$ (2ad) 5-(3'-Amino-2,6-diethoxy-4'-methyl-biphenyl-4-ylmethyl)-pyrimidine-2,4-diamine 5-(2,6-Diethoxy-4'-methyl-3'-nitro-biphenyl-4-ylmethyl)-pyrimidine-2,4-diamine (105 mg; 0.25 mmol) is dissolved in acetic acid conc. (6 ml), water (0.3 ml) and ethanol (1.5 ml) and hydrogenated over Pd/C 10% (85 mg). The catalyst is then filtered off with suction and rinsed thoroughly with ethanol and the solvent is evaporated off. The residue is taken up in water (20 ml) and the pH is adjusted to approx. 9–10 with NH$_4$OH conc., whereupon the product precipitates out. After stirring for 30 minutes, the product which has precipitated out is filtered off with suction, washed with water and dried under a high vacuum.

Yield: 77 mg (78%) 5-(3'-amino-2,6-diethoxy-4'-methyl-biphenyl-4-ylmethyl)-pyrimidine-2,4-diamine as a brown powder. MS (ISP): 394.3 (M+H)$^+$ (2ae) 4'-(2,4-Diamino-pyrimidin-5-ylmethyl)-2',6'-diethoxy-3-fluoro-biphenyl-4-ol Starting from 5-(3,5-diethoxy-4-iodo-benzyl)-pyrimidine-2,4-diamine (example 1) (300 mg, 0.72 mmol), 4-benzyloxy-3-fluoro-phenylboron acid (445 mg; 1.81 mmol) and tetrakis-triphenylphosphine-palladium (50 mg; 0.043 mmol) in dimethylformamide (20 ml) and a 2 M aqueous potassium phosphate solution (2.1 ml), 10 mg (30%) 5-(4'-benzyloxy-2,6-diethoxy-3'-fluoro-biphenyl-4-ylmethyl)-pyrimidine-2,4-diamine are obtained as a colourless powder analogously to example 2a after chromatography over silica gel with methylene chloride/methanol/NH$_4$OH conc. (90/10/1).

MS (ISP): 489.3 (M+H)$^+$ 5-(4'-Benzyloxy-2,6-diethoxy-3'-fluoro-biphenyl-4-ylmethyl)-pyrimidine-2,4-diamine (110 mg; 0.23 mmol) is hydrogenated over Pd/C 10% (80 mg) in ethanol (3 ml), conc. acetic acid (9 ml) and water (1 ml). The catalyst is filtered off with suction and the solution is evaporated. The residue is taken up in a little water, the pH is brought to 9–10 with NH$_4$OH conc. and the solid which has precipitated out is filtered off with suction, washed with water and dried under a high vacuum.

Yield: 52 mg (58%) 4'-(2,4-diamino-pyrimidin-5-ylmethyl)-2',6'-diethoxy-3-fluoro-biphenyl-4-ol as a colourless powder.

MS (ISP): 399.3 (M+H)$^+$ (2af) 5-(2,6-Diethoxy-3'-methylsulphonyl-biphenyl-4-ylmethyl)-pyrimidine-2,4-diamine Starting from 5-(3,5-diethoxy-4-iodo-benzyl)-pyrimidine-2,4-diamine (example 1) (178 mg; 0.43 mmol), 3-methylsulphonyl-phenylboron acid (140 mg; 0.86 mmol) and tetrakis-triphenylphosphine-palladium (69 mg; 0.060 mmol) in dimethoxyethane (4 ml), ethanol (3 ml) and sodium carbonate (387 mg; 3.6 mmol) in water (4.5 ml), 10 mg (63%) 5-(2,6-diethoxy-3'-methylsulphanyl-biphenyl-4-ylmethyl)-pyrimidine-2,4-diamine are obtained as a greyish powder analogously to example 2a after crystallization from methanol.

MS (ISP): 411.2 (M+H)$^+$

Starting from 5-(2,6-diethoxy-3'-methylsulphanyl-biphenyl-4-ylmethyl)-pyrimidine-2,4-diamine (205 mg; 0.5 mmol), 73 mg (33%) 5-(2,6-diethoxy-3'-methylsulphonyl-biphenyl-4-ylmethyl)-pyrimidine-2,4-diamine are obtained as a colourless powder analogously to example (2i).

MS (ISP): 443.2 (M+H)$^+$ (2ag) 4'-(2,4-Diamino-pyrimidin-5-ylmetyl)-2',6'-diethoxy-biphenyl-4-carbaldehyde Starting from 5-(3,5-diethoxy-4-iodo-benzyl)-pyrimidine-2,4-diamine (example 1) (621 mg; 0.15 mmol) and 4-formyl-phenylboron acid (300 mg; 2.0 mmol), 570 mg (72%) 4'-(2,4-diamino-pyrimidin-5-ylmethyl)-2',6'-diethoxy-biphenyl-4-carbaldehyde are obtained as a colourless powder.

MS (ISP): 393.2 (M+H)$^{+M.p.:}$ 178–182° C.

EXAMPLE 3

Preparation of Compounds of the Formula III, Equation 1, by Method B (Stille Coupling with Organostannane)

(3a) 2-[5-[4-(2,4-Diamino-pyrimidin-5-ylmethyl)-2,6-diethoxy-phenyl]-thiophen-2-ylmethoxyl]-1-morpholin-4-yl-ethanone 5-(3,5-Diethoxy-4-iodo-benzyl)-pyrimidine-2,4-diamine (example 1) (828 mg; 2 mmol); tris-(dibenzylidene-acetone)-dipalladium-chloroform complex ($Pd_2(dba)_3 \cdot CHCl_3$) (83 mg; 0.08 mmol), copper iodide (38 mg; 0.2 mmol) and triphenylarsene (Ph3As) (245 mg; 0.8 mmol) are heated to 120° C. in 1-methyl-2-pyrrolidone (10 ml) under argon. A solution of 1-morpholin-4-yl-2-(5-trimethylstannanyl-thiophen-2-ylmethoxy)-ethanone (970 mg; 2.4 mmol) in 1-methyl-2-pyrrolidone (NMP) (5 ml) is added dropwise at 120° C. in the course of hour. The reaction mixture is then filtered, washed thoroughly with methanol and concentrated. The residue is chromatographed over silica gel with methylene chloride/methanol/ammonia (95/5/0.5) and then crystallized from methanol.

Yield: 69 mg (23%) 2-[5-[4-(2,4-diamino-pyrimidin-5-ylmethyl)-2,6-diethoxy-phenyl]-thiophen-2-ylmethoxy]-1-morpholin-4-yl-ethanone as a colourless powder.

MS (ISP): 528.3 $(M+H)^+$

The 1-morpholin-4-yl-2-(5-trimethylstannanyl-thiophen-2-ylmethoxy)-ethanone employed is prepared as follows (stages a–b):

Stage a) (5-Trimethylstannanyl-thiophen-2-yl)-methanol

2-Thiophene-methanol (4.8 ml; 50 mmol) is dissolved in tetrahydrofaran over a molecular sieve under argon. The reaction mixture is cooled to −78° C. and a 1.6 M solution of n-butyl-lithium in tetrahydrofuran (62.5 ml; 100 mmol) is added dropwise such that the temperature does not exceed −70° C. The mixture is then subsequently stirred for one hour at −78° C. and half an hour at room temperature. The reaction mixture is then poured on to a saturated aqueous sodium chloride solution (50 ml) and extracted with ether (3×50 ml). The combined organic phases are washed with a saturated aqueous sodium chloride solution (2×30 ml), dried over sodium sulphate, filtered with suction and concentrated. The residue is purified by means of bulb tube distillation at 122–124° C./0.6 mbar.

Yield: 9.6 g (69%) of a yellow oil.

Stage b) 1-Morpholin-4-yl-2-(5-trimethylstannanyl-thiophen-2-ylmethoxy)-ethanone (5-Trimethylstannanyl-thiophen-2-yl)-methanol (6.51 g; 23.5 mmol) and sodium iodide (3.46 g; 23.2 mmol) are dissolved in tetrahydrofuran (100 ml) at room temperature under argon and the solution is cooled to −78° C. A 1.6 M n-butyllithium solution in n-hexane (14.7 ml; 23.5 mmol) is then added dropwise in the course of 10 minutes and the mixture is stirred for a further 60 minutes at −78° C. Hexamethylphosphoramide (8.33 ml, 46.48 mmol) and 4-(chloroacetyl)morpholine (4.58 g; 28 mmol) are then added dropwise in succession. The reaction mixture is then subsequently stirred at room temperature for 18 hours. After this period of time diisopropylamine (4 ml) is added dropwise and the mixture is stirred for one hour at room temperature. The reaction mixture is then poured on to an aqueous saturated ammonium chloride solution (150 ml) and extracted with diethyl ether (3×200 ml). The combined organic phases are washed with a saturated aqueous sodium chloride solution (2×80 ml), dried over sodium sulphate, filtered with suction and concentrated. The residue is chromatographed over silica gel with n-hexane/ethyl acetate 1/1.

Yield: 1.03 g (9%) 1-morpholin-4-yl-2-(5-trimethylstannanyl-thiophen-2-ylmethoxy)-ethanone as a yellowish oil.

MS: 390 (M−CH3)

The following are prepared analogously [examples 3(b) and 3(c)]:

(3b) 2-[5-[4-(2,4-Diamino-pyrimidin-5-ylmethyl)-2,6-diethoxy-phenyl]-thiophen-2-ylmethoxy]-1-thiomorpholin-4-yl-ethanone Starting from 207 mg; 0.5 mmol 5-(3,5-diethoxy-4-iodo-benzyl)-pyrimidine-2,4-diamine (example 1) (207 mg; 0.5 mmol) and 1-thiomorpholin-4-yl-2-(5-trimethyl-stannanyl-thiophen-2-ylmethoxy)-ethanone (3×210 mg; 3×0.5 mmol), 24 mg (9%) 2-[5-[4-(2,4-diamino-pyrimidin-5-ylmethyl)-2,6-diethoxy-phenyl]-thiophen-2-ylmethoxy]-1-thiomorpholin-4-yl-ethanone are obtained as a beige powder.

M.p.: >180° C. (decomposition) MS (ISP): 544.2 (M+H)

The 1-thiomorpholin-4-yl-2-(5-trimethylstannanyl-thiophen-2-ylmethoxy)-ethanone employed is prepared analogously to example (3a) (stage b)) starting from (5-trimethylstannanyl-thiophen-2-yl)-methanol (7.66 g; 27.67 mmol; described, in example (3a), stage a)), sodium iodide (4.07 g; 27.34 mmol) and 2-chloro-1-thiomorpholiri-4-yl-ethanone (5.92 g; 32.94 mmol)

Yield: 1.6 g (12%) 1-thiomorpholin-4-yl-2-(5-trimethylstannanyl-thiophen-2-ylmethoxy)-ethanone as a yellow oil. MS: 421 (M); 406 (M−$CH_3$)

(3c) 2-[5-[4-(2,4-Diamino-pyrimidin-5-ylmethyl)-2,6-diethoxy-phenyl]-thionhen-2-ylmethoxy]-1-piperidin-1-yl-ethanone Starting from 5-(3,5-diethoxy-4-iodo-benzyl)-pyrimidine-2,4-diamine (example 1) (828 mg; 2.0 mmol) and 1-piperidin-1-yl-2-(5-trimethylstannanyl-thiophen-2-ylmethoxy)-ethanone (3×1.6g; 3×4.0 mmol), 85 mg (5%) 2-[5-[4-(2,4-diamino-pyrimidin-5-ylmethyl)-2,6-diethoxy-phenyl]-thiophen-2-ylmethoxy]-1-piperidin-1-yl-ethanone are obtained as a colourless powder.

M.p.: 155–160° C. MS (ISP): 526,0.3 $(M+H)^+$

The 1-piperidin-1-yl-2-(5-trimethylstannanyl-thiophen-2-ylmethoxy)-ethanone employed is prepared analogously to example (3a) (stage b)) starting from (5-trimethylstannanyl-thiophen-2-yl)-methanol (6.98 g; 25.2 mmol; described in example (3a) stage a)), sodium iodide (3.71 g; 24.9 mmol) and 1-chloroacetyl-piperidine (4.85 g; 30 mmol).

Yield: 4.4 g (37%) 1-piperidin-1-yl-2-(5-trirnethylstannanyl-thiophen-2-ylmethoxy)-ethanone as a colourless oil. MS: 403 (M); 388 (M−$CH_3$)

(3d) 5-[4-(2,6-Dimethyl-pyridin-4-yl)-3,5-diethoxy-benzyl]-pyrimidine-2,4-diamine 5-(3,5-Diethoxy-4-iodo-benzyl)-pyrimidine-2,4-diamine (example 1) (414 mg; 1 mmol), 2,6-dimethyl-4-trimethyltin-pyridine (404 mg; 1.5 mmol), bis(triphenyl-phosphine) palladium dichloride (20 mg) and a few crystals of 2,6-di-tert-butyl-4-methylphenol are dissolved in dimethylformamide (5 ml) and the solution is stirred for 24 hours at 140° C. while gassing with argon. The reaction mixture is concentrated, a little water is added to the residue obtained, the pH is adjusted to 8 by addition of NH₄OH conc. and the entire mixture is filtered with suction. The mother liquor is concentrated and the residue is chromatographed over silica gel (30 g) with methylene chloride/methanol/NH₄OH conc. (19/1/0.05). 26 mg (6.6%) 5-[4-(2,6-dimethyl-pyridin-4-yl)-3,5-diethoxy-benzyl]-pyrimidine-2,4-diamine are obtained as a yellow powder.

MS(ISP): 394.3 (M+H)⁺

The following is prepared analogously to example (3d):

(3e) 5-[3,5-Diethoxy-4-(6-methylsulphanyl-pyridin-3-yl)-benzyl]-pyrimidine-2,4-diamine Starting from 5-(3,5-diethoxy-4-iodo-benzyl)-pyrimidine-2,4-diamine (example 1) (2.07 . . . [sic]; 5.0 mmol) and 2-methylsulphanyl-5-trimethylstannanyl-pyridine (2.12 g; 7.5 mmol), 420 mg (21%) 5-[3,5-diethoxy-4-(6-methylsulphanyl-pyridin-3-yl)-benzyl]-pyrimidine-2,4-diamine are obtained as a light-yellow powder.

MS (ISP): 412.3 (M+H)⁺

EXAMPLE 4

Preparation of Compounds of the Formula III, Equation 1, by Method C (Suzuki Coupling with in situ Generation of R²—B(OH)₂)

(4a) 4'-(2,4-Diamino-pyrimidin-5-ylmethyl)-2',6'-diethoxy-biphenyl-4-carbonitrile 4-Bromo-benzonitrile (186 mg; 1 mmol), bis(pinacolato)diboron (279 mg; 1.1 mmol), potassium acetate (294 mg; 3 mmol) and 1,1'-bis(diphenylphosphino)ferrocene-dichloropalladium(II) (PdCl₂(dppf)) (46 mg; 0.06 mmol) are stirred in dimethylformamide (6 ml; dried over a molecular sieve) at a bath temperature of 80° C. for 3 hours while gassing with argon. After cooling to room temperature, dimethylformamide (20 ml; dried over a molecular sieve), tetrakis-triphenylphosphine-palladium (90 mg; 0.078 mmol), 5-(3,5-diethoxy-4-iodo-benzyl)-pyrimidine-2,4-diamine (example 1) (331 mg; 0.8 mmol) and a 2 M aqueous potassium phosphate solution (4 ml) are added. The reaction mixture is stirred for approx. 1.5 hours at 80° C., cooled to room temperature and concentrated. The residue obtained is chromatographed over silica gel (100 g) with methylene chloride/methanol/NH₄OH (19/1/0.05)0.61 mg (20%) 4'-(2,4-diamino-pyrimidin-5-ylmethyl)-2',6'-diethoxy-biphenyl-4-carbonitrile are obtained as a beige powder.

MS(ISP): 390.1 (M+H)⁺

The following are prepared analogously (examples 4(b)-(4u), 4(x), 4(z), 4(ab), (4ae), 4(f), any amounts of the reaction participants which deviate from example 4(a) being stated specifically):

(4b) N-[4'-(2,4-Diamino-pyrimidin-5-ylmethyl)-2',6'-diethoxy-biphenyl-4-yl]-methanesulphonamide Starting from N-(4-bromo-phenyl)-methanesulphonamide (250 mg; 1 mmol) and 5-(3,5-diethoxy-4-iodo-benzyl)-pyrimidine-2,4-diamine (example 1) (331 mg; 0.8 mmol), 133 mg (36%) N-[4'-(2,4-diamino-pyrimidin-5-ylmethyl)-2',6'-diethoxy-biphenyl-4-yl]-methanesulphonamide are obtained as a light-beige powder

MS (ISP): 458.2 (M+H)⁺

(4c) 5-(4'-Amino-2,6-diethoxy-biphenyl-4-ylmethyl)-pyrimidine-2 4-diamine

Starting from N-(4-bromo-phenyl)-2,2,2-trifluoro-acetamide (536 mg; 2 mmol) and 5-(3,5-diethoxy-4-iodo-benzyl)-pyrimidine-2,4-diamine (example 1) (662 mg; 1.6 mmol), 89 mg (15%) 5-(4'-amino-2,6-diethoxy-biphenyl-4-ylmethyl)-pyrimidine-2,4-diamine are obtained as a pale brown powder after treatment overnight with 1 N sodium hydroxide solution (0.55 ml; 0.55 mmol) and ethanol (15 ml) at 70° C.

MS (ISP): 380.4 (M+H)⁺

(4d) 5-[3,5-Diethoxy-4-(6-morpholin-4-ylmethyl-pyridin-3-yl)-benzyl]-pyrimidine-2,4-diamine Starting from 4-(5-bromo-pyridin-2-ylmethyl)-morpholine (280 mg; 1.08 mmol), bis(pinacolato)diboron (305 mg; 1.2 mmol), potassium acetate (321 mg; 3.27 mmol) and 1,1'-bis(diphenylphosphino)ferrocene-dichloropalladium(II) (PdCl₂(dppf)) (46 mg; 0.06 mmol) and from 5-(3,5-diethoxy-4-iodo-benzyl)-pyrimidine-2,4-diamine (example 1) (361 mg; 0.872 mmol), 43 mg (10%) 5-[3,5-diethoxy-4-(6-morpholin-4-ylmethyl-pyridin-3-yl)-benzyl]-pyrimidine-2,4-diamine are obtained as a colourless powder.

MS (ISP): 465.3 (M+H)⁺.

(4e) N-[4'-(2,4-Diamino-pyrimidin-5-ylmethyl)-2',6'-diethoxy -3-methyl-biphenyl-4yl]-acetamide Starting from N-[4-bromo-2-methylJ-acetanilide (274 mg; 1.2 mmol), bis(pinacolato)diboron (336 mg; 1.32 mmol), potassium acetate (354 mg; 3.6 mmol) and 1,1'-bis(diphenylphosphino)ferrocene-dichloro-palladium(II) (PdCl₂(dppf)) (35 mg; 0.05 mmol) in dimethylformamide, and then 5-(3,5-diethoxy-4-iodo-benzyl)-pyrimidine-2,4-diamine (example 1) (414 mg; 1 mmol), tetrakis-triphenylphosphine-palladium (83.3 mg; 0.07 mmol), aqueous 2 M potassium phosphate solution (3.36 ml; 6.7 mmol) in dimethylformamide, 115 mg (22%) N-[4'-(2,4-diamino-pyrimidin-5-ylmethyl)-2',6'-diethoxy-3-methyl-biphenyl-4-yl]-acetamide are obtained as brown crystals.

MS (ISP): 436.3 (M+H)⁺

(4f) 5-(4'-Amino-2,6-diethoxy-3'-methyl-biphenyl-4ylmethyl)-pyximidine-2,4-diamine Starting from N-(4-bromo-2-methyl-phenyl)-2,2,2-trifluoroacetamide (670 mg; 2.5 mmol), bis(pinacolato)diboron (698 mg; 2.75 mmol), potassium acetate (736 mg; 7.5 mmol) and 1,1'-bis(diphenylphosphino)ferrocene-dichloropalladium(II) (PdCl₂(dppf)) (73 mg; 0.1 mmol) in dimethylformamide, thereafter 5-(3,5-diethoxy-4-iodo-benzyl)-pyrimidine-2,4-diamine (example 1) (828 mg; 2 mmol), tetrakis-triphenylphosphine-palladium (173.3 mg; 0.15 mmol), aqueous 2 M potassium phosphate solution (7 ml; 14 mmol) in dimethylformamide, 56 mg (10%) 5-(4'-amino-2,6-diethoxy-3'-methyl-biphenyl-4-ylmethyl)-pyrimidine-2,4-diamine are obtained as pale brown crystals

MS (ISP): 394.3 (M+H)⁺

N-(4-Bromo-2-methyl-phenyl)-2,2,2-trifluoroacetamide was prepared from 4-bromo-2-methyl-aniline analogously to example (4l) (below).

(4g) N-[4'-(2,4-Diamino-pyrimidin-5-ylmethyl)-2',6'-diethoxy-biphenyl-4-yl]-2-morpholin-4-yl-acetamide Starting from N-(4-bromo-phenyl)-4-morpholine-acetamide (299 mg; 1 mmol) and 5-(3,5-diethoxy-4-iodo-benzyl)-pyrimidine-2,4-diamine (example 1) (331 mg 0.8 mmol), 70 mg (17%) N-[4'-(2,4-diamino-pyrimidin-5-

(4h) 4-Amino-4'-(2,4-diamino-pyrimidin-5-ylmethyl)-2',6'diethoxy-biphenyl-3-carbonitrile Starting from 2-amino-5-benzonitrile (940 mg; 3.85 mmol) and 5-(3,5-diethoxy-4-iodo-benzyl)-pyrimidine-2,4-diamine (example 1) (1.27 g; 3.06 mmol), 845 mg (68%) 4-amino-4'-(2,4-diamino-pyrimidin-5-ylmethyl)-2',6'-diethoxy-biphenyl-3-carbonitrile are obtained as a green powder

MS (ISP): 405.4 (M+H)+

(4i) 5-(3'-Amino-2,6-diethoxy-4'-methoxy-biphenyl-4-ylmethyl)-pyrimidine-2,4-diamine Starting from N-(3-bromo-6-methoxy-phenyl)-2,2,2-trifluoroacetamide (450 mg; 1.5 mmol), bis(pinacolato) diboron (380 mg; 1,5 mmol), potassium acetate (442 mg; 3 mmol) and 1,1'-bis(diphenylphosphino)ferrocene-dichloropalladium(II) (PdCl$_2$(dppf)) (72 mg; 0.06 mmol) in dimethylformamide (10 ml), thereafter 5-(3,5-diethoxy-4-iodo-benzyl)-pyrimidine-2,4-diamine (example 1) (415 mg; 1 mmol), tetrakis-triphenylphosphine-palladium (87 mg; 0,1 mmol) and aqueous 2 M potassium phosphate solution (3 ml; 6 mmol) in dimethylformamide (30 ml), 225 mg 5-(3'-amino-2,6-diethoxy-4'-methoxy-biphenyl-4-ylmethyl)-pyrimidine-2,4-diamine are obtained as pale brown crystals

MS (ISP): 410.4 (M+H)+

N-(3-Bromo-6-methoxy-phenyl)-2,2,2-trifluoroacetamide is prepared from 3-bromo-6-methoxy-aniline analogously to example (4l) (below).

(4j) 5-(3'-Amino-2,6-diethoxy-4'-morpholino-4-ylmethy-biphenyl)-pyrimidine-2,4-diamine Starting from N-(5-bromo-2-methylmorpholine-phenyl)-2,2,2-trifluoroacetamide (550 mg; 1.5 mmol), bis(pinacolato)diboron (380 mg; 1.5 mmol), potassium acetate (442 mg; 3 mmol) and 1,1'-bis(diphenylphosphino)ferrocene-dichloropalladium(II) (PdCl$_2$(dppf)) (72 mg; 0.06 mmol) in dimethylformamide (10 ml), thereafter 5-(3,5-diethoxy-4-iodo-benzyl)-pyrimidine-2,4-diamine (example 1) (415 mg; 1 mmol), tetrakis-triphenylphosphine-palladium (87 mg; 0.1 mmol) and aqueous 2 M potassium phosphate solution (3 ml; 6 mmol) in dimethylformamide (30 ml), 375 mg (78%) 5-(3'-amino-2,6-diethoxy-4'-methyl-morpholino-4-ylmethyl-biphenyl)-pyrimidine-2,4-diamine are obtained as a beige solid

MS (ISP): 479.4 (M+H)+

N-(5-Bromo-2-methylmorpholin-phenyl)-2,2,2-trifluoroacetamide is prepared from 5-bromo-2-methylmorpholine-aniline analogously to example (4l).

(4k) 5-[3,5-Diethoxy-4-(2-morpholin-4-yl-pyrimidin-5-yl)-benzyl]-pyrimidine-2,4-diamine Starting from 4-(5-bromo-2-pyrimidin-yl)-morpholine (244 mg; 1 mmol), bis(pinacolato)diboron (279 mg; 1.1 mmol), potassium acetate (294 mg; 3 mmol) and 1,1'-bis(dtiphenylphosphino)ferrocene-dichloropalladium(II) (PdCl$_2$(dppf)) (24 mg; 0.035 mmol) and from 5-(3,5-diethoxy-4-iodo-benzyl)-pyrimidine-2,4-diamine (example 1) (373 mg; 0.9 mmol), 49 mg (12%) 5-[3,5-diethoxy-4-(2-morpholin-4-yl-pyrimidin-5-yl)-benzyl]-pyrimidine-2,4-diamine are obtained as a colourless powder MS (ISP): 452.3 (M+H)+ M.p. 196–199° C.

(4l) 5-(4'-Amino-2,6-diethoxy-3'-methoxy-biphenyl-4-ylmethyl)-pyrimidine-2,4-diamine Starting from N-(4-iodo-2-methoxphenyl)-2,2,2-trifluoroacetamide (700 mg; 1.5 mmol), bis(pinacolato) diboron (380 mg; 1.5 mmol), potassium acetate (442 mg; 4 mmol) and 1,1'-bis(diphenylphosphino)ferrocene-dichloropalladium(II) (PdCl$_2$(dppf)) (72 mg; 0.06 mmol) in dimethylformamide (10 ml), thereafter 5-(3,5-diethoxy-3-iodo-benzyl)-pyrimidine-2,4-diamine (example 1) (415 mg; 1 mmol), tetrakis-triphenylphosphine-palladium (87 mg; 0,1 mmol) and aqueous 2 M potassium phosphate solution (3 ml; 6 mmol) in dimethylformamide (30 ml), 250 mg (61%) 5-(3'-amino-2,6-diethoxy-4'-methyl-biphenyl-4-ylmethyl)-pyrimidine-2,4-diamine are obtained as a beige solid

MS (ISP): 410.4 (M+H)+

N-(4-Iodo-2-methoxy-phenyl)-2,2,2-trifluoroacetamide is prepared as follows:

2-Methoxy-aniline (1 g; 8.12 mmol) is dissolved in a 2/1 methanol/methylene chloride mixture. Calcium carbonate (1.5 g) and benzyl-trimethyl-ammonium dichlorate (3.1 g; 8.93 mmol) are added at room temperature. After stirring for 2 days, the solvent is evaporated off and the residue is chromatographed over silica gel with n-hexane/ethyl acetate (8/2). The pure fractions are combined and the solvent is evaporated off. 1.76 g (87%) 4-iodo-3-methoxy-aniline are obtained as a brown oil. The entire amount is diluted with methylene chloride (30 ml), and pyridine (1.6 ml; 19.9 mmol) and trifluoroacetic anhydride (1.12 ml; 7.96 mnmol) are added and the mixture is stirred for one hour at room temperature. The reaction solution is poured on to aqueous hydrochloric acid (1 M; 20 ml) and the mixture is extracted twice with ethyl acetate (20 ml). The combined organic phases are dried over sodium sulphate, filtered and concentrated. The residue is chromatographed over silica gel with n-hexane/ethyl acetate (7/3). The pure fractions are combined and the solvent is evaporated off.

Yield: 2.10 g (92%) as a white solid MS: 345 (M)

(4m) 5-(3,5-Diethoxy-4-quinolin-6-yl-benzyl)-pyrimidine-2,4-diamine

Starting from trifluoromethanesulphonic acid 6-quinolinyl ester (424 mg; 1.53 mmol), bis(pinacolato) diboron (279 mg; 1.1 mmol), potassium acetate (450 mg; 4.6 mmol), 1,1'-bis(diphenylphosphino)ferrocene-dichloropalladium(II) (PdCl$_2$(dppf)) (8 mg; 0.025 mmol) and from 5-(3,5-diethoxy-4-iodo-benzyl)-pyrimidine-2,4-diamine (example 1) (414 mg; 1 mmol), 66 mg (12%) 5-(3,5-diethoxy-4-quinolin-6-yl-benzyl)-pyrimidine-2,4-diamine are obtained as a colourless powder.

MS (ISP): 416.2 (M+H)+M.p.: 232–236° C.

(4n) 5-(3'-Amino-2,6-diethozy-4'-fluoro-biphenyl-4-ylmethyl)-pyrimidine-2,4-diamine Starting from N-(3-bromo-4-fluoro-phenyl)-2,2,2-trifluoroacetamide (200 mg; 0.7 mmol), bis(pinacolato) diboron (266 mg; 1.05 mmol), potassium acetate (206 mg; 2.1 mmol) and 1,1'-bis(diphenylphosphino)ferrocene-dichloropalladium(II) (PdCl$_2$(dppf)) (31 mg; 0.04 mmol) in dimethylformamide (10 ml), thereafter 5-(3,5-diethoxy-4-iodo-benzyl)-pyrimidine-2,4-diamine (example 1) (232 mg; 0.56 mmol), tetra-(triphenyl-phosphine)-palladium (48 mg; 0.04 mmol) and aqueous 2 M potassium phosphate solution (2.1 ml; 4.2 mmol) in dimethylformamide (30 ml), 102 mg (37%) 5-(3'-amino-2,6-diethoxy-4'-fluoro-biphenyl-4-ylmethyl)-pyrimidine-2,4-diamine are obtained as a pale brown solid

MS (ISP): 398.3 (M+H)+

The N-(3-bromo-4-fluoro-phenyl)-2,2,2-trifluoroacetamide employed is prepared from 3-bromo-4-fluoro-aniline analogously to example (4l).

(4o) 4'-(2,4-Diamino-gyrimidin-5-ylmethyl)-2',6'-diethoxy-biphenyl-4-sulphonic acid amide Starting from 4-bromobenzenesulphonamide (236 mg; 1 mmol) and 5-(3,5-diethoxy-4-iodo-benzyl)-pyrimidine-2,4-diamine (example 1) (331 mg; 0.8 mmol), 46 mg (13%) 4'-(2,4-diamino-pyrimidin-5-ylmethyl)-2',6'-diethoxy-biphenyl-4-sulphonic acid amide are obtained as a grey powder.

MS (ISP): 444.2 (M+H)+

(4p) N-[4'-(2,4-Diamino-pyrimidin-5-ylmethl)-2',6'-diethoxy-biphen-4-yl]-acetamide Starting from 4-bromoacetanilide (214 mg; 1 mmol) and 5-(3,5-diethoxy-4-iodo-benzyl)-pyrimidine-2,4-diamine (example 1) (331 mg; 0.8 mmol), 136 mg (40%) N-[4'-(2,4-diamino-pyrimidin-5-ylmethyl)-2',6'-diethoxy-biphenyl-4-yl]-acetamide are obtained as a grey powder.

MS (ISP): 422.2 (M+H)+

(4g) 5-[4-(6-Amino-pyridin-3-yl)-3,5-diethoxy-benzyl]-pyrimidine-2,4-diamine

Bis-(triphenylphosphine)-palladium(II) dichloride (42 mg; 0.036 mnnol) is suspended in dioxane (2 ml) while gassing with argon, and 5-brozno-2-(2,2,5,5-tetramethyl-[1,2,5]azadisilolidin-1-yl)-pyridine (0.63 g; 2 mmol) in dioxane (6 ml) and triethylamine (0.607 g; 6 mmol) are added. After stirring for 15 minutes at room temperature, a 1 M solution of 4,4,5,5-tetramethyl-1,3,2-dioxaborolane (bis(pinacolato)diboron) in dioxane (3 ml; 3 mmol) is added and the reaction mixture is heated under reflux for 6 hours. The solvents are evaporated on a rolling evaporator and the residue is dried under a high vacuum for 2 hours. 720 mg of crude 2-(2,2,5,5-tetramethyl[1,2,5]azadisilolidin-1-yl)-5-(4,4,5,5-tetramethyl (1,3,2]dioxaborolan-2-yl)-pyridine are obtained. The crude intermediate product is dissolved in 6 ml dimethylformamide, while gassing with argon, and tetrakis-triphenylphosphine-palladium (50 mg; 0.043 mmol), 5-(3,5-diethoxy-4-iodo-benzyl)-pyrimidine-2,4-diamine (example 1) (414 mg; 1 mmol) and 2 M potassium phosphate solution (6 ml) are added to the solution formed. The reaction mixture is then boiled under reflux for 5 hours. The reaction mixture is stirred with water (50 ml) and extracted three times with 25 ml methylene chloride each time. The combined organic phases are dried over magnesium sulphate and concentrated. The residue is chromatographed over silica gel (50 g) with methylene chloride/methanol (17/3). The pure fractions are combined and concentrated and the residue is dried under a high vacuum.

Yield: 0.32 g (84%) 5-[4-(6-amino-pyridin-3-yl)-3,5-diethoxy-benzyl]-pyrirnidine-2,4-diamine as a beige powder.

MS (EI): 380 (M+). M.p. 215–218° C.

(4r) 5-(4'-Amino-2,6-diethoxy-3'-fluoro-biphenyl-4–3dmethyl)-Ryrimidine-2,4-diamine Starting from N-(4-bromo-3-fluoro-phenyl)-2,2,2-trifluoroacetamide (700 mg; 2.45 mmol), bis(pinacolato) diboron (932 mg; 3.67 mmol), potassium acetate (721 mg; 7.34 mmol) and 1,1'-bis(diphenylphosphino)ferrocene-dichloropalladium(II) (PdCl₂(dppf)) (107 mg 0.15 mmol) in dimethylformamide (16 ml), thereafter 5-(3,5-diethoxy-4-iodo-benzyl)-pyrimidine-2,4-diamine (example 1) (760 mg; 1.84 mmol), tetrakis-triphenylphosphine-palladium (170 mg; 0.15 mmol) and aqueous 2 M potassium phosphate solution (7.4 ml; 14.8 mmol) in dimethylformamide (48 ml), 307 mg (42%) 5-(4'-amino-2,6-diethoxy-3'-fluoro-a iphenyl-4-ylmethyl)-pyrimidine-2,4-diamine are obtained as a grey solid.

MS (ISP): 398.3 (M+H)+

The N-(4-bromo-3-fluoro-phenyl)-2,2,2-trifluoroacetamide employed is prepared from 4-bromo-3-fluoro-aniline analogously to example (4l).

(4s) (RS)-3-[4'-(2,4-Diamino-pyrimidin-5-ylmethyl)-2',6'-diethoxy-biphenyl-4-yl]-5-methoxymethyl-oxazolidin-2-one Starting from (RS)-3-(4-iodophenyl)-5-(methoxymethyl)-oxazolidin-2-one (333 mg; 1 mmol) and 5-(3,5-diethoxy-4-iodo-benzyl)-pyrimidine-2,4-diamine (example 1) (331 mg; 0.8 mmol), 194 mg (49%) (RS)-3-[4'-(2,4-diamino-pyrimidin-5-ylmethyl)-2',6'-diethoxy-biphenyl-4-yl]-5-methoxymethyl-oxazolidin-2-one are obtained as a beige powder.

MS (ISP): 494.3 (M+H)+

(4t) 5-(5'-Amino-2,6-diethoxy-3'-fluoro-biphenyl-4-ylmethyl )-pyrimidine-2,4-diamine Starting from N-(5-iodo-3-fluoro-phenyl)-2,2,2-trifluoroacetamide (600 mg; 1.8 mmol), bis(pinacolato) diboron (595 mg; 2.34 mmol), potassium acetate (530 mg; 5.41 mol [sic]) and 1,1'-bis(diphenylphosphino)ferrocene-dichloropalladium(II) (PdCl₂(dppf)) (80 mg; 0.11 mmol) in dimethylformamide (10 ml), the reaction mixture is poured on to water and extracted with ethyl acetate. The combined organic phases are washed with a saturated aqueous sodium chloride solution, dried over magnesium sulphate, filtered with suction and concentrated and the residue is employed directly in the next step. After reaction with 5-(3,5-diethoxy-4-iodo-benzyl)-pyrimidine-2,4-diamine (example 1) (523 mg; 1.26 mmol), tetrakis-triphenylphosphine-palladium (125 mg; 0.11 mmol) and aqueous 2 M sodium carbonate (18 ml; 36 mmol) in a 5/1 dimethoxyethanelethanol mixture (30 ml), 321 mg (45%) 5-(5'-amino-2,6-diethoxy-3'-fluoro-biphenyl-4-ylmethyl)-pyrimidine-2,4-diamine are obtained as a brown solid.

MS (ISP): 398.4 (M+H)+

The N-(5-iodo-3-fluoro-phenyl)-2,2,2-trifluoroacetamide employed is prepared as follows:

3-Iodo-5-fluoro-1-nitrobenzene (5.2 g; 19.48 mmol) is dissolved in a 4/3 water/tetrahydrofuran mixture. Powdered iron (8.7 g; 156 mmol), followed by acetic acid (4.5 ml) are added at room temperature and the suspension formed is stirred overnight at 40° C. The reaction mixture is filtered over diatomaceous earth and poured on to water. The mixture is extracted with ethyl acetate and the combined organic phases are dried over sodium sulphate, filtered and concentrated. The residue is chromatographed over silica gel with n-hexane/ethyl acetate (3/1). The pure fractions are combined and the solvent is evaporated off. The residue is diluted with methylene chloride (30 ml), and pyridine (4,0 ml; 49.5 mmol) and trifluoroacetic anhydride (3.44 ml; 24.7 mmol) are added and the mixture is stirred for one hour at room temperature. The reaction solution is poured on to aqueous hydrochloric acid (1 M; 50 ml) and the mixture is extracted twice with ethyl acetate (50 ml). The combined organic phases are dried over sodium sulphate, filtered and concentrated. The residue is chromatographed over silica gel with n-hexanelethyl acetate (9/1). The pure fractions are combined and the solvent is evaporated off.

Yield: 5.40 g (98%) as a white solid.

MS: 333 (M)

(4u) 4'-(2,4-Diamino-pyrimidin-5-ylmethyl)-2',6'-diethoxy-biphenyl-3-carbaldehyde Starting from 3-bromobenzaldehyde (515 mg; 3 mmol), bis(pinacolato)diboron (1.14 g; 4.5 mmol), potassium acetate (883 mg; 9 mmol), bis(triphenylphosphine) palladium(II) dichloride (142 mg; 0.2 mmol) and from 5-(3,5-diethoxy-4-iodo-benzyl)-pyrimidine-2,4-diamine (exampDle 1) (931 mg; 2.25 mmol), 838 mg (95%) 4'-(2,4-diamino-pyrimidin-5-ylmethyl)-2',6'-diethoxy-biphenyl-3-carbaldehyde are obtained as a pale yellow powder.

MS (ISP): 393.2 (M+H)$^+$.

(4v) 5-[2,6-Diethoxy-4'-[(2,2,2-trifluoroethylamino)-methyl]-biphenyl-4-ylmethyl]-pyrimidine-2,4-diamine A solution of 2,2,2-trifluoroethylamine (0.477 ml; 6 mmol) in 4 ml methanol is adjusted to pH 6 with glacial acetic acid, and 4'-(2,4-diamino-pyrimidin-5-ylmethyl)-2',6'-diethoxy-biphenyl-4-carbaldehyde (392 mg; 1 mmol) is added. The reaction mixture is then cooled to 0° C. and sodium cyanoborohydride (38 mg; 0.6 mmol) is added. After half and hour at 0° C., the mixture is stirred for 3 h at room temperature. After evaporation of the reaction mixture, the residue is stirred in 20 m water and the mixture is adjusted to pH 8 with 1 N aqueous sodium hydroxide solution. The substance which has precipitated out is filtered off with suction and dried under a high vacuum. The residue is stirred in 20 ml methylene chloride and filtered off with suction again and dried. 105 mg (22%) 5-{2,6-Diethoxy-4'-[(2,2,2-trifluoro-ethylamino)-methyl]-biphenyl-4-ylmethyl}-pyrimidine-2,4-diamine are obtained as a colourless powder.

MS (ISP): 476.2 (M+H)$^+$ M.p. 146–149° C.

(4w) 1-[4'-(2,4-Diamino-pyrimidin-5-lmethyl)-2',6'-diethoxy-biphenyl-4-ylmethyl]-pyrazolidin-3-one 3-Pyrazolidinone hydrochloride (123 mg; 1 mmol) is dissolved in 2.5 ml water, sodium bicarbonate (84 mg; 1 mmol) is added and the mixture is stirred for 15 min. A solution of 4'-(2,4-diamino-pyrimidin-5-ylmethyl)-2',6'-diethoxy-biphenyl-4-carbaldehyde (392 mg; 1 immol) in 2.5 ml methanol is added to this solution and the reaction mixture is heated for 24 h at 80° C. The reaction mixture is then cooled to room temperature and the precipitate is filtered off with suction, washed with 5 ml water and dried. The crude residue (360 mg) is dissolved in 10 ml methanol, platinum dioxide (10 mg; 0.044 mmol) is added and hydrogenation is then carried out at room temperature under a normal pressure of hydrogen. After 48 h the reaction mixture is filtered. The filtrate is concentrated and the residue is chromatographed over silica gel (50 g) with methylene chloride/methanol (4/1). The pure fractions are combined and concentrated and the residue is dried under a high vacuum.

Yield : 74 mg (21%) 1-[4'-(2,4-diamino-pyrimidin-5-ylmethyl)-2',6'-diethoxy-biphenyl-4-ylmethyl]-pyrazolidin-3-one as a colourless powder. MS (EI): 463.3 (M$^+$) M.p. 102–105° C.

(4x) 5-[3,5-Diethoxy-4-(2-morpholin-4-ylmethyl-pyrimidin-5-yl)-benzyl]-pyrimidine-2,4-diamine Analogously to example (4a), starting from 4-(5-bromo-pyrimidin-2-ylmethyl)-morpholine (500 mg; 1.94 mmol), ), bis(pinacolato)diboron (739 mg; 2.9 mmol), potassium acetate (572 mg; 9 mmol), bis(triphenylphosphine) palladium(II) dichloride (91 mg; 0.13 mmol) and from 5-(3,5-diethoxy-4-iodo-benzyl)-pyrimidine-2,4-diamine (example 1) (600 mg; 1.45 mmol), 112 mg (17%) 5-[3,5-diethoxy-4-(2-morpholin-4-ylmethyl-pyrimidin-5-yl)-benzyl]-pyrimidine-2,4-diamine are obtained as a pale yellow powder.

MS (ISP): 466.3 (M+H)$^{+M.p.}$ 200–206° C. (decomp.)

(4y) 5-(2,6-Diethoxy-4'-pyrrolidin-1-ylmethyl-biphenyl-4-ylmethyl)-pyrimidine-2,4-diamine Analogously to example (4v), 124 mg (28%) 5-(2,6-diethoxy-4'-pyrrolidin-1-ylmethyl-biphenyl-4-ylmethyl)-pyrimidine-2,4-diamine are obtained as a colourless powder from 4'-(2,4-diamino-pynmidin-5-ylmethyl)-2',6'-diethoxy-biphenyl-4-carbaldehyde (392 mg; 1 mmol) and pyrrolidine (427 mg; 6 mmol).

MS (ISP): 448.4 (M+H)$^{+M.p.}$ 144–146° C.

(4z) 5-(2,6-Diethoxy-3'-fluoro-4'-morpholin-4-ylmethyl-biphenyl-4-ylmethy-pyrimidine-2,4-diamine Analogously to example (4a), starting from 4-(4-bromo-2-fluoro-benzyl)-morpholine (274 mg; 1 mmol), bis (pinacolato)diboron (380 mg; 1.5 mmol), potassium acetate (294 mg; 3 mmol), bis(triphenylphosphine)palladium(II) dichloride (47 mg; 0.07 mmol) and from 5-(3,5-diethoxy-4-iodo-benzyl)-pyrimidine-2,4-diamine (example 1) (248 mg; 0.6 mmol), 166 mg (34%) 5-(2,6-diethoxy-3'-fluoro-4'-morpholin-4-ylmethyl-biphenyl-4-ylmethyl)-pyrimidine-2,4-diamine are obtained as a pale yellow powder.

MS (ISP): 482.4 (M+H)$^{+M.p.}$ 113–116° C. (decomp.)

(4aa) 5-(2,6-Diethoxy-3'-fluoro-4'-pyrrolidin-1-ylmethyl-biphenyl-4-ylmethyl)-pyrimidine-2,4-diamine Analogously to example (4v), 281 mg (55%) 5-(2,6-diethoxy-3'-fluoro-4'-pyrrolidin-1-ylmethyl-biphenyl-4-ylmethyl)-pyrimidine-2,4-diamine are obtained as a colourless powder from 4'-(2,4-diamino-pyrimidin-5-ylmethyl)-2',6'-diethoxy-3-fluoro-biphenyl-4-carbaldehyde (450 mg; 1.1 mmol) and pyrrolidine (467 mg; 6.6 mmol).

MS (ISP): 466.3 (M+H)$^+$ M.p. 131–134° C.

(4ab) 5-(2,6-Diethoxy-4'-methylamino-biphenyl-4-ylmethyl)-pyrimidine-2,4-diamine N-(4-Bromophenyl)-2,2,2-trifluoro-N-methyl-acetamide (1.32 g; 5.2 mmol), bis(pinacolato)diboron (1.57 g; 14.1 mmol), potassium acetate (1.38 g; 14.1 mmol) and 1,1'-bis (diphenylphosphino) ferrocene-dichloropalladium(II) (PdCl$_2$(dppf)) (228 mg; 0.29 mmol) are stirred in dimethoxyethane (47 ml; dried over a molecular sieve) at a bath temperature of 80° C. for 17 hours while gassing with argon. After cooling to room temperature, bis(pinacolato) diboron (250 mg; 0.995 mmol) and bis(diphenylphosphino) ferrocene-dichloropalladium(II) (PdCl$_2$(dppf)) (31 mg; 0.039 mmol) are added again and the mixture is stirred again for 1 hour at a bath temperature of 80° C. under argon. After cooling to room temperature, dimethylformarnide (95 ml), tetrakis-triphenylphosphine-palladium (416 mg; 0.36 mmol), 5-(3,5-diethoxy-4-iodo-benzyl)-pyrimidine-2,4-diamine (example 1) (1.56 g; 3.76 mmol) and a 2 M aqueous potassium phosphate solution (18.8 ml) are added. The reaction mixture is stirred for 7 hours at 80° C., cooled to room temperature and concentrated. Water (300 ml) is added to the residue and the product which has precipitated out is filtered off with suction. The tacky filter cake is dissolved in methanol and the solution is evaporated. Azeotropic distillation is carried out twice with methanol and the substance is dried under a high vacuum. The crude product obtained is chromatographed twice over silica gel (125 g) with methylene chloride/methanol/$NH_4OH$ conc. 19/110.05. The pure fractions are combined, the solvent is concentrated, the residue is stirred with methanol (10 ml), filtered off with suction and dried under a high vacuum. 570 mg (26%) 5-(2,6-diethoxy-4'-methylamino-biphenyl-4-ylmethyl)-pyrimidine-2,4-diamine are obtained as a light-yellow powder.

MS(ISP): 394.4 $(M+H)^+$ (4ac) 5-(2,6-Diethoxy-4'-{[N-(2-fluoro-ethyl)-N-methyl-amino]-methyl}-biphenyl-4-ylmethyl)-pyrimidine-2,4-diamine From 5-{2,6-diethoxy-4'-[(2-fluoro-ethylamino)-methyl]-biphenyl-4-ylmethyl}-pyrimidine-2,4-diamine (213 mg; 0.48 mmol), 87 mg (39%) 5-(2,6-diethoxy-4'-{[N-(2-fluoro-ethyl)-N-methyl-amino]-methyl}-biphenyl-4-ylmethyl)-pyrimidine-2,4-diamine are obtained as a colourless powder after treatment with 0.1 ml 35% aqueous formaldehyde and reduction with sodium borohydride (18 mg; 0.48 mmol).

MS (ISP): 454.5 $(M+H)^+$ M.p. 145–148° C.

(4ad) 5-(2,6-Diethoxy-3'-fluoro-4'-{[N-(2-fluoro-ethyl)-N-methyl-amino]-methyl}-biphenyl-4-ylmethyl)-pyrimidine-2,4-diamine From 5-{2,6-diethoxy-3'-fluoro-4'-[(2-fluoro-ethylamino)-methyl]-biphenyl-4-ylmethyl}-pyrimidine-2,4-diamine (example (4ah)) (145 mg; 0.32 mmol), 134 mg (89%) 5-(2,6-diethoxy-3'-fluoro-4'-{[N-(2-fluoro-ethyl)-N-methyl-amino]-methyl}-biphenyl-4-ylmethyl)-pyrimidine-2,4-diamine are obtained as a colourless powder after treatment with 0.1 ml of a 35% aqueous formaldehyde solution and reduction with sodium borohydride (12 mg; 0.32 mmol).

MS (ISP): 472.3 $(M+H)^+$
M.p. 127–129° C.

(4ae) 5-(5'-Amino-2,6-diethoxy-3'-methyl-biphenyl-4-ylmethyl)-pyrimidine-2,4-diamine Starting from N-(5-bromo-3-methyl-phenyl)-2,2,2-trifluoroacetamide (600 mg; 1.6 mmol), bis(pinacolato)diboron (608 mg, 2.39 mmol), potassium acetate (470 mg; 4.79 mmol) and (diphenylphosphino)-dichloropalladium(II) (67 mg; 0.10 mmol) in dioxane (10 ml), the reaction mixture is poured on to water and extracted with ethyl acetate. The combined organic phases are washed with a saturated aqueous sodium chloride solution, dried over magnesium sulphate, filtered with suction and concentrated and the residue is employed directly in the next step. After reaction with 5-(3,5-diethoxy-4-iodo-benzyl)-pyrimidine-2,4-diamine (example 1) (330 mg; 1.26 mmol), tetrakis-triphenylphosphine-palladium (55 mg; 0.05 mmol) and aqueous 2 M sodium carbonate solution (4 ml; 8 mmol) in a 5/1 dimethoxyethanefethanol mixture (30 ml), 102 mg (32%) 5-(5'-amino-2,6-diethoxy-3'-methyl-biphenyl-4-ylmethyl)-pyrimicine-2,4-diamine are obtained as a yellow foam.

MS (ISP): 394.4 $(M+H)^+$ (4af) 4'-(2,4-Diamino-pyrimidin-5-ylmethyl)-2',6'-diethoxy-3-fluoro-biphenyl-4-carbaldehyde Analogously to example (4a), starting from 4-bromo-2-fluoro-benzaldehyde (406 mg; 2 mmol), ), bis(pinacolato)diboron (762 mg; 3 mmol), potassium acetate (589 mg; 6 mmol), bis(triphenylphosphine)palladium(II)dichloride (94 mg; 0.13 mmol) and from 5-(3,5-diethoxy-4-iodo-benzyl)-pyrimidine-2,4-diamine (example 1) (414 mg; 1 mmol) 132 mg (32%) 4'-(2,4-diamino-pyrimidin-5-ylmethyl)-2',6'-diethoxy-3-fluoro-biphenyl-4-carbaldehyde are obtained as a pale beige powder.

MS (ISP): 411.3 $(M+H)^+$.

4ag) 5-{2,6-Diethoxy-4'-[(2-fluoro-ethylamino)-methyl]-biphenyl-4-ylmethyl}-pyrimidine-2,4-diamine Analogously to example (4v), 170 mg (38%) 5-{2,6-diethoxy-4'-[(2-fluoro-ethylamino)-methyl]-biphenyl-4-ylmethy}-pyrimidine-2,4-diamine are obtained as a colourless powder from 4'-(2,4-diamino-pyrimidin-5-ylmethyl)-2',6'-diethoxy-biphenyl-4-carbaldehyde (392 mg; 1 mmol) and 2-fluoroethylamine hydrochloride (597 mg; 6 mmol).

MS (ISP): 440.5 $(M+H)^+$ M.p. 150–153° C.

(4ah) 5-{2,6-Diethoxy-3'-fluoro-4'-[(2-fluoro-ethylamino)-methyl]-biphenyl-4-ylmethyl}-pyrimidine-2,4-diamine Analogously to example (4v), 237 mg (52%) 5-{2,6-diethoxy-3'-fluoro-4'-[(2-fluoro-ethylamino)-methyl]-biphenyl-4-ylmethyl}-pyrimidine-2,4-diamine are obtained as a colourless powder from 4'-(2,4-diamino-pyrimidin-5-ylmethyl)-2',6'-diethoxy-3-fluoro-biphenyl-4-carbaldehyde (410 mg; 1 mmol) and 2-fluoroethylamine hydrochloride (597 mg; 6 mmol).

MS (ISP): 458.5 $(M+H)^+$ M.p. 151–154° C.

EXAMPLE 5

Preparation of Compounds of the Formula III from Educts of the Formula (II), Equation 1, by Method A (Suzuki Coupling with $R^2$—$B(OH)_2$)

(5a) 5-(2,6-Diethoxy-3'-methoxy-biphenyl-4-ylmethyl)-pyrimidine-2,4-diamine

Tetrakis-triphenylphosphine-palladium (57 mg; 0.050 mmol) is suspended in dimethoxyethane (1 ml), while gassing with argon, and 2,4-diamino-5-(4-bromo-3,5-diethoxybenzyl)pyrimidine (367 mg; 1 mmol) in dimethoxyethane (6 ml) is added. After stirring for a quarter of an hour at room temperature, 3-methory-phenylboron acid (228 mg; 1.5 mmol) in ethanol (1.5 ml) is added, the mixture is stirred for a further 5 minutes at room temperature, an aqueous 2 M sodium carbonate solution (4.2 ml; 8.5 mmol) is added and the mixture is then boiled under reflux (bath temperature 85° C.) for 2.5 hours. The reaction mixture is concentrated and the residue is stirred with water and a little methanol and filtered off with suction. The filter cake is stirred with water, filtered off with suction and dried under a high vacuum.

Yield : 340 mg (86%) 5-(2,6-diethoxy-3'-methoxy-biphenyl-4-ylznethyl)-pyrimidine-2,4-diamine as a grey powder.

MS (ISP): 395.4 (M+H)+

The following are prepared analogously:

(5b) 5-(2,6-Diethoxy-4'-methoxy-biphenyl-4-ylmethyl)-pyrimidine-2,4-diamine

Starting from 2,4-diamino-5-(4-bromo-3,5-diethoxybenzyl)pyrimidine (367 mg; 1 mmol) and 4-methoxy-phenylboron acid (304 mg; 2.0 mmol), 91 mg (23%) 5-(2,6-diethoxy-4'-methoxy-biphenyl-4-ylmethyl)-pyrimidine-2,4-diamine are obtained as a light-yellowish powder after chromatography over silica gel (100 g) with methylene chloride/methanol/NH$_4$OH conc. (19/1/0.05).

MS (ISP): 395.5 (M+H)+

(5c) N-[4'-(2,4-Diamino-pyrimidin-5-ylmethyl)-2',6'-diethoxy-biphenyl-3-yl]-acetamide Starting from from [sic] 2,4-diamino-5-(4-bromo-3,5-diethoxybenzyl)pyrimidine (367 mg; 1 mmol) and 4-acetamido-phenylboron acid (268 mg; 1.5 mmol), 158 mg (38%) N-[4'-(2,4-diamino-pyrimidin-5-ylmethyl)-2',6'-diethoxy-biphenyl-3-yl]-acetamide are obtained in the form of a light-grey powder after stirring with water and recrystallization from hot methanol.

MS (ISP): 422.5 (M+H)+

(5d) 4'-(2,4-Diamino-pyrimidin-5-ylmethyl)-2',6'-diethoxy-biphenyl-3-ol

Starting from 2,4-diamino-5-(4-bromo-3,5-diethoxybenzyl)pyrimidine (735 mg; 2 mmol) and 3-hydroxy-phenylboron acid (413 mg; 3.0 mmol), 634 mg (83%) 4'-(2,4-diamino-pyrimidin-5-ylmethyl)-2',6'-diethoxy-biphenyl-3-ol are obtained as a beige powder after successive stirring with water and methylene chloride.

MS (ISP): 381.2 (M+H)+

EXAMPLE 6

Preparation of The Compound of the Formula IV, Equation 1, Wherein $R^1$ Denotes Ethoxy 5-(3-Benzyloxy-5-ethoxy-4-iodo-benzyl)-pyrimidine-2,4-diamine (Key Intermediate Product)

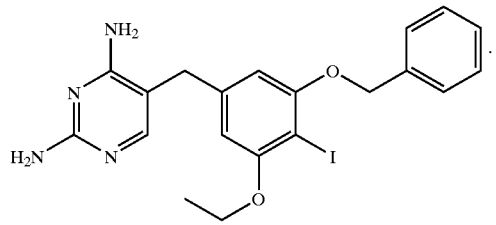

This compound is prepared by the following reaction sequence (stages a)-f)):

Stage a) 3-Benzyloxy-5-hydroxy-4-iodo-benzeic [sic] acid methyl ester 3,5-Dihydroxy-4-iodo-benzoic acid methyl ester (example 1, stage b) (1,000 g; 3.4 mol) is initially introduced into dimethylformamide (9 l) under argon, and benzyl chloride (455 ml; 3.95 mol) is added. The reaction mixture is then cooled to 0–5° C. and potassium tert-butylate (840 g; 7.48 mol) in dimethylformamide (3.651) is added at between 0–5° C. in the course of 1 hour. After stirring for one hour at this temperature, the reaction mixture is poured onto water and the pH is adjusted to 5 by addition of a 1 N aqueous hydrochloric acid solution (approx. 4 l). The mixture is then extracted with ethyl acetate (15 l) and the organic phase is washed with a sodium chloride solution (1 kg. sodium chloride in 10 l water), dried over sodium sulphate (1 kg) and filtered. The first aqueous phase is re-extracted with ethyl acetate (10 l), dried over sodium sulphate and filtered. The organic phases are combined and concentrated, the residue is taken up in toluene (5 l) and the mixture is chromatographed over silica gel (8 kg) with toluene (160 l) The pure fractions are concentrated to a volume of approx. 5 l and the concentrate is cooled to 0–5° C., while stirring. The crystals which have precipitated out are filtered off with suction, after stirring for 2 hours, and rinsed with 1 l of cold toluene and dried under a high vacuum.

Yield: 812 g (63%) 3-benzyloxy-5-hydroxy-4-iodo-benzoic acid methyl ester as colourless crystals.

M.p.: 131° C.

Stage b) 3-Benzyloxy-5-ethoxy-4-iodo-benzoic acid methyl ester

3-Benzyloxy-5-hydroxy-4-iodo-benzoic acid methyl ester (801 g; 2.085 mol) is dissolved in acetone (8.9 l), and potassium carbonate (344 g; 2.49 mol) is added. Thereafter, ethyl iodide (206 ml; 2.55 mol) is added and the reaction mixture is stirred under reflux for 16 hours. After cooling to room temperature, the salts are filtered off with suction and the filtrate is concentrated. The crude product obtained is taken up in methylene chloride (5 l), the mixture is poured on to water (5 l) and the organic phase is separated off and rinsed with water (5 l). The aqueous phases are re-extracted with methylene chloride (1 l), the combined organic phases are concentrated and the residue is crystallized from ethyl acetate at 0–5° C. The crystals are filtered off with suction, washed with cold ethyl acetate (2×0.5 l) and dried under a high vacuum.

Yield: 787 g (93%) 3-benzyloxy-5-ethoxy-4-iodo-benzoic acid methyl ester as a colourless powder. M.p.: 126° C.

Stage c) (3-Benzyloxy-5-ethoxy-4-iodo-phenyl)-methanol

3-Benzyloxy-5-ethoxy-4-iodo-benzoic acid methyl ester (780 g; 1.892 . . . [sic]) is initially introduced into tetrahydrofuran (4.7 l) under argon and the iixture is cooled to 0–5° C. A 1.2 M diisobutylaluminium hydride solution (DIBAH) in toluene (3.9 l; 4.68 mol) is then added dropwise such that the temperature does not rise above 0–5° C. (approx. 75 minutes). After 1 hour, the cooling bath is removed and the reaction mixture is poured on to a 1 M aqueous citric acid solution (1,732 g citric acid in 9 l water) in the course of 2 hours with vigorous stirring. After the aqueous phase has been separated off, the organic phase is rinsed with water (9 l) and evaporated. The residue is dissolved in methylene chloride (15 l) and this is then slowly replaced by n-hexane (3.7 l) by distilling off. The suspension is then cooled to 0° C. and, after 1 hour at this temperature, filtered with suction and the residue is rinsed with n-hexane (0.5 l) and dried under a high vacuum.

Yield: 716 g (98%) (3-benzyloxy-5-ethoxy-4-iodo-phenyl)-methanol as a colourless powder.

M.p.: 85° C.

Stage d) 3-Benzyloxy-5-ethoxy-4-iodo-benzaldehyde (3-Benzyloxy-5-ethoxy-4-iodo-phenyl)-methanol (710 g; 1.848 mol) is dissolved in methylene chloride (7.1 l) under argon, and manganese(IV) oxide (919 g;, 10.57 mol) is added. The suspension is stirred for 17 hours under reflux, cooled to room temperature and filtered and the residue is rinsed with methylene chloride (5 l). The solvent is then replaced with n-hexane (3.5 l) by distilling off and the solution is then cooled to 0–5° C., while stirring. After 1 hour, the suspension is filtered with suction and the crystals are washed with n-hexane (2×1 l) and dried under a high vacuum.

Yield: 656 g (93%) 3-benzyloxy-5-ethoxy-4-iodo-benzaldehyde as a pale beige powder. M.p.: 104° C.

Stage e) (Z/E)-2-(3-Benzyloxy-5-ethoxy-4-iodo-benzyl)-3-phenylamino-acrylonitrile 3-Benzyloxy-5-ethoxy-4-iodo-benzaldehyde (650 g; 1.7 mol) is initially introduced into dimethylsulphoxide (510 ml) and tert-butanol (1,300 ml) under argon, 3-anilino-propionitrile (300 g; 2.02 mol) is added and the mixture is heated to 25–30° C. with an oil bath. Thereafter, potassium tert-butylate (231 g; 1.99 mol) in dimethylsulphoxide (790 ml) is added dropwise in the course of 15 minutes and the solution formed is then heated to 60° C. in the course of 1 hour. After 45 minutes at this temperature, the mixture is evaporated, the oil obtained is dissolved in methylene chloride (7 l) and the solution is washed with a saturated aqueous sodium chloride solution (7 l). The aqueous phase is re-extracted with methylene chloride (2 l) and the combined organic phases are evaporated on a rolling evaporator. Methanol (5 l) is added during the concentration. The suspension formed is cooled to 0–5° C. and, after stirring for one hour at this temperature, filtered with suction and the residue is rinsed with cold methanol (0.5 l) and dried under a high vacuum.

Yield :409 g of a yellow powder. A further 372 g of a yellow powder are obtained from the mother liquor after filtration over silica gel (1,400 g) and elution with toluene (5 l), and, after crystallization from methanol/methylene chloride (same method as above) give a further 93.8 g (yellow powder) and then 84 g (beige powder) of product Overall yield: 576.3 g (67%) (ZIE)-2-(3-benzyloxy-5-ethoxy-4-iodo-benzyl)-3-phenylamino-acrylonitrile

MS (EI): 510 (M)

Stage f) 5-(3-Benzyloxy-5-ethoxy-4-iodo-benzyl)-pyrimidin-2,4-diamine

Guanidine hydrochloride (364 g; 3.73 mol) is dissolved in ethanol (4.3 l) under argon, and a solution of potassium tert-butylate (465 g; 4.01 mol) in ethanol (2.8 l) is added. After approx. 20 minutes, (Z/E)-2-(3-benzyloxy-5-ethoxy-4-iodo-benzyl)-3-phenylamino-acrylonitrile (580.8 g; 1.11 mol) is added. The suspension formed is stirred for 20 hours at 70° C. and water (2,100 ml) is added. The reaction mixture is then cooled to 0–5° C. and stirred for 1 hour at this temperature. The suspension is filtered with suction and the filter cake is rinsed successively with ethanol (2.8 l), water (2.8 l) and n-hexane (2.8 l) and dried. The crude product is crystallized from methanol/methylene chloride (8/2).

Yield : 470 g (88%) MS: 476 (M)

EXAMPLE 7

Preparation of Compounds of the Formula VII, Equation 1, from the Corresponding Compounds of the Formula VI by Alkylation of the Free Hydroxyl Group (7a) 5-(3'-Amino-6-cyclopropylmethoxy-2-ethoxy-biphenyl-4-ylmethyl)-pirimidine-2,4-diamine
(Method α: Alkylation with Bromide)

3'-Amino-4-(2,4-diamino-pyrimidin-5-ylmethyl)-6-ethoxy-biphenyl-2-ol (351 mg; 1 mmol) is dissolved in dimethylformamide (22.5 ml; dried over a molecular sieve), while gassing with argon, and potassium tert-butylate (172 mg; 1.5 mmol) is added at room temperature. After the mixture has been stirred for one hour, bromomethyl-cyclopropane (0.124 ml; 1.3 mmol) is added and stirring is continued for 1 hour at a bath temperature of 60° C. The reaction mixture is then cooled to room temperature and concentrateds The residue is taken up in water/ethyl acetate and the mixture is poured into a separating funnel and extracted by shaking. The aqueous phase is separated off and re-extracted once with ethyl acetate. The combined organic phases are washed with an aqueous saturated sodium chloride solution, dried over magnesium sulphate, filtered with suction and concentrated. The residue is chromatographed over silica gel (21 g) with methylene chloride/methanol/$NH_4OH$ conc. (19/1/0.05). The pure fractions are concentrated and the residue is stirred with diethyl ether (10 ml) for 1 hour, filtered off with suction, rinsed with diethyl ether and dried under a high vacuum.

Yield: 203 mg (52%) 5-(3'-amino-6-cyclopropylmethoxy-2-ethoxy-biphenyl-4-ylmethyl)-pyrimidine-2,4-diamine as a beige powder.

MS(ISP): 406.4 $(M+H)^+$ NMR $^1H$: (250 MHz, δ, TMS, DMSO): 0.15 (m; 2H); 0.39 (m; 2H); 1.00 (m; 1H); 1.12 (t; J=6.9; 3H); 3.55 (s; 2H); 3.68 (d; J=6.5; 2H); 3.87 (q; J=6.9; 2H); 4.85 (s; 2H); 5.69 (s; 2H); 6.10 (s; 2H); 6.39 (m; 3H); 6.56 (s; 2H); 6.93 (m; 1H); 7.55 (s; 1H).

The following are prepared analogously:

(7b) {1-[3'-Amino-4-(2,4-diamino-pyrimidin-5-ylmethyl)-6-ethoxy-biphenyl-2-yloxymethyl]-cydopropyl}-acetonitrile (Method α)

Starting from 3'-amino-4-(2,4-diamino-pyrimidin-5-ylmethyl)-6-ethoxy-biphenyl-2-ol (150 mg; 0.427 mmol) and (1-bromomethyl-cyclopropyl)-acetonitrile (97 mg; 0.555 mmol), 121 mg (64%) {1-[3'-amino-4-(2,4-diamino-pyrimidin-5-ylmethyl)-6-ethoxy-biphenyl-2-yloxymethyl]-cydopropyl}-acetonitrile are obtained as a pale beige powder.

MS (ISP): 445.4 $(M+H)^+$

The (1-bromomethyl-cyclopropyl)-acetonitrile employed is prepared as follows, starting from (1-hydroxymethyl-cydopropyl)-acetonitrile:

(1-Hydroxymethyl-cyclopropyl)-acetonitrile (1.29 g; 11.6 mmol) and triphenylphosphine (3.08 g; 11.8 mmol) are dissolved in dimethylformamide (8 ml; dried over a molecular sieve), while stirring, and the solution is cooled to 0–5° C. N-Bromosuccinimide (2.1 g; 11.8 mmol) is then added in portions in the course of 40 minutes. Stirring is then continued for 1.5 hours at this temperature, methanol (0.2 ml) and water (8 ml) are added and the mixture is stirred at room temperature for 10 minutes The reaction mixture is then extracted with n-pentane (3×40 ml). Thecombined organic phases are washed with a 5% aqueous sodium bicarbonate solution (40 ml) and concentrated. The oil obtained is employed without further purification.

MS: 173 (M)

(7c) 5-[3'-Amino-6-ethoxg-2-[(1-methoxymethyl-cyclopropyl)-methoxy]-biphenyl-4-yimethyl]-pyrimidine-2,4-diamine (Method α)

Starting from 3'-amino-4-(2,4-diamino-pyrimidin-5-ylmethyl)-6-ethoxy-biphenyl-2-ol (527 mg; 1.5 mmol) and 1-bromomethyl-1-methoxymethylcyclopropane (350 mg; 1.97 mmol), 353 mg (52%) 5-[3'-amino-6-ethoxy-2-[(1-methoxymethyl-cydopropyl)-methoxy]-biphenyl-4-ylmethyl]-pyrimidine-2,4-diamine are obtained as a solid orange foam.

MS (ISP): 450.4 (M+H)+

The 1-bromomethyl-1-methoxymethylcydopropane employed is prepared as follows starting from 1,1-cyclopropanedimethanol (stages a)-b)):

Stage a) 1-Methoxymethyl-cydopropyl)-methanol 1,1-Cyclopropanedimethanol (1.02 g; 10 mmol) is dissolved in dimethylformamide (20 ml; dried over a molecular sieve) and, after addition of potassium tert-butylate (1.14 g, 10 mmol), the mixture is stirred at room temperature for 1 hour. The reaction mixture is then cooled to 0–5° C. and a solution of rmethyl iodide (0.63 ml; 10 mmol) in dimethylformamide (5 ml; dried over a molecular sieve) is then added dropwise. After stirring at this temperature for 50 minutes, the reaction mixture is poured on to a mixture of a saturated aqueous $NH_4Cl$ solution (100 ml) and diethyl ether (400 ml), while stirring. After separation of the phases, the aqueous phase is re-extracted with diethyl ether (400 ml) and the combined organic phases are washed with a saturated aqueous sodium chloride solution (2×100 ml), dried over magnesium sulphate, filtered with suction and concentrated. The crude product obtained is chromatographed over silica gel (50 g) with diethyl ether.

Yield : 493 mg (39%) (1-methoxymethyl-cyclopropyl)-methanol as a pale yellow oil. NMR (1H, 250 MHz in $CDCl_3$) in ppm: 0.5–0.6 (multiplet, 4H); 3.37 (multiplet, 5H); 3.54 (s,2H)

Stage b) 1-Bromomethyl-1-methoxymethylcydopropane

Prepared analogously to (1-bromomethyl-cydopropyl)-acetonitrile (example 7b).

Starting from (1-methoxyymethyl-cyclopropyl)-methanol (490 mg; 4.2 mmol), 341 mg (45%) 1-bromomethyl-1-methoxymethylcyclopropane are obtained as a colourless oil.

NMR (1H, 250 MHz in $CDCl_3$) in ppm: 0.6–0.8 (multiplet, 4H); 3.35 (s, 2H); 3.38 (s, 3H); 3.49 (s, 2H)

(7d) 5-(3'-Amino-6-cycloventloxy-2-ethoxy-biphenyl-4-ylmethyl)-pyrimidine-2,4-diamine (Method α)

Starting from 3'-amino-4-(2,4-diamino-pyrimidin-5-ylmethyl)-6-ethoxy-biphenyl-2-ol (176 mg; 0.5 mmol) and bromo-cydopentane (0.121 ml; 1.21 mmol), 92 mg (44%) 5-(3'-amino-6-cycopentyloxy-2-ethoxy-biphenyl-4-ylmethyl)-pyrimidine-2,4-diamine are obtained as a solid yellow foam.

MS (ISP): 420.3 (M+H)+

(7e) 5-(3'-Amino-6-qdobutoxy-2-ethoxy-biphenyl-4-ylmethyl)-pyrimidine-2,4-diamine (Method α)

Starting from 3'-amino-4-(2,4-diamino-pyrimidin-5-ylmethyl)-6-ethoxy-biphenyl-2-ol (176 mg; 05 mmol) and bromo-cyclobutane (0.061 ml; 0.65 mmol), 71 mg (35%) 5-(3'-amino-6-cyobutox)-2-ethoxy-biphenyl-4-ylmethyl)-pyrimidine-2,4-diamine are obtained as a solid yellow foam.

MS (ISP): 406.4 (M+H)+

(7f) (E)-5-[3'-Amino-4-(2,4-diamino-p yrimidin-5-ylmeth )-6-ethoxy-biphenyl-2-yloxy]-4,4-dimethyl-pent-2-ene-nitrile (Method α)

Starting from 3'-amino-4-(2,4-diamino-pyrimidin-5-ylmethyl)-6-ethoxy-biphenyl-2-ol (351 mg; 1.0 mmol) and (E)-5-bromo-4,4-dimethyl-pent-2-ene-nitrile (245 mg; 1.3 mmol), 42 mg (9%) (E)- and/or (Z)-5-[3'-amino-4-(2,4-diamino-pyrimidin-5-ylmethyl)-6-ethoxy-biphenyl-2-yloxy]-4,4-dimethyl-pent-2-ene-nitrile are obtained as a solid yellow foam.

MS (ISP): 459.5 (M+H)+

The (E)-5-bromo-4,4-dimethyl-pent-2-ene-nitrile employed is prepared as follows:

1-Bromo-2,2-dimethyl-3-propanal (710 mg; 4.3 mmol) and (triphenylphos-phoranylidene)acetonitrile (1.4 g; 4.73 mmol) are dissolved in acetonitrile (20 ml) and dimethylformamide (5 ml) and the solution is stirred for 18 hours at room temperature. The reaction mixture is concentrated, the residue is stirred with n-hexane, the triphenylphosphine oxide which has precipitated out is filtered off with suction, the filtrate is concentrated and the residue is purified by means of bulb tube distillation.

Yield: 312 mg (39%) (E)-5-bromo-4,4-dimethyl-pent-2-ene-nitrile as a colourless oil. MS: 187 (M); 188 (M+H)+

(7g) 5-[3'-Amino-6-ethoxy-2-(2-pyridin-2-yl-ethoxy)-biphenyl-4-ylmethyl]-pyrimidine-2,4-diamine (Method β: Alkylation with Mesylate)

Prepared analogously to example (7i) below.

Starting from 3'-amino-4-(2,4-diamino-pyrimidin-5-ylmethyl)-6-ethoxy-biphenyl-2-ol (702 mg; 2.0 mmol), 2-(2-pyridyl)ethyl mesylate (three portions of 402 mg each; 2 mmol) and potassium carbonate (three portions of 414 mg each; 3.0 mmol) in boiling acetonitrile (80 ml), 100 mg (11%) 5-[3'-amino-6-ethoxy-2-(2-pyridin-2-yl-ethoxy)-biphenyl-4-ylmethyl]-pyrimidine-2,4-diamine are obtained as a beige powder.

MS (ISP) ): 457.4 (M+H)+

(7h) (RS)-5-[3'-Amino-6-ethoxy-2-[2-(tetrahydro-pyran-2-yl)-ethoxy]-biphenyl-4-ylmethyl]-2yrimidine-2,4-diamine (Method α)

Starting from 3'-amino-4-(2,4-diamino-pyrimidin-5-ylmethyl)-6-ethoxy-biphenyl-2-ol (211 mg; 0.6 mmol) and (tetrahydro-pyran-2-yl)-ethyl bromide (151 mg; 0.78 mmol), 194 mg (70%) (RS)-5-[3'-amino-6-ethoxy-2-[2-(tetrahydro-pyran-2-yl)-ethoxy]-biphenyl-4-ylmethyl]-pyrimidine-2,4-diamine are obtained as a solid yellow foam.

MS (ISP): 464.3 (M+H)+

(7i) 5-[3'-Amino-6-ethoxy-2-(2,2,2-trifluoro-ethoxy)-biphenyl-4-ylmethyl]-pyrimidine-2,4-diamine (Method β)

3'-Amino-4-(2,4-diamino-pyrimidin-5-ylmethyl)-6-ethoxy-biphenyl-2-ol (527 mg; 1.5 mmol) is suspended in acetonitrile (60 ml; dried over a molecular sieve), potassium carbonate (621 mg; 4.5 mmol) is added and the mixture is heated to a bath temperature of 100° C. 2,2,2-Trifluoroethyl methanesulphonate (0.353 ml; 3.0 mmol) is added and the mixture is boiled under reflux for 3 hours. After this period of time, potassium carbonate (414 mg; 3 mmol) and 2,2,2-trifluoroethyl methanesulphonate (0.353 ml; 3.0 mmol) are again added and the mixture is stirred under reflux for a further 2 hours. The same procedure is repeated four more times at intervals of two hours. The suspension is then filtered with suction and the filtrate is concentrated. The residue is chromatographed over silica gel (120 g) with methylene chloride/methanol/$NH_4OH$ (1/1 mixture of 90/10/1 and 19/1/0.05).

Yield: 33 mg (5%) 5-[3'-amino-6-ethoxy-2-(2,2,2-trifluoro-ethoxy)-biphenyl-4-ylmethyl]-pyrimidine-2,4-diamine as a colourless powder.

MS (ISP) ): 434.4 (M+H)+

In this chromatography process the end product of example 14a is also obtained as a second component.

(7j) 5-{3'-Amino-2-ethoxy-6-[2-(tetrahydro-pyran-4-yl)-ethoxy]-biphenyl-4-ylmethyl}-pyrimidine-2,4-diamine (Method α)

Starting from 3'-amino-4-(2,4-diamino-pyrimidin-5-ylmethyl)-6-ethoxy-biphenyl-2-ol (211 mg; 0.6 mmol) and 4-(2-bromoethyl)-tetrahydropyran (151 mg; 0.78 mmol), 166 mg (60%) 5-{3'-amino-2-ethoxy-6-[2-(tetrahydropyran-4-yl)-ethoxy]-biphenyl-4-ylmethyl}-pyrimidine-2,4-diamine are obtained as a solid yellow foam.

MS (ISP): 464.3 (M+H)$^+$

The starting compound 3'-amino-4-(2,4-diamino-pyrimidin-5-ylmethyl)-6-ethoxy-biphenyl-2-ol is prepared from 5-(3-benzyloxy-5-ethoxy-4-iodo-benzyl)-pyrimidine-2,4-diamine (example 6) in 2 stages a) and b)) as in equation 1, (IV)→(V)→(VI):

Stage a) 5-(3'-Amino-2-benzyloxy-6-ethoxy-biphenyl-4-ylmethyl)-pyrimidine-2,4-diamine is prepared analogously to example (2a) (Suzuki coupling with boron acid).

Starting from 5-(3-benzyloxy-5-ethoxy-4-iodo-benzyl)-pyrimidine-2,4-diamine (example 6) (25.76 g; 54 mmol) and 3-amino-phenylboron acid monohydrate (12.8 g; 81.1 mmol), 21.3 g (82%) 5-(3'-amino-2-benzyloxy-6-ethoxy-biphenyl-4-ylmethyl)-pyrimidine-2,4-diamine are obtained as a colourless foam.

MS: 441 (M)

Stage b) 3'-Amino-4-(2,4-diamino-pyrimidin-5-ylmethyl)-6-ethoxy-biphenyl-2-ol 5-(3'-Amino-2-benzyloxy-6-ethoxy-biphenyl-4-ylmethyl)-pyrimidine-2,4-diamine (17.51 g; 39.7 mmol) is hydrogenated in ethanol (66 ml) and acetic acid conc. (198 ml) over Pd/C 10% (8.1 g) for 20 hours. The catalyst is filtered off and the mother liquor is concentrated. The residue is taken up in water and the pH is adjusted to 10 by addition of NH$_4$OH conc. The suspension is filtered with suction and the crystals are washed thoroughly with water and dried under a high vacuum.

Yield: 11 g (79%) 3'-amino-4-(2,4-diamino-pyrimidin-5-ylmethyl)-6-ethoxy-biphenyl-2-ol as a pale brown powder.

MS (ISP): 352.3 (M+H)$^+$

EXAMPLE 8

Preparation of Compounds of the Formula VII, Equation 1, from Educts of the Formula (VI) with Subsequent Splitting Off of the Protective Group and Optional Derivatization (8a) 4'-(2,4-Diamino-pylimidin-5-ylmethyl)-6'-ethoxy-2'-(3-methoxy-2,2-dimethyl-propoxy)-biphenyl-4-ol 4'-(2,4-Diamino-pyrimidin-5-ylmethyl)-2'-ethoxy-6'-(1-methoxymethyl-cydopropylmethoxy)-biphenyl-4-ol (235 mg; 0.52 mmol) is hydrogenated in ethanol/acetic acid conc./water (4/1/0.1) (10 ml) over PtO$_2$ (6×35 mg) at 100° C. The reaction mixture is cooled to room temperature, the catalyst is filtered off with suction and the filtrate is concentrated. The residue is stirred in water, the pH is adjusted to pH 9 by addition of NH$_4$OH conc., stirring is continued for 30 minutes and the mixture is filtered with suction. The grey crude product is then chromatographed over silica gel (20 g) with methylene chloride/methanol/NH$_4$OH conc. (19/1/0.05). 104 mg (44%) 4'-(2,4-diamino-pyrimidin-5-ylmethyl)-6'-ethoxy-2'-(3-methoxy-2,2-dimethyl-propoxy)-biphenyl-4-ol are obtained as a colourless powder.

MS (ISP): 453.5 (M+H)$^+$

The 4'-(2,4-diamino-pyrimidin-5-ylmethyl)-2'-ethoxy-6'-(1-methoxymethyl-cydopropylmethoxy)-biphenyl-4-ol employed is prepared starting from 4-(2,4-diamino-pyrimidin-5-ylmethyl)-6-ethoxy-4'-methoxymethoxy-biphenyl-2-ol as follows by the following sequence (stages a)-b)):

Stage a) 5-[6-Ethoxy-4'-methoxymethoxy-2-(1-methoxymethyl-cyclopropylmethoxy)-biphenyl-4-ylmethyl]-pyrimidine-2,4-diamine Analogously to Example 7 (Alkylation with Bromide, Method α):

4-(2,4-Diamino-pyrimidin-5-ylmethyl)-6-ethoxy-4'-methoxymethoxy-biphenyl-2-ol (850 mg; 2.15 mmol) is dissolved in dimethylformamide (40 ml; dried over a molecular sieve) while gassing with argon, and potassium tert-butylate (362 mg; 3.22 mmol) is added at room temperature. After the mixture has been stirred for one hour, 1-bromomethyl-1-methoxymethyl-cyclopropane (0.5 g; 2.8 mmol) is added and the mixture is stirred for 3 hours at a bath temperature of 80° C. The reaction mixture is then cooled to room temperature and concentrated. Water is added to the residue and the mixture is extracted twice with methylene chloride. The aqueous phase is re-extracted once with ethyl acetate. The combined organic phases are concentrated and the residue is chromatographed over silica gel (120 g) with methylene chloride/methanol/NH$_4$OH conc. (19/1/0.5). The pure fractions are concentrated and the residue is stirred with diethyl ether/n-hexane (1/1), filtered off with suction and dried under a high vacuum.

Yield: 487 mg (46%) 5-[6-ethoxy-4'-methoxymethoxy-2-(1-methoxymethyl-cydopropylmethoxy)-biphenyl-4-ylmethyl]-pyrimidine-2,4-diamine as a beige powder.

MS(ISP): 495.3 (M+H)$^+$

Stage b) 4'-(2,4-Diamino-pyrimidin-5-ylmethyl)-2'-ethoxy-6'-(1-methoxymethyl-cydopropylmethoxy)-biphenyl-4-ol 5-[6-Ethoxy-4'-methoxymethoxy-2-(1-methoxymethyl-cyclopropylmethoxy)-biphenyl-4-ylmethyl]-pyrimidine-2,4-diamine (471 mg; 953 mmol) is stirred in methanol (25 ml) and a 3 M hydrochloric acid solution in methanol (5.5 ml; 16.5 mmol) for 30 minutes at a bath temperature of 60° C. The reaction mixture is concentrated and the residue is stirred with water. The pH is adjusted to 9 by addition of NHOH conc. After stirring for 2 hours at room temperature, the suspension is filtered with suction and the residue is washed thoroughly with water and recrystallized from ethyl acetate.

Yield: 305 mg (71%) 4'-(2,4-diamino-pyrimidin-5-ylmethyl)-2'-ethoxy-6'-(1-methoxymethyl-cyclopropylmethoxy)-biphenyl-4-ol as a beige powder.

MS (ISP): 451.4 (M+H)$^+$.

The following compounds are prepared analogously from 4-(2,4-diamino-pyrimidin-5-ylmethyl)-6-ethoxy-4'-methoxymethoxy-biphenyl-2-ol:

(8b) (E)-5-[4-(2,4-Diamino-pyrimidin-5-ylmethyl)-6-ethoxy-4'-hydroxy-biphenyl-2-yloxy]-4,4-dimethyl-pent-2-ene-nitrile Stage a) (E)-5-[4-(2,4-Diamino-pyrimidin-5-ylmethyl)-6-ethoxy-4'-methoxymethoxy-biphenyl-2-yloxy]-4,4-dimethyl-pent-2-ene-nitrile Analogously to Example 7 (Method α):

Starting from 4-(2,4-diamino-pyrimidin-5-ylmethyl)-6-ethoxy-4'-methoxymethoxy-biphenyl-2-ol (890 mg; 2.25 mmol) and (E)-5-bromo-4,4-dimethyl-pent-2-ene-nitrile (described in example (7f)) (549 mg; 2.92 mmol), 271 mg (23%) (E)-5-[4-(2,4-diamino-pyrimidin-5-ylmethyl)-6-ethoxy-4'-methoxymethoxy-biphenyl-2-yloxy]-4,4-dimethyl-pent-2-ene-nitrile are obtained as a pale brown powder.

MS (ISP): 504.3 (M+H)⁺

Stage b) (E)-5-[4-(2,4-Diamino-pyrimidin-5-ylmethyl)-6-ethoxy-4'-hydroxy-biphenyl-2-yloxy]-4,4-dimethyl-pent-2-ene-nitrile Starting from (E)-5-[4-(2,4-diamino-pyrimidin-5-ylmethyl)-6-ethoxy-4'-methoxymethoxy-biphenyl-2-yloxy]-4,4-dimethyl-pent-2-ene-nitrile (250 mg; 0.497 mmol), 202 mg (88%) (E)-5-[4-(2,4-diamino-pyrimidin-5-ylmethyl)-6-ethoxy-4'-hydroxy-biphenyl-2-yloxy]-4,4-dimethyl-pent-2-ene-nitrile are obtained as a pale brown powder.

MS (ISP): 460.4 (M+H)⁺

(8c) {1-[4-(2,4-Diamino-pyrimidin-5-ylmethyl)-6-ethoxy-4'-hydroxy-biphenyl-2-yloxymethyl]-cyclopropyl}-acetonitrile Stage a) [1-[4-(2,4-Diamino-pyrimidin-5-ylmethyl)-6-ethoxy-4'-methoxymethoxy-biphenyl-2-yloxymethyl]-cyclopropyl]-acetonitrile Analogously to Example 7 (Method α):

Starting from 4-(2,4-diamino-pyrimidin-5-ylmethyl)-6-ethoxy-4'-methoxymethoxy-biphenyl-2-ol (594 mg; 1.5 mmol) and (1-bromomethyl-cydopropyl)-acetonitrile (340 mg; 195 mmol), 558 mg (76%) [1-[4-(2,4-diamino-pyrimidin-5-ylmethyl)-6-ethoxy-4'-methoxymethoxy-biphenyl-2-yloxymethyl]-cyclopropyl]-acetonitrile are obtained as a pale brown powder.

MS (ISP): 490.3 (M+H)⁺

Stage b) {1-[4-(2,4-Diamino-pyrimidin-5-ylmethyl)-6-ethoxy-4'-hydroxy-biphenyl-2-yloxymethyl]-cyclopropyl}-acetonitrile Starting from [1-[4-(2,4-diamino-pyrimidin-5-ylmethyl)-6-ethoxy-4'-methoxymethoxy-biphenyl-2-yloxymethyl]-cyclopropyl]-acetonitrile (520 mg; 1.06 mmol), 312 mg (66%) {1-[4-(2,4-diamino-pyrimidin-5-ylmethyl)-6-ethoxy-4'-hydroxy-biphenyl-2-yloxymethyl]-cycopropyl}-acetonitrile are obtained as a brown powder.

MS (ISP): 446.3 (M+H)⁺

(8d) (E)-3-[1-[4-(2,4-Diamino-pyrimidin-5-ylmethyl)-6-ethoxy-4'-hydrozy-biphenyl-2-yloxymethyl]-cyopropyl]-acrylonitrile (E)-3-[1-[4-(2,4-Diamino-pyrimidin-5-ylmethyl)-6-ethoxy-4'-methoxymethoxy-biphenyl-2-yloxymethyl]-cyclopropyl]-acrylonitrile (350 mg; 0.698 mmol) is stirred in methanol (12 ml) and a 3 M hydrochloric acid solution in methanol (3.4 ml) for 30 minutes at a bath temperature of 60° C. The methanol is evaporated off, the residue is dissolved in water (33 ml) and the pH is adjusted to approx. 9 by addition of NH₄OH conc., whereupon the substance precipitates out. After stirring for 2 hours the mixture is filtered with suction and the residue is washed with water and dried under a high vacuum. 295 mg (92%) (E)-3-[1-[4-(2,4-diamino-pyrimidin-5-ylmethyl)-6-ethoxy-4'-hydroxy-biphenyl-2-yloxymethyl]-cyclopropyl]-acrylonitrile are obtained as a colourless powder.

MS (ISP): 458.4 (M+H)⁺

The (E)-3-[1-[4-(2,4-diamino-pyrimidin-5-ylmethyl)-6-ethoxy-4'-methoxymethoxy-biphenyl-2-yloxymethyl]-cyclopropyl]-acrylonitrile employed is prepared by the following sequence (stages a)-b)):

Stage a) {1-[4-(2,4-Diamino-pyrimidin-5-ylmethyl)-6-ethoxy-4'-methoxymethoxy-biphenyl-2-yloxymethyl]-cyclopropyl}-methanol Analogously to Example 7 (Method α):

4-(2,4-Diamino-pyrimidin-5-ylmethyl)-6-ethoxy-4'-methoxymethoxy-biphenyl-2-ol (2.5 g; 6.31 mmol) is dissolved in dimethylformamide (125 ml; dried over a molecular sieve) and potassium tert-butylate (920 mg; 8.2 mmol) is added at room temperature. A solution of [(1-bromomethyl-cyclopropyl)methoxymethyl]-benzene (2.253 g; 8.83 mmol) in dimethylformamide (3 ml) is then added and the mixture is stirred for 100 minutes at a bath temperature of 60° C. The reaction mixture is concentrated, diluted with water (100 ml) and extracted with methylene chloride (120 ml) and re-extracted (50 ml). The combined organic phases are concentrated and the residue is chromatographed over silica gel (300 g) with methylene chloride/methanol/NH₄OH conc. (19/1/0.05). The combined pure fractions are concentrated and the residue is dissolved in acetic acid conc. (40 ml) and ethanol (10 ml) and hydrogenated over Pd/C 10% (900 mg). The reaction mixture is filtered with suction and the filtrate is concentrated. The residue is stirred with water (50 ml) and the pH is adjusted to approx. 10 by addition of NH₄OH conc. The product which has precipitated out is filtered off with suction and the residue is washed with a little water and dried under a high vacuum. 2.24 g (95%) {1-[4-(2,4-diamino-pyrimidin-5-ylmethyl)-6-ethoxy-4'-methoxymethoxy-biphenyl-2-yloxymethyl]-cyclopropyl}-methanol are obtained as a colourless powder.

MS (ISP): 481.4 (M+H)⁺

Stage b) (E)-3-[1-[4-(2,4-Diamino-pyrimidin-5-ylmethyl)-6-ethoxy-4'-methoxymethoxy-biphenyl-2-yloxymethyl]-cydopropyl]-acrylonitrile {1-[4-(2,4-Diamino-primidin-5-ylmethyl)-6-ethoxy-4'-methoxymethoxy-biphenyl-2-yloxymethyl]-cyclopropyl}-methanol (1.6 g; –3.33 mmol) is dissolved in methylene chloride (260 ml) and dimethylformamide (68 ml), MnO₂ (9.9 g) is added and the mixture is stirred for 5 hours at a bath temperature of 40° C. under argon. The reaction mixture is cooled to room temperature and filtered with suction, the solvent is concentrated and the residue is dried under a high vacuum. The residue is dissolved in acetonitrile,(40 ml), triphenylphosphoranylidene-acetonitrile (1.35 g; 4.5 mmol) is added and the mixture is then stirred for 6 hours at room temperature. The reaction mixture is concentrated and the residue is chromatographed over silica gel (140 g) with methylene chloridelmethanol/NH₄OH conc. 19/1/0.05. The pure fractions are combined and concentrated (210 mg) and the residue is chromatographed again over silica gel (42 g) with methylene chloride/methanol/NH₄OH conc. 90/10/1.

Yield: 148 mg (47%) (E)-3-[1-[4-(2,4-diamino-pyrimidin-5-ylmethyl)-6-ethoxy-4'-methoxymethoxy-biphenyl-2-yloxymethyl]-cydopropyl]-acrylonitrile as a colourless solid foam.

MS (ISP): 502.3 (M+H)⁺

(8e) 4'-(2,4-Diamino-pyrimidin-5-ylmethyl)-6'-ethoxy-2'-[2-(tetrahydrogyran-4-yl)-ethoxy]-biphenyl-4-ol Stage a) 5-{6-Ethoxy-4'-methoxymethoxy-2-[2-(tetrahydropyran-4-yl)-ethoxy]-biphenyl-4-ylmethyl}-pyrimidine-2,4-diamine Analogously to Example 7 (Method α):

Starting from 4-(2,4-diamino-pyrimidin-5-ylmethyl)-6-ethoxy-4'-methoxymethoxy-biphenyl-2-ol (396 mg; 1 mmol) and 4-(2-bromoethyl)-tetrahydro-pyran (251 mg; 1.3 mmol), 520 mg (73%) 5-{6-ethoxy-4'-methoxymethoxy-2-[2-(tetrahydropyran-4-yl)-ethoxy]-biphenyl-4-ylmethyl}-pyrimidine-2,4-diamine are obtained as a yellow powder, which is employed directly in the next stage.

Stage b) 4'-(2,4-Diamino-pyrimidin-5-ylmethyl)-6'-ethoxy-2'-[2-(tetrahydropyran-4-yl)-ethoxy]-biphenyl-4-ol Starting from 5-{6-ethoxy-4'-methoxymethoxy-2-(tetrahydropyran-4-yl)-ethoxy]-biphenyl-4-ylmethyl}- pyrimidine-2,4-diamine (520 mg; 1.02 mmol), 358 mg (76%) 4'-(2,4-diamino-pyrimidin-5-ylmethyl)-6'-ethoxy-2'-[2-(tetrahydropyran-4-yl)-ethoxy]-biphenyl-4-ol are obtained as a colourless powder.
MS (ISP): 465.3 (M+H)⁺

(8f) 1-[4-(2,4-Diamino-pyrimidin-5-ylmethyl)-6-ethoxy-4'-hydroxy-biphenyl-2-yloxymethyl]-cyclopropanecarbonitrile Stage a) 1-[4-(2,4-Diamino-pyrimidin-5-ylmethyl)-6-ethoxy-4'-methoxymethoxy-biphenyl-2-yloxymethyl]-cyclopropanecarbonitrile Analogously to Example 7 (Method α):
Starting from 4-(2,4-diamino-pyrimidin-5-ylmethyl)-6-ethoxy-4'-methoxymethoxy-biphenyl-2-ol (396 mg; 1 mmol) and 1-(bromomethyl)-2,3-cydopropanecarbonitrile (184 mg; 1.15 mmol), 328 mg (69%) 1-[4-(2,4-diamino-pyrimidin-5-ylmethyl)-6-ethoxy-4'-methoxymethoxy-biphenyl-2-yloxymethyl]-cyclopropanecarbonitrile are obtained as a beige powder after successive stirring with water and methanol.
MS (ISP): 476.2 (M+H)⁺

Stage b) 1-[4-(2,4-Diamino-pyrimidin-5-ylmethyl)-6-ethoxy-4'-hydroxy-biphenyl-2-yloxymethyl]-cyclopropanecarbonitrile Starting from 1-[4-(2,4-diamino-pyrimidin-5-ylmethyl)-6-ethoxy-4'-methoxymethoxy-biphenyl-2-yloxymethyl]-cyclopropanecarbonitrile (300 mg; 0.63 mmol), 100 mg (37%) 1-[4-(2,4-diamino-pyrimidin-5-ylmethyl)-6-ethoxy-4'-hydroxy-biphenyl-2-yloxymethyl]-cyclopropanecarbonitrile are obtained as a colourless powder.
MS (ISP): 432.4 (M+H)⁺

(8g) 4'-(2,4-Diamino-pyrimidin-5-ylmethyl)-6'-ethoxy-2'-(2-pyridin-2-yl-ethoxy)-biphenyl-4-ol Stage a) 5-[6-Ethoxy-4'-methoxymethoxy-2-(2-pyridin-2-yl-ethoxy)-biphenyl-4-ylmethyl]-pyrimidine-2,4-diamine Analogously to Example 7 (Method β):
Starting from 4-(2,4-diamino-pyrimidin-5-ylmethyl)-6-ethoxy-4'-methoxymethoxy-biphenyl-2-ol (396 mg; 1 mmol) and 2-(2-pyridyl)ethyl mesylate (four portions of 400 mg each; 2 mmol) and potassium carbonate (four portions of 414 mg each; 3.0 mmol) in boiling acetonitrile (40 ml), 187 mg (37%) 5-[6-ethoxy-4'-methoxymethoxy-2-(2-pyridin-2-yl-ethoxy)-biphenyl-4-ylmethyl]-pyrimidine-2,4-diamine are obtained as a beige powder.
MS (ISP) ): 502.3 (M+H)⁺

Stage b) 4'-(2,4-Diamino-pyrimidin-5-ylmethyl)-6'-ethoxy-2'-(2-pyridin-2-yl-ethoxy)-biphenyl-4-ol Starting from 5-[6-ethoxy-4'-methoxymethoxy-2-(2-pyridin-2-yl-ethoxy)-biphenyl-4-ylmethyl]-pyrimidine-2,4-diamine (180 mg; 0.36 mmol), 151 mg (92%) 4'-(2,4-diamino-pyrimidin-5-ylmethyl)-6'-ethoxy-2'-(2-pyridin-2-yl-ethoxy)-biphenyl-4-ol are obtained as a colourless powder.
MS (ISP): 458.4 (M+H)⁺

(8h) 2'-Cyclopropylmethoxy-4'-(2,4-diamino-pyrimidin-5-ylmethyl)-6'-ethoxy-biphenyl-4-ol Stage a) 5-(2-Cydopropylmethoxy-6-ethoxy-4'-methoxymethoxy-biphenyl-4-ylmethyl)-pyrimidine-2,4-diamine Analogously to Example 7 (Method α):
Starting from 4-(2,4-diamino-pyrimidin-5-ylmethyl)-6-ethoxy-4'-methoxymethoxy-biphenyl-2-ol (396 mg; 1.0 mmol) and bromomethyl-cydopropane (0.114 ml; 1.2 mmol), 214 mg (53%) 5-(2-cyclopropylmethoxy-6-ethoxy-4'-methoxymethoxy-biphenyl-4-ylmethyl)-pyrimidine-2,4-diamine are obtained as a yellowish powder.
MS (ISP): 451.3 (M+H)⁺

Stage b) 2'-Cyclopropylmethoxy-4'-(2,4-diamino-pyrimidin-5-ylmethyl)-6'-ethoxy-biphenyl-4-ol Starting from 5-(2-cyclopropylmethoxy-6-ethoxy-4'-methoxymethoxy-biphenyl-4-ylmethyl)-pyrimidine-2,4-diamine (150 mg; 0.33 mmol), 118 mg (84%)) 2'-cyclopropymethoxy-4'-(2,4-diamino-pyrimidin-5-ylmethyl)-6'-ethoxy-biphenyl-4-ol are obtained as a beige powder.
MS (ISP): 407.3 (M+H)⁺

(8i) 2'-Cyclobutylmethoxy-4'-(2,4-diamino-pyrimidin-5-ylmethyl)-6'-ethoxy-biphenyl-4-ol Stage a) 5-(2-Cydobutylmethoxy-6-ethoxy-4'-methoxymethoxy-biphenyl-4-ylmethyl)-pyrimidine-2,4-diamine Analogously to Example 7 (Method α):
Starting from 4-(2,4-diamino-pyrimidin-5-ylmethyl)-6-ethoxy-4'-methoxymethoxy-biphenyl-2-ol (396 mg; 1.0 mmol) and bromomethyl-cydobutane (0.135 ml; 1.2 mmol), 192 mg (41%) 5-(2-cydobutylmethoxy-6-ethoxy-4'-methoxymethoxy-biphenyl-4-ylmethyl)-pyrimidine-2,4-diamine are obtained as a colourless powder
MS (ISP): 465.2 (M+H)⁺

Stage b) 2'-Cyclobutylmethoxy-4'-(2,4-diamino-pyrimidin-5-ylmethyl)-6'-ethoxy-biphenyl-4-ol Starting from 5-(2-cydobutylmethoxy-6-ethoxy-4'-methoxymethoxy-biphenyl-4-ylmethyl)-pyrimidine-2,4-diamine (150 mg; 0.32 mmol), 123 mg (90%)) 2'-cyclobutylmethoxy-4'-(2,4-diamino-pyrimidin-5-ylmethyl)-6'-ethoxy-biphenyl-4-ol are obtained as a beige powder.
MS (ISP): 421.2 (M+H)⁺

(8j) 2'-Cyclopentylox-4'-(2,4-diamino-pyrimidin-5-ylmethyl)-6'-ethoxy-biphenyl-4-ol Stage a) 5-(2-Cyclopentyloxy-6-ethoxy-4'-methoxymethoxy-biphenyl-4-ylmethyl)-pyrimidine-2,4-diamine Analogously to Example 7 (Method α):
Starting from 4-(2,4-diamino-pyrimidin-5-ylmethyl)-6-ethoxy-4'-methoxymethoxy-biphenyl-2-ol (396 mg; 1.0 mmol) and bromocyclopentane (0.128 ml; 1.2 mmol), 226 mg (48%) 5-(2-cycopentyloxy-6-ethoxy-4'-methoxymethoxy-biphenyl-4-ylmethyl)-pyrimidine-2,4-diamine are obtained as a beige powder.
MS (ISP): 465.3 (M+H)⁺

Stage b) 2'-Cydopentyloxy-4'-(2,4-diamino-pyrimidin-5-ylmethyl)-6'-ethoxy-biphenyl-4-ol Starting from 5-(2-cyclopentylmethoxy-6-ethoxy-4'-methoxymethoxy-biphenyl-4-ylmethyl)-pyrimidine-2,4-diamine (150 mg; 0.323 mmol), 120 mg (88%)) 2'-cyclopentylmethoxy-4'-(2,4-diamino-pyrimidin-5-ylmethyl)-6'-ethoxy-biphenyl-4-ol are obtained as a beige powder.
MS (ISP): 421.3 (M+H)⁺

(8k) 2'-Cyclobutoxy-4'-(2,4-diamino-pyrimidin-5-ylmethyl)-6'-ethoxy-biphenyl-4-ol Stage a) 5-(2-Cyclobutoxy-6-ethoxy-4'-methoxymethoxy-biphenyl-4-ylmethyl)-pyrimidine-2,4-diamine Analogously to Example 7 (Method α):
Starting from 4-(2,4-diamino-pyrimidin-5-ylmethyl)-6-ethoxy-4'-methoxymethoxy-biphenyl-2-ol (396 mg; 1.0 mmol) and bromocydobutane (0.113 ml; 1.2 mmol), 268 mg (60%) 5-(2-cyclobutoxy-6-ethoxy-4'-methoxymethoxybiphenyl-4-ylmethyl)-pyrimidine-2,4-diamine are obtained as a yellow powder.

MS (ISP): 451.3 (M+H)$^+$

Stage b) 2'-Cydobutoxy-4'-(2,4-tiamino-pyrimidin-5-ylmethyl)-6'-ethoxy-biphenyl-4-ol Starting from 5-(2-Cyclopentyloxy-6-ethoxy-4'-methoxymethoxy-biphenyl-4-ylmethyl)-pyrimidine-2,4-diamine (175 mg; 0.415 mmol), 151 mg (86%) 2'-cydobutoxy-4'-(2,4-diamino-pyrimidin-5-ylmethyl)-6'-ethoxy-biphenyl-4-ol are obtained as a yelowish powder.

MS (ISP): 407.3 (M+H)$^+$ (8l 2'-(2-Cydopropyl-ethoxy)-4'-(2,4-diamino-pyrimidin-5-ylmethyl)-6'-ethoxy-biphenyl-4-ol Stage a) 5-[2-(2-Cydopropyl-ethoxy)-6-ethoxy-4'-methoxymethoxy-biphenyl-4-ylmethyl]-pyrimidine-2,4-diamine Analogously to Example 7 (Method α):

Starting from 4-(2,4-diamino-pyrimidin-5-ylmethyl)-6-ethoxy-4'-methoxymethoxy-biphenyl-2-ol (396 mg; 1.0 mmol) and 2-bromoethylcyclopropane (193 mg; 1.3 mmnol), 261 mg (56%) 5-[2-(2-cydopropyl-ethoxy)-6-ethoxy-4'-methoxymethoxy-biphenyl-4-ylmethyl]-pyrimidine-2,4-diamine are obtained as a beige powder.

MS (ISP): 465.2 (M+H)$^+$

Stage b) 2'-(2-Cydopropyl-ethoxy)-4'-(2,4-diamino-pyrimidin-5-ylmethyl)-6'-ethoxy-biphenyl-4-ol Starting from 5-[2-(2-cyclopropyl-ethoxy)-6-ethoxy-4'-methoxymethoxy-biphenyl-4-ylmethyl]-pyrimidine-2,4-diamine (190 mg; 0.409 mmol), 152 mg (88%) 2'-(2-cyclopropyl-ethoxy)-4'-(2,4-diamino-pyrimidin-5-ylmethyl)-6'-ethoxy-biphenyl-4-ol are obtained as a beige powder.

MS (ISP): 421.3 (M+H)$^{30}$ (8m) 4'-(2,4-Diamino-pyrimidin-5-ylmethyl)-6'-ethoxy-2'-(2-pyridin-2-yl-ethoxy)-biphenyl-4-ol Stage a) 5-(6-Ethoxy-2-isopropoxy-4'-methoxymethoxy-biphenyl-4-ylmethyl)-pyrimidine-2,4-diamine Analogously to Example 7 (Method α):

Starting from 4-(2,4-diamino-pyrimidin-5-ylmethyl)-6-ethoxy-4'-methoxymethoxy biphenyl-2-ol (396 mg; 1.0 mmol) and 2-bromopropane (0.122 ml; 1.3 mmol), 241 mg (55%) 5-(6-ethoxy-2-isopropoxy-4'-methoxymethoxy-biphenyl-4-ylmethyl)-pyrimidine-2,4-diamine are obtained as a beige powder.

MS (ISP): 439.3 (M+H)$^+$

Stage b) 4'-(2,4-Diamino-pyrimidin-5-ylmethyl)-6'-ethoxy-2'-isopropy-biphenyl-4-ol Starting from 5-(6-ethoxy-2-isopropoxy-4'-methoxymethoxy-biphenyl-4-ylmethyl)-pyrimidine-2,4-diamine (200 mg; 0.458 mmol), 170 mg (94%) 4'-(2,4-diamino-pyrimidin-5-ylmethyl)-6'-ethoxy-2'-isopropoxy-biphenyl-4-ol are obtained as a beige powder.

MS (ISP): 395.2 (M+H)$^+$ (8n) 4'-(2,4-Diamino-pyrimidin-5-ylmethyl)-6'-ethoxy-2'-isobutoxy-biphenyl-4-ol Stage a) 5-(6-Ethoxy-2-isobutoxy-4'-methoxymethoxy-biphenyl-4-ylmethyl)-pyrimidine-2,4-diamine Analogously to Example 7 (Method α):

Starting from 4-(2,4-diamino-pyrimidin-5-ylmethyl)-6-ethoxy-4'-methoxymethoxy-biphenyl-2-ol (396 mg; 1.0 mmol) and isobutyl bromide (0.141 ml; 1.3 mmol), 278 mg (61%) 5-(6-ethoxy-2-isobutoxy-4'-methoxymethoxy-biphenyl-4-ylmethyl)-pyrimidine-2,4-diamine are obtained as a yellowish powder.

MS (ISP): 453.4 (M+H)$^+$

Stage b) 4'-(2,4-Diamino-pyrimidin-5-ylmethyl)-6'-ethoxy-2'-isobutoxy-biphenyl-4-ol Starting from 5-(6-ethoxy-2-isobutoxy-4'-methoxymethoxy-biphenyl-4-ylmethyl)-pyrimidine-2,4-diamine (240 mg; 0.530 mmol), 184 mg (85%) 4'-(2,4-diamino-pyrimidin-5-ylmethyl)-6'-ethoxy-2'-isobutoxy-biphenyl-4-ol are obtained as a light-yellowish powder.

MS (ISP): 409.3 (M+H)$^+$ (8o) 4'-(2,4-Diamino-pyrimidin-5-ylmethyl)-6'-ethoxy-2'-[(1-methyl-cyclopropyl)-methoxy]-biphenyl-4-ol Stage a) 5-[6-Ethoxy-4'-methoxymethoxy-2-[(1-methyl-cyclopropyl)-methoxy]-biphenyl-4-ylmethyl]-pyrimidine-2,4-diamine Analogously to Example 7 (Method α):

Starting from 4-(2,4-diamino-pyrimidin-5-ylmethyl)-6-ethoxy-4'-methoxymethoxy-biphenyl-2-ol (396 mg; 1.0 mmol) and 1-bromomethyl-1-methylcydopropane (208 mg; 1.4 mmol), 291 mg (62%) 5-[6-ethoxy-4'-methoxymethoxy-2-[(1-methyl-cydopropyl)-methoxy]-biphenyl-4-ylmethyl]-pyrimidine-2,4-diamine are obtained as a yellowish powder.

MS (ISP): 465.2 (M+H)$^+$

Stage b) 4'-(2,4-Diamino-pyrimidin-5-ylmethyl)-6'-ethoxy-2'-[(1-methyl-cydopropyl)-methoxy]-biphenyl-4-ol Starting from 5-[6-ethoxy-4'-methoxymethoxy-2-[(1-methyl-cyclopropyl)-methoxy]-biphenyl-4-ylmethyl]-pyrimidine-2,4-diamine (280 mg; 0.602 mmol), 123 mg (49%) 4'-(2,4-diamino-pyrimidin-5-ylmethyl)-6'-ethoxy-2'-[(1-methyl-cydopropyl)-methoxy]-biphenyl-4-ol are obtained as a colourless powder.

MS (ISP): 421.2 (M+H)$^+$ (8p) 4'-(2,4-Diamino-pyrimidin-5-ylmethyl)-6'-ethoxy-2'-(3-hydroxy-2,2-dimethyl-propoxgyl-biphenyl-4-ol Stage a) 5-{2-[2,2-Dimethyl-3-(tetrahydro-pyran-2-yloxy)-propoxy]-6-ethoxy-4'-methoxymethoxy-biphenyl-4-ylmethyl}-pyrimidine-2,4-diamine 4-(2,4-Diamino-pyrimidin-5-ylmethyl)-6-ethoxy-4'-mcthoxymethoxy-biphenyl-2-ol (1.19; 3.0 mmol) is suspended in water (15 ml), and a 1 M aqueous KOH solution (3.0 ml; 3 mmol) and ethanol (15 ml) are added at room temperature. The solution is concentrated and the residue is stirred with acetone, filtered off with suction and dried under a high vacuum. 1.09 g of a yellowish powder are obtained. 400 mg (0.92 mmol) of this are taken and dissolved in dimethylformamide (10 ml; dried over a molecular sieve), and 2-(3-bromo-2,2-dimethylpropoxy)tetrahydro-2H-pyran (300 mg; 1.19 mmol) is added. The reaction mixture is heated at 150° C. for 20 hours and then cooled to room temperature and concentrated. The residue is stirred with water and the mixture is extracted twice with methylene chloride. The combined organic phases are dried over magnesium sulphate and chromatographed over silica gel (100 g) with methylene chloride/methanol/NH$_4$OH conc. (19/1/0.05). 144 mg (18%) 5-{2-[2,2-dimethyl-3-(tetrahydro-pyran-2-yloxy)-propoxy]-6-ethoxy-4'-methoxymethoxy-biphenyl-4-ylmethyl)-pyrimidine-2,4-diamine are obtained as an oily residue.

MS (ISP): 567.3 (M+H)$^+$

Stage b) 4'-(2,4-Diamino-pyrimidin-5-ylmethyl)-6'-ethoxy-2'-(3-hydroxy-2,2-dimethyl-propoxy)-biphenyl-4-ol Starting from 5-{2-[2,2-dimethyl-3-(tetrahydro-pyran-2-yloxy)-propoxy]-6-ethoxy-4'-methoxymethoxy-biphenyl-4-ylmethyl}-pyrimidine-2,4-diamine (106 mg; 0.187 mmol), 68 mg (80%) 4'-(2,4-diamino-pyrmidin-5-ylmethyl)-6'- ethoxy-2'-(3-hydroxy-2,2-dimethyl-propoxy)-biphenyl-4-ol are obtained as a brownish powder analogously to example (8a), stage (b).

MS (ISP): 439.2 (M+H)+

(8q) 4'-(2,4-Diamino-pyrimidin-5-ylmethyl)-6'-ethoxy-2'-[2-(4-methyl-thiazol-5-yl)-ethoxy]-biphenyl-4-ol Stage a) 5-{6-Ethoxy-4'-methoxymethoxy-2-[2-(4-methyl-thiazol-5-yl)-ethoxy]-biphenyl-4-ylmethyl}-pyrimidine-2,4-diamine Analogously to Example 7 (Method β):

Starting from 4-(2,4-diamino-pyrimidin-5-ylmethyl)-6-ethoxy-4'-methoxymethoxy-biphenyl-2-ol (594 mg; 1.5 mmol) and (4-methyl-thiazol-5-yl)ethanol-methanesulphonate (four portions of 400 mg each; 2 mmol) and potassium carbonate (three portions of 664 mg each; 3.0 mmol) in boiling acetonitrile (67 ml), 629 mg (56%) 4'-(2,4-diamino-pyrimidin-5-ylmethyl)-6'-ethoxy-2'-[2-(4-methyl-thiazol-5-yl)-ethoxy]-biphenyl-4-ol obtained as a yellow powder.

MS (ISP) ): 522.2 (M+H)+

Stage b) 4'-(2,4-Diamino-pyrimidin-5-ylmethyl)-6'-ethoxy-2'-[2-(4-methyl-thiazol-5-yl)-ethoxy]-biphenyl-4-ol Starting from 5-{6-ethoxy-4'-methoxymethoxy-2-[2-(4-methyl-thiazol-5-yl)-ethoxy]-biphenyl-4-ylmethyl}-pyrimidine-2,4-diamine (608 mg; 1.16 mmol), 496 mg (90%) 4'-(2,4-diamino-pyrimidin-5-ylmethyl)-6'-ethoxy-2'-[2-(4-methyl-thiazol-5-yl)-ethoxy]-biphenyl-4-ol are obtained as a colourless powder.

MS (ISP): 478.3 (M+H)+

(8r) 5-[6-Ethoxy-2-(3-methoxy-cyclopentyloxy)-4'-hydroxy-biphenyl-4-ylmethyl]-pyrimidine-2,4-diamine Stage a) 5-[6-Ethoxy-2-(3-methoxy-cyclopentyloxy)-4'-methoxymethoxy-biphenyl-4-ylmethyl]-pyrimidine-2,4-diamine Analogously to Example 7 (Method α):

Starting from 5-(6-ethoxy-2-hydroxy-4'-methoxymethoxy-biphenyl-4-ylmethyl)-pyrimidine-2,4-diamine (400 mg; 1.0 mmol), 1-bromo-3-methoxy-cyclopentane, potassium tert-butylate (272 mg; 2.42 mmol) in dimethylformamide, 155 mg (31%) 5-[6-ethoxy-2-(3-methoxy-dclopentyloxy)-4'-methoxymethoxy-biphenyl-4-ylmethyl]-pyrimidine-2,4-diamine are obtained as a yellow solid.

MS (ISP): 495.3 (M+H)+

Stage b) 5-[6-Ethoxy-2-(3-methoxy-cyclopentyloxy)-4'-hydroxy-biphenyl-4-ylmethyl]-pyrimidine-2,4-diamine Starting from 5-[6-ethoxy-2-(3-methoxy-cydopentyloxy)-4'-methoxymethoxy-biphenyl-4-ylmethyl]-pyrimidine-2,4-diamine (196 mg; 0.4 mmol), 98 mg (58%) 5-[6-ethoxy-2-(3-methoxy-cyclopentyloxy)-4'-hydroxy-biphenyl-4-ylmethyl]-pyrimidine-2,4-diamine are obtained as a yellow solid.

MS (ISP): 451.4 (M+H)+

The 1-bromo-3-methoxy-cyclopentane employed is prepared as follows (stages a)-d)):

Stage a) 1-(tert-Butyldimethyl-silanyloxy)-3-hydroxy-cyclopentane 1,3-Dihydroxycydopentane (4.5 g; 44.06 mmol) is dissolved in tetrahydrofuran (40 ml), and sodium hydride (50% in oil) (2.11 g; 44.06 mmol) is added. The mixture is stirred vigorously at room temperature (a white "pulp" forms). tert-Butyl-dimethyl-chlorosilane (6.64 g; 44.06 mmol) is then added and the mixture is stirred at room temperature overnight. The reaction mixture is poured on to a saturated potassium bicarbonate solution (100 ml). The mixture is extracted twice with ether and the organic phase is dried over sodium sulphate, filtered and concentrated.

The residue is chromatographed over silica gel with n-hexanelethyl acetate (3/1). The pure fractions are combined and the solvent is evaporated off.

Yield: 3.24 g (34%) 1-(tert-butyldimethyl-silanyloxy)-3-hydroxy-cyclopentane as a yellow liquid.

MS: 216 (M)

Stage b) 1-(tert-Butyldimethyl-silanyloxy)-3-methoxy-cyclopentane:

1-(tert-Butyldimethyl-silanyloxy)-3-hydroxy-cyclopentane (3.24 g; 14.97 mmol) is dissolved in tetrahydrofuran (30 ml), and potassium tert-butylate (3.36 g; 29.94 mmol) is added. The mixture is stirred for half an hour at room temperature, methyl iodide (1.86 ml; 29.94 mmol) is added and the mixture is stirred for a further two hours. The reaction mixture is then poured on to water (100 ml) and the mixture is extracted twice with ethyl acetate. The organic phase is dried over sodium sulphate, filtered and concentrated. The residue is chromatographed over silicasith n-hexane/ethyl acetate (97/3). The pure fractions are combined and the solvent is evaporated off.

Yield: 3.09 g (89%) 1-(tert-butyldimethyl-silanyloxy)-3-methoxy-cyclopentane as a yellowish liquid. NMR (1H, 250 Mz in DMSO) in ppm: 0.0 (s, 6H); 0.82 (s, 9H); 1.3–2.0 (m, 6H); 3.11 (s, 3H); 3.81 (m, 1H); 4.3 (m, 1H)

Stage c) 1-Hydroxy-3-methoxy-cydopentane:

1-(tert-Butyldimethyl-silanyloxy)-3-methoxy-cyclopentane (3.08 g; 13.37 mmol) is dissolved in tetrahydrofuran (40 ml), a 1 M tetrabutylammonium fluoride solution in tetrahydrofuran (29.4 ml; 29.4 mmol) is added and the mixture is stirred for four hours at room temperature. The reaction mixture is concentrated. The residue is chromatographed over silica gel with n-hexane/ethyl acetate (4/6). The pure fractions are combined and the solvent is evaporated off.

Yield: 1.65 g (quantitative) 1-hydroxy-3-methoxy-cyclopentane as a yellowish liquid.

NMR (1H, 250 Mz in DMSO) in ppm, 1.4–2.0 (6H); 3.18 (s, 3H); 3.8–3.9 (m, 1H); 4.2 (m, 1H); 4.5 (d, 1H)

Stage d) 1-Bromo-3-methoxy-cyclopentane

1-Hydroxy-3-methoxy-cydopentane (1.65 g; 13.37 mmol) is dissolved in methylene chloride (40 ml), and carbon tetrabromide (5.54 g; 16.71 mmol) is added. The reaction mixture is cooled to 0° C. and triphenylphosphine (5.26 g; 20.05 mmol) is added in portions. After half an hour at 0° C. and half an hour at room temperature, the reaction mixture is poured on to ice-water (100 ml). The mixture is extracted twice with ethyl acetate and the organic phase is dried over sodium sulphate, filtered and concentrated. The residue is chromatographed over silica gel with n-hexane/ethyl acetate (9/1). The pure fractions are combined and the solvent is evaporated off.

Yield: 2.76 g (quantitative) 1-bromo-3-methoxy-cyclopentane as a yellowish liquid. MS: 178 (M)

(8s) 4'-(2,4-Diamino-pyrimidin-5-ylmethyl)-6'-ethga-2'-(2,2,2-trifluoro-ethoxy-biphenyl-4-ol Prepared Analogously to Example 7i (Method β):

Starting from 4-(2,4-diamino-pyrimidin-5-ylmethyl)-6-ethoxy-4'-methoxymethoxy-biphenyl-2-ol (594 mg; 1.5 mmol) and 2,2,2-trifluoroethyl methanesulphonate (0.70 ml; 6 mmol), 419 mg (62%) of a white powder are obtained after chromatography over silica gel (90 g) with methylene chloride/methanol/NH$_4$OH conc. (1/1 mixture of 90/10/1 and 19/1/0.05). This powder is dissolved in methanol (20 ml), a 3 M aqueous hydrochloric acid solution is added and the mixture is stirred for 20 minutes at 60° C. The solution is concentrated, the residue is taken up in water and the mixture is adjusted tb pH 9 with NH₄OH conc. and chromatographed over silica gel (100 g) with methylene chloride/methanol/NH₄OH conc. (19/1/0.05). 74 mg (20%) 4'-(2,4-diamino-pyrimidin-5-ylmethyl)-6'-ethoxy-2'-(2,2,2-trifluoro-ethoxy)-biphenyl-4-ol are obtained as a colourless powder.

MS (ISP): 435.3 (M+H)⁺

The same batch also gives methanesulphonic acid 4-(2,4-diamino-pyriridin-5-ylmethyl)-6-ethoxy-4'-hydroxy-biphenyl-2-yl ester (example 15a)

(8t) (RS)-4'-(2,4-Diamino-pyrimidin-5-ylmethyl)-6'-ethoxy-2'-[2-(tetrahydro-pyran-2-yl)-ethoxy]-biphenyl-4-ol Stage a) (RS)-5-[6-Ethoxy-4'-methoxymethoxy-2-[2-(tetrahydro-pyran-2-yl)-ethoxy]-biphenyl-4-ylmethyl]-pyrimidine-2,4-diamine Analogously to Example 7 (Method α):

Starting from 4-(2,4-diamino-pyrimidin-5-ylmethyl)-6-ethoxy-4'-methoxyinethoxy-biphenyl-2-ol (198 mg; 0.5 mmol) and (tetrahydro-pyran-2-yl)-ethyl bromide (126 mg; 0.65 nmnol), 197 mg (77%) (RS)-5-[6-ethoxy-4'-methoxymethoxy-2-[2-(tetrahydro-pyran-2-yl)-ethoxy]-biphenyl-4-ylmethyl]-pyrimidine-2,4-diamine are obtained as a solid yellow foam.

MS (ISP): 509.0 (M+H)⁺

Stage b) (RS)-4'-(2,4-Diamino-pyrimidin-5-ylmethyl)-6'-ethoxy-2'-[2-(tetrahydro-pyran-2-yl)-ethoxy]-biphenyl-4-ol Starting from (RS)-5-[6-ethoxy-4'-methoxymethoxy-2-[2-(tetrahydro-pyran-2-yl)-ethoxy]-biphenyl-4-ylmethyl]-pyrimidine-2,4-diamine (194 mg; 0.38 mmol), 170 mg (96%) (RS)-4'-(2,4-diamino-pyrimidin-5-ylmethyl)-6'-thoxy-2'-[2-(tetrahydro-pyran-2-yl)-ethoxy]-biphenyl-4-ol are obtained as a pale yellow powder.

MS (ISP): 465.3 (M+H)⁺

(8u) rac-(E)-{2-[4-(2,4-Diamino-pyrimidin-5-ylmethyl)-6-ethoxy-4'-hydroxy-biphenyl-2-yloxy]-cyclopentyl}-acetonitrile Stage a) rac-(E)-{2-[4-(2,4-Diamino-pyrimidin-5-ylmethyl)-6-ethoxy-4'-methoxymethoxy-biphenyl-2-yloxy]-cydopentyl}-acetonitrile (coupling under Mitsunobu conditions)

5-(6-Ethoxy-2-hydroxy-4'-methoxymethoxy-biphenyl-4-ylmethyl)-pyrimidine-2,4-diamine (50 mg; 0.13 mmol) is dissolved in dimethylformamide (10 ml), and triphenylphosphine (660 mg; 2.52 mmol), rac-(Z)-(2-hydroxy-cyclopentyl)-acetonitrile (70 mg; 0.56 mmol) and triethylamine (0.5 ml; 3.59 mmol) are added, while stirring. DEAD (diethyl azodicarboxylate) (448 mg; 2.57 mmol) is then added and stirring of the mixture is continued. The reaction mixture is then poured on to water and extracted with ethyl acetate and the extract is dried over sodium sulphate, filtered with suction and concentrated. The crude product is chromatographed over silica gel with methylene chloride/methanol (19/1).

Yield: 50 mg (79%) rac-(E)-{2-[4-(2,4-diamino-pyrimidin-5-ylmethyl)-6-ethoxy-4'-methoxymetboxy-biphenyl-2-yloxy]-cydopentyl}-acetonitrile as a colourless wax.

MS (ISP): 504.3 (M+H)⁺

Stage b) rac-(E)-{2-[4-(2,4-Diamino-pyrimidin-5-ylmethyl)-6-ethoxy-4'-hydroxy-biphenyl-2-yloxy]-cydopentyl}-acetonitrile Starting from rac-(E)-{2-[4-(2,4-diamino-pyrimidin-5-ylmethyl)-6-ethoxy-4'-methoxymethoxy-biphenyl-2-yloxy]-cyclopentyl}-acetonitrile, 88 mg (34%) rac-(E)-{2-[4-(2,4-diamino-pyrimidin-5-ylmethyl)-6-ethoxy-4'-hydroxy-biphenyl-2-yloxy]-cyclopentyl}-acetonitrile are obtained as a white solid.

MS (ISP): 460.4 (M+H)⁺

The rac-(Z)-(2-hydroxy-cydopentyl)-acetonitrile employed is prepared as follows:

rac-(Z)-2-Hydroxy-cyclopentane-carboxylic acid ethyl ester (5.06 g; 32 mmol) is dissolved in dimethylformamide (20 ml), imidazole (5.44 g; 80 mznol) and tert-butyl-dimethyl-chlorosilane (6.19 g; 35 mmol) are added at room temperature and the mixture is then stirred for 15 hours. The reaction mixture is poured on to water (100 ml) and extracted three times with n-hexane. The combined organic phases are dried over sodium sulphate, filtered and concentrated. The rac-(Z)-2-(tert-butyl-dimethyl-silanyloxy)-cyclopentane-carboxylic acid ethyl ester obtained (8.7 g; 32 mmol) is dissolved in tetrahydrofuran (100 ml), diisobutylaluminium hydride (DIBAH) (1.2 M solution in toluene; 76 ml; 91 mmol) is added at 0° C. and the mixture is stirred for three hours. Methanol (10 ml) is cautiously added dropwise, with vigorous stirring, followed by a 2 M potassium sodium tartrate solution (100 ml). After half an hour the organic phase is separated off, washed with water, dried over sodium sulphate, filtered and concentrated. The rac-(Z)-2(tert-butyl-dimethyl-silanyloxy)-1-hydroxymethyl-cyclopentane obtained (3.57 g; 15.5 mmol) is dissolved in methylene chloride (70 ml), and dimethylaminopyridine (5.67 g; 46.5 mmol) and tosyl chloride (8.87 g; 46.5 mmol) are added and the mixture is stirred overnight. The reaction mixture is poured on to aqueous hydrochloric acid (1 M) (100 ml) and extracted three times with n-hexane. The combined organic phases are dried over sodium sulphate, filtered and concentrated. The residue is chromatographed over silica gel with n-hexane/ethyl acetate (8/2). The pure fractions are combined and the solvent is evaporated off. The tosylate obtained (5.5 g; 15.5 mmol) is dissolved in dimethylsulphoxide (35 ml), sodium cyanide (1.37 g; 28 mmol) is added and the mixture is heated at 90° C. for 1.5 hours. The reaction mixture is poured on to water (100 ml) and extracted twice with ethyl acetate. The combined organic phases are dried over sodium sulphate, filtered and concentrated. The residue is chromatographed over silica gel with n-hexane/ethyl acetate (8/2). The pure fractions are combined and the solvent is evaporated off. The rac-(Z)-[2-(tert-butyl-dimethyl-silanyloxy)-cyclopentyl]-acetonitrile obtained (3.5 g; 14.6 mmol) is diluted in a 1/1 acetonitrile/tetrahydrofuran mixture (40 ml), 40% hydrofluoric acid (11.3 ml) is added and the mixture is stirred for one hour. The reaction mixture is poured on to a saturated sodium bicarbonate solution (200 ml) and extracted twice with ethyl acetate. The combined organic phases are dried over sodium sulphate, filtered and concentrated.

Yield: 2.0 g (76%) rac-(Z)-(2-hydroxy-cyclopentyl)-acetonitrile as a colourless liquid. MS: 125 (M)

(8v) rac-(E)-5-[6-Ethoxy-4'-hydroxy-2-(2-methoxymethyl-cyclopentyloxy)-biphenyl-4-ylmethyl]-pyrimidine-2,4-diamine Stage a) rac-(E)-5-[6-Ethoxy-4'-methoxymethoxy-2-(2-methoxymethyl-cyclopentyloxy)-biphenyl-4-ylmethyl]-pyrimidine-2,4-diamine Prepared analogously to example 8u (stage a)) (coupling under Mitsunobu conditions).

Starting from 5-(6-ethoxy-2-hydroxy-4'-methoxymethoxy-biphenyl-4-ylmethyl)-pyrimidine-2,4- diamine (250 mg; 0.63 mmol) and rac-(Z)-2-methoxymethyl-cydopentanol (492 mg; 2.84 mmol), 380 mg (92%) rac-(E)-5-[6-ethoxy-4'-methoxymethoxy-2-(2-methoxymethyl-cyclopentyloxy)-biphenyl-4-ylmethyl]-pyrimidine-2,4-diamine are obtained as a yellowish wax.

MS (ISP): 509.5 (M+H)$^+$

Stage b) rac-(E)-5-[6-Ethoxy-4'-hydroxy-2-(2-methoxymethyl-cydopentyloxy)-biphenyl-4-ylmethyl]-pyrimidine-2,4-diamine Starting from rac-(E)-5-[6-ethoxy-4'-methoxyrnethoxy-2-(2-methoxymethyl-cyclopentyloxy)-biphenyl-4-ylmethyl]-pyrimidine-2,4-diamine (370 mg; 0.57 mmol), 150 mg (57%) rac-(E)-5-[6-ethoxy-4'-hydroxy-2-(2-methoxymethyl-cydopentyloxy)-biphenyl-4-ylmethyl]-pyrimidine-2,4-diamine are obtained as a white solid.

MS (ISP): 465.3 (M+H)$^+$

The rac-(Z)-2-methoxymethyl-cyclopentanol employed is prepared as follows:

rac-(Z)-2(tert-Butyl-dimethyl-silanyloxy)-1-hydroxymethyl-cyclopentane (0.5 g; 2.17 mmol) (preparation in example 8u) is dissolved in methylene chloride (20 ml). 2,6-Di-tert-butylpyridine (1.0 ml; 4.34 mmol) and methyl trifluoromethanesulphonate (0.736 ml; 6.5 mmol) are added and the reaction mixture is heated for two hours under reflux conditions. The reaction mixture is poured on to dilute aqueous hydrochloric acid (1 M) (30 ml) and extracted twice with methylene chloride. The combined organic phases are dried over sodium sulphate, filtered and concentrated. A 1/1 tetrahydrofuran/acetonitrile mixture (5 ml) and 40% aqueous hydrofluoric acid (2 ml) are added to the rac-(Z)-2(tert-butyl-dimethyl-silanyloxy)-1-methoxymethyl-cydopentane obtained and the mixture is stirred for three hours. The reaction mixture is poured on to a saturated aqueous sodium bicarbonate solution (20 ml). The mixture is extracted twice with ethyl acetate and the combined organic phases are dried over sodium sulphate, filtered with suction and concentrated.

Yield: 0.24 g (84%) rac-(Z)-2-methoxymethyl-cyclopentanol as a colourless oil. MS (EI): 112 (M-H$_2$O)

(8w) {3-[4-(2,4-Diamino-pyhmidin-5-ylmethyl)-6-ethoxy-4'-hydroxy-biphenyl-2-yloxy]-cyclopentyl}-acetonitrile Stage a) 5{3-[4-(2,4-Diamino-pyrimidin-5-ylmethyl)-6-ethoxy-4'-methoxymethoxy-biphenyl-2-yloxy]-cydopentyl}-acetonitrile Prepared analogously to example 8u (stage a) (coupling under Mitsunobu conditions).

Starting from 5-(6-ethoxy-2-hydroxy-4'-methoxymethoxy-biphenyl-4-ylmethyl)-pyrimidine-2,4-diamine (250 mg; 0.63 mmol) and (3-hydroxy-cyclopentyl)-acetonitrile (190 mg; 1.51 mmol), 155 mg (49%) 5{3-[4-(2,4-diamino-pyrimidin-5-ylmethyl)-6-ethoxy-4'-methoxymethoxy-biphenyl-2-yloxy]-cydopentyl}-acetonitrile are obtained as a yellowish foam.

MS (ISP): 504.3 (M+H)$^+$

Stage b) {3-[4-(2,4-Diamino-pyrimidin-5-ylmethyl)-6-ethoxy-4'-hydroxy-biphenyl-2-yloxy]-cyclopentyl}-acetonitrile Starting from 5{3-[4-(2,4-diamino-pyrimidin-5-ylmethyl)-6-ethoxy-4'-methoxymethoxy-biphenyl-2-yloxy]-cyclopentyl}-acetonitrile (150 mg; 0.30 mmol), 107 mg (78%) {3-[4-(2,4-diamino-pyrimidin-5-ylmethyl)-6-ethoxy-4'-hydroxy-biphenyl-2-yloxy]-cyclopentyl}-acetonitrile are obtained as a white solid.

MS (ISP): 460.4 (M+H)$^+$

The (3-hydroxy-cydopentyl)-acetonitrile employed is prepared as follows:

3-(Oxo-cyclopentyl)-acetonitrile (0.9 g; 8.25 mmol) is dissolved in methanol (15 ml), and cerium(III) chloride (3.38 g; 9.07 mmol) is added. Sodium borohydride (0.343 g; 9.1 mmol) is added at 0° C. and the mixture is stirred for a quarter of an hour at 0° C. and half an hour at room temperature. The reaction mixture is poured on to water (30 ml). The mixture is extracted twice with ethyl acetate and the combined organic phases are dried over sodium sulphate, filtered and concentrated. The residue is chromatographed over silica gel with n-hexane/ethyl acetate (1/1). The pure fractions are combined and the solvent is evaporated off.

Yield : 0.752 g (82%) (3-hydroxy-cyclopentyl)-acetonitrile as a yellowish liquid. MS (EI): 125 (M)

(8x) 3-[4-(2,4-Diamino-pyximidin-5-ylmethyl)-6-ethoxy-4'-hydroxy-biphenyl-2-yloxy]-cyclopentanecarbonitrile Stage a) 3-[4-(2,4-Diamino-pyrimidin-5-ylmethyl)-6-ethoxy-4'-methoxymethoxy-biphenyl-2-yloxy]-cyclopentanecarbonitrile Analogously to Example 7 (Method α Alkylation with Bromide):

Starting from 5-(6-ethoxy-2-hydroxy-4'-methoxymethoxy-biphenyl-4-ylmethyl)-pyrimidine-2,4-diamine (400 mg; 1.01 mmol) and 1-bromo-3-cyano-cyclopentane (263 mg; 1.51 mmol), 331 mg (59%) 3-[4-(2,4-diamino-pyrimidin-5-ylmethyl)-6-ethoxy-4'-methoxymethoxy-biphenyl-2-yloxy]-cyclopentanecarbonitrile are obtained as white crystals.

(ISP): 490.3 (M+H)$^+$

Stage b) 3-[4-(2,4-Diamino-pyrimidin-5-ylmethyl)-6-ethoxy-4'-hydroxy-biphenyl-2-yloxy]-cyclopentanecarbonitrile Starting from 3-[4-(2,4-diamino-pyrimidin-5-ylmethyl)-6-ethoxy-4'-methoxymethoxy-biphenyl-2-yloxy]-cyclopentanecarbonitrile (320 mg; 0.65 mmol), 242 mg (83%) 3-[4-(2,4-diamino-pyrimidin-5-ylmethyl)-6-ethoxy-4'-hydroxy-biphenyl-2-yloxy]-cyclopentanecarbonitrile are obtained as white crystals.

MS (ISP): 446.5 (M+H)$^+$

The 1-bromo-3-cyano-cyclopentane employed is prepared as follows:

1-Hydroxy-3-cyano-cyclopentane (1.0 g; 9 mmol) is dissolved in methylene chloride (30 ml), and carbon tetrabromide (3.73 g; 11.25 mmol) is added. Triphenylphosphine (3.54 g; 13.5 mmol) is added at 0°0 C. and the mixture is then stirred for a quarter of an hour at 0° C. and half an hour at room temperature. The reaction mixture is poured on to water (30 ml) and extracted twice with ethyl acetate. The combined organic phases are dried over sodium sulphate, filtered and concentrated. The residue is chromatographed over silica gel with n-hexanelethyl acetate (8/2). The pure fractions are combined and the solvent is evaporated off.

Yield: 0.757 g (48%) 1-bromo-3-cyano-cyclopentane as a yellowish liquid. MS (EI): 173 (M)

(8y) 5-[6-Ethoxy-2((trans)-2-methoxy-cyclopentyloxy)-4'-hydroxy-biphenyl-4-ylmethtl]-pyrimidine-2,4-diamine Stage a) 5-[6-Ethoxy-2((trans)-2-methoxy-cyclopentyloxy)-4'-methoxymethoxy-biphenyl-4-ylmethyl]-pyrimidine-2,4-diamine Prepared Analogously to Example 8u (Stage a) (Coupling Under Mitsunobu Conditions).

Starting from 4-(2,4-diamino-pyrimidin-5-ylmethyl)-6-ethoxy-4'-methoxymethoxy-biphenyl-2-ol (390 mg; 0.98 mmol) and (cis)-2-methoxy-cyclopentanol (547 mg; 2.21 mmol), 400 mg (82%) 5-(6-ethoxy-2((trans)-2-methoxycyclopentyloxy)-4'-methoxymethoxy-biphenyl-4-ylmethyl)-pyrimidine-2,4-diamine are obtained as a yellowish foam.

MS (ISP): 495.3 (M+H)+

Stage b) 5-[6-Ethoxy-2((trans)-2-methoxy-cyclopentyloxy)-4'-hydroxy-biphenyl-4-ylmethyl]-pyrimidine-2,4-diamine Starting from 5-[6-ethoxy-2((trans)-2-methdxy-cyclopentyloxy)-4'-methoxymethoxy-biphenyl-4-ylmethyl]-pyrimidine-2,4-diamine (365 mg; 0.74 mmol), 260 mg (78%) 5-[6-ethoxy-2((trans)-2-methoxy-cyclopentyloxy)-4'-hydroxy-biphenyl-4-ylmethyl]-pyrimidine-2,4-diamine are obtained as a white foam.

MS (ISP): 451.3 (M+H)+

The above 4-(2,4-diamino-pyrimidin-5-ylmethyl)-6-ethoxy-4'-methoxymethoxy-biphenyl-2-ol is prepared starting from 5-(3-benzyloxy-5-ethoxy-4-iodo-benzyl)-pyrimidine-2,4-diamine (example 6 in 2 stages a) and b)): Equation 1, (IV)->(V)->(VI)

Stage a) 5-(2-Benzyloxy-6-ethoxy-4'-methoxymethoxy-biphenyl-4-ylmethyl)-pyrimidine-2,4-diamine Prepared Analogously to Example (2a) (Suzuki Coupling with Boron Acid).

Starting from 5-(3-benzyloxy-5-ethoxy-4-iodo-benzyl)-pyrimidine-2,4-diamine (example 6) (20 g; 42 mmol), 4-methoxymethoxy-phenylboron acid (15.1 g, 84 mmol), tetrakis(triphenylphosphine)palladium (2.4 g; 2.1 mmol) and a 2 M $K_3PO_4$ solution in water (115.5 ml; 231 mmol) in dimethylformamide (120 ml), 15 g (74%) 5-(2-benzyloxy-6-ethoxy-4'-methoxymethoxy-biphenyl-4-ylmethyl)-pyrimidine-2,4-diamine are obtained as a yellow foam after 17 hours at a bath temperature of 85° C.

MS ISP): 487.3 (M+H)+

Stage b) 4-(2,4-Diamino-pyrimidin-5-ylmethyl)-6-ethoxy-4'-methoxymethoxy-biphenyl-2-ol 5-(2-Benzyloxy-6-ethoxy-4'-methoxymethoxy-biphenyl-4-ylmethyl)-pyrimidine-2,4-diamine (15 g; 30.8 mmol) is hydrogenated in methanol (2,000 ml) over Pd/C 10% (7.5 g) for 6 hours. The catalyst is filtered off, the product phase is extracted by boiling twice with a mixture of methanol (300 ml) and dimethylformamide (50 ml) and the combined mother liquors are concentrated. The residue is stirred with diethyl ether, filtered off with suction and dried under a high vacuum.

Yield: 12.1 g (99%) 4-(2,4-diamino-pyrimidin-5-ylmethyl)-6-ethoxy-4'-methoxymethoxy-biphenyl-2-ol as a pale brown powder. MS (ISP): 397.2 (M+H)+

EXAMPLE 9

(9a) 5-[6-Ethoxy-4'-methoxy-2-(3-methoxy-2,2-dimethyl-propoxy)-biphenyl-4-ylmethyl]-pyrimidine-2,4-diamine Prepared Analogously to Example 7, but Starting from 4-(2,4-diamino-pyrimidin-5-ylmethyl)-6-ethoxy-4'-methoxy-biphenyl-2-ol: Equation 1, (VI)→(VII)

5-[2-Ethoxy-4'-methoxy-6-[(1-methoxymethyl-cyclopropyl)-methoxyl-biphenyl-4-ylmethyl]-pyrimidine-2,4-diamine (255 mg; 0.549 mmol) is hydrogenated in ethanol/acetic acid conc./water (4/1/0.1) (12 ml) over $PtO_2$ (3×35 mg) at 100° C. The reaction mixture is cooled to room temperature, the catalyst is filtered off with suction and the filtrate is concentrated. The residue is stirred in water, the pH is adjusted to pH 10 by addition of $NH_4OH$ conc. and the entire mixture is filtered with suction. The crude product is chromatographed over silica gel (25 g) with diethyl ether. 80 mg (31%) 5-[6-ethoxy-4'-methoxy-2-(3-Methoxy-2,2-dimethyl-propoxy)-biphenyl-4-ylmethyl]-pyrimidine-2,4-diamine are obtained as a pale brown powder.

MS (ISP): 467.3 (M+H)+

The 5-[2-ethoxy-4'-methoxy-6-[-(1-methoxymethyl-cyclopropyl)-methoxy]-biphenyl-4-ylmethyl]-pyrimidine-2,4-diamine employed is prepared as follows, starting from 4-(2,4-diamino-pyrimidin-5-ylmethyl)-6-ethoxy-4'-methoxy-biphenyl-2-ol:

4-(2,4-Diamino-pyrimidin-5-ylmethyl)-6-ethoxy-4'-methoxybiphenyl-2-ol (544 mg; 1.48 mmol) is dissolved in dimethylformamide (15 ml; dried over a molecular sieve) while gassing with argon, and potassium tert-butylate (254 mg; 2.22 mmol) is added at room temperature. After the mixture has been stirred for one hour, 1-bromomethyl-1-methoxymethyl-cyclopropane (330 mg; 1.93 mmol) is added and the entire mixture is further stirred for about 4 hours at a bath temperature of 80° C. The reaction mixture is then cooled to room temperature and concentrated. Water is added to the residue and the mixture is extracted with ethyl acetate. The aqueous phase is separated off and re-extracted once with ethyl acetate. The combined organic phases are washed twice with a saturated aqueous sodium chloride solution, dried over magnesium sulphate and concentrated. The residue is chromatographed over silica gel (154 g) with methylene chloride/methanol/$NH_4OH$ conc. (90/10/1). The pure fractions are concentrated and the residue is stirred with diethyl etherln-hexane 1:2 (18 ml), filtered off with suction, washed with a little diethyl ether and dried under a high vacuum.

Yield: 412 mg (60%) 5-[2-ethoxy-4'-methoxy-6-[(1-methoxymethyl-cyclopropyl)-methoxy]-biphenyl-4-ylmethyl]-pyrimidine-2,4-diamine as a beige powder. MS(ISP): 465.3 (M+H)+

(9b) 1-[4-(2,4-Diamino-pyrimidin-5-ylmethyl)-6-ethoxy-4'-methoxy-biphenyl-2-yloxymethyl]-clopropy]-acetonitrile Prepared Analogously to Example 8c.

Starting from 4-(2,4-diamino-pyrimidin-5-ylmethyl)-6-ethoxy-4'-methoxy-biphenyl-2-ol (183 mg; 0.5 mmol), 146.5 mg (64%) [1-[4-(2,4-diamino-pyrimidin-5-ylmethyl)-6-ethoxy-4'-methoxy-biphenyl-2-yloxymethyl]-cyclopropyl]-acetonitrile are obtained as a pale yellow powder.

MS (ISP): 460.4 (M+H)+

(9c) 3-{1-[4-(2,4-Diamino-pyrimidin-5-ylmethyl)-6-ethoxy-4'-methoxy-biphenyl-2-yloxymethyl]-cyclopropyl}-propionitrile Prepared by the following sequence (stages a–d), starting from 4-(2,4-diamino-pyrimidin-5-ylmethyl)-6-ethoxy-4'-methoxy-biphenyl-2-ol:

Stage a) 5-[6-(1-Benzyloxymethyl-cyclopropylmethoxy)-2-ethoxy-4'-methoxy-biphenyl-4-ylmethyl]-pyrimidine-2,4-diamine 4-(2,4-Diamino-pyrimidin-5-ylmethyl)-6-ethoxy-4'-methoxy-biphenyl-2-ol (476 mg; 1.3 mmol) is initially introduced into dimethylformamide (16 ml; dried over a molecular sieve), and potassium tert-butylate (224 mg; 1.95 mmol) is added at room temperature. After the mixture has been stirred for one hour, [(1-bromomethyl-cyclopropyl)-methoxymethyl]-benzene (431 mg; 1.69 mmol) is added and the mixture is then stirred for 3 hours at a bath temperature of 80° C. It is then cooled to room temperature and potassium tert-butylate (112 mg; 0.975 mmol) and [(1-bromomethyl-cyclopropyl)-methoxymethyl]-benzene (215 mg; 0.845 mmol) are added again. The reaction mixture is stirred again for 1 hour at 80° C., cooled to room temperature and concentrated. Water is added to the residue, the mixture is extracted with ethyl acetate and the extract is washed with an aqueous saturated sodium chloride solution, dried over magnesium sulphate, filtered with suction and concentrated. The crude product is chromatographed over silica gel (100 g) with methylene chloride/methanol/NH$_4$OH conc. (19/1/0.05). The pure fractions are combined and concentrated and the residue is then stirred with n-hexaneldiethyl ether 3/2 (20 ml), filtered off with suction, washed with n-hexane and dried under a high vacuum. 360 mg (48%) 5-[6-[(1-benzyloxymethyl-cyclopropyl)-methoxy]-2-ethoxy-4'-methoxy-biphenyl-4-ylmethyl]-pyrimidine-2,4-diamine are obtained as a beige powder.

MS (ISP): 541.3 (M+H)$^+$

Stage b) {1-[4-(2,4-Diamin pyrimidin-5-ylmethyl)-6-ethoxy-4'-methoxy-biphenyl-2-yloxymethyl]-cyclopropyl}-methanol 5-[6-[(1-Benzyoxymethyl-ydopropyl)-methoxy]-2-ethoxy-4'-methoxy-biphenyl-4-ylmethyl]-pyrimidine-2,4-diamine (350 mg; 0.647 mmol) is hydrogenated in acetic acid conc. (8 ml) and ethanol (2.7 ml) over Pd/C 10% (100 mg) for 4½ hours. The catalyst is filtered off with suction and washed with ethanol. The solution obtained is evaporated, water (15 ml) is added to the residue and the pH is adjusted to approx. 10 by addition of NH$_4$OH conc. The material which has precipitated out is filtered off with suction and dissolved in ethyl acetate, and the solution is washed with water, dried over magnesium sulphate and evaporated. The residue is stirred with n-hexane/diethyl ether 2/1 (15 ml), filtered off with suction, washed with n-hexane and dried under a high vacuum. 278 mg (95%) {1-[4-(2,4-diamino-pyrimidin-5-ylmethyl)-6-ethoxy-4'-methoxy-biphenyl-2-yloxymethyl]-cyclopropyl}-methanol are obtained as a colourless powder.

MS (ISP): 451.2 (M+H)$^+$

Stage c) (E)-3-[1-[4-(2,4-Diamino-pyrimidin-5-ylmethyl)-6-ethoxy-4'-methoxy-biphenyl-2-yloxymethyl]-cyclopropyl]-acrylonitrile {1-[4-(2,4-Diamino-pyrimidin-5-ylmethyl)-6-ethoxy-4'-methoxy-biphenyl-2-yloxymethyl]-cyclopropyl}-methanol (225 mg; 0.5 mmol) is stirred in methylene chloride (40 ml) and aiinethylformamide (10 ml) with MnO$_2$ (1.5 g) at a bath temperature of 40° C. for 20 hours. The suspension is filtered with suction, the residue is rinsed thoroughly with methanol and the mother liquors are concentrated. The yellow oil obtained (approx. 200 mg) is dissolved in acetonitrile (5 ml), (triphenylphosphoranylidene)acetonitrile (200 mg; 0.75 mmol) is added and the mixture is stirred for 3 days at room temperature. The reaction mixture is concentrated and the residue is chromatographed over silica gel (60 g) with methylene chloride/methanol/NH$_4$OH conc. (19/1/0.05). After stirring with n-hexane/diethyl ether (2/1), 110 mg (47%) (E)-3-[1-[4-(2,4-diamino-pyrimidin-5-ylmethyl)-6-ethoxy-4'-methoxy-biphenyl-2-yloxymethyl]-cyclopropyl]-acrylonitrile are obtained as a colourless powder.

MS (ISP): 472.3 (M+H)$^+$

Stage d) 3-{1-[4-(2,4-Diamino-pyrimidin-5-ylmethyl)-6-ethoxy-4'-methoxy-biphenyl-2-yloxymethyl]-cyclopropyl}-propionitrile Sodium borohydride (45 mg; 1.2 mmol) is added to (E)-3-[1-[4-(2,4-diamino-pyrimidin-5-ylmethyl)-6-ethoxy-4'-methoxy-biphenyl-2-yloxymethyl]-cyclopropyl]-acrylonitrile (220 mg; 0.467 mmol) in isopropanol (25 ml) and the mixture is stirred for 19 hours under reflux. The reaction mixture is concentrated, the residue is stirred with water (15 ml), the mixture is adjusted to pH 2 with 1 N aqueous hydrochloric acid and back to pH 9 with conc. NH$_4$OH and filtered with suction and the residue is dried under a high vacuum. The crude product is chromatographed over silica gel (20 g) with methylene chloride/methanol/NH$_4$OH conc. (19/1/0.05). The pure fractions are concentrated together and the residue is stirred with diethyl ether, filtered off with suction and dried under a high vacuum. 75 mg (34%) 3-{1-[4-(2,4-diamino-pyrimidin-5-ylmethyl)-6-ethoxy-4'-methoxy-biphenyl-2-yloxymethyl]-cyclopropyl}-propionitrile are obtained as a colourless powder.

MS (ISP): 474.3 (M+H)$^+$ (9d) 5-(2-Cyclopropylmethoxy-6-ethoxy-4'-methoxy-biphenyl-4-ylmethyl)-pyrimidine-2.4-diamine Prepared Analogously to Example 7a:

Starting from 4-(2,4-diamino-pyrimidin-5-ylmethyl)-6-ethoxy-4'-methoxy-biphenyl-2-ol (200 mg; 0.545 mmol), 119 mg (48%) 5-(2-cyclopropylmethoxy-6-ethoxy-4'-methoxy-biphenyl-4-ylmethyl)-pyrimidine-2,4-diamine are obtained as a colouriess powder.

MS (ISP): 421.3 (M+H)$^+$ (9e) 5-(6-Ethoxy-4'-methoxy-2-propoxy-biphenyl-4-ylmethyl)-pyrimidine-2,4-diamine Starting from 4-(2,4-diamino-pyrimidin-5-ylmethyl)-6-ethoxy-4'-methoxy-biphenyl-2-ol (200 mg; 0.545 mmol) and 1-bromopropane (0.060 ml; 0.654 mmol), 121 mg (454%) 5-(6-ethoxy-4'-methoxy-2-propory-biphenyl-4-ylmethyl)-pyrimidine-2,4-diamine are obtained as a colourless powder.

MS (ISP): 409.4 (M+H)$^+$ (9f) 5-(2-Ethoxy-6-isopropopy-4'-methoxy-biphenyl-4-ylmethyl)-pyrimidine-2,4-diamine Prepared Analogously to Example 8m (Stage a)):

Starting from 4-(2,4-diamino-pyrimidin-5-ylmethyl)-6-ethoxy-4'-methoxy-biphenyl-2-ol (200 mg; 0.545 mmol), 139 mg (62%) 5-(2-ethoxy-6-isopropoxy-4'-methoxy-biphenyl-4-ylmethyl)-pyrimidine-2,4-diamine are obtained as a beige powder.

MS (ISP): 409.4 (M+H)$^+$ (9g) 5-(2-Ethoxy-6-isobutox-4'-methoxy-biphenyl-4-ylmethyl)-pyrimidine-2,4-diamine Prepared Analogously to Example 8n (Stage a)):

Starting from 4-(2,4-diamino-pyrimidin-5-ylmethyl)-6-ethoxy-4'-methoxy-biphenyl-2-ol (200 mg; 0.545 mmol), 147 mg (64%) 5-(2-ethoxy-6-isobutoxy-4'-methoxy-biphenyl-4-ylmethyl)-pyrimidine-2,4-diamine are obtained as a beige powder.

MS (ISP): 423.3 (M+H)$^+$

The above starting compound 4-(2,4-diamino-pyrimidin-5-ylmethyl)-6-ethoxy-4'-methoxy-biphenyl-2-ol is prepared as follows: Equation 1, (IV)->(V)->(VI)

Stage a) 5-(2-Benzyloxy-6-ethoxy-4'-methoxy-biphenyl-4-ylmethyl)-pyrimidine-2,4-diamine Prepared Analogously to Example (2a) (Suzuki Coupling with Boron Acid):

Starting from 5-(3-benzyloxy-5-ethoxy-4-iodo-benzyl)-pyrimidine-2,4-diamine (example 6) (474 mg; 1 mmol) and 4-methoxy-phenylboron acid (304 mg; 2 mmol), 254 g (56%) 5-(2-benzyloxy-6-ethoxy-4'-methoxy-biphenyl-4-ylmethyl)-pyrimidine-2,4-diamine are obtained as a beige powder.

MS: 456 (M)

Stage b) 4-(2,4-Diamino-pyrimidin-5-ylmethyl)-6-ethoxy-4'-methoxy-biphenyl-2-ol 5-(2-Benzyloxy-6-ethoxy-4'- methoxy-biphenyl-4-ylmethyl)-pyrimidine-2,4-diamine (100 mg; 0.22 mmol) is hydrogenated in acetic acid conc. (3 ml) and ethanol (1 ml) over Pd/C 10% (25 mg). After 1 hour, the catalyst is filtered off with suction and rinsed with ethanol and the filtrate is concentrated. The residue is stirred with water (10 ml), after which the pH is adjusted to 8 by addition of an aqueous saturated sodium bicarbonate solution. The suspension is filtered with suction and the residue is washed with water and dried under a high vacuum. 51 mg (63%) 4-(2,4-diamino-pyrimidin-5-ylmethyl)-6-ethoxy-4'-methoxy-biphenyl-2-ol are obtained as a light-grey powder.

MS (ISP): 367.2 (M+H)$^+$

EXAMPLE 10

The Following are Prepared Analogously to Example 7 and 8: Equation 1, (VI)→(VII)

(10a) 5-(4-Benzo[1.3]dioxol-5-yl-3-cyclobutylmethoxy-5-ethoxy-benzyl)-pyrimidine-2, 4-diamine is Prepared Analogously to Example 8i (Stage a)):

Starting from 2-benzo [1,3]dioxol-5-yl-5-(2,4-diamino-pyrimidin-5-ylmethyl)-3-ethoxy-phenol (247 mg; 0.65 mmol), 198 mg (68%) 5-(4-benzo[1,3]dioxol-5-yl-3-cyclobutylmethoxy-5-ethoxy-benzyl)-pyrimidine-2,4-diamine are obtained as a yellow powder.

MS (ISP): 449.3 (M+H)$^+$ (10b) 5-(4-Benzo[1.3]dioxol-5-yl-3-cyclopropylmethoxy-5-ethoxy-benzyl)-pyrimidine-2, 4-diamine is Prepared Analogously to Example 7a (Stage a)):

Starting from 2-benzo[1,3]dioxol-5-yl-5-(2,4-diamino-pyrimidin-5-ylmethyl)-3-ethoxy-phenol (247 mg, 0.65 mmol), 195 mg (69%) 5-(4-benzo[1,3]dioxol-5-yl-3-cyclopropylmethoxy-5-ethoxy-benzyl)-pyrimidine-2,4-diamine are obtained as a yellow powder.

MS: 434 (M)

(10c) 5-(4-Benzo[1,3]dioxol-5-yl-3-ethoxy-5-isobutoxy-benzyl)-pyrimidine-2,4-diamine is Prepared Analogously to Example 8n (Stage a)).

Starting from 2-benzo[1,3]dioxol-5-yl-5-(2,4-diamino-pyrimidin-5-ylmethyl)-3-ethoxy-phenol (247 mg; 0.65 mmol), 123 mg (43%) 5-(4-benzo[1,3]dioxol-5-yl-3-ethoxy-5-isobutoxy-benzyl)-pyrimidine-2,4-diamine are obtained as a yellow powder.

MS (ISP): 437.3 (M+H)$^+$ (10d) 5-(4-Benzo[1,3]dioxol-5-yl-3-cyclopentyloxy-5-ethoxy-benzyl)-pyrimidine-2,4-diamine is Prepared Analogously to Example 7d:

Starting from 2-benzo[1,3]dioxol-5-yl-5-(2,4-diamino-pyrimidin-5-ylmethyl)-3-ethoxy-phenol (247 mg; 0.65 mmol), 136 mg (47%) 5-(4-benzo[1,3]dioxol-5-yl-3-cyclopentyloxy-5-ethoxy-benzyl)-pyrimidine-2,4-diamine are obtained as a yellow powder.

MS (ISP): 449.3 (M+H)$^+$ (10e) 5-(4-Benzo[1.31]dioxol-5-yl-3-cyclobutoxy-5-ethoxy-benzyl)-pyrmidine-2,4-diamine is Prepared Analogously to Example 7e:

Starting from 2-benzo[1,3]dioxol-5-yl-5-(2,4-diamino-pyrimidin-5-ylmethyl)-3-ethoxy-phenol (247 mg; 0.65 mmol), 113 mg (40%) 5-(4-benzo[1,3]dioxol-5-yl-3-cyclobutoxy-5-ethoxy-benzyl)-pyrimidine-2,4-diamine are obtained as a yellow powder.

MS (ISP): 435.3 (M+H)$^+$ (10f) 5-[4-Benzo[1.3]dioxol-5-yl-3-ethoxy-5-(2-methyl-allyloxy)-benzyl]-pyrimidine-2,4-diamine is Prepared Analogously to Example 7a:

Starting from 2-benzo[1,3]dioxol-5-yl-5-(2,4-diamino-pyrimidin-5-ylmethyl)-3-ethoxy-phenol (247 mg; 0.65 mmol) and 3-bromo-2-methylpropene (0.101 ml; 0.975 mml [sic]), 223 mg (79%) 5-[4-benzo[1,3]dioxol-5-yl-3-ethoxy-5-(2-methyl-allyloxy)-benzyl]-pyrimidine-2,4-diamine are obtained as a colourless powder.

MS (ISP): 435.2 (M+H)$^+$

The above starting compound 2-benzo[1,3]dioxol-5-yl-5-(2,4-diamino-pyrimidine-5-ylmethyl)-3-ethoxy-phenol is prepared as follows: Equation 1, (IV)->(V)->(VI)

Stage a) 5-(4-Benzo[1,3]dioxol-5-yl-3-benzyloxy-5-ethoxy-benzyl)-pyrimidine-2,4-diamine is Prepared Analogously to Example (2a) (Suzuki Coupling with Boron Acid):

Starting from 5-(3-benzyloxy-5-ethoxy-4-iodo-benzyl)-pyrimidine-2,4-diamine (example 6) (10 g; 21 mmol), (1,3-benzodioxol-5-yl)-boron acid (7.0 g; 42 mmol), tetrakis-triphenylphosphine-palladium (1.17 g; 1 mmol) in dimethylformamide (140 ml), ethanol (35 ml) and a 2 M $K_3PO_4$ solution in water (93 ml) for 2 hours at a bath temperature of 86° C., 9.7 g (98%) 5-(4-benzo[1,3]dioxol-5-yl-3-benzyloxy-5-ethoxy-benzyl)-pyrimidine-2,4-diamine are obtained as a yellow solid foam.

MS(ISP): 471.2 (M+H)$^+$

Stage b) 2-Benzo[1,3]dioxol-5-yl-5-(2,4-diamino-pyrimidin-5-ylmethyl)-3-ethoxy-phenol 5-(4-Benzo[1,3]dioxol-5-yl-3-benzyloxy-5-ethoxy-benzyl)-pyrimidine-2,4-diamine (900 mg; 1.9 mmol) is hydrogenated in acetic acid conc. (24 ml) and ethanol (8 ml) over Pd/C 10% (300 mg). After 3 hours, the catalyst is filtered off with suction and rinsed with ethanol and the filtrate is concentrated. The residue is stirred with water (20 ml) and the pH is adjusted to 9 by addition of $NH_4OH$ conc. The suspension is filtered with suction and the residue is washed with water and dried under a high vacuum. 533 mg (74%) 2-benzo[1,3]dioxol-5-yl-5-(2,4-diamino-pyrimnidin-5-ylmethyl)-3-ethoxy-phenol are obtained as a colourless powder.

MS (ISP): 381.2 (M+H)$^+$

EXAMPLE 11

The Following are Prepared Analogously to Example 7: Equation 1, (VI)→(VII)

(11a) 5-(4'-Amino-2-cyclopropylmethoxy-6-ethoxy-3'-methyl-biphenyl-4-ylmethyl-pyrimidine-2,4-diamine Starting from 5-(4'-Amino-6-ethoxy-2-hydroxy-3'-methyl-biphenyl-4-ylmethyl)-pyrimidine-2,4-diamine (250 mg; 0.68 mmol) and bromomethylcyclopropane (0.085 ml; 0.89 mmol), 143 mg (49%) 5-(4'-amino-2-cyclopropylmethoxy-6-ethoxy-3'-methyl-biphenyl-4-ylmethyl)-pyrimidine-2,4-diamine are obtained as a yellow foam.

MS (ISP): 420.3 (M+H)$^+$ (11b) 5-[4'-Amino-2-[(2-tetrahydropyran-4-yl)-ethoxy]-6-ethoxy-4'-methyl-biphenyl-4-ylmethyl]-pyrimidine-2,4-diamine Starting from 5-(4'-amino-6-ethoxy-2-hydroxy-4'-methyl-biphenyl-4-ylmethyl)-pyrimidine-2,4-diamine (250 mg; 0.68 mmol) and (2-tetrahydropyran-4-yl)-ethyl 1-bromide (308 mg; 1.71 mmol), 240 mg (73%) 5-{4'-amino-2-[(2-tetrahydropyran-4-yl)-ethoxy]-6-ethoxy-4'-methyl-biphenyl-4-ylmethyl}-pyrimidine-2,4-diamine are obtained as a yellow solid.

MS (ISP): 478.4 (M+H)$^+$

The above starting compound 5-(4'-amino-6-ethoxy-2-hydroxy-4'-methyl-biphenyl-4-ylmethyl)-pyrimidine-2,4-diamine is prepared as follows analogously to example 4a (Suzuki-coupling with in situ generation of $R^2$—B(OH)$_2$)) and subsequent splitting off of the benzyl group by catalytic hydrogenation: Equation 1, (IV)->(V)->(VI)

Starting from N-(4-iodo-2-methyl-phenyl)-2,2,2-trifluoroacetamide (6 g; 18.2 mmol), (bis-pinacolato) diboron (6.61 ml; 45.57 mmol), triethylamine (7.62 ml; 54.7 mmol) and (diphenylphosphino)-dichloro-palladium(II) (716 mg; 1.02 mmol) in dioxane and then 5-(3-benzyloxy-5-ethoxy-4-iodo-benzyl)-pyrimidine-2,4-diamine (example 6) (4.21 g; 8.83 mmol), tetrakis-triphenylphosphine-palladium (786 mg; 0.68 mmol), aqueous 2 M sodium carbonate solution (136 ml; 272 mmol) in 5/1 dimethoxyethane/ethanol (184 ml), 4.4 g (98%) 5-(4'-amino-2-benzyloxy-6-ethoxy-4'-methyl-biphenyl-4-ylmethyl)-pyrimidine-2,4-diamine are obtained as a brown liquid. The entire intermediate product 5-(4'-amino-2-benzyloxy-6-ethoxy-4'-methyl-biphenyl-4-ylmethyl)-pyrimidine-2,4-diamine (10.3 g; 12.57 mmol) is dissolved in dimethylformamide/methanol 1/3 and hydrogenated over Pd/C 10% (1.66 g).

Yield :4.06 g (88%) 5-(4'-amino-6-ethoxy-2-hydroxy-4'-methyl-biphenyl-4-ylmethyl)-pyrimidine-2,4-diamine as a brown solid. MS (ISP): 366.2 (M+H)$^+$

EXAMPLE 12

The Following is Prepared Analogously to Example 7: Equation 1, (VI)→(VII)

5-(3'-Amino-2-cyclopropylmethoxy-6-ethoxy-4'-methoxy-biphenyl-4-ylmethl)-pyrimidine-2,4-diamine Starting from 5-(4'-amino-6-ethoxy-2-hydroxy-4'-methoxy-biphenyl-4-ylmethyl)-pyrimidine-2,4-diamine (220 mg; 0.68 mmol) and bromomethylcyclopropane (0.138 ml; 1.44 mmol), 170 mg (65%) 5-(3'-amino-2-cyclopropylmethoxy-6-ethoxy-4'-methoxy-biphenyl-4-ylmethyl)-pyrimidine-2,4-diamine are obtained as a yellow foam.

MS (ISP): 436.4 (M+H)$^+$

The above starting compound 5-(4'-amino-6-ethoxy-2-hydroxy-4'-methoxy-biphenyl-4-ylmethyl)-pyrimidine-2,4-diamine is prepared as follows (analogously to example 4a; Suzuki coupling with in situ generation of $R^2$—B(OH)$_2$ and subsequent splitting off of the benzyl group by catalytic hydrogenation): Equation 1, (IV)->(V)->(VI)

Starting from N-(3-bromo-6-methoxy-phenyl)-2,2,2-trifluoroacetamide (5 g; 16.8 mmol), (bis-pinacolato) diboron (6.09 ml; 41.94 mmol), triethylamine (7.0 ml; 50.3 mmol) and (diphenylphosphino)-dichloro-palladium(II) (768 mg; 0.67 mmol) in dioxane, and thereafter 5-(3-benzyloxy-5-ethoxy-4-iodo-benzyl)-pyrimidine-2,4-diamine (example 6) (3.83 g; 8.04 mmol), tetra-(triphenyl-phosphine)-palladiurn (620 mg; 0.54 mmol) and aqueous 2 M sodium carbonate solution (81 ml; 162 mmol) in 5/1 dimethoxyethanelethanol (72 ml), 2.71 g (72%) 5-(3'-amino-2-benzyloxy-6-ethoxy-4'-methoxy-biphenyl-4-ylmethyl)-pyrimidine-2,4-diamine are obtained as a light-green foam. The entire intermediate product is dissolved in dimethylformamide/methanol 1/3 and hydrogenated over Pd/C 10% (0.66 g).

Yield: 0.97 g (53%) 5-(4'-amino-6-ethoxy-2-hydroxy-4'-methoxy-biphenyl-4-ylmethyl)-pyrimidine-2,4-diamine as yellow crystals. MS (ISP): 382.2 (M+H)$^+$

EXAMPLE 13

The Following is Prepared Analogously to Example 7: Equation 1, (VI)→(VII)

5-(4'-Amino-2-cyclopropylmethoxy-6-ethoxy-biphenyl-4-ylmethyl)-pyrimidine-2,4-diamine Prepared Analogously to Example 7a (Stage a)).

Starting from 4'-amino-4-(2,4-diamino-pyrimidin-5-ylmethyl)-6-ethoxy-biphenyl-2-ol (176 mg; 0,5 mmol), 110 mg (54%) 5-(4'-amino-2-cyclopropylmethoxy-6-ethoxy-biphenyl-4-ylmethyl)-pyrimidine-2,4-diamine are obtained as a yellow powder.

MS(ISP): 406.4 (M+H)$^+$

The starting compound is prepared as follows: Equation 1, (IV)->(V)->(VI)

Stage a) 5-(4'-Amino-2-benzyloxy-6-ethoxy-biphenyl-4-ylmethyl)-pyrimidine-2,4-diamine Prepared analogously to example 4a (Suzuki coupling with in situ generation of $R^2$—B(OH)$_2$)).

Trifluoroaceto-p-bromoanilide (4.02 g; 15 mmol), bis (pinacolato)diboron (5.0 g; 19.6 mmol), potassium acetate (4.41 g; 45 mmol) and 1,1'-bis(diphenylphosphino) ferrocenedichloropalladium(II) (PdCl$_2$(dppf)) (730 mg; 0.95 mnmol) are stirred in dimethoxyethane (150 ml; dried over a molecular sieve) at a bath temperature of 80° C. for 24 hours while gassing with argon. After cooling to room temperature, dimethylformamide (300 ml), tetrakis-triphenylphosphine-palladium (1.35 g; 1.17 mmol), 5-(3-benzyloxy-5-ethoxy-4-iodo-benzyl)-pyrimidine-2,4-diamine (5.7 g; 12 mmol) and a 2 M aqueous potassium phosphate solution (60 ml) are added to the reaction mixture. The reaction mixture is stirred for approx. 15 hours at 77° C., cooled to room temperature and concentrated. The residue obtained is taken up in ethanol (100 ml), a 1 N aqueous NaOH solution (40 ml) is added and the mixture is stirred under reflux for 3 hours. After cooling, the ethanol is evaporated, water (50 ml) is added, the mixture is extracted with methylene chloride (200 ml+100 ml) and the extract is washed successively with water (50 ml) and a saturated aqueous sodium chloride solution, dried over magnesium sulphate, filtered with suction and concentrated. The residue is chromatographed over silica gel (600 g) with methylene chloride/methanol/NH$_4$OH (19/1/0.05). 2.85 g (54%) 5-(4'-amino-2-benzyloxy-6-ethoxy-biphenyl-4-ylmethyl)-pyrimidine-2,4-diamine are obtained as a beige powder.

MS(ISP): 442.3 (M+H)$^+$

Stage b) 4'-Amino-4-(2,4-diamino-pyrimidin-5-ylmethyl)-6-ethoxy-biphenyl-2-ol 5-(4'-Amino-2-benzyloxy-6-ethoxy-biphenyl-4-ylethyl)-pyrimidine-2,4-diamine (2.78 g; 6.3 mmol) is hydrogenated in ethanol (150 ml) and 1 N aqueous hydrochloric acid (18.9 mnl) over Pd/C 10% (1.4 g). After approx. 20 hours, the catalyst is filtered off with suction and rinsed with ethanol and the filtrate is concentrated. The residue is stirred with water (100 ml). The pH is adjusted to 9–10 by addition of NH$_4$OH conc. The suspension is filtered with suction and the residue is washed with water and dried under a high vacuurn.: The crude product obtained is stirred in methanol (30 ml) for approx. 30 minutes, filtered off with suction, washed with methanol and dried under a high vacuum. 1.02 g (46%) 4'-amino-4-(2,4-diamino-pyrimidin-5-ylmethyl)-6-ethoxy-biphenyl-2-ol are obtained as a pale grey powder.

MS (ISP): 352.3 (M+H)$^+$

EXAMPLE 14

Preparation of Compounds of the Formula VIII, Equation 1, from Compounds of the Formula VI.

(14a) Methanesulphonic acid 3'-amino-4-(2,4-diamino-gyrimidin-5-ylmethyl)-6-ethoxy-biphenyl-2-yl ester (method 1: sulphonation with 2,2,2-trifluoroethyl ester)

3'-Amino-4-(2,4-diamino-pyrimidin-5-ylmethyl)-6-ethoxy-biphenyl-2-ol (527 mg; 1.5 mmol) is suspended in acetonitrile (60 ml; dried over a molecular sieve), potassium carbonate (621 mg; 4.5 mmol) is added and the mixture is heated to a bath temperature of 100° C. 2,2,2-Trifluoroethyl methanesulphonate (0.353 ml; 3.0 mmol) is added and the mixture is boiled under reflux for 3 hours. After this period of time, potassium carbonate (414 mg; 3 mmol) and 2,2,2-trifluoroethyl methanesulphonate (0.353 ml; 3.0 mmol) are again added and the mixture is stirred under reflux for a further 2 hours. The same procedure is repeated four more times at intervals of two hours. The suspension is then filtered with suction and the filtrate is concentrated. The residue is chromatographed over silica gel (120 g) with methylene chloride/methanol/NH$_4$OH (1/1 mixture of 90/10/1 and 19/1/0.05).

Yield: 33 mg (5%) methanesulphonic acid 3'-amino-4-(2,4-diamino-pyrimidin-5-ylmethyl)-6-ethoxy-biphenyl-2-yl ester as a colourless powder. MS ISP): 430.4 (M+H)$^+$ In this chromatography process the end product of example 7i is also obtained as a second component.

(14b) Ethanesulphonic acid 3'-amino-4-(2,4-diamino-pyrimidin-5-ylmethyl)-6-ethoxy-biphenyl-2-yl ester (Method 2: Sulphonation with Chloride)

3'-Amino-4-(2,4-diamino-pyrimidin-5-ylmethyl)-6-ethoxy-biphenyl-2-ol (176 mg; 0.5 mmol) is dissolved in dimethylformamide (11 ml; dried over a molecular sieve) under argon, and potassium tert-butylate (69 mg; 0.6 mmol) is added. After stirring for one hour at room temperature, the reaction mixture is cooled to 0–5° C. and ethanesulphonyl chloride (0.058 ml; 0.6 mmol) is added. After 2½ hours at this temperature the reaction mixture is concentrated and the residue is chromatographed over silica gel (20 g) with methylene chloride/methanol/NH$_4$OH (19/1/0.05).

Yield: 81 mg (36%) ethanesulphonic acid 3'-amino-4-(2,4-diamino-pyrimidin-5-ylmethyl)-6-ethoxy-biphenyl-2-yl ester as a yellow solid foam. MS (ISP): 444.3 (M+H)$^+$ The Following are Prepared Analogously:

(14c) Propane-2-sulphonic acid 3'-amino-4-(2,4-diamino-pyrimidin-5-ylmethyl)-6-ethoxy-biphenyl-2-yl ester (Method 2)

Starting from 3'-amino-4-(2,4-diamino-pyrimidin-5-ylmethyl)-6-ethoxy-biphenyl-2-ol (176 mg; 0.5 mmol) and 2-propanesulphonyl chloride (0.068 ml; 0.6 mmol), 74 mg (32%) propane-2-sulphonic acid 3'-amino-4-(2,4-diamino-pyrimidin-5-ylmethyl)-6-ethoxy-biphenyl-2-yl ester are obtained as a yellow powder.

MS (ISP): 458.4 (M+H)$^+$ NMR $^1$H (250 MHz, δ, TMS, DMSO): 1.01 (d; J=6.8; 6H); 1.16 (t; J=6.9; 3H); 3.03 (p; J=6.8; 1H); 3.65 (s; 2H); 3.94 (q; J=6.9; 2H); 5.03 (s; 2H); 5.73 (s; 2H); 6.16 (s; 2H); 6.3–6.55 (m; 3H); 6.84 (s; 1H); 6.9–7.1 (m; 2H); 7.58 (s; 1H).

(14d) Propane-1-sulphonic acid 3'-amino-4-(2,4-diamino-R)rimidin-5-ylmethyl)-6-ethoxy-biphenyl-2-yl ester (Method 2)

Starting from 3'-amino-4-(2,4-diamino-pyrimidin-5-ylmethyl)-6-ethoxy-biphenyl-2-ol (211 mg; 0.6 mmol) and 1-propane-sulphonyl chloride (0.082 ml; 0.72 mmol), 87 mg (32%) propane-1-sulphonic acid 3'-amino-4-(2,4-diamino-pyrimidin-5-ylmethyl)-6-ethoxy-biphenyl-2-yl ester are obtained as a yellow solid foam.

MS (ISP): 458.4 (M+H)$^+$ (14e) 3-Fluoro-4-methoxy-benzenesulphonic acid 3'-amino-4-(2,4-diamino-pyrimidin-5-ylmethyl)-6-ethoxy-biphenyl-2-yl ester (method 2)

Starting from 3'-amino-4-(2,4-diamino-pyrimidin-5-ylmethyl)-6-ethoxy-biphenyl-2-ol (100 mg; 0.28 mmol) and 3-fluoro-4-methoxy-benzenesulphonyl chloride (115 mg; 0.51 mmol), 115 mg of the title compound are obtained as a pale yellow solid.

MS (ISP): 540.3 (M+H)$^+$ (14f) Thiophene-2-sulphonic acid 3'-amino-4-(2,4-diamino-pyrimidin-5-ylmethyl)-6-ethoxy-biphenyl-2-yl ester (Method 2)

Starting from 3'-amino-4-(2,4-diamino-pyrimidin-5-ylmethyl)-6-ethoxy-biphenyl-2-ol (100 mg; 0.28 mmol) and 2-thienylsulfonyl chloride (94 mg; 0.51 mmol), 72 mg of the title compound are isolated as a yellow foam.

MS (ISP): 498.1 (M+H)$^+$ (14g) Butane-2-sulphonic acid 3'-amino-4-(2,4-diamino-pvrimidin-5-ylmethyl)-6-ethoxy-biphenyl-2-yl ester (Method 2)

Starting from 3'-amino-4-(2,4-diamino-pyrimidin-5-ylmethyl)-6-ethoxy-biphenyl-2-ol (176 mg; 0.50 mmol) and sec-butyl-sulphonyl chloride (94 mg; 0.60 mmol), 159 mg of the title compound are isolated as a white solid.

MS (ISP): 472.3 (M+H)$^+$NMR $^1$H (250 MHz, δ, TMS, DMSO): 0.78 (t, J=7.5, 3H), 0.99 (d, J=7, 3H), 1.16 (t, J=7, 3H), 1.25 (m, 1H), 1.63 (m, 1H), 2.73 (m, 1H), 3.65 (s, 2H), 3.96 (q, J=7, 2H), 5.04 (br s, 2H), 5.73 (br s, 2H), 6.17 (br s, 2H), 6.35 (d, J=7, 1H), 6.43 (s, 1H), 6.52 (br d, J=8.5, 1H), 6.82 (s, 1H), 6.94 (s, 1H), 7.01 (t, J=8, 1H), 7.59 (s, 1H).

(14h) 2-Methyl-propane-1-sulphonic acid 3'-amino-4-(2,4-diamino-Dyrimidin-5-ylmethyl)-6-ethoxy-biphenyl-2-yl ester (Method 2)

Starting from 3'-amino-4-(2,4-diamino-pyrimidin-5-ylmethyl)-6-ethoxy-biphenyl-2-ol (176 mg; 0.50 mmol) and iso-butyl-sulphonyl chloride (94 mg; 0.60 mmol), 129 mg of the title compound are isolated as pale yellow crystals.

MS (ISP): 472.3 (M+H)$^+$ (14i) 2,2-Dimethyl-propane-1-sulphonic acid 3'-amino-4-(2,4-diamino-pyrimidin-5-ylmethyl)-6-ethoxy-biphenyl-2-yl ester 3'-Amino-4-(2,4-diamino-pyrimidin-5-ylmethyl)-6-ethoxy-biphenyl-2-ol (176 mg, 0.50 mmol) are [sic] initially introduced into 3 ml abs. dimethylformamide, and 500 mg powdered molecular sieve 4 A are added. The mixture is stirred for 15 min and cooled to 0°, 69 mg (0.60 mmol) KOtBu are added and, after a further 5 min, 2,2-dimethyl-propane-1-sulphonyl chloride (102 mg; 0.50 mmol) is added. The mixture is allowed to react for 5/4 h at 0° and for 2 h at room temperature. Filtration, evaporation under reduced pressure, followed by flash chromatography with SiO$_2$ (CH$_2$Cl$_2$/MeOH/25% NH$_3$(19/1/0.05)) gives, after stirring with EtOEt, 106 mg of the tide compound as colourless crystals.

M.p.: 103° dec. MS (ISP): 486.4 (M+H)$^+$

The above starting compound 3'-amino-4-(2,4-diamino-pyrimidin-5-ylmethyl)-6-ethoxy-biphenyl-2-ol is prepared as described in example 7.

EXAMPLE 15

Analogously to example 14 (method 1 sulphonation with 2,2,2-trifluoroethyl ester or 2 sulphonation with chloride as stated), compounds of the formula VIII, equation 1, are prepared from compounds of the formula VI.

(15a) Methanesulphonic acid 4-(2,4-diamino-pyrimidin-5-ylmethyl)-6-ethoxy-4'-hydroxy-biphenyl-2-yl ester (Method 1)

Starting from 4-(2,4-diamino-pyrimidin-5-ylmethyl)-6-ethoxy-4'-methoxymethoxy-biphenyl-2-ol (594 mg; 1.5 mmol), 68 mg (19%) methanesulphonic acid 4-(2,4-diamino-pyrimidin-5-ylmethyl)-6-ethoxy-4'-hydroxy-biphenyl-2-yl ester are obtained as a colourless powder in accordance with the instructions of example 8s.

MS (ISP): 429.3 (M+H)$^+$

In the concduding chromatography, the end product of example 8s is also obtained as a second component.

(15b) Ethanesulphonic acid 4-(2,4-diamino-pyrimidin-5-ylmethyl)-6-ethoxy-4'-hydroxy-biphenyl-2-yl ester (Method 2)

Starting from 4-(2,4-diamino-pyrimidin-5-ylmethyl)-6-ethoxy-4'-methoxymethoxy-biphenyl-2-ol (248 mg; 0.63 mmol), 99 mg (36%) ethanesulphonic acid 4-(2,4-diamino-pyrimidin-5-ylmethyl)-6-ethoxy-4'-hydroxy-biphenyl-2-yl ester are obtained as a colourless powder by reaction with ethanesulphonyl chloride (0.073 ml; 0.75 mmol) and subsequent splitting off of the methoxymethyl group under acid conditions (example 8a, stage b).

MS (ISP): 445.3 (M+H)$^+$ (15c) Propane-2-sulphonic acid 4-(2,4-diamino-pyrimidin-5-ylmethyl)-6-ethoxy-4'-hydroxy-biphenyl-2-yl ester (Method 2)

Starting from 4-(2,4-diamino-pyrimidin-5-ylmethyl)-6-ethoxy-4'-methoxymethoxy-biphenyl-2-ol (238 mg; 0.60 mmol), 125 mg (45%) propane-2-sulphonic acid 4-(2,4-diamino-pyrimidin-5-ylmethyl)-6-ethoxy-4'-hydroxy-biphenyl-2-yl ester are obtained as a colourless powder by reaction with 2-propanesulphonyl chloride (0.082 ml; 0.72 mmol) and subsequent splitting off of the methoxymethyl group under acid conditions (example 8a, stage b).

MS (ISP): 459.4 (M+H)$^+$ (15d) Propane-1-sulphonic acid 4-(2,4-diamino-p rimidin-5-ylmethyl)-6-ethoxy-4'-hydroxy-biphenyl-2-yl ester (Method 2)

Starting from 4-(2,4-diamino-pyrimidin-5-ylmethyl)-6-ethoxy-4'-methoxymethoxy-biphenyl-2-ol (238 mg; 0.60 mmol), 150 mg (54%) propane-1-sulphonic acid 4-(2,4-diamino-pyrimidin-5-ylmethyl)-6-ethoxy-4'-hydroxy-biphenyl-2-yl ester are obtained as a pale yellow powder by reaction with 1-propane-sulphonyl chloride (0.164 ml; 1.44 mmol in two portions) and subsequent splitting off of the methoxymethyl group under acid conditions (example 8a, stage b).

MS (ISP): 459.4 (M+H)$^+$ (15e) Cylopropanesulphonic acid 4-(2,4-diamino-pyrimidin-5-ylmethyl)-6-ethoxy-4'-hydroxn-biphenyl-2-yl ester (Method 2)

Starting from 4-(2,4-diamino-pyrimidin-5-ylmethyl)-6-ethoxy-4'-methoxymethoxy-biphenyl-2-ol (792 mg; 2.0 mmol), 70 mg (8%) cyclopropanesulphonic acid 4-(2,4-diamino-pyrimidin-5-ylmethyl)-6-ethoxy-4'-hydroxy-biphenyl-2-yl ester are obtained as a colourless powder by reaction with cyclopropyl-sulphonyl chloride (453 mg; 3.0 mmol in two portions) and potassium carbonate (480 mg; 3.0 mmol) in dimethylformamide (20 ml) at room temperature and subsequent splitting off of the methoxymethyl group under acid conditions (example 8a. stage b).

MS (ISP): 457.3 (M+H)$^+$ (15f) 2-Methyl-propane-1-sulphonic acid 4-(2,4-diamino-pyrimidin-5-ylmethyl)-6-ethoxy-4'-hydroxy-biphenyl-2-yl ester (Method 2)

Starting from 4-(2,4-diamino-pyrimidin-5-ylmethyl)-6-ethoxy-4'-methoxymethoxy-biphenyl-2-ol (198 mg; 0.50 mmol), 151 mg of the tide compound are obtained as pale yellow crystals by reaction with iso-butylsulphonyl chloride (94 mg; 0.60 mmol) and subsequent splitting off of the methoxymethyl group under acid conditions.

MS (ISP): 473.2 (M+H)$^+$ (15g) Butane-2-sulphonic acid 4-(2,4-diamino-Dyrimidin-5-ylmethyl)-6-ethoxy-4'-hydroxy-biphenyl-2-yl ester (Method 2)

Starting from 4-(2,4-diamino-pyrimidin-5-ylmethyl)-6-ethoxy-4'-methoxymethoxy-biphenyl-2-ol (198 mg; 0.50 mmol), 112 mg of the title compound are obtained as virtually colourless crystals by reaction with sec-butyl-sulphonyl chloride (94 mg; 0.60 mmol) and subsequent splitting off of the methoxymethyl group under acid conditions.

MS (ISP): 473.3 (M+H)$^+$ (15h) 2,2-Dimethyl-propane-1-sulphonic acid 4-(2, 4-diamino-pyrimidin-5-ylmethyl)-6-ethoxy-4'-hydroxa-biphenyl-2-yl ester (Method 2)

Starting from 4-(2,4-diamino-pyrimidin-5-ylmethyl)-6-ethoxy-4'-methoxymethoxy-biphenyl-2-ol (158 mg ; 0.40 mmol), 115 mg of the tide compound are obtained as virtually colourless crystals by reaction with neopentyl-sulphonyl chloride (82 mg; 0.48 mmol) and subsequent splitting off of the methoxymethyl group under acid conditions.

MS (ISP): 487.3 (M+H)$^+$ (15i) 2-Methyl-propane-2-sulphinic acid 4-(2,4-diamino-pyrimidin-5-ylmethyl)-6-ethoxy-4'-hydroxy-biphenyl-2-yl ester (Method 2)

Starting from 4-(2,4-diamino-pyrimidin-5-ylmethyl)-6-ethoxy-4'-methoxymethoxy-biphenyl-2-ol (238 mg; 0.60 mmol), 51 mg (53%) 2-methyl-propane-2-sulphinic acid 4-(2,4-diamino-pyrimidin-5-ylmethyl)-6-ethoxy-4'-hydroxy-biphenyl-2-yl ester are obtained as a colourless powder by reaction with tert-butyl-sulphinyl chloride (101 mg; 0.72 mmol) and subsequent splitting off of the methoxymethyl group under acid conditions (example 8a, stage b).

MS (ISP): 457.5 (M+H)$^+$ (15i) 3-Fluoro-4-methoxy-benzenesulphonic acid 4-(2,4-diamino-pyrimidin-5-ylmethyl)-6-ethoxy-4'-hydroxy-biphenyl-2-yl ester (Method 2)

Starting from 4-(2,4-diamino-pyrimidin-5-ylmethyl)-6-ethoxy-4'-methoxymethoxy-biphenyl-2-ol (200 mg; 0.40 mmol), 145 mg of the tide compound are obtained as pale yellow crystals by reaction with 3-fluoro-4-methoxy-benzenesulphonyl chloride (204 mg; 0.91 mmol) and subsequent splitting off of the methoxymethyl group under acid conditions.

MS (ISP): 541.1 (M+H)$^+$

The above starting compound 4-(2,4-diamino-pyrimidin-5-ylmethyl)-6-ethoxy-4'-methoxymethoxy-biphenyl-2-ol is prepared as described in example 8.

EXAMPLE 16

Analogously to example 14, method 2, i.e. sulphonation with chloride, compounds of the formula VIII, equation 1, are prepared from compounds of the formula VI.

(16a) Methanesulphonic acid 4-(2,4-diamino-pyrimidin-5-ylmethyl)-6-ethoxy-4'-methoxy-biphenyl-2-yl ester Starting from 4-(2,4-diamino-pyrimidin-5-ylmethyl)-6-ethoxy-4'-methoxy-biphenyl-2-ol (366 mg; 1 mmol), 121 mg (27%) ) methanesulphonic acid 4-(2,4-diamino-pyrimidin-5-ylmethyl)-6-ethoxy-4'-methoxy-biphenyl-2-yl ester are obtained as a colourless powder by reaction with methanesulphonyl chloride (0.100 ml; 1.3 mmol).

MS (ISP): 445.2 (M+H)$^+$ (16b) Ethanesulphonic acid 4-(2,4-diamino-pyrimidin-5-ylmethyl)-6-ethoxy-4'-methoxy-biphenyl-2-yl ester Starting from 4-(2,4-diamino-pyrimidin-5-ylmethyl)-6-ethoxy-4'-methoxy-biphenyl-2-ol (183 mg; 0.5 mmol), 98 mg (43%) ) ethanesulphonic acid 4-(2,4-diamino-pyrimidin-5-ylmethyl)-6-ethoxy-4'-methoxy-biphenyl-2-yl ester are obtained as a pale yellow solid foam by reaction with ethanesulphonyl chloride (0.087 ml; 0.9 mmol). MS (ISP): 459.3 (M+H)$^+$ (16c) Propane-2-sulphonic acid 4-(2,4-diamino-Ryimidin-5-ylmethyl)-6-ethoxy-4'-methoxy-biphenyl-2-yl ester Starting from 4-(2,4-diamino-pyrimidin-5-ylmethyl)-6-ethoxy-4'-methoxy-biphenyl-2-ol (183 mg; 0.5 mmol), 58 mg (24%) ) propane-2-sulphonic acid 4-(2,4-diamino-pyrimidin-5-ylmethyl)-6-ethoxy-4'-methoxy-biphenyl-2-yl ester are obtained as a pale yellow powder by reaction with 2-propylsulphonyl chloride (0.136 ml; 1.2 mmol in 2 portions).

MS (ISP): 473.3 (M+H)$^+$

The above starting compound 4-(2,4-diamino-pyrimidin-5-ylmethyl)-6-ethoxy-4'-methoxy-biphenyl-2-ol is prepared as described in example 9.

EXAMPLE 17

Analogously to example 14, method 2, i.e. sulphonation with chloride, compounds of the formula VIII, equation 1, are prepared from compounds of the formula VI.

(17a) Methanesulphonic acid 2-benzof[1,3]dioxol-5-yl-5-(2,4-diamino-Ryrimidin-5-ylmethyl)-3-ethoxy-phenyl ester Starting from 2-benzo[1,3]dioxol-5-yl-5-(2,4-diamino-pyrimidin-5-ylmethyl)-3-ethoxy-phenol (380 mg; 1.0 mmol), 93 mg (20%)) methanesulphonic acid 2-benzo[1,3]dioxol-5-yl-5-(2,4-diamino-pyrimidin-5-ylmethyl)-3-ethoxy-phenyl ester are obtained as a pale yellow powder by reaction with methanesulphonyl chloride (0.100 ml; 1.3 mmol).

MS (ISP): 459.3 (M+H)$^+$ (17b) Ethanesulphonic acid 2-benzo[1.3]dioxol-5-yl-5-(2,4-diamino-Iyrimidin-5-ylmethyl)-3-ethoxy-phenyl ester Starting from 2-benzo[1,3]dioxol-5-yl-5-(2,4-diamino-pyrimidin-5-ylmethyl)-3-ethoxy-phenol (228 mg; 0.6 mmol), 182 mg (64%) ) ethanesulphonic acid 2-benzo-[1,3]dioxol-5-yl-5-(2,4-diamino-pyrimidin-5-ylmethyl)-3-ethoxy-phenyl ester are obtained as a pale yellow solid foam by reaction with ethanesulphonyl chloride (0.140 ml; 1.44 mol in 2 portions).

MS (ISP): 473.2 (M+H)$^+$ (17c) Propane-2-sulphonic acid 2-benzo[1.3]dioxol-5-yl-5-(2,4-diamino-pyrimidin-5-ylmethyl)-3-ethoxy-phenyl ester Starting from 2-benzo[1,3]dioxol-5-yl-5-(2,4-diamino-pyrimidin-5-ylmethyl)-3-ethoxy-phenol (228 mg; 0.6 mmol), 100 mg (34%) propane-2-sulphonic acid 2-benzo-[1,3]dioxol-5-yl-5-(2,4-diamino-pyrimidin-5-ylmethyl)-3-ethoxy-phenyl ester are obtained as apale yellow solid foam by reaction with 2-propanesulphonyl chloride (0.164 ml; 1.44 mmol in 2 portions).

MS (ISP): 487.2 (M+H)$^+$ (17d) Propane-1-sulphonic acid 2-benzo[1.3]dioxol-5-yl-5-(2,4-diamino-pyrimidin-5-ylmethyl)-3-ethoxy-phenyl ester Starting from 2-benzo[1,3]dioxol-5-yl-5-(2,4-diamino-pyrimidin-5-ylmethyl)-3-ethoxy-phenol (228 mg; 0.6 mmol), 100 mg (29%) propane-1-sulphonic acid 2-benzo-[1,3]dioxol-5-yl-5-(2,4-diamino-pyrimidin-5-ylmethyl)-3-ethoxy-phenyl ester are obtained as a pale yellow solid foam by reaction with 1-propanesulphonyl chloride (0.161 ml; 1.44 mmol in 2 portions).

MS (ISP): 487.2 (M+H)$^+$

The above starting compound 2-benzo[1,3]dioxol-5-yl-5-(2,4-diamino-pyrimidine-5-ylmethyl)-3-ethoxy-phenol is prepared as described in example 10.

EXAMPLE 18

Analogously to example 14, method 2, i.e. sulphonation with chloride, as in equation 1, (VI)→(VIII), the following compound . . . [sic] prepared.
Propane-2-sulphonic acid 4'-amino-4-(2,4-diamino-pyrimidin-5-ylmethyl)-6-ethoxy-biphenyl-2-yl ester, Starting from 4'-amino-4-(2,4-diamino-pyrimidin-5-ylmethyl)-6-ethoxy-biphenyl-2-ol (246 mg; 0.7 mmol), 49 mg (12%) propane-2-sulphonic acid 4'-amino-4-(2,4-diamino-pyrimidin-5-ylmethyl)-6-ethoxy-biphenyl-2-yl ester are obtained as a pale yellow solid foam by reaction with 2-propanesulphonyl chloride (0.192 ml; 1.68 mmol in 2 portions).

MS (ISP): 458.4 (M+H)$^{+NMR}$ $^1$H(250 MHz, δ, TMS, DMSO): 1.04 (d; J=6.8; 6H); 1.17 (t; J=6.8; 3H); 3.08 (p; J=6.8; 1H); 3.63 (s; 2H); 3.94 (q; J=6.8; 2H); 5.10 (s; 2H); 5.73 (s; 2H); 6.16 (s; 2H); 6.56 (d; J=8.5; 2H); 6.8–6.9 (m; 4H); 7.58 (s; 1H).

The above starting compound 4'-Amino-4-(2,4-diamino-pyrimidin-5-ylmethyl)-6-ethoxy-biphenyl-2-ol is prepared as described in example 13.

EXAMPLE 19

Preparation of Compounds of the Formula IX, Equation 1, from Compounds of the Formula VI.

(19a) Dimethyl-sulphamic acid 3'-amino-4-(2,4-diamino-pyrimidin-5-ylmethyl)-6-ethoxy-biphenyl-2-yl ester 3'-Amino-4-(2,4-diamino-pyrimidin-5-ylmethyl)-6-ethoxy-biphenyl-2-ol (200 mg; 0.57 mmol) is dissolved in dimethylformamide (11 ml; dried over a molecular sieve) under argon, and potassium tert-butylate (77 mg; 0.68 mmol) is added. After stirring for one hour at room temperature, N,N-dimethylsulphamoyl chloride (0.073 ml; 0.68 mmol) is added. After 3 hours at this temperature the reaction mixture is concentrated and the residue is chromatographed over silica gel (38 g) with methylene chloride/methanol/NH$_4$OH (1/1 mixture of 19/1/0.05 and 90/10/1).

Yield: 144 mg (55%) dimethyl-sulphamic acid 3'-amino-4-(2,4-diamino-pyrimidin-5-ylmethyl)-6-ethoxy-biphenyl-2-yl ester as a yellow solid foam. MS (ISP): 459.5 (M+H)$^+$ The Following are Prepared Analogously:

(19b) Piperidine-1-sulphonic acid 3'-amino-4-(2,4-diamino-pyrimidin-5-ylmethyl)-6-ethoxy-biphenyl-2-yl ester Starting from 3'-amino-4-(2,4-diamino-pyrimidin-5-ylmethyl)-6-ethoxy-biphenyl-2-ol (200 mg; 0.57 mmol), 131 mg (46%) piperidine-1-sulphonic acid 3'-amino-4-(2,4-diamino-pyrimidin-5-ylmethyl)-6-ethoxy-biphenyl-2-yl ester are obtained as a yellowish powder by reaction with 1-piperidinesulphonyl chloride (136 mg; 0.74 mmol).

MS (ISP): 499.3 (M+H)$^+$ (19c) Pyrrolidine-1-sulphonic acid 3'-amino-4-(2,4-diamino-pyrimidin-5-vlmethyl)-6-ethoxy-biphenyl-2-yl ester Starting from 3'-amino-4-(2,4-diamino-pyrimidin-5-ylmethyl)-6-ethoxy-biphenyl-2-ol (200 mg; 0.57 mmol), 174 mg (63%) pyrrolidine-1-sulphonic acid 3'-amino-4-(2,4-diamino-pyrimidin-5-ylmethyl)-6-ethoxy-biphenyl-2-yl ester are obtained as a yellowish powder by reaction with 1-pyrrolidinesulphonyl chloride (157 mg; 0.925 mmol).

MS (ISP): 485.4 (M+H)$^+$ (19d) N-Isopropyl-N-methyl-sulphamic acid 3'-amino-4-(2,4-diamino-pyrimidin-5-ylmethyl)-6-ethoxy-biphenyl-2-yl ester Starting from 3'-amino-4-(2,4-diamino-pyrimidin-5-ylmethyl)-6-ethoxy-biphenyl-2-ol (200 mg; 0.57 mmol), 116 mg (35%) N-isopropyl-N-methyl-sulphamic acid 3'-amino-4-(2,4-diamino-pyrimidin-5-ylmethyl)-6-ethoxy-biphenyl-2-yl ester are obtained as an orange powder by reaction with N-isopropyl-N-methyl-sulphamoyl chloride (127 mg; 0.74 mmol).

MS (ISP): 487.3 (M+H)$^+$

The N-isopropyl-N-methyl-sulphamoyl Chloride Employed is Prepared as Follows:

Sulphuryl chloride (8.1 ml, 100 mmol) is dissolved in toluene (80 ml), and a solution of N-isopropyl-N-methylamine (10.4 ml; 100 mmol) in toluene (10 ml) is added at 0–5° C. in the course of 30 minutes. The reaction mixture is then stirred for 30 minutes at the same temperature and for 2 hours at room temperature. The reaction mixture is then poured on to ice-water (approx. 150 ml) with vigorous stirring. The organic phase is separated off, washed with 1 N aqueous hydrochloric acid solution, dried over magnesium sulphate, filtered with suction and concentrated (40° C. 70–30 mbar). The crude product is then distilled.

Yield: 3.95 g (23%) N-isopropyl-N-methyl-sulphamoyl chloride as a yellow oil. Boiling point: 80° C. under 13 mbar (19e) Morpholine-4-sulphonic acid 3'-amino-4-(2,4-diamino-pyrimidin-5-ylmethyl)-6-ethoxy-biphenyl-2-yl ester Starting from 3'-amino-4-(2,4-diamino-pyrimidin-5-ylmethyl)-6-ethoxy-biphenyl-2-ol (200 mg; 0.57 mmol), 159 mg (56%) morpholine-4-sulphonic acid 3'-amino-4-(2,4-diamino-pyrimidin-5-ylmethyl)-6-ethoxy-biphenyl-2-yl ester are obtained as a yellow powder by reaction with 4-morpholinesulphonyl chloride (137 mg; 0.74 mmol).

MS (ISP): 501.3 (M+H)$^+$ (19f) N-Ethyl-N-methyl-sulphamic acid 3'-amino-4-(2,4-diamino-vyrimidin-5-ylmethyl)-6-ethoxy-biphenyl-2-yl ester Starting from 3'-amino-4-(2,4-diamino-pyrimidin-5-ylmethyl)-6-ethoxy-biphenyl-2-ol (176 mg; 0.5 mmol), 155 mg (65%) N-ethyl-N-methyl-sulphamic acid 3'-amino-4-(2,4-diamino-pyrimidin-5-ylmethyl)-6-ethoxy-biphenyl-2-yl ester are obtained as a colourless powder by reaction with N-ethyl-N-methylsulphamoyl chloride (95 mg; 0.6 mmol).

MS (ISP): 473.3 (M+H)$^+$ (19g) N-Cclopropyl-N-methyl-sulphamic acid 3'-amino-4-(2,4-diamino-Ryrimidin-5-ylmethyl)-6-ethoxy-biphenyl-2-yl ester Starting from 3'-Amino-4-(2,4-diamino-pyrimidin-5-ylmethyl)-6-ethoxy-biphenyl-2-ol (176 mg; 0.5 mmol), 154 mg (61%) N-cyclopropyl-N-methyl-sulphamic acid 3'-amino-4-(2,4-diamino-pyrimidin-5-ylmethyl)-6-ethoxy-biphenyl-2-yl ester are obtained as a colourless powder by reaction with N-cyclopropyl-N-methylsulphamoyl chloride (102 mg; 0.6 mmol).

MS (ISP): 485.3 (M+H)$^+$

The N-cyclopropyl-N-methyl-sulphamoyl chloride employed is prepared analogously to N-isopropyl-N-methyl-sulphamoyl chloride (described in example 9d):

Starting from N-cyclopropyl-N-methylamine (4.48 g; 63 mmol), 1.29 g (12%) N-cyclopropyl-N-methyl-sulphamoyl chloride are obtained as a yellow oil. Boiling point: 75–100° C. under 9 mbar.

(19h) Diethyl-sulphamic acid 3'-amino-4-(2,4-diamino-pyrimidin-5-ylmethyl)-6-ethoxy-biphenyl-2-yl ester Starting from 3'-amino-4-(2,4-diamino-pyrimidin-5-ylmethyl)-6-ethoxy-biphenyl-2-ol (176 mg; 0.5 mmol), 150 mg (55%) diethyl-sulphamic acid 3'-amino-4-(2,4-diamino-pyrimidin-5-ylmethyl)-6-ethoxy-biphenyl-2-yl ester are obtained as a colourless powder by reaction with N,N-diethylsulphamoyl chloride (103 mg; 0.6 mmol).

MS (ISP): 487.3 (M+H)$^+$

The above starting compound 3'-Amino-4-(2,4-diamino-pyrimidin-5-ylmethyl)-6-ethoxy-biphenyl-2-ol is prepared as described in example 7.

EXAMPLE 20

Analogously to example 19, compounds of the formula IX, equation 1, are prepared from compounds of the formula VI.

(20a) Dimethyl-sulphamic acid 4-(2,4-diamino-pyrimidin-5-ylmethyl)-6-ethoxy-4'-hydroxy-biphenyl-2-yl ester Starting from 4-(2,4-diamino-pyrimidin-5-ylmethyl)-6-ethoxy-4'-methoxymethoxy-biphenyl-2-ol (200 mg; 0.5 mmol), 79 mg (31%) dimethyl-sulphamic acid 4-(2,4-diamino-pyrimidin-5-ylmethyl)-6-ethoxy-4'-hydroxy-biphenyl-2-yl ester are obtained as a beige powder by reaction with N,N-dimethylsulphamoyl chloride (0.084 ml; 0.5 mmol) and subsequent splitting off of the methoxyrn-ethyl group under acid conditions (analogously to example 8a, stage b).

MS (ISP): 460.5 (M+H)$^+$ (20b) Piperidine-1-sulphonic acid 4-(2,4-diamino-pyrimidin-5-ylmethyl)-6-ethoxy-4'-hydroxy-biphenyl-2-yl ester Starting from 4-(2,4-diamino-pyrimidin-5-ylmethyl)-6-ethoxy-4'-methoxymethoxy-biphenyl-2-ol (200 mg; 0.5 mmol), 106 mg (43%) piperidine-1-sulphonic acid 4-(2,4-diamino-pyrimidin-5-ylmethyl)-6-ethoxy-4'-hydroxy-biphenyl-2-yl ester are obtained as a colourless powder by reaction with 1-piperidinesulphonyl chloride (120 mg; 0.66 mmol) and subsequent splitting off of the methoxymethyl group under acid conditions (analogously to example 8a, stage b).

MS (ISP): 500.3 (M+H)$^+$ (20c) Pyrrolidine-1-sulrbonic acid 4-(2,4-diamino-pyrimidin-5-ylmethyl)-6-ethoxy-4'-hydroxy-biphenyl-2-yl ester Starting from 4-(2,4-diamino-pyrirnidin-5-ylmethyl)-6-ethoxy-4'-methoxymethoxy-biphenyl-2-ol (200 mg; 0.5 mmol), 149 mg (62%) pyrrolidine-1-sulphonic acid 4-(2,4-diamino-pyrimidin-5-ylethyl)-6-ethoxy-4'-hydroxy-biphenyl-2-yl ester are obtained as a colourless powder by reaction with 1-pyrrolidinesulphonyl chloride (148 mg; 0.87 mmol) and subsequent splitting off of the methoxymethyl group under acid conditions (analogously to example 8a, stage b).

MS (ISP): 486.3 (M+H)$^+$ (20d) Morpholine-4-sulphonic acid 4-(2,4-diamino-pyrimidin-5-ylmethyl)-6-ethoxy-4'-hydroxy-biphenyl-2-yl ester Starting from 4-(2,4-diamino-pyrimidin-5-ylmethyl)-6-ethoxy-4'-methoxymethoxy-biphenyl-2-ol (200 mg; 0.5 mmol), 85 mg (41%) morpholine-4-sulphonic acid 4-(2,4-diamino-pyrimidin-5-ylmethyl)-6-ethoxy-4'-hydroxy-biphenyl-2-yl ester are obtained as a colourless powder by reaction with 4-morpholinesulphonyl chloride (162 mg; 0.88 mmol) and subsequent splitting off of the methoxymethyl group under acid conditions (analogously to example 8a, stage b).

MS (ISP): 502.2 (M+H)$^+$ (20e) N-Isopropyl-N-methyl-sulphamic acid 4-(2,4-diamino-pvrimidin-5-ylmethyl)-6-ethoxy-4'-hydroxy-biphenyl-2-yl ester Starting from 4-(2,4-diamino-pyrimidin-5-ylmethyl)-6-ethoxy-4'-methoxymethoxy-biphenyl-2-ol (300 mg; 0.76 mmol), 105 mg (28%) N-isopropyl-N-methyl-sulphamic acid 4-(2,4-diamino-pyrimidin-5-ylmethyl)-6-ethoxy-4'-hydroxy-biphenyl-2-yl ester are obtained as a colourless powder by reaction with N-isopropyl-N-methyl-sulphamoyl chloride (169 mg; 0.98 mmol) and subsequent splitting off of the methoxymethyl group under acid conditions (analogously to example 8a, stage b).

MS (ISP): 488.3 (M+H)$^+$

The N-isopropyl-N-methyl-sulphamoyl chloride employed is prepared as described in example 19d.

(20f) N-Cyclopropld-N-methyl-sulphamic acid 4-(2,4-diamino-pyrimidin-5-ylmethyl)-6-ethoxy-4'-hydroxy-biphenyl-2-yl ester Starting from 4-(2,4-diamino-pyrimidin-5-ylmethyl)-6-ethoxy-4'-methoxymethoxy-biphenyl-2-ol (300 mg; 0.76 mmol), 205 mg (56%) N-cyclopropyl-N-methyl-sulphamic acid 4-(2,4-diamino-pyrimidin-5-ylmethyl)-6-ethoxy-4'-hydroxy-biphenyl-2-yl ester are obtained as a colourless powder by reaction with N-cyclopropyl-N-methylsulphamoyl chloride (153 mg; 0.98 mmol) and subsequent splitting off of the methoxymethyl group under acid conditions (analogously to example 8a, stage b).

MS (ISP): 486.3 (M+H)$^+$

The N-cyclopropyl-N-methylsulphamoyl chloride employed is prepared as described in example 19g.

(20g) N-Ethyl-N-methyl-sulphamic acid 4-(2,4-diamino-pyrimidin-5-ylmethyl)-6-ethoxy-4'-hydroxy-biphenyl-2-yl ester Starting from 4-(2,4-diamino-pyrimidin-5-ylmethyl)-6-ethoxy-4'-methoxymethoxy-biphenyl-2-ol (300 mg; 0.76 mmol), 174 mg (48%) N-ethyl-N-methyl-sulphamic acid 4-(2,4-diamino-pyrimidin-5-ylmethyl)-6-ethoxy-4'-hydroxy-biphenyl-2-yl ester are obtained as a colourless powder by reaction with N-ethyl-N-methylsulphamoyl chloride (207 mg; 1.3 mmol) and subsequent splitting off of the methoxymethyl group under acid conditions (analogously to example 8a, stage b).

MS (ISP): 474.3 (M+H)$^+$ (20h) Diethyl-sulphamic acid 4-(2,4-diamino-pyrimidin-5-ylmethyl)-6-ethoxy-4'-hydroxy-biphenyl-2-yl ester Starting from 4-(2,4-diamino-pyrimidin-5-ylmethyl)-6-ethoxy-4'-methoxymethoxy-biphenyl-2-ol (200 mg; 0.5 mmol), 100 mg (41%) diethylsulphamic acid 4-(2,4-diamino-pyrimidin-5-ylmethyl)-6-ethoxy-4'-hydroxy-biphenyl-2-yl ester are obtained as a colourless powder by reaction with N,N-diethylsulphamoyl chloride (250 mg; 0.87 mmol) and subsequent splitting off of the methoxym-ethyl group under acid conditions (analogously to example 8a, stage b).

MS (ISP): 488.3 (M+H)+

The above starting compound 4-(2,4-diamino-pyrimidin-5-ylmethyl)-6-ethoxy-4'-methoxymethoxy-biphenyl-2-ol is prepared as described in example 8.

EXAMPLE 21

The following is prepared analogously to example 19: the following compound of the formula IX, equation 1, from the corresponding compound of the formula VI.
Dimethylsulphamic acid 4-(2,4-diamino-pyrimidin-5-ylmethyl)-6-ethoxy-4'-methoxy-biphenyl-2-yl ester Starting from 4-(2,4-diamino-pyrimidin-5-ylmethyl)-6-ethoxy-4'-methoxy-biphenyl-2-ol (200 mg; 0.55 mmol), 54 mg (21%) dimethylsulphamic acid 4-(2,4-diamino-pyrimidin-5-ylmethyl)-6-ethoxy-4'-methoxy-biphenyl-2-yl ester are obtained as a colourless powder by reaction with N,N-dimethyl-sulphamoyl chloride (0.105 ml; 0.97 mmol).

MS (ISP): 474.3 (M+H)+

The above starting compound 4-(2,4-diamino-pyrimidin-5-ylmethyl)-6-ethoxy-4'-methoxymethoxy-biphenyl-2-ol is prepared as described in example 9.

EXAMPLE 22

Analogously to example 19, compounds of the formula IX, equation 1, are prepared from the corresponding compounds of the formula VI:

(22a) Dimethylsulphamic acid 4'-amino-4-(2,4-diamino-pyrimidin-5-ylmethyl)-6-ethoxy-biphenyl-2-yl ester Starting from 4'-amino-4-(2,4-diamino-pyrimidin-5-ylmethyl)-6-ethoxy-biphenyl-2-ol (211 mg; 0.6 mmol), 180 mg (66%) dimethylsulphamic acid 4'-amino-4-(2,4-diamino-pyrimidin-5-ylmethyl)-6-ethoxy-biphenyl-2-yl ester are obtained as a light-yellow powder by reaction with N,N-dimethylsulphamoyl chloride (0.078 ml; 0.72 mmol).

MS (ISP): 459.5 (M+H)+

(22b) N-Ethyl-N-methyl-sulphamic acid 4'-amino-4-(2,4-diamino-pyrimidin-5-ylmethyl)-6-ethoxy-biphenyl-2-yl ester Starting from 4'-amino-4-(2,4-diamino-pyrimidin-5-ylmethyl)-6-ethoxy-biphenyl-2-ol (176 mg; 0.5 mmol), 148 mg (58%) N-ethyl-N-methyl-sulphamic add 4'-amino-4-(2,4-diamino-pyrimidin-5-ylmethyl)-6-ethoxy-biphenyl-2-yl ester are obtained as a light-yellow powder by reaction with N-ethyl-N-methylsulphamoyl chloride (95 mg; 0.6 mmol).

MS (ISP): 473.3 (M+H)+

(22c) Pyrrolidine-1-sulphonic acid 4'-amino-4-(2,4-diamino-Ryrimidin-5-ylmethyl)-6-ethoxy-biphenyl-2-yl ester Starting from 4'-amino-4-(2,4-diamino-pyrimidin-5-ylmethyl)-6-ethoxy-biphenyl-2-ol (176 mg; 0.5 mmol), 130 mg (54%) pyrrolidine-1-sulphonic acid 4'-amino-4-(2,4-diamino-pyrimidin-5-ylmethyl)-6-ethoxy-biphenyl-2-yl ester are obtained as a yellow powder by reaction with 1-pyrrolidinesulphonyl chloride (110 mg; 0.65 mmol).

MS (ISP): 485.3 (M+H)+

(22d) Morpholine-4-sulphonic acid 4'-amino-4-(2,4-diamino-pyrimidin-5-ylmethyl)-6-ethoxy-biphenyl-2-yl ester Starting from 4'-amino-4-(2,4-diamino-pyrimidin-5-ylmethyl)-6-ethoxy-biphenyl-2-ol (200 mg; 0.57 mmol), 128 mg (40%) morpholine-4-sulphonic acid 4'-amino-4-(2,4-diamino-pyrimidin-5-ylmethyl)-6-ethoxy-biphenyl-2-yl ester are obtained as a light-yellow powder by reaction with 4-morpholinesulphonyl chloride (127 mg; 0.68 mmol).

MS (ISP): 501.2 (M+H)+

(22e) N-Cyclopropyl-N-methyl-sulphamic acid 4'-amino-4-(2,4-diamino-pyrimidin-5-ylmethyl)-6-ethoxy-biphenyl-2-yl ester Starting from 4'-Amino-4-(2,4-diamino-pyrimidin-5-ylmethyl)-6-ethoxy-biphenyl-2-ol (176 mg; 0.5 mmol), 119 mg (47%) N-cyclopropyl-N-methyl-sulphamic acid 4'-amino-4-(2,4-diamino-pyrimidin-5-ylmethyl)-6-ethoxy-biphenyl-2-yl ester are obtained as a light-yellow powder by reaction with N-cyclopropyl-N-methylsulphamoyl chloride (101 mg; 0.6 mmol).

MS (ISP): 485.4 (M+H)+NMR $^1$H (250 MHz, δ, TMS, DMSO): 0.54 (m; 4H); 1.18 (t; J=6.9; 3H); 2.04 (p; J=4.9; 1H); 3.63 (s; 2H); 3.95 (q; J=6.9; 2H); 5.07 (s; 2H); 5.72 (s; 2H); 6.14 (s; 2H); 6.54 (d; J=8.4; 2H); 6.84 (s; 1H); 6.91 (s; 1H); 6.93 (d; J=8.4; 2H); 7.57 (s; 1H).

The N-cyclopropyl-N-methylsulphamoyl chloride employed is prepared as described in example 19g.

(22f) Diethylsulphamic acid 4'-amino-4-(2,4-diamino-pyrimidin-5-ylmethyl)-6-ethoxy-biphenyl-2-yl ester Starting from 4'-amino-4-(2,4-diamino-pyrimidin-5-ylmethyl)-6-ethoxy-biphenyl-2-ol (176 mg; 0.5 mmol), 113 mg (45%) diethylsulphamic acid 4'-amino-4-(2,4-diamino-pyrimidin-5-ylmethyl)-6-ethoxy-biphenyl-2-yl ester are obtained as a light-yellow powder by reaction with N,N-diethylsulphamoyl chloride (103 mg; 0.6 mmol).

MS (ISP): 487.3 (M+H)+

Theabove starting compound 4'-Amino-4-(2,4-diamino-pyrimidin-5-ylmethyl)-6-ethoxy-biphenyl-2-ol is prepared as described in example 13.

EXAMPLE 23

Analogously to example 7, the compound of the formula VII, equation 1, is prepared from the corresponding compound of the formula VI.
5-[3-Cyclopropylmethoxy-5-ethoxy-4-(5-morpholin-4-ylmethyl-thiophen-2-yl)-benzyl]-pyrimidine-2,4-diamine Analogously to example 7, starting from 5-(2,4-diamino-pyrimidin-5-ylmethyl)-3-ethoxy-2-(5-morpholin-4-ylmethyl-thiophen-2-yl)-phenol (88 mg; 0.2 mmol), potassium tert-butylate (25 mg; 0.22 mmol) and bromomethylcyclopropane (24 mg; 0.22 mmol) in dimethylformamide (4 ml, dried over a molecular sieve), 50 mg (34%) 5-[3-cyclopropylmethoxy-5-ethoxy-4-(5-morpholin-4-ylmethyl-thiophen-2-yl)-benzyl]-pyrimidine-2,4-diamine are obtained as a colourless powder.

MS (ISP): 496.2 (M+H)+

The above starting compound 5-(2,4-diamino-pyrimidin-5-ylmethyl)-3-ethoxy-2-(5-morpholin-4-ylmethyl-thiophen-2-yl)-phenol is prepared by the following sequence (a–b) starting from 5-(3-benzyloxy-5-ethoxy-4-iodo-benzyl)-pyrimidine-2,4-diamine (compound of the formula IV, equation 1, example 6): Equation 1, (IV)→(V)→(VI)

Stage a) 5-[3-Benzyloxy-5-ethoxy-4-(5-morpholin-4-ylmethyl-thiophen-2-yl)-benzyl]-pyrimidine-2,4-diamine Prepared analogously to example (2ac) starting from 5-(3-benzyloxy-5-ethoxy-4-iodo-benzyl)-pyrimidine-2,4-diamine (example 6) (1.429 g; 3 mmol) and (5-morpholin-4-ylmethyl-thiophen-2-yl)-boron acid (681 mg; 3 mmol).

Yield: 1.15 g (74%) 5-[3-benzyloxy-5-ethoxy-4-(5-morpholin-4-ylmethyl-thiophen-2-yl)-benzyl]-pyrimidine-2,4-diamine as a beige powder. M.p.: >145° C. decomposition MS(ISP): 532.3 (M+H)$^+$ Stage b) 5-(2,4-Diamino-pyrimidin-5-ylmethyl)-3-ethoxy-2-(5-morpholin-4-ylmethyl-thiophen-2-yl)-phenol 5-[3-Benzyloxy-5-ethoxy-4-(5-morpholin-4-ylmethyl-thiophen-2-yl)-benzyl]-pyrimidine-2,4-diamine (532 mg; 1 mmol) is dissolved in trifluoroacetic acid (32 ml; 400 mmol) under argon, thioanisole (1.18 ml; 10 mmol) is added and the mixture is stirred for 17 hours at room temperature. The reaction mixture is poured cautiously on to a mixture of ice-water (300 ml) and a saturated aqueous sodium bicarbonate solution (300 ml). The mixture is then extracted three times with methylene chloride and the extract is washed with a saturated aqueous sodium chloride solution, dried over sodium carbonate, filtered with suction and concentrated. The crude product obtained is chromatographed over silica gel with methylene chloride/methanol/NH$_4$OH conc. (90/10/1).

Yield: 350 mg (79%) 5-(2,4-diamino-pyrimidin-5-ylmethyl)-3-ethoxy-2-(5-morpholin-4-ylmethyl-thiophen-2-yl)-phenol as a colourless powder. M.p.: >180° C. MS(ISP): 442.3 (M+H)$^+$

EXAMPLE 24

Analogously to example 14b, (method 2, sulphonation with chloride), the following compound of the formula VIII, equation 1, is prepared from the corresponding compound of the formula VI.

Cyclopropanesulphonic acid 5-(2,4-diamino-pyrimidin-5-ylmethyl)-3-ethoxy-2-(5-morpholin-4-ylmethyl-thiophen-2-yl)-phenyl ester Starting from 5-(2,4-diamino-pyrimidin-5-ylmethyl)-3-ethoxy-2-(5-morpholin-4-ylmethyl-thiophen-2-yl)-phenol (120 mg; 0.27 mmol), 34 mg (23%) cyclopropanesulphonic acid 5-(2,4-diamino-pyrimidin-5-ylmethyl)-3-ethoxy-2-(5-morpholin-4-ylmethyl-thiophen-2-yl)-phenyl ester are obtained as a light-yellow powder by reaction with cyclopropylsulphonyl chloride (0.036 ml; 0.328 mmol).

MS (ISP): 546.2 (M+H)$^+$

The above starting compound 5-(2,4-diamino-pyrimidin-5-ylmethyl)-3-ethoxy-2-(5-morpholin-4-ylmethyl-thiophen-2-yl)-phenol is prepared as described in example 23.

EXAMPLE 25

Preparation of 5-(3-ethoxy-4-iodo-5-methoxymethoxv-benzyl)-pyrimidine-2,4-diamine (Key Intermediate Product):

Equation 2, compound (X) where R$^1$=ethyl.

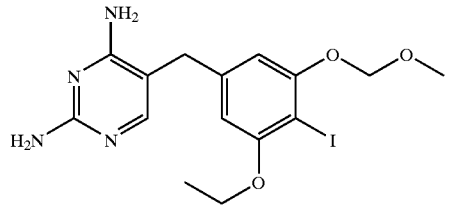

This compound is prepared by the following reaction sequence (stages a)–e)): Stage a) 3-Ethoxy-5-hydroxy-4-iodo-benzoic acid methyl ester:

3,5-Dihydroxy-4-iodo-benzoic acid methyl ester (prepared as in example 1) (60.0 g; 0.204 mol) is dissolved in dimethylformamide (600 ml), and ethyl bromide (16.25 ml; 0.224 mol) and potassium tert-butylate (50.38 g; 0.449 mol) are added at 0° C. The mixture is then stirred for one hour at room temperature. Ether (600 ml) is then added and the mixture is poured on to water (600 ml). The organic phase is separated off (it comprises chiefly 3,5-dihydroxy-4-iodo-benzoic acid methyl ester). The aqueous phase is rendered acid with hydrochloric acid (25%), while cooling, and extracted twice with ether (2 portions of 300 ml). The combined organic phases are then dried over sodium sulphate (400 g) and concentrated. The residue is stirred in a 4/1 n-hexane/ethyl acetate mixture (250 ml) and the crystals are filtered off with suction. 46 g (70%) of yellowish crystals are obtained. The mother liquor is evaporated and the residue is chromatographed over silica gel with n-hexane/ethyl acetate (7/3). The pure fractions are combined and the solvent is evaporated off. 12.1 g (18%) are additionally obtained.

Total yield: 58.1 g (88%) 3-ethoxy-5-hydroxy-4-iodo-benzoic acid methyl ester as yellowish crystals.

MS: 322 (M)

Stage b) 3-Ethoxy-4-iodo-5-methoxymethoxy-benzoic Acid Methyl Ester:

3-Ethoxy-5-hydroxy-4-iodo-benzoic acid methyl ester (58.1 g; 0.18 mmol) is dissolved in tetrahydrofuran (600 ml), and sodium hydride (15.74 g; 55%; 0.361 mmol) is added. The suspension is stirred for one hour at room temperature and then cooled to −10° C. Methoxyrnethyl chloride (27.4 ml; 0.361 mol) is then added dropwise in the course of 5 minutes and the mixture is subsequently stirred for half an hour at room temperature. The reaction mixture is poured on to water (600 ml) and extracted twice with ether (2×300 ml). The combined organic phases are then dried over sodium sulphate (400 g), filtered and concentrated. The residue is stirred in n-hexane (100 ml) and filtered off with suction.

Yield: 49.1 g (75%) 3-ethoxy-4-iodo-5-methoxymethoxy-benzoic acid methyl ester as white crystals. MS: 366 (M)

Stage c) (3-Ethoxy-4-iodo-5-methoxymethoxy-phenyl)-methanol:

Prepared Analogously to Example 1 stage d).

Starting from 3-ethoxy-4-iodo-5-methoxymethoxy-benzoic acid methyl ester (16.49 g; 0.045 Mol), diisobutylaluminium hydride 1.2 M in toluene (132 ml; 0.158 Mol), 15.6 g (3-ethoxy-4-iodo-5-methoxymethoxy-phenyl)-methanol are obtained as a colourless solid mass which is employed in the next stage without further purification.

MS (EI): 338 (M)

Stage d) 3-Ethoxy-4-iodo-5-methoxyrethoxy-benzaldehyde:

Prepared analogously to example 1(e) starting from (3-ethoxy-4-iodo-5-methoxy-methoxy-phenyl)-methanol (15.6 g; 0.045 mol) and manganese dioxide (40.16 g; 0.462 mol).

Yield: 13.76 g of red-yellowish crystals (89% over 2 stages). NMR (1H, 250 MHz in DMSO) in ppm: 1.40 (t, 3H); 3.41 (s, 3H); 4.18 (q, 2H); 5.36 (s, 2H); 7.15 (s, 1H); 7.23 (s 1H); 9.94 (s, 1H)

Stage e) 5-(3-Ethoxy-4-iodo-5-methoxymethoxy-benzyl)-pyrimidine-2,4-diamine

Potassium tert-butylate (3.33 g; 29.77 mmol) is dissolved hot in tert-butanol (33 ml) under argon, while stirring. The solution is then cooled to 40° C. and added dropwise in the course of 25 minutes to a solution comprising 3-ethoxy-4-iodo-5-methoxymethoxy-benzaldehyde (8.34 g; 24.81 mol) and 3-anilinopropionitrile (3.44 g; 23.57 mol) in dimethylsulphoxide (33 ml) at 38–40° C. (20 minutes). The reaction mixture is then stirred for 5 hours at room temperature. 33 ml of solvent are then distilled off. The reaction mixture is poured on to water (100 ml) and extracted twice with ethyl acetate (2×50 ml). The combined organic phases are then dried over sodium sulphate (100 g), filtered and concentrated. The crude intermediate product obtained is further processed directly.

Guanidine hydrochloride (7.81 g; 81.9 mmol) is dissolved in ethanol (1,500 ml), and potassium tert-butylate (10.03 g; 89.8 mmol) is added. The temperature of the reaction mixture is kept below 38° C. for one hour by gentle cooling. The crude intermediate product prepared in this way is then added and the reaction mixture is heated for 20 hours at 67–69° C. The reaction solution is poured on to water (100 ml) and extracted twice with ethyl acetate (2×50 ml). The combined organic phases are then dried over sodium sulphate (100 g), filtered and concentrated. The residue is stirred in ether (80 ml) and the crystals are filtered off with suction, washed with ether and dried under a high vacuum.

Yield: 6.82 g (64%)5-(3-ethoxy-4-iodo-5-methoxymethoxy-benzyl)-pyrimidine-2,4-diamine as yellow crystals. MS (ISP): 431.2 (M+H)$^+$

EXAMPLE 26

Starting from 4-(2,4-diamino-pyrimidin-5-ylmethyl)-6-ethoxy-4'-methylamino-biphenyl-2-ol, the compounds of the formula IX, equation 2, are prepared from the corresponding compounds of the formula VI analogously to example 19.

(26a) Dimethylsulphamic acid 4-(2,4-diamino-pyrimidin-5-ylmethyl)-6-ethoxy-4'-methylamino-biphenyl-2-yl ester Starting from 4-(2,4-diamino-pyrimidin-5-ylmethyl)-6-ethoxy-4'-methylamino-biphenyl-2-ol (183 mg; 0.5 mmol), 123 mg (48%) dimethylsulphamic acid 4-(2,4-diamino-pyrimidin-5-ylmethyl)-6-ethoxy-4'-methylamino-biphenyl-2-yl ester are obtained as a light-yellow powder by reaction with N,N-dimethylsulphamoyl chloride (0.065 ml; 0.6 mmol).

MS (ISP): 473.3 (M+H)$^+$ (26b) N-Ethyl-N-methyl-sulphamic acid 4-(2,4-diamino-pvrimidin-5-ylmethyl)-6-ethoxy-4'-methylamino-biphenyl-2-yl ester Starting from 4-(2,4-diamino-pyrimidin-5-ylmethyl)-6-ethoxy-4'-methylamino-biphenyl-2-ol (183 mg; 0.5 mmol), 130 mg (49%) N-Ethyl-N-methyl-sulphamic acid 4-(2,4-diamino-pyrimidin-5-ylmethyl)-6-etoxy-4'-met hylamino-biphenyl-2-yl ester are obtained as a colourless powder by reaction with N-ethyl-N-methyl-sulphamoyl chloride (95 mg; 0.6 mmol).

MS (ISP): 483.3 (M+H)$^+$ (26c) Morpholine-4-sulphonic acid 4-(2,4-diamino-pyrimidin-5-ylmethyl)-6-ethoxy-4'-methylamino-biphenyl-2-yl ester Starting from 4-(2,4-diamino-pyrimidin-5-ylmethyl)-6-ethoxy-4'-methylamino-biphenyl-2-ol (183 mg; 0.5 mmol), 128 mg (42%) ) morpholine-4-sulphonic acid 4-(2,4-diamino-pyrimidin-5-yimethyl)-6-ethoxy-4'-methylamino-biphenyl-2-yl ester are obtained as a colourless powder by reaction with 4-morpholinesulphonyl chloride (111 mg; 0.6 mmol).

MS (ISP): 515.3 (M+H)$^+$ NMR $^1$H: (250 MHz, δ, TMS, DMSO): 1.18 (t; J=6.9; 3H); 2.68 (d; J=5; 3H);2.81 (m; 4H); 3.44 (m; 4H); 3.64 (s; 2H); 3.95 (q; J=6.9; 2H); 5.66 (q; J=5; 1H); 5.73 (br s; 2H); 6.15 (br s; 2H); 6.54 (d; J=8.5; 2H); 6.86 (s; 1H); 6.93 (s; 1H); 6.98 (d; J=8.5; 2H); 7.58 (s; 1H).

(26d) N-Cyclopropyl-N-methyl-sulphamic acid 4-(2,4-diamino-pyrimidin-5-ylmethyl)-6-ethoxy-4'-methylamino-biphenyl-2-yl ester Starting from 4-(2,4-diamino-pyrimidin-5-ylmethyl)-6-ethoxy-4'-methylamino-biphenyl-2-ol (183 mg; 0.5 mmol), 76 mg (24%) N-cyclopropyl-N-methyl-sulphamic acid 4-(2, 4-diamino-pyrimidin-5-ylmethyl)-rethoxy-4'-methylamino-biphenyl-2-yl ester are obtained as a beige powder by reaction with N-cyclopropyl-N-methyl-sulphamoyl chloride (101 mg; 0.6 mmol).

MS (ISP): 499.3 (M+H)$^+$

The N-cyclopropyl-N-methylsulphamoyl chloride employed is prepared as described in example 19g.

(20e) Pyrrolidine-1-sulphonic acid 4-(2,4-diamino-pyrimidin-5-ylmethyl)-6-ethoxy-4'-methylamino-biphenyl-2-yl ester Starting from 4-(2,4-diamino-pyrimidin-5-ylmethyl)-6-ethoxy-4'-methylamino-biphenyl-2-ol (183 mg; 0.5 mmol), 120 mg (37%)) pyrrolidine-1-sulphonic acid 4-(2,4-diamino-pyrimidin-5-ylmethyl)-6-ethoxy-4'-methylamino-biphenyl-2-yl ester are obtained as a colourless powder by reaction with 1-pyrrolidinesulphonyl chloride (101 mg; 0.6 mmol).

MS (ISP): 499.2 (M+H)$^+$ (26f) Diethylsulphamic acid 4-(2,4-diamino-pyrimidin-5-ylmethyl)-6-ethoxy-4'-methylamino-biphenyl-2-yl ester Starting from 4-(2,4-diamino-pyrimidin-5-ylmethyl)-6-ethoxy-4'-methylamino-biphenyl-2-ol (183 mg; 0.5 mmol), 92 mg (31%) diethylsulphamic acid 4-(2,4-diamino-pyrimidin-5-ylmethyl)-6-ethoxy-4'-methylamino-biphenyl-2-yl ester are obtained as a colourless powder by reaction with N,N-diethylsulphamoyl chloride (103 mg; 0.6 mmol).

MS (ISP): 501.3 (M+H)$^+$

The 4-(2,4-diamino-pyrimidin-5-ylmethyl)-6-ethoxy-4'-methylamino-biphenyl-2-ol employed is prepared starting from 5-(3-benzyloxy-5-ethoxy-4-iodo-benzyl)-pyrimidine-2,4-diamine analogously to example 4a (Suzuki coupling with in situ generation of $R^2$—$B(OH)_2$) and subsequent splitting off of the benzyl protective group:

N-(4-Bromo-phenyl)-2,2,2-trifluoro-N-methyl-acetamide (2.68 g; 9 mmol), bis(pinacolato)diboron (2.51 g; 9.9 mmol), potassium acetate (2.65 g; 27 mmol) and 1,1'-bis (diphenylphosphino)ferrocene-dichloropalladium(II) (PdCl$_2$(dppf)) (936 mg; 0.81 mmol) are suspended in dimethoxyethane (90 ml; dried over a molecular sieve), and four times the suspension is evacuated with vigorous stirring to remove the oxygen ester and ventilated with argon. The mixture is then stirred at a bath temperature of 80° C. for 24 hours. After cooling to room temperature, dimethylformamide (170 ml), tetrakis-triphenylphosphine-palladium (936 mg; 0.81 mmol), 5-(3-benzyloxy-5-ethoxy-4-iodo-benzyl)-pyrimidine-2,4-diamine (3.42 g; 7.2 mmol) and a 2 M aqueous potassium phosphate solution (36 ml) are added to the reaction mixture. The reaction mixture is stirred for approx. 17 hours under argon at 90° C. (bath temperature), cooled to room temperature and filtered with suction and the filtrate is concentrated. Water (100 ml) is added to the residue obtained and the mixture is extracted with methylene chloride (150 ml). The organic phase is washed successively with water (100 ml and a saturated aqueous sodium chloride solution (100 ml), dried over magnesium sulphate, filtered with suction and concentrated. The residue is chromato-

89 graphed over silica gel (600 g) with methylene chloride/methanol/NH$_4$OH 19/1/0.05. 2.30 g (47%) 5-(6-benzyloxy-2-ethoxy-4'-methylamino-biphenyl-4-ylmethyl)-pyrimidine-2,4-diamine are obtained as a light-brown powder, which is employed directly in the next stage.

This product is dissolved in methanol (100 ml) and, after addition of a 1 N aqueous hydrochloric acid solution (12.8 ml), hydrogenated over Pd/C 10% (0.5 g). After approx. 1.5 hours, the catalyst is filtered off with suction and rinsed with methanol and the filtrate is concentrated. The residue is stirred with water (70 ml), after which the pH is adjusted to 9–10 by addition of NH$_4$OH conc. The suspension is filtered with suction and the residue is washed with water and dried under a high vacuum. 1.32 g (78%) 4-(2,4-diamino-pyrimidin-5-ylmethyl)-6-ethoxy-4'-methylamino-biphenyl-2-ol are obtained as a grey powder.

MS (ISP): 366.3 (M+H)$^+$

EXAMPLE 27

Analogously to example 19, the compounds of the formula IX, equation 2, are prepared from the corresponding compounds of the formula VI.

(27a) Dimethylsulphamic acid 4'-amino-4-(2,4-diamino-pyrimidin-5-ylmethyl)-6-ethoxy-3'-methyl-biphenyl-2-yl ester Starting from 4'-amino-4-(2,4-diamino-pyrimidin-5-ylmethyl)-6-ethoxy-3'-methyl-biphenyl-2-ol (182 mg; 0.5 mmol), 140 mg (55%) dimethylsulphamic acid 4'-amino-4-(2,4-diamino-pyrimidin-5-ylmethyl)-6-ethoxy-3'-methyl-biphenyl-2-yl ester are obtained as a colourless powder by reaction with N,N-dimethylsulphamoyl chloride (0.065 ml; 0.6 mmol).

MS (ISP): 473.3 (M+H)$^+$

(27b) N-Ethyl-N-methyl-sulphamic acid 4'-amino-4-(2,4-diamino-vyrimidin-5-ylmethyl)-6-ethoxy-3'-methyl-biphenyl-2-yl ester Starting from 4'-amino-4-(2,4-diamino-pyrimidin-5-ylmethyl)-6-ethoxy-3'-methyl-biphenyl-2-ol (182 mg; 0.5 mmol), 122 mg (47%) N-ethyl-N-methyl-sulphamic acid 4'-amino-4-(2,4-diamino-pyrimidin-5-ylmethyl)-6-ethoxy-3'-methyl-biphenyl-2-yl ester are obtained as a colourless powder by reaction with N-ethyl-N-methylsulphamoyl chloride (95 mg; 0.6 mmol).

MS (ISP): 487.3 (M+H)$^+$

(27c) N-Cyclopropyl-N-methyl-sulphamic acid 4'-amino-4-(2,4-diamino-pyrimidin-5-ylmethyl)-6-ethoxy-3'-methyl-biphenyl-2-yl ester Starting from 4'-amino-4-(2,4-diazmino-pyrimidin-5-ylmethyl)-6-ethoxy-3'-methyl-biphenyl-2-ol (182 mg; 0.5 mmol), 145 mg (55%) N-cyclopropyl-N-methyl-sulphamic acid 4'-amino-4-(2,4-diamino-pyrimidin-5-ylmethyl)-6-ethoxy-3'-methyl-biphenyl-2-yl ester are obtained as a light-yellow powder by reaction with N-cyclopropyl-N-methylsulphamoyl chloride (101 mg; 0.6 mmol).

MS (ISP): 499.3 (M+H)$^+$

The N-cyclopropyl-N-methylsulphamoyl chloride employed is prepared as described in example 19g.

The above starting compound 4'-amino-4-(2,4-diamino-pyrimidin-5-ylmethyl)-6-ethoxy-3'-methyl-biphenyl-2-ol is prepared as shown in equation 2, ((X)→(XI)→(VI)), i.e. analogously to example 4a (Suzuki coupling with in situ

90 generation of R$^2$—B(OH)$_2$)) and by subsequent splitting off of the methoxymethyl protective group.

N-(4-Bromo-2-methyl-phenyl)-2,2,2-trifluoro-acetamide (described in example 4f) (4.9 g; 17.5 mmol), bis (pinacolato)diboron (6.66 g; 26.25 mmol), potassium acetate (5.15 g; 52.5 mmol) and bis(triphenylphosphine)palladium (II) dichloride (PdCl$_2$(PPh$_3$)$_2$) (737 mg; 1.05 mmol) are suspended in dioxane (175 ml; dried over a molecular sieve), and four times the suspension is evacuated and ventilated with argon, with vigorous stirring. The mixture is then stirred at a bath temperature of 85° C. for 4 hours. After cooling to room temperature, the reaction mixture is concentrated and dimethoxyethane (10 ml), tetrakis-triphenylphosphine-palladium (1.21 g; 1.05 mmol), 5-(3-ethoxy-4-iodo-5-methoxymethoxy-benzyl)-pyrimidine-2,4-diamine (4.51 g; 10.5 mmol) and a 2 M aqueous sodium carbonate solution (70 ml) are added. The reaction mixture is stirred for approx. 25 hours under argon at 85° C. (bath temperature), cooled to room temperature and filtered with suction and the filtrate is concentrated. The residue obtained is dissolved in ethanol (210 ml), a 1 N aqueous sodium hydroxide solution is added and the mixture stirred is for 4½ hours in an oil bath of 50° C. The mixture is poured on to ice-water and extracted twice with ethyl acetate. The organic phases are washed with a saturated aqueous sodium chloride solution, dried over magnesium sulphate, filtered with suction and concentrated. The residue is chromatographed over silica gel (810 g) with methylene chloride/methanol/NH$_4$OH 19/1/0.05. The red powder obtained (2.6 g) is suspended in methanol (100 ml), a 4.5 N aqueous hydrochloric acid (30 ml; 137 mmol) is added and the mixture is stirred for 45 minutes in an oil bath at 60° C. The methanol is evaporated, the residue is dissolved in water (200 ml) and the pH is adjusted to approx. 10 with NH$_4$OH conc., while stirring. After stirring for 30 minutes at room temperature, the suspension is filtered with suction and the residue is washed with water and dried under a high vacuum. 2.20 g (33%) 4'-amino-4-(2,4-diamino-pyrimidin-5-ylmethyl)-6-ethoxy-3'-methyl-biphenyl-2-ol are obtained as a light-red powder.

MS (ISP): 366.3 (M+H)$^+$

This compound can also be prepared as described in example 11.

EXAMPLE 28

Analogously to example 19, the compounds of the formula IX, equation 2, are repared from the corresponding compounds of the formula VI.

(28a) Dimethylsullhamic acid 4'-amino-4-(2,4-diamino-pyrimidin-5-ylmethyl)-6-ethoxy-3'-fluoro-biphenyl-2-yl ester Starting from 4'-amino-4-(2,4-diamino-pyrimidin-5-ylmethyl)-6-ethoxy-3'-fluoro-biphenyl-2-ol (185 mg; 0.5 mmol), 145 mg (59%) dimethylsulphamic acid 4'-amino-4-(2,4-diamino-pyrimidin-5-ylmethyl)-6-ethoxy-3'-fluoro-biphenyl-2-yl ester are obtained as a colourless powder by reaction with N,N-dimethylsulphamoyl chloride (0.065 ml; 0.6 mmol).

MS (ISP): 477.3 (M+H)$^+$

(28b) N-Ethyl-N-methyl-sulphamic acid 4'-amino-4-(2,4-diamino-pyrimidin-5-ylmethyl)-6-ethoxy-3'-fluoro-biphenyl-2-yl ester Starting from 4'-amino-4-(2,4-diamino-pyrimidin-5-ylmethyl)-6-ethoxy-3'-fluoro-biphenyl-2-ol (185 mg; 0.5 mmol), 139 mg (56%) N-ethyl-N-methyl-sulphamic acid 4'-amino-4-(2,4-diamino-pyriridin-5-ylmethyl)-6ethoxy-3'-fluoro-biphenyl-2-yl ester are obtained as a light-yellow powder by reaction with N-ethyl-N-methylsulphamoyl chloride (95 mg; 0.6 mmol).

MS (ISP): 491.2 (M+H)+

(28c) N-Cyclopropyl-N-methyl-sulphamic acid 4'-amino-4-(2,4-diamino-pvrimidin-5-ylmethyl)-6-ethoxy-3'-fluoro-biphenyl-2-yl ester Starting from 4'-amino-4-(2,4-diamino-pyrimidin-5-ylmethyl)-6-ethoxy-3'-fluoro-biphenyl-2-ol (185 mg; 0.5 mmol), 126 mg (47%) N-cyclopropyl-N-methyl-sulphamic acid 4'-amino-4-(2,4-diamino-pyrimidin-5-ylmethyl)-6-ethoxy-3'-fluoro-biphenyl-2-yl ester are obtained as a colourless powder by reaction with N-cyclopropyl-N-methylsulphamoyl chloride (102 mg; 0.6 mmol).

MS (ISP): 503.3 (M+H)+

The N-cyclopropyl-N-methylsulphamoyl chloride employed is prepared as described in example 19g.

The above starting compound 4'-amino-4-(2,4-diamino-pyrimidin-5-ylmethyl)-6-ethoxy-3'-fluoro-biphenyl-2-ol is prepared analogously to 4'-amino-4-(2,4-diamino-pyrimidin-5-ylmethyl)-6ethoxy-3'-methyl-biphenyl-2-ol (precursor in example 27), cf. equation 2, (X)→(XI)→(VI)

Starting from 5-(3-ethoxy-4-iodo-5-methoxymethoxybenzyl)-pyrimidine-2,4-diamine (4.51 g; 10.5 mmol) and N-(4-bromo-2-fluoro-phenyl)-2,2,2-trifluoro-acetamide (described in example 4r) (5.0 g; 26.25 mmol), 2.0 g (29%) 4'-amino-4-(2,4-diamino-pyrimidin-5-ylmethyl)-6ethoxy-3'-fluoro-biphenyl-2-ol are obtained as a red powder after Suzuki coupling (in situ generation of $R^2$—$B(OH)_2$)) and splitting off of the protective group under acid conditions.

MS (ISP): 370.3 (M+H)+

EXAMPLE 29

Analogously to example 19, the compounds of the formula IX, equation 2, are prepared from the corresponding compounds of the formula VI:

(29a) N-Cyclopropyl-N-methyl-sulphamic acid 3'-amino-4-(2,4-diamino-pyrimidin-5-ylmethyl)-6-ethoxy-5'-fluoro-biphenyl-2-yl ester Starting from 3'-amino-4-(2,4-diamino-pyrimidin-5-ylmethyl)-6-ethoxy-5'-fluoro-biphenyl-2-ol (150 mg; 0.39 mmol), 119 mg (59%) N-cyclopropyl-N-methyl-sulphamic acid 3'-amino-4-(2,4-diamino-pyrimidin-5-ylmethyl)-6-ethoxy-5'-fluoro-biphenyl-2-yl ester are obtained as a light-yellow powder by reaction with N-cyclopropyl-N-methylsulphamoyl chloride (80 mg; 0.47 mmol).

MS (ISP): 503.2 (M+H)+

The N-cyclopropyl-N-methylsulphamoyl chloride employed is prepared as described in example 19g.

(29b) Dimethylsulphamic acid 3'-amino-4-(2,4-diamino-pyrimidin-5-ylmethyl)-6-ethoxy-5'-fluoro-biphenyl-2-yl ester Starting from 3'-amino-4-(2,4-diamino-pyrimidin-5-ylmethyl)-6-ethoxy-5'-fluoro-biphenyl-2-ol (150 mg; 0.39 mmol), 120 mg (62%) dimethylsulphamic acid 3'-amino-4-(2,4-diamino-pyrimidin-5-ylmethyl)-6-ethoxy-5'-fluoro-biphenyl-2-yl ester are obtained as a colourless powder by reaction with N,N-dimethylsulphamic chloride (0.51 ml; 0.47 mmol).

MS (ISP): 477.2 (M+H)+

(29c) N-Ethyl-N-methyl-sulphamic acid 3'-amino-4-(2,4-diamino-pyrimidin-5-ylmethyl)-6-ethoxy-5'-fluoro-biphenyl-2-yl ester Starting from 3'-amino-4-(2,4-diamino-pyrimidin-5-ylmethyl)-6-ethoxy-5'-fluoro-biphenyl-2-ol (150 mg; 0.39 mmol), 50 mg (24%) N-ethyl-N-methyl-sulphamic acid 3'-amino-4-(2,4-diamino-pyrimidin-5-ylmethyl)-6-ethoxy-5'-fluoro-biphenyl-2-yl ester are obtained as a colourless powder by reaction with N-ethyl-N-methylsulphamoyl chloride (73 mg; 0.47 mmol).

MS (ISP): 491.2 (M+H)+

The above starting compound 3'-amino-4-(2,4-diamino-pyrimidin-5-ylmethyl)-6-ethoxy-5'-fluoro-biphenyl-2-ol is prepared analogously to 4'-amino-4-(2,4-diamino-pyrimidin-5-ylmethyl)-6-ethoxy-3'-methyl-biphenyl-2-ol (precursor in example 27), cf. equation 2, (X)→(XI)→(VI)

Starting from 5-(3-ethoxy-4-iodo-5-methoxymethoxy-benzyl)-pyrimidine-2,4-diamine (1.18 g; 2.76 mmol) and N-(5-iodo-3-fluoro-phenyl)-2,2,2-trifluoroacetamide (described in example 4t) (1.53 g; 4.6 mmol), 0.554 g (42%) 3'-amino-4-(2,4-diamino-pyrimidin-5-Amethyl)-6-ethoxy-5'-fluoro-biphenyl-2-ol is obtained as a light-brown powder after Suzuki coupling (In situ generation of $R^2$—$B(OH)_2$)) and splitting off of the protective group under acid conditions.

MS (ISP): 370.3 (M+H)+

EXAMPLE 30

Analogously to example 19, the compounds of the formula IX, equation 2, are prepared from the corresponding compounds of the formula VI.

(30a) Dimethylsulphamic acid 3'-amino-4-(2,4-diamino-pyrimidin-5-ylmethyl)-6-ethoxy-4'-morpholin-4-ylmethyl-biphenyl-2-yl ester Starting from 3'-amino-4-(2,4-diamino-pyrimidin-5-ylmethyl)-6-ethoxy-4'-morpholin-4-ylmethyl-biphenyl-2-ol (185 mg; 0.4 mmol), 113 mg (50%) dimethylsulphamic acid 3'-amino-4-(2,4-diamino-pyrimidin-5-ylmethyl)-6-ethoxy-4'-morpholin-4-ylmethyl-biphenyl-2-yl ester are obtained as a colourless powder by reaction with N,N-dimethylsulphamoyl chloride (0.52 ml; 0.48 mmol).

MS (ISP): 558.3 (M+H)+

(30b) N-Cyclopropyl-N-methyl-sulphamic acid 3'-amino-4-(2,4-diamino-pyrimidin-5-ylmethyl)-6-ethoxy-4'-morpholin-4-ylmethyl-biphenyl-2-yl ester Starting from 3'-amino-4-(2,4-diamino-pyrimidin-5-ylmethyl)-6-ethoxy-4'-morpholin-4-ylmethyl-biphenyl-2-ol (185 mg; 0.4 mmol), 96 mg (40%) N-cyclopropyl-N-methyl-sulphamic acid 3'-amino-4-(2,4-diamino-pyrimidin-5-ylmethyl)-6-ethoxy-4'-morpholin-4-ylmethyl-biphenyl-2-yl ester are obtained as a light-yellow powder by reaction with N-cyclopropyl-N-methylsulphamoyl chloride (81 mg; 0.48 mmol).

MS (ISP): 584.2 (M+H)+

The N-cyclopropyl-N-methylsulphamoyl chloride employed is prepared as described in example 19g.

(30c) N-Ethyl-N-methyl-sulphamic acid 3'-amino-4-(2,4-diamino-pyrimidin-5-ylmethyl)-6-ethoxy-4'-morpholin-4-ylmethyl-biphenyl-2-yl ester Starting from 3'-amino-4-(2,4-diamino-pyrimidin-5-ylmethyl)-6-ethoxy-4'-morpholin-4-ylmethyl-biphenyl-2-ol (278 mg; 0.6 mmol), 210 mg (61%) N-ethyl-N-methyl-sulphamic acid 3'-amino-4-(2,4-diamino-pyrimidin-5-ylmethyl)-6-ethoxy-4'-morpholin-4-ylmethyl-biphenyl-2-yl ester are obtained as a light-yelow powder by reaction with N-ethyl-N-methylsulphamoyl chloride (113 mg; 0.72 mmol).

MS (ISP): 572.2 (M+H)$^+$

The above starting compound 3'-amino-4-(2,4-diamino-pyrimidin-5-ylmethyl)-6-ethoxy-4'-morpholin-4-ylmethyl-biphenyl-2-ol is prepared analogously to 4'-amino-4-(2,4-diamino-pyrimidin-5-ylmethyl)-6-ethoxy-3'-methyl-biphenyl-2-ol (precursor in example 27), cf. equation 2, (X)→(XI)→(VI)

Starting from 5-(3-ethoxy-4-iodo-5-methoxymethoxy-benzyl)-pyrimidine-2,4-diamine (2.11 g; 4.9 mmol) and N-(5-bromo-2-morpholin-4-ylmethyl-phenyl)-2,2,2-trifluoro-acetamide (described in example 4j) (3.0 g; 8.17 mmol), 1.36 g (36%) 3'-amino-4-(2,4-diamino-pyrimidin-5-ylmethyl)-6-ethoxy-4'-morpholin-4-ylmethyl-biphenyi-2-ol are obtained as a beige powder after Suzuki coupling (in situ generation of R$^2$—B(OH)$_2$)) and splitting off of the protective group under acid conditions.

MS (ISP): 451.4 (M+H)$^+$

EXAMPLE 31

Analogously to example 19, the compounds of the formula IX, equation 2, are prepared from the corresponding compounds of the formula VI.

(31a) Dimethylsulphamic acid 3'-amino-4-(2,4-diamino-pyrimidin-5-ylmethyl)-6-ethoxy-4'-methyl-biphenyl-2-yl ester Starting from 3'-amino-4-(2,4-diamino-pyrimidin-5-ylmethyl)-6-ethoxy-4'-methyl-biphenyl-2-ol (183 mg; 0.5 mmol), 128 mg (52%) dimethylsulphamic acid 3'-amino-4-(2,4-diamino-pyrimidin-5-ylmethyl)-6-ethoxy-4'-methyl-biphenyl-2-yl ester are obtained as a colourless powder by reaction with N,N-dimethylsulphamoyl chloride (0.064 ml; 0.6 mmol).

MS (ISP): 473.3 (M+H)$^{+NMR}$ $^1$H: (400 MHz, δ, TMS, DMSO): 1.17 (t; J=6.8; 3H); 2.06 (s; 3H); 2.46 (s; 6H); 3.64 (s; 2H); 3.95 (q; J=6.8; 2H); 4.74 (s; 2H); 5.69 (s; 2H); 6.11 (s; 2H); 6.37 (d; J=7.2; 1H); 6.52 (s; 1H); 6.84 (s; 1H); 6.90 (m; 2H); 7.57 (s; 1H).

(31b) N-Ethyl-N-methyl-sulphamic acid 3'-amino-4-(2,4-diamino-pyrimidin-5-ylmethyl)-6-ethoxy-4'-methyl-biphenyl-2-yl ester Starting from 3'-amino-4-(2,4-diamino-pyrimidin-5-ylmethyl)-6-ethoxy-4'-methyl-biphenyl-2-ol (183 mg; 0.5 mmol), 149 mg (59%) N-ethyl-N-methyl-sulphamic acid 3'-amino-4-(2,4-diamino-pyrimitin-5-ylmethyl)-6-ethoxy-4'-methyl-biphenyl-2-yl ester are obtained as a colourless powder by reaction with N-ethyl-N-methylsulphamoyl chloride (95 mg; 0.6 mmol).

MS (ISP): 487.3 (M+H)$^+$

The above starting compound 3'-amino-4-(2,4-diamino-pyrimidin-5-ylmethyl)-6-ethoxy-4'-methyl-biphenyl-2-ol is prepared analogously to 4'-amino-4-(2,4-diamino-pyrimidin-5-ylmethyl)-6-ethoxy-3'-methyl-biphenyl-2-ol (precursor in example 27), cf. equation 2, (X)→(XI) (VI)

Starting from 5-(3-ethoxy-4-iodo-5-methoxymethoxy-benzyl)-pyrimidine-2,4-diamine (2.11 g; 4,9 mmol) and N-(5-bromo-2-methyl-phenyl)-2,2,2-trifluoro-acetamide (prepared from 5-bromo-2-methyl-aniline analogously to example 41) (2.3 g; 8.17 mmol), 0.963 g (30%) 3'-amino-4-(2,4-diamino-pyrimidin-5-ylmethyl)-6-ethoxy-4'-methyl-biphenyl-2-ol is obtained as a beige powder after Suzuki coupling (in situ generation of R$^2$—B(OH)$_2$) and splitting off of the protective group under acid conditions.

MS (ISP): 366.2 (M+H)$^+$

EXAMPLE 32

Analogously to example 4, the compounds of the formula VIII, equation 2, are prepared from the corresponding compounds of the formula XIII by method A, i.e. Suzuki coupling with R$^2$—B(OH)$_2$.

(32a) Pronane-1-sulophonic acid 3'-amino-4-(2,4-diamino-pyrimidin-5-ylmethyl)-6-ethoxy-4'-morpholinemethyl-4-ylmethyl-biphenyl-2-yl ester Starting from N-(5-bromo-2-morpholinemethyl-4-ylmethyl-phenyl)-2,2,2-trifluoro-acetamide (400 mg; 1.09 mmol), bis(pinacolato)diboron (414 mg; 1.63 mmol), potassium acetate (321 mg; 3.27 mmol) and 1,1'-bis(diphenylphosphino)ferrocene-dichloro-palladium(II) (PdCl$_2$(dppf)) (48 mg; 0.06 mmol) in 20 ml dimethylformamide, and then propane-1-sulphonic acid 5-(2,4-diamino-pyrimidin-5-ylmethyl)-3-ethoxy-2-iodo-phenyl ester (375 mg; 0.76 mmol), tetrakis-triphenylphosphine-palladium (76 mg; 0.07 mmol), aqueous 2 M potassium phosphate solution (3.3 ml; 6.6 mmol) and 20 ml dimethylformamide, 97 mg (23%) propane-1-sulphonic acid 3'-amino-4-(2,4-diamino-pyrimidin-5-ylmethyl)-6-ethoxy-4'-morpholinemethyl-4-ylmethyl-biphenyl-2-yl ester are obtained as a brown foam.

MS (ISP): 557.2 (M+H)$^+$ (32b) Propane-1-sulphonic acid 4'-amino-4-(2,4-diamino-pyrimidin-5-)lmethyl)-6-ethoxy-3'-methyl-4-ylmethyl-biphenyl-2-yl ester Starting from N-(4-bromo-2-methyl)-2,2,2-trifluoro-acetamide (516 mg; 1.83 mmol), bis(pinacolato)diboron (697 mg; 2.74 mmol), potassium acetate (539 mg; 5.5 mmol) and 1,1'-bis(diphenylphosphino)ferrocene-dichloro-palladium(II) (PdCl$_2$(dppf)) (80 mg; 0.11 mmol) in dimethylformamide, and then propane-1-sulphonic acid 5-(2,4-diamino-pyrimidin-5-ylmethyl)-3-ethoxy-2-iodo-phenyl ester (613 mg; 1.28 mmol), tetrakis-triphenylphosphine-palladium (127 mg; 0.11 mmol), aqueous 2 M potassium phosphate solution (5.5 ml; 11 mmol) and 20 ml dimethylformamide, 106 mg (17%) propane-1-sulphonic acid 4'-amino-4-(2,4-diamino-pyrimidin-5-ylmethyl)-6-ethoxy-3'-methyl-4-ylmethyl-biphenyl-2-yl ester are obtained as a brown foam.

MS (ISP): 472.2 (M+H)$^+$ (32c) Propane-1-sulphonic acid 3'-amino-4-(2,4-diamino-pyrimidin-5-ylmethyl-6-ethoxy-4'-fluoro-4-ylmethyl-biphenyl-2-yl ester Starting from N-(3-bromo-4-fluoro-phenyl)-2,2,2-trifluoroacetamide (350 mg; 1.22 mmol), bis (pinacolato)diboron (466 mg; 1.84 mmol), potassium acetate (360 mg; 3.67 mmol) and 1,1'-bis(diphenylphosphino)ferrocene-dichloro-palladium(II) (PdCl$_2$(dppf)) (54 mg; 0.07 mmol) in 20 ml dimethylformamide, and then propane-1-sulphonic acid 5-(2,4-diamino-pyrimidin-5-ylmethyl)-3-ethoxy-2-iodo-phenyl ester (402 mg; 0.82 mmol), tetrakis-triphenylphosphine-palladium (85 mg; 0.07 mmol), aqueous 2 M potassium phosphate solution (3.7 ml; 7.4 mmol) and 20 ml dimethylformamide, 92 mg (24%) propane-1-sulphonic acid 3'-amino-4-(2,4-diamino-pyrimidin-5-ylmethyl)-6-ethoxy-4'-fluoro-4-ylmethyl-biphenyl-2-yl ester are obtained as a brown solid.

MS (ISP): 476.2 (M+H)$^+$ (32d) Propane-1-sulphonic acid 3'-amino-4-(2,4-diamino-pyrimidin-5-ylmethyl)-6-ethoxy-4'-methoxy-4-ylmethyl-biphenyl-2-yl ester N-(3-Bromo-6-methoxy-phenyl)-2,2,2-trifluoroacetamide (894 mg; 3 mmol), bis(pinacolato)diboron (1,143 mg; 4.5 mmol), potassium acetate (883 mg; 9 mmol) and 1,1'-bis(diphenylphosphino)-dichloro-palladium(II) (126 mg; 0.18 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-1-sulphonic acid 5-(2,4-diamino-pyrimidin-5-ylmethyl)-3-ethoxy-2-iodo-phenyl ester (370 mg; 0.75 mmol), tetrakis-triphenylphosphine-palladium (52 mg; 0.05 mmol) and aqueous 2 M sodium carbonate solution (5.6 ml; 11.2 mmol) in a 4/1 dimethoxyethane/ethanol mixture (15 ml). 300 mg (82%) propane-1-sulphonic acid 3'-amino-4-(2,4-diamino-pyrimidin-5-ylmethyl)-6-ethoxy-4'-methoxy-4-ylmethyl-biphenyl-2-yl ester are obtained as a brown foam.

MS (ISP): 488.3 (M+H)$^+$ (32e) Propane-1-sulphonic acid 4'-amino-4-(2,4-diamino-pyrimidin-5-ylmethyl)-6-ethoxy-3'-fluoro-4-ylmethyl-biphenyl-2-yl ester N-(4-Bromo-3-fluoro-phenyl)-2,2,2-trifluoroacetamide (858 mg; 3 mmol), bis-(pinacolato)diboron (1,143 mg; 4.5 mmol), potassium acetate (883 mg; 9 mmol) and (diphenylphosphino)-dichloro-palladium(II) (126 mg; 0.18 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-1-sulphonic acid 5-(2,4-diamino-pyrimidin-5-ylmethyl)-3-ethoxy-2-iodo-phenyl ester (332 mg; 0.67 mmol), tetrakis-triphenylphosphine-palladium (47 mg; 0.04 mmol) and aqueous 2 M sodium carbonate solution (5 ml; 10 mmol) in a 4/1 dimethoxyethane/ethanol mixture (15 ml). 174 mg (54%) propane-1-sulphonic acid 4'-amino-4-(2,4-diamino-pyrimidin-5-ylmethyl)-6-ethoxy-3'-fluoro-4-ylmethyl-biphenyl-2-yl ester are obtained as a brown foam.

MS (ISP): 476.2 (M+H)$^+$ (32f) Propane-1-sulphonic acid 3'-amino-4-(2,4-diamino-pyrimidin-5-ylmethyl)-6-ethoxy-5'-fluoro-4-ylmethyl-biphenyl-2-yl ester N-(5-Iodo-3-fluoro-phenyl)-2,2,2-trifluoroacetamide (prepared as in example 4t) (999 mg; 3 mmol), bis (pinacolato)diboron (1,143 mg; 4.5 mmol), potassium acetate (883 mg; 9 mmol) and (diphenylphosphino)-dichloro-palladium(II) (126 mg; 0.18 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-1-sulphonic acid 5-(2,4-diamino-pyrimidin-5-ylmethyl)-3-ethoxy-2-iodo-phenyl ester (332 mg; 0.67 mmol), tetrakis-triphenylphosphine-palladium (47 mg; 0,04 mmol) and aqueous 2 M sodium carbonate solution (5 ml; 10 mmol) in a 4/1 dimethoxyethanelethanol mixture (15 ml). 202 mg (63%) propane-1-sulphonic acid 3'-amino-4-(2,4-diamino-pyrimidin-5-ylmethyl)-6-ethoxy-5'-fluoro-4-ylmethyl-biphenyl-2-yl ester are obtained as a light-yellow foam.

MS (ISP): 476.2 (M+H)$^+$ (32g) Propane-1-sulphonic acid 3'-amino-4-(2,4-diamino-pyrimidin-5-ylmethyl)-6-ethoxy-4'-dimethylaminomethyl-4-ylmethyl-biphenyl-2-yl ester N-(5-Bromo-2-dimethylaminomethyl-4-ylmethyl-phenyl)-2,2,2-trifluoro-acetamide (1.16 g; 3.57 mmol), bis(pinacolato)diboron (1,360 mg; 5.35 mmol), potassium acetate (1,050 mg; 10.7 mmol) and (diphenylphosphino)-dichloro-palladium(II) (150 mg; 0.21 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-1-sulphonic acid 5-(2,4-diamino-pyrimidin-5-ylmethyl)-3-ethoxy-2-iodo-phenyl ester (395 mg, 0.80 mmol), tetrakis-triphenylphosphine-palladium (56 mg; 0,05 mmol) and aqueous 2 M sodium carbonate solution (6 ml; 12 mmol) in a 4/1 dimethoxyethane/ethanol mixture (15 ml). 166 mg (40%) propane-1-sulphonic acid 3'-amino-4-(2,4-diamino-pyrimidin-5-ylmethyl)-6-ethoxy-5'-fluoro-4-ylmethyl-biphenyl-2-yl ester are obtained as an orange foam.

MS (ISP): 515.3 (M+H)$^+$

The Above Starting Compound propane-1-sulphonic acid 5-(2,4-diamino-pyrimidin-5-ylmethyl)-3-ethoxy-2-iodo-phenyl ester is Prepared as Follows (Stages a–b), cf. Equation 2, (X)→(XII)→(XIII)

Stage a) 5-(3-Ethoxy-5-hydroxy-4-iodo-benzyl)-pyrimidine-2,4-diamine 5-(3-Ethoxy-4-iodo-5-methoxymethoxy-benzyl)-pyrimidine-2,4-diamine (20 g; 46.48 mmol) is suspended in methanol (900 ml) and the suspension is heated to 50° C., while stirring and gassing with argon. 4.5 M hydrochloric acid in methanol (62 ml; 279 mmol) is added to the suspension, whereupon a solution forms. After 30 minutes the reaction mixture is cooled to 5° C. with an ice bath, the pH is adjusted to 10 with NH$_4$OH conc. and the volume is reduced to approx. 1/10 on a rolling evaporator. The suspension obtained is cooled in an ice bath, water (350 ml) is added and the mixture is stirred for 30 minutes. The suspension is then filtered with suction and the residue is washed with water and dried under a high vacuum.

Yield: 16.74 g (93%) 5-(3-ethoxy-5-hydroxy-4-iodo-benzyl)-pyrimidine-2,4-diamine obtained as colourless crystals. MS (ISP): 387.1 (M+H)$^+$ Stage b) Propane-1-sulphonic acid 5-(2,4-diamino-pyrimidin-5-ylmethyl)-3-ethoxy-2-iodo-phenyl ester 5-(3-Ethoxy-5-hydroxy-4-iodo-benzyl)-pyrimidine-2,4-diamine (907 mg; 2.35 mmol) is dissolved in dimethylformamide (25 ml), potassium tert-butylate (395 mg; 3.52 mmol) is added, and n-propanesulphonyl chloride (0.395 ml; 3.52 mmol) is added at 0° C. The mixture is then stirred for one hour at room temperature. The reaction mixture is evaporated and the residue is chromatographed over silica gel with methylene chloride/methanol (19/1) and 0.5% ammonia. The pure fractions are combined and the solvent is evaporated off.

Yield: 813 mg (49%) propane-1-sulphonic acid 5-(2,4-diamino-pyrimidin-5-ylmethyl)-3-ethoxy-2-iodo-phenyl ester as a yellowish wax MS (ISP): 493.1 $(M+H)^+$

EXAMPLE 33

Analogously to example 4), compounds of the formula VIII, equation 2, are prepared from the corresponding compounds of the formula III.

(33a) Propane-2-sulphonic acid 3'-amino-4-(2,4-diamino-pyrimidin-5-ylmethyl)-6-ethoxy-4'-methoxy-4-ylmethyl-biphenyl-2-yl ester N-(3-Bromo-6-methoxy-phenyl)-2,2,2-trifluoroacetamide (894 mg; 3 mmol), bis(pinacolato) diboron (1,143 mg; 4,5 mmol), potassium acetate (883 mg; 9 mmol) and 1,1'-bis(diphenylphosphino)-dichloro-palladium(II) (126 mg; 0.18 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-2-sulphonic acid 5-(2,4-diamino-pyrimidin-5-ylmethyl)-3-ethoxy-2-iodo-phenyl ester (370 mg; 0.75 mmol), tetrakis-triphenylphosphine-palladium (52 mg; 0.05 mmol), aqueous 2 M sodium carbonate solution (5.6 ml; 11.2 mmol) in a 4/1 dimethoxyethane/ethanol mixture (15 ml). 59 mg (16%) propane-2-sulphonic acid 3'-amino-4-(2,4-diamino-pyrimidin-5-ylmethyl)-6-ethoxy-4'-methoxy-4-ylmethyl-biphenyl-2-yl ester are obtained as a light-green foam. MS (ISP): 488.3 $(M+H)^+$

(33b) Propane-2-sulphonic acid 4'-amino-4-(2,4-diamino-pyrimidin-5-ylmethyl)-6-ethoxy-3'-fluoro-4-ylmethyl-biphenyl-2-yl ester Starting from [sic] N-(4-bromo-3-fluoro-phenyl)-2,2,2-trifluoroacetamide (858 mg; 3 mmol), bis(pinacolato) diboron (1,143 mg; 4.5 mmol), potassium acetate (883 mg; 9 mmol) and (diphenylphosphino)-dichloro-palladium(II) (126 mg; 0.18 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-2-sulphonic acid 5-(2,4-diamino-pyrimidin-5-ylmethyl)-3-ethoxy-2-iodo-phenyl ester (406 mg; 0.82 mmol), tetrakis-triphenylphosphine-palladium (58 mg; 0.05 mmol), aqueous 2 M sodium carbonate solution (6.2 ml; 12.4 mmol) in a 4/1 dimethoxyethanelethanol mixture (15 ml). 195 mg (56%) propane-2-sulphonic acid 4'-amino-4-(2,4-diamino-pyrimidin-5-ylmethyl)-6-ethoxy-3'-fluoro-4-ylmethyl-biphenyl-2-yl ester are obtained as white crystals.

MS (ISP): 476.2 $(M+H)^+$

(33c) Propane-2-sulphonic acid 3'-amino-4-(2,4-diamino-pyrimidin-5-ylmethyl)-6-ethoxy-5'-fluoro-4-ylmethyl-biphenyl-2-yl ester Starting from [sic] N-(5-iodo-3-fluoro-phenyl)-2,2,2-trifuoroacetamide (prepared as in example 4t) (999 mg; 3 mmol), bis(pinacolato)diboron (1,143 mg; 4.5 mmol), potassium acetate (883 mg; 9 mmol) and (diphenylphosphino)-dichloro-palladium(II) (126 mg; 0.18 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-2-sulphonic acid 5-(2,4-diamino-pyrimidin-5-ylmethyl)-3-ethoxy-2-iodo-phenyl ester (406 mg; 0.82 mmol), tetrakis-triphenylphosphine-palladium (58 mg; 0.05 mmol), aqueous 2 M sodium carbonate solution (6.2 ml; 12.4 mmol) in a 4/1 dimethoxyethane/ethanol mixture (15 ml). 197 mg (50%) propane-2-sulphonic acid 3'-amino-4-(2,4-diamino-pyrimidin-5-ylmethyl)-6-ethoxy-5'-fluoro-4-ylmethyl-biphenyl-2-yl ester are obtained as a white solid.

MS (ISP): 476.2 $(M+H)^+$

(33d) Propane-2-sulphonic acid 3'-amino-4-(2,4-diamino-pyrimidin-5-ylmethyl)-6-ethoxy-4'-morpholinemethyl-4-ylmethyl-biphenyl-2-yl ester N-(5-Bromo-2-morpholinemethyl-4-ylmethyl-phenyl)-2,2,2-trifluoro-acetamide (500 mg; 1.36 mmol), bis (pinacolato)diboron (519 mg; 2.04 mmol), potassium acetate (401 mg; 4.09 mmol) and (diphenylphospbino)-dichloro-palladium(II) (88 mg; 0.08 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with propane-2-sulphonic acid 5-(2,4-diamino-pyrimidin-5-yl)methyl)-3-ethoxy-2-iodo-phenyl ester (336 mg; 0.68 mmol), tetrakis-triphenylphosphine-palladium (94 mg; 0.08 mmol) and aqueous 2 M sodium carbonate solution (10 ml; 20 mmol) in a 4/1 dimethoxyethanelethanol mixture (15 ml), 104 mg (27%) propane-2-sulphonic acid 3'-amino-4-(2,4-diamino-pyrimidin-5-ylmethyl)-6-ethoxy-4'-morpholinemethyl-4-ylmethyl-biphenyl-2-yl ester are obtained as a brown foam.

MS (ISP): 557.3 $(M+H)^+$

(33e) Propane-2-sulphonic acid 4'-amino-4-(2,4-diamino-pyrimidin-5-ylmethyl)-6-ethoxy-3'-methyl-biphenyl-2-yl ester N-(4-Bromo-2-methyl)-2,2,2-trifluoro-acetamide (600 mg; 2.13 mmol), bis-(pinacolato)diboron (810 mg; 3.20 mmol), potassium acetate (626 mg; 6.38 mmol) and (diphenylphosphino)-dichioro-palladium(II) (89 mg; 0.13 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with propane-2-sulphonic acid 5-(2,4-diaminopyrimidin-5-ylmethyl)-3-ethoxy-2-iodo-phenyl ester (524 mg; 1.06 mmol), tetrakis-triphenylphosphine-palladium (147 mg; 0.13 mmol) and aqueous 2 M sodium carbonate solution (16 ml; 32 mmol) in a 4/1 dimethoxyethanelethanol mixture (15 ml), 229 mg (60%) propane-2-sulphonic acid 4'-amino-4-(2,4-diamino-pyrimidin-5-ylmethyl)-6-ethoxy-3'-methyl-biphenyl-2-yl ester are obtained as light-brown crystals.

MS (ISP): 472.3 (M+H)$^+$ NMR $^1$H: (250 MHz, δ, TMS, DMSO): 1.13 (d; J=6.8; 6H); 1.16 (t; J=6.9; 3H); ); 2.04 (s; 3H); 3.03 (Sept.; J=6.8, 1H); 3.63 (s; 2H); 3.94 (q; J=6.9; 2H); 4.88 (s(br); 2H); 5.72 (s(br); 2H); 6.15 (s(br); 2H); 6.60 (d; J=7.6; 1H); 6.78 (d; J=8.0; 1H); 6.81 (s; 1H); 6.84 (s; 1H); 6.90 (s; 1H); 7.57 (s; 1H).

(33f) Propane-2-sulphonic acid 3'-amino-4-(2,4-diamino-pyrimidin-5-ylmethyl)-6-ethoxy-4'-dimethylaminomethyl-biphenyl-2-yl ester N-(5-Bromo-2-dimethylaminomethyl-4-ylmethyl-phenyl)-2,2,2-trifluoro-acetamide (1.16 g; 3.57 mmol), bis(pinacolato)diboron (1,360 mg; 5.35 mmol), potassium acetate (1,050 mg; 10.7 mmol) and (diphenylphosphino)-dichloro-palladium(II) (150 mg; 0.21 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with propane-2-sulphonic acid 5-(2,4-diamino-pyrimidin-5-ylmethyl)-3-ethoxy-2-iodo-phenyl ester (483 mg; 0.98 mmol), tetrakis-triphenylphosphine-palladium (68 mg; 0.06 mmol) and aqueous 2 M sodium carbonate solution (7.4 ml; 14.8 mmol) in a 4/1 dimethoxyethanelethanol mixture (15 ml). 123 mg (24%) propane-2-sulphonic acid 3'-amino-4-(2,4-diamino-pyrimidin-5-ylmethyl)-6-ethoxy-4'-dimethylaminomethyl-biphenyl-2-yl ester are obtained as a white foam.

MS (ISP): 515.3 (M+H)$^+$

The following is prepared analogously to example 2a (Suzuki coupling with boron acid):

(33g) Propane-2-sulphonic acid 5-(2,4-diamino-pyrimidin-5-ylmethyl)-3-ethoxy-2-(6-methyl-pyridin-3-yl)-phenyl ester Starting from propane-2-sulphonic acid 5-(2,4-diamino-pyrimidin-5-ylmethyl)-3-ethoxy-2-iodo-phenyl ester (246 mg; 0.5 mmol) and 2-methylpyridinyl-5-boron acid (205 mg; 1.5 mmol), 146 mg (64%) propane-2-sulphonic acid 5-(2,4-diamino-pyrimidin-5-ylmethyl)-3-ethoxy-2-(6-methyl-pyridin-3-yl)-phenyl ester are obtained as a light-yellow powder.

MS (ISP): 458.5 (M+H)$^+$

The Above Starting Compound propane-2-sulphonic acid 5-(2,4-diamino-pyrimidin-5-ylmethyl)-3-ethoxy-2-iodo-phenyl ester is Prepared as Follows, cf. Equation 2, (XII) →(XIII)

5-(3-Ethoxy-5-hydroxy-4-iodo-benzyl)-pyrimidine-2,4-diamine (see example 32 stage a)) (5.9 g; 15.28 mmol) is dissolved in dimethylformamide (150 ml), and potassium tert-butylate (2.57 g; 22.92 mmol) is added. Propane-2-sulphonyl chloride (2.56 ml; 22.92 mmol) is added at 0° C. The mixture is then stirred for one hour at room temperature. The reaction mixture is evaporated and the residue is chromatographed over silica gel with methylene chloride/methanol (19/1) and 0.5% ammonia. The pure fractions are combined and the solvent is evaporated off.

Yield: 4.16 g (55%) propane-2-sulphonic acid 5-(2,4-diamino-pyrimidin-5-ylmethyl)-3-ethoxy-2-iodo-phenyl ester as an orange solid. MS (ISP): 493.1 (M+H)$^+$

EXAMPLE 34

Analogously to example 2a, the compound of the formula VIII, equation 2, is prepared from the corresponding compounds of the formula XIII.

(34a) Cyclopropanesulphonic acid 3'-amino-4-(2,4-diamino-pyrimidin-5-ylmethyl)-6-ethoxy-bilphenyl-2-yl ester Starting from cyclopropanesulphonic acid 5-(2,4-diamino-pyrimidin-5-ylmethyl)-3-ethoxy-2-iodo-phenyl ester (190 mg; 0.387 mmol) and 3-amino-phenylboron acid (87 mg; 0.564 mmol), 69 mg (39%) cyclopropanesulphonic acid 3'-amino-4-(2,4-diamino-pyrimidin-5-ylmethyl)-6-ethoxy-biphenyl-2-yl ester are obtained as a colourless powder.

MS (ISP): 456.5 (M+H)$^+$

The following are prepared analogously to example 4:

(34b) Cyclopropanesulphonic acid 4-(2,4-diamino-Ryrimidin-5-ylmethyl)-6-ethoxy-4'-methylamino-biphenyl-2-yl ester Starting from cyclopropanesulphonic acid 5-(2,4-diamino-pyrimidin-5-ylmethyl)-3-ethoxy-2-iodo-phenyl ester (450 mg; 0.920 mmol) and N-(4-bromo-phenyl)-2,2,2-trifluoro-N-methyl-acetamide (405 mg; 1.15 mmol) (first step in 11.5 ml dimethoxyethane instead of dimethylformamide), 114 mg (16%) cyclopropanesulphonic acid 4-(2,4-diamino-pyrimidin-5-ylmethyl)-6-ethoxy-4'-methylamino-biphenyl-2-yl ester are obtained as a colourless powder.

MS (ISP): 470.2 (M+H)$^+$ (34c) Cyclopropanesulphonic acid 3'-amino-4-(2,4-diamino-pyrimidin-5-ylmethyl)-6-ethoxy-5'-fluoro-biphenyl-2-yl ester Starting from cyclopropanesulphonic acid 5-(2,4-diamino-pyrimidin-5-ylmethyl)-3-ethoxy-2-iodo-phenyl ester (294 mg; 0.60 mmol) and N-(5-iodo-3-fluoro-phenyl)-2,2,2-trifluoroacetamide (preparation described in example 4t) (333 mg; 1.0 mmol) (first step in 12 ml dioxane instead of dimethylformarmide with bis-triphenylphosphine-palladium dichloride (56 mg; 0.08 mmol) and second step in dimethoxyethane (8 ml) and ethanol (2 ml) with tetrakis-triphenylphosphine-palladium (69 mg; 0.06 mmol)), 147 mg (30%) cyclopropanesulphonic acid 3'-amino-4-(2,4-diamino-pyrimidin-5-ylmethyl)-6-ethoxy-5'-fluoro-biphenyl-2-yl ester are obtained as a colourless powder.

MS (ISP): 474.2 (M+H)$^+$ (34d) Cyclopropanesulphonic acid 4'-amino-4-(2,4-diamino-pyrimidin-5-ylmethyl)-6-ethoxy-3'-methyl-biphenyl-2-yl ester Starting from cyclopropanesulphonic acid 5-(2,4-diamino-pyrimidin-5-ylmethyl)-3-ethoxy-2-iodo-phenyl ester (294 mg; 0.6 mmol) and N-(4-bromo-2-methyl-phenyl)-2,2,2-trifluoroacetamide (282 mg; 1.0 mmol) (first step in 12 ml dioxane instead of dimethylformamide with bis-triphenylphosphine-palladium dichloride (56 mg; 0.08 mmol) and second step in dimethoxyethane (8 ml) and ethanol (2 ml) with tetrakis-triphenylphosphine-palladium (69 mg; 0.06 mmol)), 151 mg (30%) cyclopropanesulphonic acid 4'-amino-4-(2,4-diamino-pyrimidin-5-ylmethyl)-6-ethoxy-3'-methyl-biphenyl-2-yl ester are obtained as a colourless powder.

MS (ISP): 470.3 (M+H)$^+$

N-(4-Bromo-2-methyl-phenyl)-2,2,2-trifluoroacetamide is prepared from 4-bromo-2-methyl-aniline (analogously to example 4l).

(34e) Cyclopropanesulphonic acid 3'-amino-4-(2,4-diamino-pyrimidin-5-ylmethyl)-6-ethoxy-4'-morpholin-4-ylmethyl-biphenyl-2-yl ester Starting from cyclopropanesulphonic acid 5-(2,4-diamino-pyrimidin-5-ylmethyl)-3-ethoxy-2-iodo-phenyl ester (294 mg; 0.6 mmol) and N-(5-bromo-2-methylmorpholine-phenyl)-2,2,2-trifluoro-acetamide (367 mg; 1.0 mmol) (first step in 10 ml dioxane and second step in dimethoxyethane (10 ml) and ethanol (2 ml)), 262 mg (46%) cyclopropanesulphonic acid 3'-amino-4-(2,4-diamino-pyrimidin-5-ylmethyl)-6-ethoxy-4'-morpholin-4-ylmethyl-biphenyl-2-yl ester are obtained as a colourless powder.

MS (ISP): 555.2 (M+H)$^+$

N-(5-Bromo-2-methylmorpholine-phenyl)-2,2,2-trifluoro-acetamide is prepared from 5-bromo-2-methylmorpholine-aniline (analogously to example 4l).

(34f) Cyclopropanesulphonic acid 3'-amino-4-(2,4-diamino-pyrimidin-5-ylmethyl)-6-ethoxy-4'-methyl-biphenyl-2-yl ester Starting from cyclopropanesulphonic acid 5-(2,4-diamino-pyrimidin-5-ylmethyl)-3-ethoxy-2-iodo-phenyl ester (294 mg; 0.6 mmol) and N-(5-bromo-2-methyl-phenyl)-2,2,2-trifluoro-acetamide (prepared from 5-bromo-2-methyl-aniline analogously to example 4l) (367 mg; 1.0 mmol) (first step in 10 ml dimethoxyethane and second step in dimethoxyethane (10 ml) and ethanol (2 ml)), 187 mg (38%) cyclopropanesulphonic acid 3'-amino-4-(2,4-diamino-pyrimidin-5-ylmethyl)-6-ethoxy-4'-methyl-biphenyl-2-yl ester are obtained as a beige powder.

MS (ISP): 470.3 (M+H)$^+$

The Above Starting Compound cyclopropanesulphonic acid 5-(2,4-diamino-pyrimidin-5-ylmethyl)-3-ethoxy-2-iodo-phenyl ester is Prepared as Follows, cf. Equation 2, (XII)→(XIII)

5-(3-Ethoxy-5-hydroxy-4-iodo-benzyl)-pyrimidine-2,4-diamine (see example 32 stage a)) (360 mg; 0.932 mmol) is dissolved in dimethylformamide (30 ml), and potassium tert-butylate (125 mg; 1.12 mmol) is added at room temperature. Cyclopropanesulphonyl chloride (2.56 ml; 22.92 mmol) is added at 0° C. The mixture is then stirred for 4½ h hours at 0–5° C. The reaction mixture is evaporated and the residue is chromatographed over silica gel (45 g) with methylene chloridelmethanol/NH$_4$OH conc. (1/1 mixture of 19/1/0.05 and 90/10/1) The pure fractions are combined and the solvent is evaporated off.

Yield: 210 mg (46%) cyclopropanesulphonic acid 5-(2,4-diamino-pyrimidin-5-ylmethyl)-3-ethoxy-2-iodo-phenyl ester are obtained as a colourless solid. MS (ISP): 491.1 (M+H)$^+$

EXAMPLE 35

Analogously to example 4, or as described in example 35(a), compounds of the formula VIII, equation 2, are prepared from the corresponding compounds of the formula III.

(35a) Butane-2-sulphonic acid 4'-amino-4-(2,4-diamino-pyrimidin-5-ylmethyl)-6ethoxy-biphenyl-2-yl ester Bis(pinacolato)diboron (322 mg, 1.26 mmol), N-(4-bromo-phenyl)-2,2,2-trifluoro-acetamide (225 mg, 0.84 mmol), potassium acetate (249 mg, 0.254 mmol) and tetrakis-triphenylphosphine-palladium (59 mg, 0.051 mmol) are dissolved in 12 ml abs. dioxane, four times the solution is evacuated and gassed with argon, and the mixture is then kept at 80° C. for 2 h. An HPLC analysis indicates complete conversion of the aromatic bromide. The mixture is evaporated under reduced pressure, the residue is dried for 1 hour under a greatly reduced pressure, and butane-2-sulphonic acid 5-(2,4-diamino-pyrimidin-5-ylmethyl)-3-ethoxy-2-iodo-phenyl ester (214 mg, 0.422 mmol), 59 mg fresh tetrakis-triphenylphosphine-palladium, 7.5 ml dimethoxyethane, 1.75 ml EtOH, 6 ml 2 N aqueous Na$_2$CO$_3$ are added and the mixture is allowed to react for 2 hours at 75° C. The mixture is cooled, poured on to ice and extracted with ethyl acetate, and the extract is washed with saturated aqueous sodium chloride solution, dried over MgSO$_4$ and evaporated to dryness. Flash chromatography over SiO$_2$ (CH$_2$Cl$_2$/MeOH/25% NH$_3$(19/1/0.05) gives 114 mg of the tide compound as a brownish foam.

MS (ISP): 472.2 (M+H)$^+$ NMR $^1$H(250 MHz, δ, TMS, DMSO): 0.79 (t, J=7,3H), 1.01 (d, J=7, 3H), 1.17 (t, J=7, 3H), 1.27 (m, 1H), 1.63 (m, 1H), 2.74 (m, 1H), 3.63 (s, 2H), 3.93 (q, J=7, 2H), 5.08 (br s, 2H), 5.71 (br s, 2H), 6.13 (br s, 2H), 6.55 (d, J=9, 2H), 6.81 (s, 1H), 6.89 (d, J=9, 2H), 6.91 (s, 1H), 7.58 (s, 1H).

(35b) Butane-2-sulphonic acid 4'-amino-4-(2,4-diamino-pyrimidin-5-ylmethyl)-6-ethoxy-3'-fluoro-biphenyl-2-yl ester Starting from 241 mg (0.84 mmol) N-(4-bromo-2-fluoro-phenyl)-2,2,2-trifluoro-acetamide and 214 mg (0.422 mmol) butane-2-sulphonic acid 5-(2,4-diamino-pyrimidin-5-ylmethyl)-3-ethoxy-2-iodo-phenyl ester, 85 mg of the tide compound are obtained as a pale brown powder.

MS (ISP): 490.3 (M+H)$^+$ (35c) Butane-2-sulphonic acid 3'-amino-4-(2,4-diamino-pyrimidin-5-ylmethyl)-6-ethoxy-4'-morpholin-4-ylmethyl-biphenyl-2-yl ester Starting from 308 mg (0.84 mmol) N-(5-bromo-2-morpholin-4-ylmethyl-phenyl)-2,2,2-trifluoro-acetamide and 214 mg (0.422 mmol) butane-2-sulphonic acid 5-(2,4-diamino-pyrimidin-5-ylmethyl)-3-ethoxy-2-iodo-phenyl ester, 139 mg of the title compound are obtained as pale brown crystals.

MS (ISP): 571.2 (M+H)$^+$ (35d) Butane-2-sulphonic acid 3'-amino-4-(2,4-diamino-gyrimidin-5-ylmethyl)-6-ethoxy-4'-methoxy-biphenyl-2-yl ester Starting from 197 mg (0.66 mmol) N-(5-bromo-2-methoxy-phenyl)-2,2,2-trifluoro-acetamide and 168 mg (0.33 mmol) butane-2-sulphonic acid 5-(2,4-diamino-pyrimidin-5-ylmethyl)-3-ethoxy-2-iodo-phenyl ester, 41 mg of the title compound are obtained as pale brown crystals.

MS (ISP): 502.3 (M+H)$^+$ (35e) Butane-2-sulphonic acid 4'-amino-4-(2,4-diamino-pyrimidin-5-ylmethyl)-6-ethoxy-3'-methyl-biphenyl-2-yl ester Starting from 191 mg (0.68 mmol) N-(4-bromo-2-methyl-phenyl)-2,2,2-trifluoro-acetamide and 173 mg (0.34 mmol)

butane-2-sulphonic acid 5-(2,4-diamino-pyrirmidin-5-ylmethyl)-3-ethoxy-2-iodo-phenyl ester, 53 mg of the title compound are obtained as a pale brown foam after two chromatography operations.

MS (ISP): 486.3 (M+H)$^+$ NMR 1H (250 MHz, δ, TMS, DMSO): 0.77 (t, J=7, 3H), 1.00 (d, J=7, 3H), 1.16 (t, J=7, 3H), 1.25 (m, 1H), 1.62 (m, 1H), 2.04 (s, 3H), 2.70 (m, 1H), 3.62 (s, 2H), 3.93 (q, J=7, 2H), 4.9 (br d, 2H), 5.73 (br s, 2H), 6.15 (br s, 2H), 6.60 (d, J=9, 1H), 6.78 (d, J=9, 1H), 6.80 (s, 1H), 6.80 (s, 1H), 6.92 (s, 1H), 7.58 (s, 1H).

(35f) Butane-2-sulphonic acid 4-(2,4-diamino-pyrimidin-5-ylmethyl)-6-ethoxy-4'-(2-hydroxy-ethylamino)-biphenyl-2-yl ester Starting from 370 mg (0.87 mmol) N-(4-bromo-phenyl)-N-[2-(tert-butyl-dimethyl-silanyloxy)-ethyl]-2,2,2-trifluoro-acetamide and 220 mg (0.43 mmol) butane-2-sulphonic acid 5-(2,4-diamino-pyrimidin-5-ylmethyl)-3-ethoxy-2-iodo-phenyl ester, 35 mg of the tide compound are obtained as a colourless foam after splitting off of the tert-butyl-dimethylsilanyl protective group under acid conditions ((4.5 N HCl [MeOH]).

MS (ISP): 516.3 (M+H)$^+$

The N-(4-bromo-phenyl)-N-[2-(tert-butyl-dimethyl-silanyloxy)-ethyl]-2,2,2-trifluoro-acetamide required for this is prepared as follows:

N-(4-Bromo-phenyl)-2,2,2-trifluoro-acetamide (1.12 g, 4.18 mmol) are [sic] initially introduced into 8.5 ml abs. dimethylformamide, and 1.2 g powdered molecular sieve 4 A are added. The mixture is stirred for 15 min, 612 mg (5.45 mmol) KOtBu are added and, after a further 5 min, 1.44 g (5.02 mmol) tert-butyl-(2-iodo-ethoxy)-dimethyl-silane are added. The mixture is allowed to react for 36 hours at 70° C. and is cooled. Filtration, extraction with ethyl acetate, washing with water, drying over MgSO$_4$, evaporation under reduced pressure, followed by flash chromatography with SiO$_2$ (n-hexane/ethyl acetate 9/1) gives 887 mg of the title compound as a colourless oil.

MS (EI): 410.412 (M-CH$_3$)$^+$

The Above Starting Compound butane-2-sulphonic acid 5-(2,4-diamino-pyrimidin-5-ylmethyl)-3-ethoxy-2-iodo-phenyl ester is Prepared as Follows, cf. Equation 2, (XII) →(XIII)

5-(2,4-Diamino-pyrimidin-5-ylmethyl)-3-ethoxy-2-iodo-phenol (example 32 stage a)) (40 mg; 0.104 mmol) are [sic] dissolved in 2.1 ml abs. tetrahydrofuran, 160 mg molecular sieve 4A and 14 mg (0.125 mmol) KOtBu are added and the mixture is stirred for 20 min. It is then cooled to −20° C. and 20 mg (0.127 mmol) sec-butyl-sulphonyl chloride are added. After 30 min the temperature is increased to +10° C. and the mixture is allowed to react for a further 2 hours. The reaction mixture is diluted with a mixture of CH$_2$Cl$_2$/MeOH/25% NH$_3$(90/10/1), filtered and evaporated and the crude product is purified by means of flash chromatography on SiO$_2$ (CH$_2$Cl$_2$/MeOH/25% NH$_3$(19/1/0.05). 27 mg of the tide compound are obtained here as a colourless powder.

MS (ISP): 507.2 (M+H)$^+$

EXAMPLE 36

Analogously to example 4, compounds of the formula VIII, equation 2, are prepared from the corresponding compounds of the formula III.

(36a) 2-Methyl-propane-1-sulphonic acid 4'-amino-4-(2,4-diamino-pyrimidin-5-ylmethyl)-6-ethoxy-3'-methyl-biphenyl-2-yl ester Starting from 191 mg (0.68 mmol) N-(4-bromo-2-methyl-phenyl)-2,2,2-trifluoro-acetamide and 173 mg (0.34 mmol) 2-methyl-propane-1-sulphonic acid 5-(2,4-diamino-pyrimidin-5-ylmethyl)-3-ethoxy-2-iodo-phenyl ester, 109 mg of the title compound are obtained as a brown solid after chromatography and stirring in 5 ml ether.

MS (ISP): 486.4 (M+H)$^+$ (36b) 2-Methyl-propane-1-sulphonic acid 4'-amino-4-(2,4-diamino-pyrimidin-5-ylmethyl)-6-ethoxy-3'-fluoro-biphenyl-2-yl ester Starting from 241 mg (0.84 mmol) N-(4-bromo-2-fluoro-phenyl)-2,2,2-trifluoro-acetamide and 215 mg (0.42 mmol) 2-methyl-propane-1-sulphonic acid 5-(2,4-diamino-pyrimidin-5-ylmethyl)-3-ethoxy-2-iodo-phenyl ester, 164 mg of the title compound are obtained as a pale brown foam.

MS (ISP): 490.3 (M+H)$^+$ (36c) 2-Methyl-propane-1-sulphonic acid 4'-amino-4-(2,4-diamino-pyrimidin-5-ylmethyl)-6-ethoxy-biphenyl-2-yl ester Starting from 225 mg (0.84 mmol) N-(4-bromo-phenyl)-2,2,2-trifluoro-acetamide and 214 mg (0.42 mmol) 2-methyl-propane-1-sulphonic acid 5-(2,4-diamino-pyrimidin-5-ylmethyl)-3-ethoxy-2-iodo-phenyl ester, 78 mg of the tide compound are obtained as a brown foam after two chromatography operations.

MS (ISP): 472.2 (M+H)$^+$ (36d) 2-Methyl-prooane-1-sulphonic acid 3'-amino-4-(2,4-diamino-pyrimidin-5-ylmethyl)-6-ethoxy-4'-methoxy-biphenyl-2-yl ester Starting from 250 mg (0.84 mmol) N-(5-bromo-2-methoxy-phenyl)-2,2,2-trifluoro-acetamide and 214 mg (0.42 mmol) 2-methyl-propane-1-sulphonic acid 5-(2,4-diamino-pyrimidin-5-ylmethyl)-3-ethoxy-2-iodo-phenyl ester, 56 mg of the title compound are obtained as a pale brown foam.

MS (ISP): 502.3 (M+H)$^+$ (36e) 2-Methyl-propane-1-sulphonic acid 4-(2,4-diamino-pyrimidin-5-ylmethyl)-6-ethoxy-4'-(2-hydroxy-ethylamino)-biphenyl-2-yl ester Starting from 397 mg (0.93 mmol) N-(4-bromo-phenyl)-N-[2-(tert-butyl-dimethyl-silanyloxy)-ethyl]-2,2,2-trifluoro-acetamide and 220 mg (0.47 mmol) 2-methyl-propane-1-sulphonic acid 5-(2,4-diamino-pyrimidin-5-ylmethyl)-3-ethoxy-2-iodo-phenyl ester, 165 mg of the title compound are obtained as a pale beige foam after splitting off of the tert-butyl-dimethylsilanyl protective group under acid conditions (HCl/MeOH).

MS (ISP): 516.3 (M+H)$^+$

The Above Starting Compound 2-methyl-propane-1-sulphonic acid 5-(2,4-diamino-pyrimidin-5-ylmethyl)-3-ethoxy-2-iodo-phenyl ester is Prepared as Follows:

5-(2,4-Diamino-pyrimidin-5-ylmethyl)-3-ethoxy-2-iodo-phenol (579 mg, 1.5 mmol) are [sic] initially introduced into 15 ml abs. dimethylformamide, and 2.4 g powdered molecular sieve 4A and 202 mg (1.8 mmol) KOtBu are added. The mixture is stirred for 10 min at room temperature and 480 mg (3 mmol) isobutylsulphonyl chloride are then added at 0° C. After 2 hours, the mixture is filtered and the residue is rinsed thoroughly with ethyl acetate. The combined filtrates are evaporated under reduced pressure. Flash chromatography over SiO$_2$ (CH$_2$Cl$_2$/MeOH/25% NH$_3$(19/1/0.05)) gives 521 mg of the title compound as pale yellow crystals; MS (ISP): 507.2 (M+H)$^+$

EXAMPLE 37

Analogously to example 4, or as described in example 37(a), compounds of the formula VIII, equation 2, are prepared from the corresponding compounds of the formula XIII.

(37a) 2,2-Dimethyl-propane-1-sulphonic acid 4'-amino-4-(2,4-diamino-pyrimidin-5-ylmethyl)-6-ethoxy-3'-fluoro-biphenyl-2-yl ester Bis-(pinacolato)diboron (318 mg, 1.25 mmol), N-(4-bromo-2-fluoro-phenyl)-2,2,2-trifluoro-acetamide (238 mg, 0.83 mmol), potassium acetate (246 mg, 0.251 mmol) and tetrakis-triphenylphosphine-palladium (94 mg, 0.08 mmol) are dissolved in 12 ml abs. dioxane, four times the solution is evacuated and gassed with argon, and the mixture is then kept at 80° C. overnight. An HPLC analysis indicates complete conversion of the aromatic bromide. The mixture is evaporated under reduced pressure, the residue is dried under greatly reduced pressure and 2,2-dimethyl-propane-1-sulphonic acid 5-(2,4-diamino-pyrimidin-5-ylmethyl)-3-ethoxy-2-iodo-phenyl ester (217 mg, 0.42 mmol), 58 mg fresh tetrakis-triphenylphosphine-palladium, 7.5 ml dimethoxyethane, 1.75 ml EtOH, 6 ml 2 N aqueous sodium carbonate solution are added, and the mixture is degassed again and allowed to react overnight at 75° C. The mixture is cooled, poured on to ice and extracted with ethyl acetate, and the extract is washed with saturated NaCl, dried over $MgSO_4$ and evaporated to dryness. Flash chromatography over $SiO_2$ ($CH_2Cl_2$/MeOH/25% $NH_3$(19/1/0.05) gives, after stirring with diethyl ether, 69 mg of the title compound as a pale brown foam.

MS (ISP): 504.3 $(M+H)^+$;

(37b) 2,2-Dimethyl-propane-1-sulphonic acid 3'-amino-4-(2,4-diamino-pyrimidin-5-ylmethyl)-6-ethoxy-4'-methoxy-biphenyl-2-yl ester Starting from 197 mg (0.66 mmol) N-(5-bromo-2-methoxy-phenyl)-2,2,2-trifluoro-acetamide and 173 mg (0.33 mmol) 2,2-dimethyl-propane-1-sulphonic acid 5-(2,4-diamino-pyrimidin-5-ylmethyl)-3-ethoxy-2-iodo-phenyl ester, 46 mg of the title compound are obtained as a brownish solid after two chromatography operations.

MS (ISP): 516.3 $(M+H)^+$

(37c) 2,2-Dimethyl-propane-1-sulphonic acid 4'-amino-4-(2,4-diamino-pyrimidin-5-ylmethyl)-6-ethoxy-biphenyl-2-yl ester Starting from 272 mg (1.01 mmol) N-(4-bromo-phenyl)-2,2,2-trifluoro-acetamide and 265 mg (0.51 mmol) 2,2-dimethyl-propane-1-sulphonic acid 5-(2,4-diamino-pyrimidin-5-ylmethyl)-3-ethoxy-2-iodo-phenyl ester, 56 mg of the title compound are isolated as a yellowish foam after two chromatography operations.

MS (ISP): 486.4 $(M+H)^+$

(37d) 2,2-Dimethyl-propane-1-sulphonic acid 4-(2,4-diamino-pyrimidin-5-ylmethyl)-6-ethoxy-4'-(2-hydroxy-ethylamino)-biphenyl-2-yl ester Bis-(pinacolato)diboron (336 mg, 1.32 mmol), N-(4-bromo-phenyl)-N-[2-(tert-butyl-dimethyl-silanyloxy)-ethyl]-2,2,2-trifluoro-acetamide (451 mg, 1.06 mmol), potassium acetate (311 mg, 3.17 mmol) and $PdCl_2$(dppf) (39 mg, 0.05 mmol) are dissolved in 7 ml abs. dioxane, twice the solution is evacuated and gassed with argon, and the mixture is then kept at 80° C. overnight. 275 mg (0.53 mmol) 2,2-dimethyl-propane-1-sulphonic acid 5-(2,4-diamino-pyrimidin-5-ylmethyl)-3-ethoxy-2-iodo-phenyl ester, 61 mg tetrakis-triphenylphosphine-palladium and 1.75 ml 2 M $K_3PO_4$ are added and the mixture is degassed again and allowed to react overnight at 80° C. The mixture is cooled, poured on to ice and extracted with ethyl acetate, and the extract is washed with saturated aqueous sodium chloride solution, dried over $MgSO_4$ and evaporated to dryness. Flash chromatography twice over $SiO2$ ($CH_2Cl_2$/MeOH/25% $NH_3$(19/1/0.05) gives 152 mg of product, which is deaved as follows to give the free alcohol:

The product is dissolved in 1 ml tetrahydrofuran, and 1 ml 4.5 M HCl (MeOH) is added. After 45 min the mixture is neutralized with 10% aqueous sodium carbonate solution and extracted with ethyl acetate, and the extract is washed with conc. aqueous sodium chloride solution, dried over $MgSO_4$ and evaporated. Flash chromatography over $SiO2$ ($CH_2Cl_2$/MeOH/25% $NH_3$(19/11/0.05) gives, after stirring with diethyl ether, 37 mg of the tide compound as virtually white crystals.

MS (ISP): 530.2 $(M+H)^+$;

The Above Starting Compound dimethyl-propane-1-sulphonic acid 5-(2,4-diamino-pyrimidin-5-ylmethyl)-3-ethoxy-2-iodo-phenyl ester is Prepared as Follows:

5-(2,4-Diamino-pyrimidin-5-ylmethyl)-3-ethoxy2-iodo-phenol (1,000 mg; 2.59 mmol) are [sic] initially introduced into 50 ml abs. tetrahydrbifuran, 4.0 g powdered molecular sieve 4A and 407 mg (3.63 mmol) KOtBu are added and the mixture is stirred for 45 min. It is then cooled to −20° C. and 618 mg (3.62 mmol) 2,2-dimethyl-propane-1-sulphonyl chloride are added. After 60 min at −20° C., 4 hours at 0° C. and 12 hours at +8° C., the reaction mixture is diluted with a mixture of $CH_2Cl_2$/MeOH/25% $NH_3$(90/10/1), filtered and evaporated and the crude product is purified by means of flash chromatography on $SiO2$ ($CH_2Cl_2$/MeOH/25% $NH_3$ (19/1/0.05). 552 mg of the tide compound are obtained here as a colourless powder.

MS (ISP): 521.1 $(M+H)^+$

EXAMPLE 38

Analogously to example 2, the compound of the formula VIII, equation 2, wherein $R^2$ is amino, is prepared from the corresponding compound of the formula XIII.

(38a) Cyclopropylmethane-sulphonic acid 3'-amino-4-(2,4-diamino-pyrimidin-5-ylmethyl)-6ethoxy-biphenyl-2-yl ester Starting from cyclopropylmethane-sulphonic acid 5-(2,4-diamino-pyrimidin-5-ylmethyl)-3-ethoxy-2-iodo-phenyl ester (250 mg; 0.5 mmol), 3-aminophenylboron acid (108 mg; 0.7 mmol), tetrakis-triphenylphosphine-palladium (34 mg; 0.03 mmol) and aqueous 2 M sodium carbonate solution (3.7 ml; 7.4 mmol) in a 4/1 dimethoxyethane/ethanol mixture (10 ml), 205 mg (88%) cyclopropylmethane-sulphonic acid 3'-amino-4-(2,4-diamino-pyrimidin-5-ylmethyl)-6-ethoxy-biphenyl-2-yl ester are obtained as a yellow foam.

MS (ISP): 470.2 $(M+H)^+$

The following are prepared analogously to example 4:

(38b) Cyclopropylmethane-sulphonic acid 4'-amino-4-(2,4-diamino-pyrimidin-5-ylmethyl)-6-ethoxy-3'-fluoro-4-ylmethyl-biphenyl-2-yl ester N-(4-Bromo-3-fluoro-phenyl)-2,2,2-trifluoroacetamide (1.0 g; 3.5 mmol), bis-(pinacolato)diboron(1,332 mg; 5.2 mmol), potassium acetate (1,030 mg; 10.5 mmol) and (diphenylphosphino)-diclloro-palladium(II) (147 mg; 0.21 mmol) in 60 ml dioxane are stirred at 80° C. for 3 hours. Half of this batch is concentrated, water is added to the residue, the mixture is extracted with ethyl acetate and the combined organic phases are washed with a saturated aqueous sodium chloride solution, dried over magnesium sulphate, filtered with suction and concentrated.

The product obtained in this way is treated with cyclopropylmethane-sulphonic acid 5-(2,4-diamino-pyrimidin-5-ylmethyl)-3-ethoxy-2-iodo-phenyl ester (441 mg; 0.87 mmol), tetra-(triphenyl-phosphine)-palladium (121 mg; 0.10 mmol), aqueous 2 M sodium carbonate solution (13 ml; 26 mmol) in a 4/1 dimethoxyethane/ethanol mixture (15 ml). 249 mg (58%) Cyclopropylmethane-sulphonic acid 4'-amino-4-(2,4-diamino-pyrimidin-5-ylmethyl)-6-ethoxy-3'-fluoro-4-ylmethyl-biphenyl-2-yl ester are obtained as a violet foam.

MS (ISP): 488.3 (M+H)$^+$ (38c) Cyclopropylmethane-sulphonic acid 4'-amino-4-(2,4-diamino-pyrimidin-5-ylmethyl)-6-ethoxg-3'-methyl-biphenyl-2-yl ester N-(4-Bromo-2-methyl)-2,2,2-trifluoro-acetaraide (600 mg; 2.13 mmol), bis-(pinacolato)diboron (810 mg; 3.20 mmol), potassium acetate (626 mg; 638 mmol) and (diphenylphosphino)-dichloro-palladium(II) (89 mg; 0.13 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with cyclopropylmethane-sulphonic acid 5-(2,4-diamino-pyrimidin-5-ylmethyl)-3-ethoxy-2-iodo-phenyl ester (469 mg; 0.93 mmol), tetrakis-triphenylphosphine-palladium (129 mg; 0.11 mmol) and aqueous 2 M sodium carbonate solution (14 ml; 28 mmol) in a 4/1 dimethoxyethane/ethanol mixture (15 ml), 315 mg (70%) cyclopropylmethane-sulphonic acid 4'-amino-4-(2,4-diamino-pyrimidin-5-ylmethyl)-6ethoxy-3'-methyl-biphenyl-2-yl ester are obtained as a brown foam.

MS (ISP): 484.3 (M+H)$^+$ (38d) Cyclopropylmethane-sulphonic acid 3'-amino-4-(2,4-diamino-pyrimidin-5-ylmethyl)-6-ethoxy-4'-morpholinemethyl-biphenyl-2-yl ester N-(5-Bromo-2-morpholinemethyl-4-ylmethyl-phenyl)-2,2,2-trifluoro-acetamide (500 mg; 1.36 mmol), bis(pinacolato)diboron (519 mg; 2.04 mmol), potassium acetate (401 mg; 4.09 mmol) and (diphenylphosphino)-dichloro-palladium(II) (88 mg; 0.08 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with cyclopropylmethane-sulphonic acid 5-(2,4-diamino-pyrimidin-5-ylmethyl)-3-ethoxy-2-iodo-phenyl ester (308 mg; 0.61 mmol), tetra-(triphenyl-phosphine)-palladium (85 mg; 0.07 mmol), aqueous 2 M sodium carbonate solution (9 ml; 18 mmol) in a 4/1 dimethoxyethane/ethanol mixture (15 ml), 254 mg (73%) cyclopropylmethane-sulphonic acid 3'-amino-4-(2,4-diamin6-pyrimidin-5-ylmethyl)-6ethoxy-4'-morpholinemethyl-biphenyl-2-yl ester are obtained as a white foam.

MS (ISP): 569.3 (M+H)$^+$

The Above Starting Compound cyclopropylmethane-sulphonic acid 5-(2,4-diamino-pyrimidin-5-ylmethyl)-3-ethoxy-2-iodo-phenyl ester is Prepared as Follows, cf. Equation 2, (XII)→(XIII)

5-(3-Ethoxy-5-hydroxy-4-iodo-benzyl)-pyrimidine-2,4-diamine (see example 32 stage a) (250 mg; 0.67 mmol) is dissolved in tetrahydrofuran (6 ml), and potassium tert-butylate (109 mg; 0.97 mmol) is added. Cyclopropylmethane-sulphonyl chloride (200 mg; 1.29 mmol) is added at 0° C. The mixture is then stirred for one hour at room temperature. The reaction mixture is evaporated and the residue is chromatographed over silica gel with methylene chloride/methanol (19/1) and 0.5% ammonia. The pure fractions are combined and the solvent is evaporated off.

Yield: 185 mg (57%) Cyclopropylmethane-sulphonic acid 5-(2,4-diamino-pyrimidin-5-ylmethyl)-3-ethoxy-2-iodo-phenyl ester as a white solid. MS (ISP): 504 (M+H)$^+$

EXAMPLE 39

Analogously to example 2a, the compound of the formula VIII, equation 2, wherein $R^2$ is amino, is prepared from the corresponding compound of the formula XIII.

(39a) (2-Methoxy-2-methyl-propane)-1-sulphonic acid 3'-amino-4-(2,4-diamino-pyrimidin-5-ylmethyl)-6-ethoxy-biphenyl-2-yl ester Starting from (2-methoxy-2-methyl-propane)-1-sulphonic acid 5-(2,4-diamino-pyrimidin-5-ylmethyl)-3-ethoxy-2-iodo-phenyl ester (250 mg; 0.5 mmol), 3-Amino-phenylboron acid (108 mg; 0.7 mmol), tetrakis-triphenylphosphine-palladium (34 mg; 0.03 mmol) and aqueous 2 M sodium carbonate solution (3.5 ml; 7.0 mmol) in a 4/1 dimethoxyethane/ethanol mixture (15 ml), 108 mg (46%) (2-methoxy-2-methyl-propane)-1-sulphonic acid 3'-amino-4-(2,4-diamino-pyrimidin-5-ylmethyl)-6-ethoxy-biphenyl-2-yl ester are obtained as a yellow foam.

MS (ISP): 502.3 (M+H)$^+$

The following are prepared analogously to example 4:

(39b) (2-Methoxy-2-methyl-propane)-1-sulphonic acid 4'-amino-4-(2,4-diamino-pyrimidin-5-ylmethyl)-6-ethoxy-3'-methyl-biphenyl-2-yl ester Starting from [sic] N-(4-bromo-3-methyl-phenyl)-2,2,2-trifluoroacetamide (1.05 g; 3.7 mmol), bis(pinacolato)diboron (1.42 g; 5.58 mmol), potassium acetate (1.09 g; 11.2 mmol) and (diphenylphosphino)-dichloro-palladium(II) (157 mg; 0.22 mmol) in in [sic] 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with (2-methoxy-2-methyl-propane)-1-sulphonic acid 5-(2,4-diamino-pyrimidin-5-ylmethyl)-3-ethoxy-2-iodo-phenyl ester (499 mg; 0.93 mmol), tetrakis-triphenylphosphine-palladium (64 mg; 0.06 mmol) and aqueous 2 M sodium carbonate solution (6.9 ml; 13.8 mmol) in a 4/1 dimethoxyethane/ethanol mixture (15 ml). 243 mg (51%) (2-methoxy-2-methyl-propane)-1-sulphonic acid 4'-amino-4-(2,4-diamino-pyrimidin-5-ylmethyl)-6-ethoxy-3'-methyl-biphenyl-2-yl ester are obtained as a brown foam.

MS (ISP): 516.3 (M+H)+

(39c) (2-Methoxg-2-methyl-propane)-1-sulphonic acid 4'-amino-4-(2,4-diamino-pyrimidin-5-ylmethyl)-6-ethoxy-3'-fluoro-4-ylmethyl-biphenyl-2-yl ester N-(4-Bromo-3-fluoro-phenyl)-2,2,2-trifluoroacetamide (1.0 g; 3.5 mmol), bis-(pinacolato)diboron (1,332 mg; 5.2 mmol), potassium acetate (1,030 mg; 10.5 mmol) and (diphenylphosphino)-dichloro-palladium(II) (147 mg; 0.21 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with (2-methoxy-2-methyl-propane)-1-sulphonic acid 5-(2,4-diamino-pyrimidin-5-ylmethyl)-3-ethoxy-2-iodo-phenyl ester (320 mg; 0.60 mmol), tetrakis-triphenylphosphine-palladium (42 mg; 0.04 mmol) and aqueous 2 M sodium carbonate solution (4.5 ml; 9 mmol) in a 4/1 dimethoxyethane/ethanol mixture (15 ml). 167 mg (54%) (2-methoxy-2-methyl-propane)-1-sulphonic acid 4'-amino-4-(2,4-diamino-pyrimidin-5-ylmethyl)-6-ethoxy-3'-fluoro-4-ylmethyl-biphenyl-2-yl ester are obtained as a white foam.

MS (ISP): 520.2 (M+H)+

(39d) (2-Methoxy-2-methyl-propane)-1-sulphonic acid 3'-amino-4-(2,4-diamino-pyrimidin-5-ylmethyl)-6-ethoxy-4'-morpholinemethyl-biphenyl-2-yl ester N-(5-Bromo-2-morpholinemethyl-4-ylmethyl-phenyl)-2,2,2-trifluoro-acetamide (894 mg; 2.43 mmol), bis(pinacolato)diboron (927 mg; 3.65 mmol), potassium acetate (717 mg; 7.3 mmol) and (diphenylphosphino)-dichloro-palladium(II) (103 mg; 0.146 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with (2-methoxy-2-methyl-propane)-1-sulphonic acid 5-(2,4-diamino-pyrimidin-5-ylmethyl)-3-ethoxy-2-iodo-phenyl ester (326 mg; 0.61 mmol), tetrakis-triphenylphosphine-palladium (42 mg; 0.04 mmol) and aqueous 2 M sodium carbonate solution (4.5 ml; 9 mmol) in a 4/1 dimethoxyethane/ethanol mixture (15 ml). 158 mg (43%) 2-methoxy-2-methyl-propane)-1-sulphonic acid 3'-amino-4-(2,4-diamino-pyrimidin-5-ylmethyl)-6-ethoxy-4'-morpholinemethyl-biphenyl-2-yl ester are obtained as a white solid.

MS (ISP): 601.1 (M+H)+

The Above Starting Compound (2-methoxy-2-methyl-propane)-1-sulphonic acid 5-(2,4-diamino-pyrimidin-5-ylmethyl)-3-ethoxy-2-iodo-phenyl ester is Prepared as Follows, cf. Equation 2, (XII)→(XIII)

5-(3-Ethoxy-5-hydroxy-4-iodo-benzyl)-pyrimidine-2,4-diamine (see example 32 stage a) (2,170 mg; 5.63 mmol) is dissolved in tetrahydrofuran (60 ml), and potassium tert-butylate (947 mg; 8.44 mmol) is added at room temperature. The mixture is then cooled to 0° C. and 2-methoxy-2-methyl-propane-1-sulphonyl chloride (2.1 g; 11.25 mmol) is added. After one hour at room temperature, the reaction mixture is evaporated and the residue is chromatographed over silica gel with methylene chloride/methanol (19/1) and 0.5% ammonia. The pure fractions are combined and the solvent is evaporated off.

Yield: 1,710 mg (57%) (2-methoxy-2-methyl-propane)-1-sulphonic acid 5-(2,4-diamino-pyrimidin-5-ylmethyl)-3-ethoxy-2-iodo-phenyl ester as a beige solid. MS (ISP): 537.1 (M+H)+

The (2-methoxy-2-methyl-propane)-1-sulphonyl chloride Employed is Prepared as Follows (Stages a–b):
Stage a) 2,2'-Dithiobis-(1,1-dimethylethyl methyl ether)

1,1-Dimethyl-thiiran (1.00 g; 10.2 mmol) is dissolved in methanol (50 ml), dichloro-dicyano-benzoquinone (2.32 g; 10.2 mmol) is added and the mixture is heated under reflux for 6 hours. The reaction mixture is evaporated and the residue is chromatographed over silica gel with n-hexane/ethyl acetate (8/2). The pure fractions are combined and the solvent is evaporated off.

Yield: 870 mg (71%) 2,2'-dithiobis-(1,1-dimethylethyl methyl ether) are obtained as a yellow oil. MS (EI): 238 (M)

Stage b) (2-Methoxy-2-methyl-propane)-1-sulphonyl chloride 2,2'-Dithiobis-(1,1-dimethylethyl methyl ether) (2.00 g; 8.4 mmol) is dissolved in ether (250 ml), and iodosobenzene (10.8 g; 33.6 mmol) and hydrochloric acid (14 ml; 37%) are added at room temperature. After one hour the reaction mixture is poured on to a saturated sodium carbonate solution and extracted twice with ether. The organic phase is dried over sodium sulphate, the salts are filtered off and the solvent is evaporated off. The residue is chromatographed over silica gel with n-hexane/ethyl acetate (8/2). The pure fractions are combined and the solvent is evaporated off.

Yield: 2.44 g (78%) (2-methoxy-2-methyl-propane)-1-sulphonyl chloride as a light-yellow liquid. MS (EI): 171 (M-$CH_3$)

EXAMPLE 40

Analogously to example 2, the compound of the formula VIII, equation 2, is prepared from the corresponding compounds of the formula XIII.

(40a) Cyclobutane-sulphonic acid 3'-amino-4-(2,4-diamino-pyrimidin-5-ylmethyl)-6-ethoxy-biphenyl-2-yl ester Starting from cyclobutane-sulphonic acid 5-(2,4-diamino-pyrimidin-5-ylmethyl)-3-ethoxy-2-iodo-phenyl ester (250 mg; 0.5 mmol), 3-aminophenylboron acid (115 mg; 0.7 mmol) tetrakis-triphenylphosphine-palladium (34 mg; 0.03 mmol) and aqueous 2 M sodium carbonate solution (3.7 ml; 7.4 mmol) in a 4/1 dimethoxyethane/ethanol mixture (10 ml), 157 mg (67%) cyclobutane-sulphonic acid 3'-amino-4-(2,4-diamino-pyrimidin-5-ylmethyl)-6-ethoxy-biphenyl-2-yl ester are obtained as a yellow foam.

MS (ISP): 470.3 (M+H)+

(40b) Cylobutane-sulphonic acid 4'-amino-4-(2,4-diamino-pyrimidin-5-ylmethyl)-6-ethoxy-3'-fluoro-4-ylmethyl-biphenyl-2-yl ester 33 N-(4-Bromo-3-fluoro-phenyl)-2,2,2-trifluoroacetamide (900 mg; 3.15 mmol), bis-(pinacolato) diboron (1,198 mg; 4.7 mmol), potassium acetate (926 mg; 9.44 mmol) and (diphenylphosphino)-dichloro-palladium (II) (132 mg; 0.19 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

Since [sic] product obtained in this way istreated with cyclobutane-sulphonic acid 5-(2,4-diamino-pyrimidin-5-ylmethyl)-3-ethoxy-2-iodo-phenyl ester (397 mg; 0.79 mmol), tetrakis-triphenylphosphine-palladium (109 mg; 0.09 mmol) and aqueous 2 M sodium carbonate solution (12 ml; 24 mmol) in a 4/1 dimethoxyethane/ethanol mixture (15 ml). 314 mg (81.8%) cyclobutane-sulphonic acid 4'-amino-4-(2,4-diamino-pyrimidin-5-ylmethyl)-6-ethoxy-3'-fluoro-4-ylmethyl-biphenyl-2-yl ester are obtained as a light-brown foam.

MS (ISP): 488.3 (M+H)$^+$ (40c) Cyclobutane-sulphonic acid 4'-amino-4-(2,4-diamino-pyrimidin-5-ymethyl)-6-ethoxy-3'-methyl-biphenyl-2-yl ester N-(4-Bromo-2-methyl)-2,2,2-trifluoro-acetamide (600 mg; 2.13 mmol), bis(pinacolato)diboron (810 mg; 3.20 mmol), potassium acetate (626 mg; 6.38 mmol) and (diphenylphosphino)-dichloro-palladium(II) (89 mg; 0.13 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with cyclobutane-sulphonic acid 5-(2,4-diamino-pyrimidin-5-ylmethyl)-3-ethoxy-2-iodo-phenyl ester (358 mg; 0.71 mmol), tetrakis-triphenylphosphine-palladium (98 mg; 0.09 mmol) and aqueous 2 M sodium carbonate solution (10.6 ml; 21.2 mmol) in a 4/1 dimethoxyethane/ethanol mixture (15 ml), 153 mg (44.6%) cyclobutane-sulphonic acid 4'-amino-4-(2,4-diamino-pyrimidin-5-ylmethyl)-6-ethoxy-3'-methyl-biphenyl-2-yl ester are obtained as a brown foam.

MS (ISP): 484.4 (M+H)$^+$ NMR $^1$H: (250 MHz, δ, TMS, DMSO): 1.17 (t; J=6.6; 3H); 2.05 (s; 3H); 1.65–2.16 (m; 6H); 3.62 (s; 2H); 3.65 (m, 1H); 3.94 (q; J=6.6; 2H); 4.90 (s(br); 2H); 5.72 (s(br); 2H); 6.15 (s(br); 2H); 6.61 (d; J=7.6; 1H); 6.79 (s; 1H); 6.81 (d; J=7.6; 1H); 6.83 (s; 1H); 1H); 6.91 (s; 1H); 7.57 (s; 1H).

(40d) Cyclobutane-sulphonic acid 3'-amino-4-(2,4-diamino-pyrimidin-5-ylmethyl)-6-ethoxy-4'-morpholinomethyl-biphenyl-2-yl ester N-(5-Bromo-2-morpholinemethyl-phenyl)-2,2,2-trifluoro-acetamide (450 mg; 1.23 mmol), bis(pinacolato) diboron (466 mg; 1.84 mmol), potassium acetate (361 mg; 3.68 mmol) and (diphenylphosphino)-dichloro-palladium (II) (52 mg; 0.07 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with cyclobutane-sulphonic acid 5-(2,4-diamino-pyrimidin-5-ylmethyl)-3-ethoxy-2-iodo-phenyl ester (310 mg; 0.61 mmol), tetrakis-triphenylphosphine-palladium (43 mg; 0.04 mmol) and aqueous 2 M sodium carbonate solution (4.5 ml; 9 mmol) in a 4/1 dimethoxyethane/ethanol mixture (15 ml), 259 mg (74%) cyclobutane-sulphonic acid 3'-amino-4-(2,4-diamino-pyrimidin-5-ylmethyl)-6-ethoxy-4'-morpholinomethyl-biphenyl-2-yl ester are obtained as a white foam.

MS (ISP): 569.3 (M+H)$^+$ (40e) Cyclobutane-sulphonic acid 3'-amino-4-(2,4-diamino-pyrimidin-5-ylmethyl)-6-ethoxy-5'-fluoro-biphenyl-2-yl ester N-(5-Iodo-3-fluoro-phenyl)-2,2,2-trifluoroacetamide (prepared as in example 4t) (326 mg; 0.98 mmol), bis (pinacolato)diboron (373 mg; 1.47 mmol), potassium acetate (288 mg; 294 mmol) and (diphenylphosphino)-dichloro-palladium(II) (PdCl$_2$(PPh$_3$)$_2$) (41 mg; 0.06 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reacion with cyclobutane-sulphonic acid 5-(2,4-diamino-pyrimidin-5-ylmethyl)-3-ethoxy-2-iodo-phenyl ester (247 mg; 0.49 mmol), tetrakis-triphenylphosphine-palladium (34 mg; 0.03 mmol) and aqueous 2 M sodium carbonate solution (3.65 ml; 7.3 mmol) in a 4/1 dimethoxyethane/ethanol mixture (15 ml), 154 mg (65%) cyclobutane-sulphonic acid 3'-amino-4-(2,4diamino-pyrimidin-5-ylmethyl)-6-ethoxy-5'-fluoro-biphenyl-2-yl ester are obtained as a white foam.

MS (ISP): 488.3 (M+H)$^+$

The Above Starting Compound cyclobutane-sulphonic acid 5-(2,4-diamino-pyrimidin-5-ylmethyl)-3-ethoxy-2-iodo-phenyl ester is Prepared as Follows, cf. Equation 2, (XII)→(XIII)

5-(3-Ethoxy-5-hydroxy-4-iodo-benzyl)-pyrimidine-2,4-diamine (see example 32 stage a) (2,800 mg; 7.25 mmol) is dissolved in tetrahydrofuran (50 ml), potassium tert-butylate (1,220 mg; 10.8 mmol) is added and the mixture is cooled to −20° C. Thereafter, cyclobutane-sulphonyl chloride (2.24 g; 14.5 mol) is added and the mixture is then stirred for one hour at −20° C. The reaction mixture is poured on to ice-water and extracted twice with ethyl acetate. The organic phase is dried over sodium sulphate, the salts are filtered off and the solvent is evaporated off. The residue is chromatographed over silica gel with methylene chloride/methanol (19/1) and 0.5% ammonia. The pure fractions are combined and the solvent is evaporated off.

Yield: 2,180 mg (59.6%) cyclobutane-sulphonic acid 5-(2,4-diamino-pyrimidin-5-ylmethyl)-3-ethoxy-2-iodo-phenyl ester as yellow crystals. MS (ISP): 505.1 (M+H)$^+$ The cyclobutane-sulphonyl chloride Employed is Prepared as Follows (Stages a–b-c):

Stage a) Cyclobutane-sulphonic acid n-butyl ester

4-Chloro-n-butane-1-sulphonic acid n-butyl ester (68.10 g; 298 mmol) is dissolved in tetrahydrofuran (1.5 L), and n-butyllithium (205 ml; 1.6 M in tetrahydrofuran; 327 mmol) is added at −70° C. in the course of 1.5 hours. After stirring at room temperature for half an hour, water (15 ml) is added and the reaction mixture is concentrated. The residue is diluted with a saturated aqueous sodium chloride solution and extracted twice with ethyl acetate. The organic phase is dried over sodium sulphate, the salts are filtered off and the solvent is evaporated off. The residue is chromatographed over silica gel with n-hexane/ethyl acetate (8/2). The pure fractions are combined and the solvent is evaporated off.

Yield: 14.81 g (25.9%) cyclobutane-sulphonic acid n-butyl ester as a yellow oil. MS (ISP): 136 (M-C$_4$H$_8$)$^+$ NMR (250 MHz; J in Hz; CDCl$_3$)in ppm 4.21(t; J=6.5; 2H); 3.90 (quint.; J=8.0; 1H); 2.54 (m; 2H); 2.34 (m; 2H); 2.02 (m; 2H); 1.68 (m; 2H); 1.4 (sext.; J=7.2; 2H); 0.95 (t; J=7.2; 3H).

Stage b) Potassium cyclobutane-sulphonate

Cyclobutane-sulphonic acid n-butyl ester (14.81 g; 77 mmol) is dissolved in a 1/1 dimethoxyethane/water mixture (220 ml), potassium thiocyanate (7.78 g; 80 mmol) is added and the mixture is boiled under reflux for 20 hours. The reaction mixture is concentrated to half The aqueous phase is separated off, washed twice with ether and evaporated. The residue is stirred with ethanol (200 ml) at −10° C. and the white crystals are filtered off with suction.

Yield: 10.77 g (80.2%) potassium cyclobutane-sulphonate as white crystals. MS (ISN): 135.2 (M−K)⁻

Stage c) Cyclobutane-sulphonyl chloride

Potassium cyclobutane-sulphonate (10.76 g; 62 mmol) is suspended in methylene chloride (50 ml), dimethylformamide (0.5 ml), as a catalyst, and thionyl chloride (49.3 ml; 68 mmol) are added and the mixture is boiled under reflux for 20 hours. The reaction mixture is concentrated, water is added to the residue and the mixture is extracted with ether. The organic phase is washed with a saturated aqueous sodium chloride solution, dried over sodium sulphate, filtered with suction and concentrated.

Yield: 8.44 g (88%) cyclobutane-sulphonyl chloride as a light-brown liquid GC-MS (ISP): 55 (M−SO$_2$Cl)⁺ NMR (250 MHz; J in Hz; CDCl$_3$)in ppm 4.43 (quint.; J=7.7; 1H); 2.69 (m; 2H); 2.50 (m; 2H); 2.09 (m; 2H).

EXAMPLE 41

Analogously to example 4, as shown in equation 2, compounds of the formula XIII are prepared from compounds of the formula VIII.

Equation 2, (XIII)→(VIII)

(41a) Tetrahydropyran-4-sulphonic acid 4'-amino-4-(2,4-diamino-pyrimidin-5-ylmethyl)-6-ethoxy-3'-methyl-biphenyl-2-yl ester N-(4-Bromo-2-methyl)-2,2,2-trifluoro-acetamide (800 mg; 2.84 mmol), bis(pinacolato)diboron (1.08 g; 4.25 mmol), potassium acetate (835 mg; 8.51 mmol) and (diphenylphosphino)-dichloro-palladium(II) (119 mg; 0.17 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with tetrahydropyran-4-sulphonic acid 5-(2,4-diamino-pyrimidin-5-ylmethyl)-3-ethoxy-2-iodo-phenyl ester (379 mg; 0.71 mmol), tetrakis-triphenylphosphine-palladium (49 mg; 0.04 mmol) and aqueous 2 M sodium carbonate solution (5.3 ml; 10.6 mmol) in a 4/1 dimethoxyethane/ethanol mixture (15 ml). 261 mg (72%) tetrahydropyran-4-sulphonic acid 4'-amino-4-(2,4-diamino-pyrimidin-5-ylmethyl)-6-ethoxy-3'-methyl-biphenyl-2-yl ester are obtained as a brown foam.

MS (ISP): 514.3 (M+H)⁺

(41b) Tetrahydronyran-4-sulphonic acid 4'-amino-4-(2,4-diamino-pyrimidin-5-ylmethyl)-6-ethoxy-3'-fluoro-biphenyl-2-yl ester N-(4-Bromo-3-fluoro-phenyl)-2,2,2-trifluoroacetamide (900 mg; 3.15 mmol), bis-(pinacolato)diboron (1,198 mg; 4.7 mmo),potassium acetate (926 mg; 9.44 mmol) and (diphenylphosphino)-dichloro-palladium(II) (132 mg; 0.19 mmol) in 60 ml dioxane are stirred at 80° C. for 3 hours. Half of this batch is concentrated, water is added and the mixture is extracted with ethyl acetate. The combined organic phases are washed with a saturated aqueous sodium chloride solution, dried over magnesium sulphate, filtered with suction and concentrated.

The product obtained in this way is treated with tetrahydropyran-4-sulphonic acid 5-(2,4-diamino-pyrimidin-5-ylmethyl)-3-ethoxy-2-iodo-phenyl ester (421 mg; 0.79 mmol), tetrakis-triphenylphosphine-palladium (55 mg; 0.05 mmol) and aqueous 2 M sodium carbonate solution (6 ml; 12 mmol) in a 4/1 dimethoxyethane/ethanol mixture (15 ml). 245 mg (60%) tetrahydropyran-4-sulphonic acid 4'-amino-4-(2,4-diamino-pyrimidin-5-ylmethyl)-6-ethoxy-3'-fluoro-biphenyl-2-yl ester are obtained as a brown foam.

MS (ISP): 518.3 (M+H)⁺

The following is prepared analogously to example 2a:

(41c) Tetrahydropyran-4-sulphonic acid 3'-amino-4-(2,4-diamino-pyrimidin-5-ylmethyl)-6-ethoxy-biphenyl-2-yl ester Starting from tetrahydropyran-4-sulphonic acid 5-(2,4-diamino-pyrimidin-5-ylmethyl)-3-ethoxy-2-iodo-phenyl ester (250 mg; 0.5 mmol), 3-aminophenylboron acid (109 mg; 0.7 mmol) tetrakis-triphenylphosphine-palladium (34 mg; 0.03 mmol) and aqueous 2 M sodium carbonate solution (3.5 ml; 7.0 mmol) in a 4/1 dimethoxy-ethane/ethanol mixture (10 ml), 167 mg (71%) tetrahydropyran-4-sulphonic acid 3'-amino-4-(2,4-diamino-pyrimidin-5-ylmethyl)-6-ethoxy-biphenyl-2-yl ester are obtained as a white foam.

MS (ISP): 500.3 (M+H)⁺

The Above Starting Compound tetrahydropyran-4-sulphonic acid 5-(2,4-diamino-pyrimidin-5-ylmethyl)-3-ethoxy-2-iodo-phenyl ester is Prepared as Follows, cf. Equation 2, (XII)→(XIII)

5-(3-Ethoxy-5-hydroxy-4-iodo-benzyl)-pyrimidine-2,4-diamine (see example 32 stage a) (2,300 mg; 5.96 mmol) is dissolved in tetrahydrofuran (70 ml), potassium tert-butylate (1,000 mg; 8.9 mmol) is added and the mixture is cooled to −20° C. Tetrahydropyran-4-sulphonyl chloride (2.2 g; 11.9 mmol) is added at this temperature and the mixture is then stirred for one hour at −20° C. The reaction mixture is poured on to ice-water and extracted twice with ethyl acetate. The organic phase is dried over sodium sulphate, the salts are filtered off and the solvent is evaporated off. The residue is chromatographed over silica gel with methylene chloride 1 methanol (19/1) and 0.5% ammonia. The pure fractions are co mbidand the solvent is evaporated off.

Yield: 1,370 mg (43%) tetrahydropyran-4-sulphonic acid 5-(2,4-diamino-pyrimidin-5-ylmethyl)-3-ethoxy-2-iodo-phenyl ester as a white solid.

MS (ISP): 535.2 (M+H)⁺

The tetrahydropyran-4-sulphonyl chloride Employed is Prepared as Follows (Stages a–b):

Stage a) 4,4'-Dithiobis-tetrahydro-pyran

Sodium sulphide (42.2 g; 35%; 188.8 mmol) and sulphur (3.33 g; 104 mmol) are suspended in water (120 ml) and the suspension is stirred for 1.5 hours at 60° C. Benzene (250 ml), followed by tetrabutylammonium bromide (0.61 g; 1.89 mmol) and 4-bromo-tetrahydropyran (7.79 g; 47.2 mmol) are added and the entire mixture is stirred at 60° C. for four hours. The reaction mixture is poured on to ice-water and extracted twice with ether. The organic phase is dried over sodium sulphate, the salts are filtered off and the solvent is evaporated off.

Yield: 2.41 g (44%) 4,4'-dithiobis-tetrahydropyran as a yellow oil. MS (ISP): 234 (M)⁺

Stage b) Tetrahydropyran-4-sulphonyl chloride 4,4'-Dithiobis-tetrahydropyran (2.41 g; 10.3 mmol) is dissolved in ether (250 ml), iodosobenzene (13.25 g; 41.1 mmol) and hydrochloric acid (117 ml; 37%) are added at room temperature and the mixture is stirred for one hour. The reaction mixture is poured on to a saturated aqueous sodium carbonate solution and extracted twice with ether. The combined organic phases are dried over sodium sulphate, the salts are filtered off and the solvent is evaporated off. The residue is chromatographed over silica gel with n-hexane/ethyl acetate (7/3). The pure fuictions are combined and the solvent is evaporated off.

Yield: 2.47 g (65%) tetrahydropyran-4-sulphonyl chloride as a light-yellow liquid. MS (ISP): 149 (M-Cl)$^+$

EXAMPLE 42

Analogously to example 2, the compounds of the formula VIII, equation 2, are prepared from the corresponding compounds of the formula XIII.

(42a) Tetrahydrofuran-2-yl-methanesulphonic acid 3'-amino-4-(2,4-diamino-pyrimidin-5-ylmethyl)-6-ethoxy-biphenyl-2-yl ester Starting from tetrahydrofuran-2-yl)-methanesulphonic acid 5-(2,4-diamino-pyrimidin-5-ylmethyl)-3-ethoxy-2-iodo-phenyl ester (220 mg; 0.5 mmol), 3-aminophenyl-boron acid (98 mg; 0.63 mmol), tetrakis-triphenylphosphine-palladium (29 mg; 0.03 mmol) and aqueous 2 M sodium carbonate solution (3.2 ml; 6.4 mmol) in a 4/1 dimethoxyethane/ethanol mixture (10 ml) (52%) tetrahydrofuran-2-yl-methanesulphonic acid 3'-amino-4-(2, 4-diamino-pyrimidin-5-ylmethyl)-6-ethoxy-biphenyl-2-yl ester are obtained as a yellow foam.

MS (ISP): 500.3 (M+H)$^+$ (42b) Tetrahydrofuran-2-yl-methanesulphonic acid 4'-amino-4-(2,4-diamino-primidin-5-ylmethyl)-6-ethoxy-3'-fluoro-biphenAl-2-yl ester N-(4-Bromo-3-fluoro-phenyl)-2,2,2-trifluoroacetamide (471 mg; 1.65 mmol), bis-(pinacolato)diboron (628 mg; 2.47 mmol), potassium acetate (485 mg; 4.9 mmol) and (diphenylphosphino)-dichloro-palladium(II) (69 mg; 0.10 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with tetrahydrofuran-2-yl-methanesulphonic acid 5-(2, 4-diamino-pyrimidin-5-ylmethyl)-3-ethoxy-2-iodo-phenyl ester (220 mg; 0.41 mmol), tetrakis-triphenylphosphine-palladium (57 mg; 0.05 mmol) and aqueous 2 M sodium carbonate solution (4.1 ml; 8.2 mmol) in a 4/1 dimethoxy-ethanelethanol mixture (10 ml), 170 mg (80%) tetrahydrofuran-2-yl-methanesulphonic acid 4'-amino-4-(2, 4-diamino-pyrimidin-5-ylmethyl)-6-ethoxy-3'-fluoro-biphenyl-2-yl ester are obtained as a brown foam.

MS (ISP): 518.3 (M+H)$^+$ (42c) Tetrahydrofuran-2-yl-methanesulphonic acid 4'-amino-4-(2,4-diamino-pyrimidin-5-ylmethyl)-6-ethoxy-3'-methyl-biphenyl-2-yl ester N-(4-Bromo-2-methyl)-2,2,2-trifluoro-acetamide (465 mg; 1.65 mmol), bis-(pinacolato)diboron (627 mg; 2.47 mmol), potassium acetate (485 mg; 4.94 mmol) and (diphenylphosphino)-dichloro-palladium(II) (69 mg; 0.10 mmol) in 60 ml dioxane are stirred at 80° C. for 3 hours. The reaction mixture is concentrated, water is added to the residue and the mixture is extracted with ethyl acetate. The combined organic phases are washed with a saturated aqueous sodium chloride solution, dried over magnesium sulphate, filtered with suction and concentrated. After reaction with tetrahydrofuran-2-yl-methanesulphonic acid 5-(2, 4-diamino-pyrimidin-5-ylmethyl)-3-ethoxy-2-iodo-phenyl ester (220 mg; 0.71 mmol), tetrakis-triphenylphosphine-palladium (57 mg; 0.05 mmol) and aqueous 2 M sodium carbonate solution (4.1 ml; 8.2 mmol) in 4/1 dimethoxyethane/ethanol (20 ml), 66 mg (31%) tetrahydrofuran-2-yl-methanesulphonic acid 4'-amino-4-(2, 4-diamino-pyrimidin-5-ylmethyl)-6-ethoxy-3'-methyl-biphenyl-2-yl ester are obtained as a brown foam.

MS (ISP): 514.3 (M+H)$^+$

The Above Starting Compound tetrahydrofuran-2-yl-methanesulphonic acid 5-(2,4-diamino-pyrimidin-5-ylmethyl)-3-ethoxy-2-iodo-phenyl ester is Prepared as Follows, cf. Equation 2, (XII)→(XIII)

5-(3-Ethoxy-5-hydroxy-4-iodo-benzyl)-pyrimidine-2,4-diamine (see example 32 stage a) (3.00 g; 7.77 mmol) is dissolved in tetrahydrofuran (50 ml), potassium tert-butylate (1.31 g; 11.65 mmol) is added and the mixture is cooled to −20° C. Tetrahydrofuran-2-yl-methanesulphonyl chloride (4.3 g; 23.3 mmol) is added at this temperature and the mixture is stirred for one hour at −20° C. The reaction mixture is poured on to ice-water and extracted twice with ethyl acetate. The combined organic phases are dried over sodium sulphate, the salts are filtered off and the solvent is evaporated off. The residue is chromatographed over silica gel with methylene chloride/methanol (19/1) and 0.5% ammonia. The pure fractions are combined and the solvent is evaporated off.

Yield: 1,690 mg (41%) tetrahydrofuran-2-yl-methanesulphonic acid 5-(2,4-diamino-pyrimidin-5-ylmethyl)-3-ethoxy-2-iodo-phenyl ester as a yellow foam.

MS (ISP): 535.2 (M+H)$^+$

The tetrahydrofuran-2-yl-methanesulphonyl chloride Employed is Prepared as Follows (Stages a,b):
Stage a) Dithio-bis-(tetrahydrofuran-2-yl)-methan-yl Sodium sulphide (72.9 g; 35%; 327 mmol) and sulphur (5.77 g; 180 mmol) are suspended in water (130 ml) and the suspension is stirred for 1.5 hours at 60° C. Benzene (300 ml), followed by tetrabutylammonium bromide.(1.06 g; 3.27 mmol) and tetrahydrofuran-2-yl-methyl bromide (15 g; 81.8 mmol) are added and the mixture is stirred at 60° C. for four hours. The reaction mixture is poured on to ice-water and extracted twice with ether. The organic phase is dried over sodium sulphate, the salts are filtered off and the solvent is evaporated off.

Yield: 10.2 g (100%) dithio-bis-(tetrahydrofuran-2-yl)-methan-yl as a pale brown liquid. MS (ISP): 234 (M)$^+$
Stage b) Tetrahydrofuran-2-yl-methanesulphonyl chloride Dithiobis-(tetrahydrofuran-2-yl)-methan-yl (4.07 g; 32.6 mmol) is dissolved in ether (300 ml). iodosobenzene (42 g; 130 mmol) and hydrochloric acid (55 ml; 37%) are added at room temperature and the entire mixture is stirred for one hour. The reaction mixture is poured on to a saturated sodium carbonate solution and extracted twice with ether. The organic phases are dried over sodium sulphate, the salts are filtered off and the solvent is evaporated off. The residue is chromatographed over silica gel with n-hexanelethyl acetate (7/3). The pure fractions are combined and the solvent is evaporated off.

Yield: 6.76 g (56%) tetrahydrofuran-2-yl-methanesulphonyl chloride as a slightly pale brown liquid. NMR (250 MHz; J in Hz; CDCl₃)in ppm: 4.58 (m; 1H); 4.02–3.75 (m; 4H); 2.25 (m; 1H); 1.99 (m; 2H); 1.76 (m; 1H).

EXAMPLE 43

Analogously to example 2 (nos. 43a, 43b, 43d) or example 4 (no. 43c), compounds of the formula IX are prepared from the corresponding compounds of the formula XIV, cf. equation 2.

(43a) Dimethylsulphamic acid 4-(2,4-diamino-pyrimidin-5-ylmethyl)-6-ethoxy-4'-methylsulphanyl-biphenyl-2-yl ester Starting from dimethylsulphamic acid 5-(2,4-diamino-pyrimidin-5-ylmethyl)-3-ethoxy-2-iodo-phenyl ester (509 mg; 1.0 mmol) and 4-(methylthio)phenylboron acid (269 mg; 1.55 mmol), 410 mg (71%) dimethylsuiphamic acid 4-(2,4-diamino-pyrimidin-5-ylmethyl)-6-ethoxy-4'-methylsulphanyl-biphenyl-2-yl ester are obtained as a colourless powder.

MS (ISP): 490.3 (M+H)$^+$

(43b) Dimethylsulphamic acid 4-(2,4-diamino-pyrimidin-5-ylmethyl)-6-ethoxy-biphenyl-2-yl ester Starting from dimethylsulphamic acid 5-(2,4-diamino-pyrimidin-5-ylmethyl)-3-ethoxy-2-iodo-phenyl ester (280 mg; 0.57 mmol) and phenylboron acid (118 mg; 0.96 mmol),206 mg (82%) dimethylsulphamic acid 4-(2,4-diamino-pyrimidin-5-ylmethyl)-6-ethoxy-biphenyl-2-yl ester are obtained as a colourless powder.

MS (ISP): 444.4 (M+H)$^+$

(43c) Dimethylsulphamic acid 4'-amino-3'-cyano-4-(2,4-diamino-gvrimidin-5-ylmethyl)-6-ethoxy-biphenyl-2-yl ester Starting from dimethylsulphamic acid 5-(2,4-diamino-pyrimidin-5-ylmethyl)-3-ethoxy-2-iodo-phenyl ester (148 mg; 0.3 mmol) and 2-amino-5-iodo-benzonitrile (143 mg; 0.59 mmol), 12 mg (4%) dimethyl-sulphamic acid 4'-amino-3'-cyano-4-(2,4-diamino-pyrimidin-5-ylmethyl)-6-ethoxy-biphenyl-2-yl ester are obtained as a colourless powder.

MS (ISP): 484.4 (M+H)$^+$

(43d) Dimethylsulphamic acid 5-(2,4-diamino-pyrimidin-5-ylmethyl)-3-ethoxy-2-(1H-indol-5-yl)-phenyl ester Starting from dimethylsulphamic acid 5-(2,4-diamino-pyrimidin-5-ylmethyl)-3ethoxy-2-iodo-phenyl ester (470 mg; 0.95 mmol) and 5-(1H-indolyl)-boron acid (230 mg; 1.43 mmol), 373 mg (81%) dimethylsulphamic acid 5-(2,4-diamino-pyrimidin-5-ylmethyl)-3-ethoxy-2-(1H-indol-5-yl)-phenyl ester are obtained as a colourless powder.

MS (ISP): 483.3 (M+H)$^+$

The Above Starting Compound dimethylsulphamic acid 5-(2,4-diamino-pyrimidin-5-ylmethyl)-3-ethoxy-2-iodo-phenyl ester is Prepared as Follows, cf. Equation 2, (XII) →(XIII)

5-(3-Ethoxy-5-hydroxy-4-iodo-benzyl)-pyrimidine-2,4-diamine (see example 32) (386 mg; 1.0 mmol) is dissolved in dimethylformamide (31 ml), potassium tert-butylate (137 mg; 1.2 mmol) is added at room temperature and the mixture is stirred for one houL N,N-Dimethylsulphamoyl chloride (0.129 ml; 1.2 mmol) is then added at 0° C. and the mixture is stirred for 3 hours at 0–5° C. The reaction mixture is evaporated and the residue is chromatographed over silica gel (43 g) with methylene chloride/methanol/NH₄OH conc. (19/11/0.05). The pure fractions are combined and the solvent is evaporated off. The residue obtained is stirred with diethyl ether, filtered off with suction and dried under a high vacuum.

Yield: 229 mg (46%) dimethylsulphamic acid 5-(2,4-diamino-pyrimidin-5-ylmethyl)-3-ethoxy-2-iodo-phenyl ester as a colourless solid. MS (ISP): 494.1 (M+H)$^+$

EXMAPLE 44

N-[4'-(2,4-Diamino-pyrimidin-5-ylmethyl)-2',6'-diethoxy-biphenyl-3-yl]-methanesulphonamide This Compound is Prepared Starting from 5-(3'-Amino-2,6-diethoxy-biphenyl-4-ylmethyl)-pyrimidine-2,4-diamine (Example (2a)):

5-(3'-Amino-2,6-diethoxy-biphenyl-4-ylmethyl)-pyrimidine-2,4-diamine (228 mg; 0.6 mmol) is dissolved in dimethylformamide (6 ml; dried over a molecular sieve), triethylamine (0.090 ml; 0.66 mmol) is added at room temperature, and the mixture is cooled to 0° C. and a solution of methanesulphonyl chloride (0.051 ml; 0.66 mmol) in dimethylformamide (1.0 ml) is added in the course of 5 minutes. After 1 hour at 0–5° C. the reaction mixture is concentrated and the residue is taken up in water, after which the pH is adjusted to 10 by addition of NH₄OH conc. After stirring for 15 minutes the mixture is filtered with suction and the residue is dried under a high vacuum and chromatographed over silica gel (60 g) with methylene chloride/methanol/NH₄OH conc. (19/1/0.05).

Yield: 161 mg (58%) N-[4'-(2,4-diamino-pyrimidin-5-ylmethyl)-2',6'-diethoxy-biphenyl-3-yl]-methanesulphonamide as a colourless powder. MS (ISP): 458.2 (M+H)$^+$

EXAMPLE 45

Methanesulphonic acid 4'-(2,4-diamino-pyrimidin-5-ylmethyl)-2',6'-diethoxy-biphenyl-4-yl ester This compound is prepared starting from 4'-(2,4-diamino-pyrimidin-5-ylmethyl)-2',6'-diethoxy-biphenyl-4-ol (Example (2t)) Analogously to Example 44:

Starting from 4'-(2,4-diamino-pyrimidin-5-ylmethyl)-2',6'-diethoxy-biphenyl-4-ol (300 mg; 0.79 mmol), potassium tert-butylate (instead of triethylamine; 133 mg; 1.18 mmol) in dimethylformamide (10 ml), and from methanesulphonyl chloride (0.080 ml; 1.03 mmol) in dimethylformamide (5.0 ml) at room temperature, 102 mg (22%) methanesulphonic acid 4'-(2,4-diamino-pyrimidin-5-ylmethyl)-2',6'-diethoxy-biphenyl-4-yl ester are obtained as a colourless powder.

MS (ISP): 459.4 (M+H)$^+$

EXAMPLE 46

2-[4'-(2,4-Diamino-pylimidin-5-ylmethyl)-2',6'-diethoxy-biphenyl-4-yloxy]-acetamide This Compound is Prepared Starting from 4'-(2,4-diamino-pyrimidin-5-ylmethyl)-2',6'-diethoxy-biphenyl-4-ol (Example (2t)):

A molecular sieve (0.5 g) and then potassium tert-butylate (180 mg; 1.6 mmol) are added at room temperature to 4'-(2,4-diamino-pyrimidin-5-ylmethyl)-2',6'-diethoxybiphenyl-4-ol (380 mg; 1.0 mmol) in dimethylformamide (10 ml). After stirring for 15 minutes, 2-bromoacetamide (193 mg; 1.4 mmol) is added. After 70 minutes the reaction mixture is concentrated and the residue is chromatographed over silica gel (60 g) with methylene chloride/methanol/ NH$_4$OH conc. (90/10/1).

Yield: 190 mg (43%) 2-[4'-(2,4-diamino-pyrimidin-5-ylmethyl)-2',6'-diethoxy-biphenyl-4-yloxy]-acetamide as a colourless powder. MS (ISP): 438.3 (M+H)$^+$

EXAMPLE 47

3-{1-[4-(2,4-Diamino-pyrimidin-5-yjmethyl)-6-ethoxy-4'-hydroxy-biphenyl-2-loxymethyl]-cycloprropyl}-propionitrile This Compound is Prepared Starting from (E)-3-[1-[4-(2,4-diamino-pyrimidin-5-ylmethyl)-6-ethoxy-4'-hydroxy-biphenyl-2-yloxymethyl]-cyclopropyl]-acrylonitrile (example 8d):

(E)-3-[1-[4-(2,4-Diamino-pyrimidin-5-ylmethyl)-6-ethoxy-4'-hydroxy-biphenyl-2-yloxymethyl]-cyclopropyl]-acrylonitrile (example 8d) (190 mg; 0.415 mmol) is suspended in isopropyl alcohol (20 ml), and sodium borohydride (103 mg; 2.69 mmol) is added in portions in the course of approx. 10 minutes. The mixture is then boiled under reflux for 23 hours under argon, cooled to room temperature and concentrated. The residue is stirred with water (27 nil) and the pH is adjusted to 2 with 1 N aqueous hydrochloric acid. The pH is then adjusted to 9 by addition of NH$_4$OH conc. and the suspension obtained is stirred for one hour at room temperature and filtered with suction. The solid is washed with a little water and dried under a high vacuum.

Yield: 180 mg (94%) 3-{1-[4-(2,4-diamino-pyrimidin-5-ylmethyl)-6ethoxy-4'-hydroxy-biphenyl-2-yloxymethyl]-cyclopropyl}-propionitrile. MS (ISP): 460.4 (M+H)$^+$

EXAMPLE 48

5-[4-(2,4-Diamino-pyrimidin-5-ylmethyl) 6-ethoy-4'-hydro-biPhenyl-2-xyloxy]-4,4-dimethyl-pentanenitrile This Compound is Prepared Starting from (E)-5-[4-(2,4-diamino-pyrimidin-5-ylmethyl)-6-ethoxy-4'-hydroxy-biphenyl-2-yloxy]-4,4-dimethyl-pent-2-enenitrile (Example (8b)) Analogously to Example 47:

Starting from (E)-5-[4-(2,4-diamino-pyrimidin-5-ylmethyl)-6-ethoxy-4'-hydroxy-biphenyl-2-yloxy]-4,4-dimethyl-pent-2-enenitrile (110 mg; 0.239 mmol), 85 mg (77%) 5-[4-(2,4-Diamino-pyrimidin-5-ylmethyl)-6-ethoxy-4'-hydroxy-biphenyl-2-yloxy]-4,4-dimethyl-pentanenitrile are obtained as a pale brown powder.

MS (ISP): 462.3 (M+H)$^+$

EXAMPLE 49

5-[3,5-Diethoxy-4-(1,2,3,4-tetrahydro-quinolin-6-yl)-benzyl]-pyrimidine-2,4-diamine Nickel(II) chloride hexahydrate (200 mg; 0.84 mmol) is added to a solution of 5-(3,5-diethoxy-4-quinolin-6-yl-benzyl)-pyrinidine-2,4-diamine (example (4m)) (200 mg; 0.48 mmol) in 5.5 ml MeOH while gassing with argon. Sodium borohydride (73 mg, 1.93 mmol) is added in portions. The mixture is stirred at room temperature for 3 hours. After evaporation of the reaction mixture, the residue is stirred in 20 ml 10% aqueous hydrochloric acid for 10 minutes. The solution is adjusted to pH 10 with 25% aqueous ammonia solution and extracted three times with 25 ml methylene chloride each time. The combined organic phases are dried over magnesium sulphate and concentrated. The crude product is chromatographed over silica gel with methylene chloride/methanol (19/1). 125 mg (62%) 5-[3,5-diethoxy-4-(1,2,3,4-tetrahydro-quinolin-6-yl)-benzyl]-pyrimidine-2,4-diamine are obtained as a colourless powder.

MS (ISP): 420.3 (M+H)$^+$.

EXAMPLE 50

5-[2,6-Diethoxy-3'-(2-methoxy-ethoxy)-biphenyl-4-ylmethyl]-pyrimidine-2,4-diamine This Compound is Prepared Starting from 4'-(2,4-diamino-pyrimidin-5-ylmethyl)-2',6'-diethoxy-biphenyl-3-ol (Example (5d)):

4'-(2,4-Diamino-pyrimidin-5-ylmethyl)-2',6'-diethoxy-biphenyl-3-ol (200 mg; 0.526 mmol) is suspended in dimethylformamide (5 ml; dried over a molecular sieve), and potassium tert-butylate (83 mg; 0.736 mmol) is added at room temperature. 2-Bromoethyl methyl ether (0.059 ml; 0.63 mmol) in dimethylformamide (5 ml; dried over a molecular sieve) is added in the course of 35 minutes to the solution formed. After stirring at room temperature for 12 hours, the reaction mixture is concentrated and the residue is stirred successively with water (twice) and diethyl ether, filtered off with suction and dried under a high vacuum.

Yield: 180 mg (78%) 5-[2,6-diethoxy-3'-(2-methoxy-ethoxy)-biphenyl-4-ylmethyl]-pyrimidine-2,4-diamine as a light-beige powder. MS (ISP): 439.4 (M+H)$^+$

EXAMPLE 51

5-(3'-Amino-2,6-di-n-propoxy-biphenyl-4-ylmethyl)-pyrimidine-2,4-diamine

Prepared Analogously to Example 2a) (Suzuki Coupling with Boron Acid):

Starting from 5-(4-iodo-3,5-di-n-propoxy-benzyl)-pyrimidine-2,4-diamine (200 mg; 0.45 mmol) and 3-aminophenyl-boron acid (175 mg; 1.13 mmol), 110 mg (60%) 5-(3'-amino-2,6-di-n-propoxy-biphenyl-4-ylmethyl)-pyrimidine-2,4-diamine are obtained as a colourless powder.

MS (ISP): 408.4 (M+H)$^+$

The Above Starting Compound 5-(4-iodo-3,5-di-n-propoxy-benzyl)-pyrimidine-2,4-diamine is Prepared by the Following Sequence (Stages a)-f)):

Stage a) 4-Iodo-3,5-di-n-propoxy-benzoic acid methyl ester 3,5-Dihydroxy-4-iodo-benzoic acid methyl ester (example 1, stage b) (5 g; 17 mmol) is dissolved in dimethylformamide (125 ml), and potassium tert-butylate (3.81 g; 34 mmol) is added at room temperature. After stirring for one hour, n-propyl bromide (5.0 g, 40 mol) in dimethylformamide (5 ml) is added dropwise in the course of one hour. The reaction mixture is then heated to 40° C. and stirred for 48 hours at this temperature. The reaction mixture is cooled to room temperature, the solvent is evaporated, water and 1 N aqueous hydrochloric acid are added to the residue and the mixture is extracted with ethyl acetate. The organic phases are washed with an aqueous saturated sodium chloride solution, dried over magnesium sulphate and concentrated.

Yield: 4.2 g (68%) 4-iodo-3,5-dipropoxy-benzoic acid methyl ester as a yellow powder. MS: 378 (M)

Stage b) (4-Iodo-3,5-di-n-propoxy-phenyl)-methanol
Prepared Analogously to Example 6, Stage c):
Starting from 4-iodo-3,5-di-n-propoxy-benzoic acid methyl ester (4.2 g; 11 mmol), 3.8 g (99%) (4-iodo-3,5-di-n-propoxy-phenyl)-methanol are obtained as a colourless powder after crystallization from n-hexane.
MS: 350 (M)

Stage c) 4-Iodo-3,5-di-n-propoxy-benzaldehyde
Prepared Analogously to Example 6, Stage d):
Starting from (4-iodo-3,5-di-n-propoxy-phenyl)-methanol (3.8 g; 11 mmol), 3.36 g (87%) 4-iodo-3,5-di-n-propoxy-benzaldehyde are obtained as a colourless powder.
MS: 348 (M)

Stage d) (E/Z)-2-(4-Iodo-3,5-di-n-propoxy-benzyl)-3-phenylamino-acrylonitrile
Prepared Analogously to Example 6, Stage e):
Starting from 4-iodo-3,5-di-n-propoxy-benzaldehyde (3.36 g; 9.6 mmol), 3.0 g (65%) (E/Z)-2-(4-iodo-3,5-di-n-propoxy-benzyl)-3-phenylamino-acrylonitrile are obtained as a brown, very viscous oil after chromatography over silica gel with ethyl acetate/n-hexane 7/3.
MS (ISP); 477.2 (M+H)$^+$ Stage e) 5-(4-Iodo-3,5-di-n-propoxy-benzyl)-pyrimidine-2,4-diamine
Prepared Analogously to Example 6, Stage f):
Starting from (E/Z)-2-(4-iodo-3,5-di-n-propoxy-benzyl)-3-phenylamino-acrylonitrile (3.0 g; 6.2 mmol), 1.8 g (65%) 5-(4-iodo-3,5-di-n-propgxy-benzyl)-pyrimidine-2,4-diamine are obtained as a beige powder after chromatography over silica gel with methylene chloride/methanol/NH4OH conc. (90/10/1).
MS (ISP): 443.2 (M+H)$^+$

EXAMPLE 52

4'-(2,4-Diamino-pyrimidin-5-ylmethyl)-2',6'-digropobiphenyl-3-ol

Prepared Analogously to Example 2a) (Method A Suzuki Coupling with Boron Acid):
Starting from 5-(4-iodo-3,5-di-n-propoxy-benzyl)-pyrimidine-2,4-diamine (100 mg; 0.22 mmol) and 3-hydroxyphenyl-boron acid (78 mg; 0.56 mmol), 153 mg (73%) 4'-(2,4-diamino-pyrimidin-5-ylmethyl)-2',6'-dipropoxy-biphenyl-3-ol are obtained as a colourless powder.
MS (ISP): 409.3 (M+H)$^+$ The Above Starting Compound 5-(4-iodo-3,5-dipropoxy-benzyl)-pyrimidine-2,4-diamine is Prepared as Described in Example 51.

EXAMPLE 53

4'-(2,4-Diamino-pyrimidin-5-ylmethyl)-6'-ethoxy-2'-n-propoxy-biphenyl-3-ol

Prepared Analogously to Example (7a):
Starting . . . [sic] 4'-(2,4-diamino-pyrimidin-5-ylmethyl)-6'-ethoxy-2'-hydroxy-biphenyl-3-yl acetate (300 mg; 0.76 mmol) and 1-bromo-n-propane (0.07 ml; 0.912 mmol), 70 mg (23%) 4'-(2,4-diamino-pyrimidin-5-ylmethyl)-6'-ethoxy-2'-propoxy-biphenyl-3-ol are obtainred as a colourless powder after treatment with aqueous saturated sodium bicarbonate solution (2 ml) and methanol (5 ml) for 2 hours at room temperature.
MS (ISP): 395.3 (M+H)$^+$ The Above Starting Compound 4'-(2,4-diamino-pyrimidin-5-ylmethyl)-6'-ethoxy-2'-hydroxy-biphenyl-3-yl acetate is Prepared by the Following Sequence (Stages a)-c)):

Stage a) 2'-Benzyloxy-4'-(2,4-diamino-pyrimidin-5-ylmethyl)-6'-ethoxy-biphenyl-3-ol
Prepared Analogously to Example 2a (Suzuki Coupling with Boron Acid):
Starting from 5-(3-benzyloxy-5-ethoxy-4-iodo-benzyl)-pyrimidine-2,4-diamine (example 6) (3.4 g; 7.12 mmol) and 3-hydroxyphenyl-boron acid (1.97 g; 14.3 mmol), 2.34 g (74%) 2'-benzyloxy-4'-(2,4-diamino-pyrimidin-5-ylmethyl)-6'-ethoxy-biphenyl-3-ol are obtained as a colourless powder.
MS (ISP): 443.3 (M+H)$^+$ Stage b) 2'-Benzyloxy-4'-(2,4-diamino-pyrimidin-5-ylmethyl)-6'-ethoxy-biphenyl-3-yl acetate
Potassium tert-butylate (602 mg; 5.36 mmol) in dimethylformamide (40 ml) is added to 2'-benzyloxy-4'-(2,4-diamino-pyrjmidin-5-ylmethyl)-6'-ethoxbiphenyl-3-ol (1.9 g; 4.3 mmol) in dimethylformamide (40 ml) at 0–5° C. After stirring for 15 minutes at this temperature, acetic anhydride (0.406 ml; 4.3 mmol) is added. After 3 hours at 0–5° C. potassium tert-butylate (60 mg; 0.53 mmol) and then acetic anhydride (0.08 ml; 0.85 mmol) are added again and stirring is continued for 16 hours at room temperature. The reaction mixture is concentrated, the residue is stirred with water and the mixture is filtered with suction. The crude product is recrystallized from isopropanol.
Yield: 1.57 g (75%) 2'-benzyloxy-4'-(2,4-diamino-pyrimidin-5-ylmethyl)-6'-ethoxy-biphenyl-3-yl acetate as a colourless powder. MS (ISP): 485.3 (M+H)$^+$ Stage c) 4'-(2,4-Diamino-pyrimidin-5-ylmethyl)-6'-ethoxy-2'-hydroxy-biphenyl-3-yl) acetate
2'-Benzyloxy-4'-(2,4-diamino-pyrimidin-5-ylmethyl)-6'-ethoxy-biphenyl-3-yl acetate (1.5 g; 3.09 mmol) is hydrogenated in acetic acid conc. (45 ml) and ethanol (15 ml) over Pd/C 10% (380 mg) for 2 hours. The catalyst is filtered off with suction and rinsed with ethanol and the solvent is evaporated off. The residue is stirred with water and the pH is adjusted to 7 by addition of aqueous saturated sodium bicarbonate solution. The suspension formed is filtered with suction and the residue is dried under a high vacuum.
Yield: 1.05 g (86%) 4'-(2,4-diamino-pyrimidiri-5-ylmethyl)-6'-ethoxy-2'-hydroxy-biphenyl-3-yl acetate as a colourless powder. MS (ISP): 495.2 (M+H)$^+$

EXAMPLE 54

2'-Cyclopropanomethoxy-4'-(2,4-diamino-pyrimidin-5-ylmethyl)-6'-ethoxy-biphenyl-3-ol Prepared Analogously to Example 55:
Starting from 4'-(2,4-diamino-pyrimidin-5-ylmethyl)-6'-ethoxy-2'-hydroxy-biphenyl-3-yl acetate (300 mg; 0.76 mmol) and bromomethyl-cyclopropane (123 mg; 0.91 mmol), 101 mg (31%) 2'-cyclopropylmethoxy-4'-(2,4-diamino-pyrimidin-5-ylmethyl)-6'-ethoxy-biphenyl-3-ol are obtained as a colourless powder.
MS (ISP): 407.3 (M+H)$^+$ The Above Starting Compound 4'-(2,4-diamino-pyrimidin-5-ylmethyl)-6'-ethoxy-2'-hydroxy-biphenyl-3-yl acetate is prepared as described in example 53.

EXAMPLE 55

2-[2'-Cyclopropylmethoxy-4'-(2,4-diamino-pyrimidin-5-ylmethyl)-6'-ethoxy-biphenyl-4-yloxy]-ethanol Prepared Analogously to Example 46:
Starting from 2'-cyclopropylmethoxy-4'-(2,4-diamino-pyrimidin-5-ylmethyl)-6'-ethoxy-biphenyl-4-ol (example 8h) (406 mg; 1 mmol) and 2-(2-chloroethoxy)-tetrahydro-2H-pyran (0.47 ml; 3.2 mmol), 95 mg (21%) 2-[2'-cyclopropylmethoxy-4'-(2,4-diamino-pyrimidin-5-ylmethyl)-6'-ethoxy-biphenyl-4-yloxy]-ethanol are obtained as a light-yellow powder after splitting off of the protective group under acid conditions (HCl 3N in methanol at room temperature).

MS (ISP): 451.3 (M+H)$^+$

EXAMPLE 56

5-[2-Cyclopropylmethyl-6-ethoxy-4'-(2-morpholin-4-yl-ethoxy)-biphenyl-4-ylmethyl]-pyrimidine-2,4-diamine Prepared Analogously to Example 46:

Starting from 2'-cyclopropylmethoxy-4'-(2,4-diamino-pyrimidin-5-ylmethyl)-6'ethoxy-biphenyl-4-ol (example 8h) (300 mg; 0.74 mmol) and 4-(2-chloroethyl)-morpholine hydrochloride (170 mg; 0.89 mmol), 129 mg (25%) 5-[2-cyclopropylmethoxy-6-ethoxy-4'-(2-morpholin-4-yl-ethoxy)-biphenyl-4-ylmethyl]-pyrimidine-2,4-diamine are obtained as a colourless powder.

MS (ISP): 520.3 (M+H)$^+$

EXAMPLE 57

Methanesulphonic acid 2'-cylopropylmethoxy-4'-(2,4-diamino-pyrimidin-5-ylmethyl)-6'-ethoxy-biphenyl-4-yl ester Prepared Analogously to Example 45:

Starting from 2'-qdopropylmethoxy-4'-(2,4-diamino-pyrimidin-5-ylmethyl)-6'-ethoxy-biphenyl-4-ol (example 8h) (300 mg; 0.74 mmol) and methanesulphonyl chloride (0.063 ml; 0.81 mmol), 152 mg (42%) methanesulphonic acid 2'-cyclopropylmethoxy-4'-(2,4-diamino-pyrimidin-5-ylmethyl)-6'-ethoxy-biphenyl-4-yl ester are obtained as a colourless powder.

MS (ISP): 485.2 (M+H)$^+$

EXAMPLE 58

4'-(2,4-Diamino-pyrimidin-5-ylmethyl)-6'-ethoxy-2'-(propane-2-sulphonyloxy)-biphenyl-4-yl acetate Prepared Analogously to Example 45:

Starting from propane-2-sulphonic acid 4-(2,4-diamino-pyrimidin-5-ylmethyl)-6-ethoxy-4'-hydroxy-biphenyl-2-yl ester (example 15c) (137 mg; 0.30 mmol), potassium tert-butylate (42 mg; 0.37 mmol) and acetic anhydiide (0.028 ml; 0.30 mmol) in dimethylformamide (3.5 ml) at 0–5° C. (15 minutes) and then room temperature (3 hours), 39 mg (27%) 4'-(2,4-diamino-pyrimidin-5-ylmethyl)-6'-ethoxy-2'-(propane-2-sulphonyloxy)-biphenyl-4-yl acetate are obtained as a colourless powder.

MS (ISP): 501.3 (M+H)$^+$

EXAMPLE 59

[2'-Cycloproplmethoxy-4'-(2,4-diamino-pyrimidin-5-ylmethyl)-6'-ethoxy-biphenyl-4-yloxy]-acetonitrile Prepared Analogously to Example 46:

Starting from 2'-cyclopropylmethoxy-4'-(2,4-diamino-pyrimidin-5-ylmethyl)-6'-ethoxy-biphenyl-4-ol (example 8h) (203 mg; 0.5 mmol) and bromoacetonitrile (0.06 ml; 0.9 mmol), 85 mg (38%) [2'-cyclopropylmethoxy-4'-(2,4-diamino-pyrimidin-5-ylmethyl)-6'-ethoxy-biphenyl-4-yloxy]-acetonitrile are obtained as a beige powder.

MS (ISP): 446.3 (M+H)$^+$

EXAMPLE 60

Dimethylsulphamic acid 4-(2,4-diamino-pyrimidin-5-ylmethyl)-6-ethoxy-4'-methanesulphonyl-biphenyl-2-yl ester Prepared Analogously to Example 2b:

Starting from dimethylsulphamic acid 4-(2,4-diamino-pyrimidin-5-ylmethyl)-6-ethoxy-4'-methylsulphanyl-biphenyl-2-yl ester (example 43a) (342 mg; 0.7 mmol) and m-chloroperbenzoic acid (403 mg; 2.12 mmol), 340 mg (84%) dimethylsulphamic acid 4-(2,4-diamino-pyrimidin-5-ylmethyl)-6-ethoxy-4'-methanesulphonyl-biphenr-2-yl) ester are obtained as a beige powder.

MS (ISP): 522.1 (M+H)$^+$

EXAMPLE 61

(61a) 2-Methyl-propane-1-sulphonic acid 4-(2,4-diamino-pyrimidin-5-ylmethyl)-6-ethoxy-4'-(2-hydroxy-ethoxy)-biphenyl-2-yl ester 2-Methyl-propane-1-sulphonic acid 4-(2,4-diamino-pyrimidin-5-ylmethyl)-6-ethoxy-4'-hydroxy-biphenyl-2-yl ester (example 15f) (85 mg, 0.18 mmol) are [sic] initialy introduced into 2 ml absolute dimethylformamide, 280 mg powdered molecular sieve (4A) and 37 mg (0.32 mmol) potassium tert-butylate are added and the mixture is stirred for 10 min. It is then cooled to 0° C. and 93 mg (0.32 mmol) tert-butyl-(2-iodo-ethoxy)-dimethyl-silane are added. After 10 min at 0° C. and 1 h at room temperature, the reaction mixture is diluted with a mixture of $CH_2Cl_2$/MeOH/25% $NH_3$(90/10/1), filtered and evaporated and the crude product is purified by means of flash chromatography over $SiO_2$ ($CH_2Cl_2$/MeOH/25% $NH_3$(19/1/0.05). 66 mg of the silyl ether of the above compound are obtained here as a colourless oil, which is hydrolysed as follows:

It is dissolved in 1.2 ml tetrahydrofuran, and 1.2 ml 3 N HCl in methanol are added. After 15 min the mixture is neutralized with 10% sodium carbonate solution and extracted with ethyl acetate, and the extract is washed with concentrated aqueous sodium chloride solution, dried over magnesium sulphate and evaporated. Stirring in diethyl ether gives 42 mg of the title compound as a white solid.

MS (ISP): 517.4 (M+H)$^+$

The Following is Prepared Analogously:

(61b) Butane-2-sulphonic acid 4-(2,4-diamino-pyrimidin-5-ylmethyl)-6-ethoxy-4'-(2-hydroxy-ethoxy-biphenyl-2-yl ester Starting from 105 mg (0.22 mmol) 2-methyl-propane-1-sulphonic acid 4-(2,4-diamino-pyrimidin-5-ylmethyl)-6-ethoxy-4'-hydroxy-biphenyl-2-yl ester and 115 mg (0.40 mmol) tert-butyl-(2-iodo-ethoxy)-dimethyl-silane, 56 mg of the title compound are obtained as a colourless foam after splitting off of the silyl protective group under acid conditions.

MS (ISP): 517.3 (M+H)$^+$

EXAMPLE 62

4'-(2,4-Diamino-pyrimidin-5-ylmethyl)-2'-dimethylsulphamoylxy-6'-ethoxy-biphenyl-4-yl acetate Prepared Analogously to Example 45:

Starting from dimethylsulphamic acid 4-(2,4-diamino-pyrimidin-5-ylmethyl)-6-ethoxy-4'-hydroxy-biphenyl-2-yl ester (example 20a) (250 mg; 0.54 mmol), potassium tert-butylate (91 mg; 0.81 mmol) and acetic anhydride (0.061 ml; 0.65 mmol) in dimethylformamide (6 ml) at 0–5° C. (30 minutes) and then room temperature (65 hours), 133 mg (49%) are obtained as a colourless powder.

MS (ISP): 502.2 (M+H)$^+$

EXAMPLE 63

2-Methyl-propane-1-sulphonic acid 4-(2,4-diamino-pyrimidin-5-ylmethyA)-6-ethoxy-4'-(2-methoxethoxy)-biphenyl-2-yl ester 2-Methyl-propane-1-sulphonic acid 4-(2,4-diamino-pyrimidin-5-ylmethyl)-6-ethoxy-4'-hydroxy-biphenyl-2-yl ester (100 mg, 0.21 mmol) are [sic] initially introduced into 2.1 ml abs. dimethylformamide, 320 mg powdered molecular sieve 4A and, after 15 min, 43 mg (0.38 mmol) potassium tert-butylate are added and the mixture is stirred for a further 5 minutes. It is subsequently cooled to 0° C. and 55 mg (0.30 mol) 1-iodo-2-methoxy-ethane are then added. After 1.5 h at 0° C. the reaction mixture is diluted with a mixture of CH$_2$Cl$_2$/MeOH/25% NH$_3$(90/10/1), filtered and evaporated and the crude product is purified by means of flash chromatography over SiO$_2$ (CH$_2$Cl$_2$/MeOH/25% NH$_3$(19/1/0.05). 70 mg of the title compound are obtained here as a colourless foam.

MS (ISP): 531.3 (M+H)$^+$

EXAMPLE 64

Preparation of compounds of the formula VIII, equation 2, from the corresponding compounds of the formula VI.

(64a) Methanesulphonic acid 4-(2,4-diamino-pyrimidin-5-ylmethyl)-6-ethoxy-3'-fluoro-4'-morpholin-4-ylmethyl-biphenyl-2-yl ester 4-(2,4-Diamino-pyrimidin-5-ylmethyl)-6-ethoxy-3'-Auoro-4'-morpholin-4-ylmethyl-biphenyl-2-ol (250 mg, 0.55 mmol) is suspended in 11 ml tetrahydrofuran, 0.5 g powdered molecular sieve is added and the mixture is stirred at room temperature for 15 min. Potassium tert-butylate (93 mg; 0.83 mmol) is added and the suspension is stirred again for 1 hour at room temperature. The beige suspension is then cooled to –20° C., and methanesulphonyl chloride (126 mg; 1.1 mmol) is added. The reaction mixture is stirred for 4 hours at 0° C. and then concentrated. The residue is chromatographed over silica gel with methylene chloride/MeOH (99:1). 99 mg (33%) methanesulphonic acid 4-(2,4-diamino-pyrimidin-5-ylmethyl)-6-ethoxy-3'-fluoro-4'-morpholin-4-ylmethyl-biphenyl-2-yl ester are obtained as a light-yellow powder.

MS (ISP): 523.3 (M+H)$^+$.

(64b) Dimethylsulphamic acid 4-(2,4-diamino-pyrimidin-5-ylmethUl)-6-ethoxy-3'-fluoro-4'-morpholin-4-ylmethyl-biphenyl-2-yl ester, equation 1, (VI)→(IX)

4-(2,4-Diamino-pyrimidin-5-ylmethyl)-6-ethoxy-3'-fluoro-4'-morpholin-4-ylmethyl-biphenyl-2-ol (250 mg, 0.55 mmol) are [sic] suspended in 11 ml tetrahydrofuran, 0.5 g powdered molecular sieve are added and the mixture is stirred for 15 minutes at room temperature. Potassium tert-butylate (93 mg; 0.83 mmol) is added and the suspension is stirred again for 1 hour at room temperature. The beige suspension is then cooled to –20° C., and N,N-dimethylsulphamoyl chloride (158 mg; 1.1 mmol) is added. The reaction mixture is stirred for 4 hours at 0° C. and 2 hours at 10° C and then concentrated. The residue is chromatographed over silica gel with methylene chloride/MeOH (99:1). 151 mg (49%) dimethylsulphamic acid 4-(2,4-diamino-pyrimidin-5-ylmethyl)-6-ethoxy-3'-fluoro-4'-morpholin-4-ylmethyl-biphenyl-2-yl ester are obtained as a light-yellow powder.

MS (ISP): 561.3 (M+H)$^+$.

The Above Starting Compound 4-(2,4-diamino-pyrimidin-5-ylmethyl)-6-ethoxy-3'- fluoro-4'-morpholin-4-ylmethyl-biphenyl-2-ol is Prepared by the Following Sequence (Stages a)-c)).

Stage a) 4'-(2,4-Diamino-pyrimidin-5-ylmethyl)-6'-ethoxy-3-fluoro-2'-methoxymethoxy-biphenyl-4-carbaldehyde Analogously to example (4a), starting from 4-bromo-2-fluoro-benzaldehyde (1,015 g; 5 mmol),), bis(pinacolato)diboron (1,395 g; 5.5 mmol), potassium acetate (1.08 g; 11 mmol), bis(triphenylphosphine) palladium(II) dichloride (150 mg; 0.21 mmol) and from 5-(3-ethoxy-4-iodo-5-methoxymethoxy-benzyl)-pyrimidine-2,4-diamine (example 25) (1,075 g; 2.5 mmol), 980 mg (92%) 4'-(2,4-diamino-pyrimidin-5-ylmethyl)-6'-ethoxy-3-fluoro-2'-methoxymethoxy-biphenyl-4-carbaldehyde are obtained as a pale yellow powder.

MS (ISP): 427.4 (M+H)$^+$.

Stage b) 5-(6-Ethoxy-3'-fluoro-2-methoxymethoxy-4'-morpholin-4-ylmethyl-biphenyl-4-ylmethyl)-pyrimidine-2,4-diamine Analogously to example (4v), from 4'-(2,4-diamino-pyrimidin-5-ylmethyl)-6'-ethoxy-3-fluoro-2'-methoxymethoxy-biphenyl-4-carbaldehyde (900 mg; 2.11 mmol) and morpholine (1.1 g; 12.6 mmol), 699 mg (66%) 5-(6-ethoxy-3'-fluoro-2-methoxymethoxy-4'-morpholin-4-ylmethyl-biphenyl-4-ylmethyl)-pyrimidine-2,4-diamine are obtained as a light-yellow powder.

MS (ISP): 498.4 (M+H)$^+$.

Stage c) 4-(2,4-Diamino-pyrimidin-5-ylmethyl)-6-ethoxy-3'-fluoro-4'-morpholin-4-ylmethyl-biphenyl-2-ol A solution of 5-(6-ethoxy-3'-fluoro-2-methoxymethoxy-4'-morpholin-4-ylmethyl-biphenyl-4-ylmethyl)-pyrimidine-2,4-diamine (120 mg; 0.24 mmol) in 20 ml methanol is heated to 50° C., 2.7 ml 4.5 M hydrochloric acid in methanol are then added and the mixture is stirred for 1 hour at this temperature. The pale yellow solution is cooled to 0° C., adjusted to pH 10 with 25% aqueous ammonia solution and concentrated to a volume of 2 ml. 20 ml water are added to the residue and the mixture is extracted three times with 50 ml methylene chloride each time. The combined organic phases are dried over magnesium sulphate and concentrated. 57 mg (52%) 4-(2,4-diamino-pyrimidin-5-ylmethyl)-6-ethoxy-3'-fluoro-4'-morpholin-4-ylmethyl-biphenyl-2-ol are obtained as a colourless powder.

MS (ISP): 454.5 (M+H)$^+$.

EXAMPLE 65

Dimethylsulphamic acid 4-(2,4-diamino-pyrimidin-5-ylmethyl)-6-ethoxy-4'-morpholin-4-ylmethyl-biphenyl-2-yl ester Analogously to example (64b), starting from 4-(2,4-diamino-pyrimidin-5-ylmethyl)-6-ethoxy-4'-morpholin-4- ylmethyl-biphenyl-2-ol (290 mg; 0.67 mmol) and N,N-dimethylsulphamoyl chloride (191 mg; 1.33 mmol), 282 mg (78%) dimethyl-sulphamic acid 4-(2,4-diamino-pyrimidin-5-ylmethyl)-6-ethoxy-4'-morpholin-4-ylmethyl-biphenyl-2-yl ester are obtained as a yellow foam.

MS (ISP): 543.3 (M+H)$^+$.

The Above Starting Compound 4-(2,4-diamino-pyrimidin-5-ylmethyl)-6-ethoxy-4'-morpholin-4-ylmethyl-biphenyl-2-ol is Prepared by the Following Sequence (Stages a)-c)):

Stage a) 4'-(2,4-Diamino-pyrimidin-5-ylmethyl)-6'-ethoxy-2'-methoxymethoxy-biphenyl-4-carbaldehyde Analogously to example (2ag), starting from 1.075 g (2.5 mmol) 5-(3-ethoxy-4-iodo-5-methoxymethoxy-benzyl)-pyrimidine-2,4-diamine (example 25) and 4-formyl-phenylboron acid (562 mg; 3.75 mmol), 956 mg (93%) 4'-(2,4-diamino-pyrimidin-5-ylmethyl)-6'-ethoxy-2'-methoxymethoxy-biphenyl-4-carbaldehyde are obtained as a beige foam.

MS (ISP): 409.4 (M+H)$^+$.

Stage b) 5-(6-Ethoxy-2-methoxymethoxy-4'-morpholin-4-ylmethyl-biphenyl-4-ylmethyl)-pyrimidine-2,4-diamine Analogously to example (4v), from 4'-(2,4-diamino-pyrimidin-5-ylmethyl)-6'-ethoxy-2'-methoxymethoxy-biphenyl-4-carbaldehyde (950 mg; 2.33 mmol) and morpholine (1.21 g; 13.95 mmol), 746 mg (67%)5-(6-ethoxy-2-methoxymethoxy-4'-morpholin-4-ylmethyl-biphenyl-4-ylmethyl)-pyrimidine-2,4-diamine are obtained as a white powder.

MS (ISP): 480.4 (M+H)$^+$.

Stage c) 4-(2,4-Diamino-pyrimidin-5-ylmethyl)-6-ethoxy-4'-morpholin-4-ylmethyl-biphenyl-2-ol Analogously to example (64b) (preparation of the starting compound, stage c)), from 5-(6-ethoxy-2-methoxymethoxy-4'-morpholin-4-ylmethyl-biphenyl-4-ylmethyl)-pyrimidine-2,4-diamine (0.74 g; 1.54 mmol) and hydrochloric acid in methanol, 0.587 g (87%) 4-(2,4-diamino-pyrimidin-5-ylmethyl)-6-ethoxy-4'-morpholin-4-ylmethyl-biphenyl-2-ol is obtained as a white powder.

MS (ISP): 436.5 (M+H)$^+$.

EXAMPLE 66

Dimethylsulphamic acid 4-(2,4-diamino-pyrimidin-5-ylmethyl)-6-ethoxy-4'-{[N-(2-fluoro-ethyl)-N-methyl-amino]-methyl}-binhenyl-2-yl ester, cf. equation 2, (X)→(XI)→(VI)→(IX).

Analogously to example (64b), starting from 4-(2,4-diamino-pyrimidin-5-ylmethyl)-6-ethoxy-4'-{[N-(2-fluoro-ethyl)-N-methyl-amino]-methyl}-biphenyl-2-ol (150 mg; 0.35 mmol) and N,N-dimethylsulphamoyl chloride (101 mg; 0.71 mmol), 44 mg (23%) dimethylsulphamic acid 4-(2,4-diamino-pyrimidin-5-ylmethyl)-6-ethoxy-4'-{[N-(2-fluoro-ethyl)-N-methyl-amino]-methyl}-biphenyl-2-yl ester are obtained as a yellow foam.

MS (ISP): 533.3 (M+H)$^+$.

The Above Starting Compound 4-(2,4-diamino-pyrimidin-5-ylmethyl)-6-ethoxy-4'-{[N-(2-fluoro-ethyl)-N-methyl-amino]-methyl}-biphenyl-2-ol is Prepared by the Following Sequence (Stages a)-c)):

Stage a) 5-{6-Ethoxy-4'-[(2-fluoro-ethylamino)-methyl]-2-methoxymethoxy-biphenyl-4-ylmethyl}-pyrimidine-2,4-diamine Analogously to example (4v), from 4'-(2,4-diamino-pyrimidin-5-ylmethyl)-6'-ethoxy-2'-methoxymethoxy-biphenyl-4-carbaldehyde (example 65, stage a)) (1 g; 2.45 mmol) and 2-fluoroethylamine hydrochloride (1.46 g; 14.69 mmol), 1,059 g (95%) 5-{6-ethoxy-4'-[(2-fluoro-ethylamino)-methyl]-2-methoxymethoxy-biphenyl-4-ylmethyl}-pyrimidine-2,4-diamine are obtained as a white powder.

MS (ISP): 456.4 (M+H)$^+$.

Stage b) 5-(6-Ethoxy-4'-{[N-(2-fluoro-ethyl)-N-methyl-amino]-methyl}-2-methoxymethoxy-biphenyl-4-ylmethyl}-pyrimidine-2,4-diamine Analogously to example (4ad), from 5-{6-ethoxy-4'-[(2-fluoro-ethylamino)-methyl]-2-methoxymethoxy-biphenyl-4-ylmethyl}-pyrimidine-2,4-diamine (0.835 g; 1.83 mmol) and 0.61 ml 35% aqueous formaldehyde, 0.422 g (49%) 5-(6-ethoxy-4'-{[N-(2-fluoro-ethyl)-N-methyl-amino]-methyl}-2-methoxymethoxy-biphenyl-4-ylmethyl)-pyrimidine-2,4-diamine is obtained as a white foam by reduction with sodium borohydride.

MS (ISP): 470.4 (M+H)$^+$.

Stage c) 4-(2,4-Diamino-pyrimidin-5-ylmethyl)-6-ethoxy-4'-{[N-(2-fluoro-ethyl)-N-methyl-amino]-methyl}-biphenyl-2-ol Analogously to example (64b) (preparation of the starting compound, stage c)), from 5-(6-ethoxy-4'-{[N-(2-fluoro-ethyl)-N-methyl-amino]-methyl}-2-methoxymethoxy-biphenyl-4-ylmethyl)-pyrimidine-2,4-diamine (0.46 g; 0.98 mmol) and hydrochloric acid in methanol, 305 mg (73%) 4-(2,4-diamino-pyrimidin-5-ylmethyl)-6-ethoxy-4'-{[N-(2-fluoro-ethyl)-N-methyl-amino]-methyl}-biphenyl-2-ol are obtained as a white powder.

MS (ISP): 426.5 (M+H)$^+$.

| Tablet | |
|---|---|
| Example A | |
| Sulphamethoxazole | 400 mg |
| Compound of the formula A as the dihydrochloride | 80 mg |
| PRIMOJEL (starch derivative) | 6 mg |
| POVIDONE K30 (polyvinylpyrrolidone) | 8 mg |
| Magnesium stearate | 6 mg |
| Total weight | 500 mg |
| Example B | |
| Comound of the formula A, e.g. as the hydrochloride | 100 mg |
| Maize starch | 15 mg |
| Talc | 3 mg |
| Magnesium stearate | 2 mg |
| | 120 mg |

What is claimed is:

1. A compound selected from the group consisting of compounds of the formula

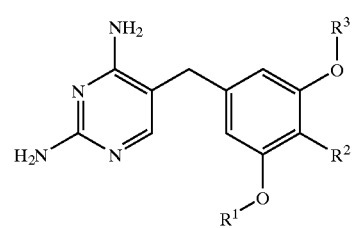

in which
R$^1$ is C$_2$–C$_3$ alkyl;

$R_2$ is phenyl, naphthyl or heterocyclyl bonded via one of its C atoms, where the heterocyclyl and phenyl, groups are unsubstituted or mono- or polysubstituted by halogen, cyano, alkyl, alkoxy, hydroxyl, nitro, amino, alkylamino, dialklamino, alkanoylamino, formyl, alkanoyloxy, cyanoalky, cyanoalkoxy, hydroxyalkyl, alkoxyalkyl, hydroxyalkoxy, hydroxyalkylamino, alkoxyalkoxy, carbamoylalkoxy, alkylaminoalkyl, dialkylaminoalkyl halogenoalkylaminoalkyl, N-alkyl-N-halogenoalky-aminoalkyl, alkylsulphanyl (alkylthio), alkylsulphinyl, alkylsulphonyl, alkylsulphonyloxy, alkylsulphonylamino, $R_7$, $R_7$-alkyl, $R_7$-alkoxy, $R_7$-carbonylalkoxyalkyl or $R_7$-alkanoylamino, or are also substituted by two adjacent substituents which together form a fused-5- or 6-membered heteromylic radical; and $R_7$ is heterocyclyl or alkyl containing up to 6 carbon atoms; and where the napthyl group is unsubstituted or mono- or polyhydroxysubstituted; and $R^3$ is $C_2$–C6 alkyl, $C_2$–C6 alkenyl, cycloalkyl, cycloalkylalkyl, heterocyclylalkyl, alkylsulphonyl, phenylsulphonyl, cycloalkylsulphonyl, cycloalkylalkylsulphonyl, cycloalkylalkylsulphamoyl, heterocyclylsulphonyl, heterocyclylallylsulphonyl or dialkylsulphamoyl, where the cycloalkyl, cycloalkylalkyl, heterocyclyalkyl, cycloalkylsulphonyl, cycloalkalkysulphonyl, heterocyclylsulphonyl, heterocyclylalkylsulphonyl, phenylsulphonyl or cycloalkylalkylsulphamoyl substituents are unsubstituted or substituted with alkyl, alkoxy, bydroxyalkyl, alkoxyalkyl, cyano, cyanoalkyl or cyanoalkenyl; wherein alkl, alkoxy and alkenyl can contain up to 6 carbon atoms, and where the $C_2$–C6 alkyl, $C_2$–C6 alkenyl, alkylsulphonyl and dialkylsulphamoyl substituents are unsubstituted or substituted by haldgen, cyano, hydroxyl or alkoxy having up to 6 carbon atoms; and with heterocyclyl being a 5 or 6 membered heterocyclic ring containing from 1 to 4 heteroatoms selected from the group consisting of oxygen, nitrogen or sulfur;

and acid addition salts of these compounds.

2. The compound of claim 1, wherein $R^2$ is naphthyl unsubstituted or substituted by hydroxyl.

3. The compound of claim 1, wherein $R^7$ is a heterocyclyl group unsubstituted or substituted by halogen, alkyl, alkoxyalkyl, hydroxyalkyl, alkanoyl, alkanoylaminoalkyl or oxo; wherein alkyl, alkoxy and alkanoyl, containing up to 6 carbon atoms.

4. The compound of claim 1, wherein $R^3$ is $C_2$–C6 alkyl, alkenyl, alkylsulphonyl or dialkylsulphamoyl which groups are unsubstituted or substituted by halogen, cyano, hydroxyl or alkoxy having up to 6 carbon atoms.

5. The compound of claim 1, wherein $R^3$ is cycloalkyl, cycloalkylalkyl, heterocyclylalkyl, cycloalkylsulphonyl, cycloalkylalkylsulphonyl, heterocyclylsulphonyl or heterocyclylalkylsulphonyl, which groups are unsubstituted or substituted by alkyl, alkoxy, hydroxyalkyl, alkoxyalkyl, cyano, cyanoalkyl or cyanoalkenyl, wherein alkyl, alkoxy and alkenyl, have up to 6 carbon atoms.

6. The compound of claim 1 selected from the group consisting of compounds of the formula

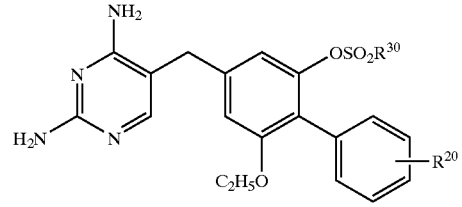

A1 in which $R^{20}$ is $C_1$–C6 alkyl, $C_1$–C6 alkoxy, amino, $C_1$–C6 alkylamino, fluorine or chlorine and $R^{30}$ represents is $C_1$–C6 alkyl, $C_3$–C6 cycloalkyl; di-($C_1$–C6 alkyl)amino, N—($C_3$–C6 cycloalkyl)-N—($C_1$–C6 alkyl)amino or a 5- or 6-membered, saturated N-heterocyclic radical linked by the nitrogen in the heterocyclic ring, and acid addition salts of these compounds.

7. The compound of claim 6, wherein $R^{20}$ is methyl, methoxy, amino, methylamino or fluorine.

8. The compound of claim 6, wherein $R^{30}$ is isopropyl, sec-butyl, cyclobutyl, dimethylamino, N-cyclopropyl-N-methyl-amino or morpholino.

9. The compound of claim 1 wherein the compound is selected from the from consisting of compounds of the formula

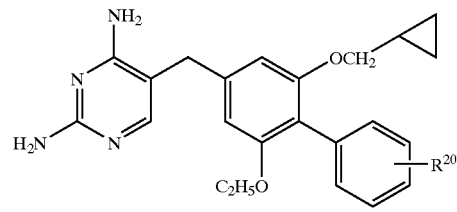

A2 in which $R^{20}$ denotes $C_1$–C6 alkyl, $C_1$–C6 alkoxy, amino, $C_1$–C6 alkylamino, fluorine or chlorine, and acid addition salts of these compounds.

10. The compound of claim 9, wherein $R^{20}$ is methyl, methoxy, amino, methylamino or fluorine.

11. The compound of claim 1 wherein the compounds are selected from the group consisting of compounds of the formula

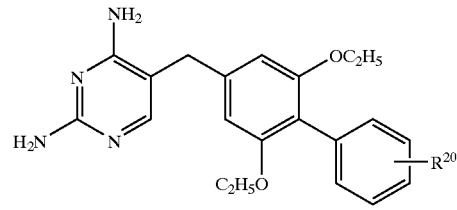

A3 in which $R^{20}$ denotes $C_1$–C6 alkyl, $C_1$–C6 alkoxy, amino, $C_1$–C6 alkylamino, fluorine or chlorine, and acid addition salts of these compounds.

12. The compound of claim 11, wherein $R^{20}$ represents methyl, methoxy, amino, methylamino or fluorine.

13. Butane-2-sulphonic acid 4'-amino-4-(2,4-diamino-pyrimidin-5-ylmethyl)-6-ethoxy-biphenyl-2-yl ester or acid addition salts of this compound.

14. Cyclobutane-sulphonic acid 4'-amino-4-(2,4-diamino-pyrimidin-5-ylmethyl)-6-ethoxy-3'-methyl-biphenyl-2-yl ester or acid addition salts of this compound.

15. Morpholino-4-sulphonic acid 4-(2,4-diamino-pyrimidin-5-ylmethyl)-6-ethoxy-4'-methylamino-biphenyl-2-yl ester or acid addition salts of this compound.

16. Dimethyl-sulphamic acid 3'-amino-4-(2,4-diamino-pyrimidin-5-ylmethyl)-6-ethoxy-4'-methyl-biphenyl-2-yl ester for acid addition salts of this compound.

17. Propane-2-sulphonic acid 4'-amino-4-(2,4-diamino-pyrimidin-5-ylmethyl)-6-ethoxy-biphenyl-2-yl ester or acid addition salts of this compound.

18. Butane-2-sulphonic acid 4'-amino-3-(2,4-diamino-pyrimidin-5-ylmethyl)-6-ethoxy-biphenyl-2-yl ester or acid addition salts of this compound.

19. N-Cyclopropyl-N-methyl-sulphamic acid 4'-amino-4-(2,4-diamino-pyrimidin-5-ylmethyl)-6-ethoxy-biphenyl-2-yl ester or acid addition salts of this compound.

20. Propane-2-sulphonic acid 4'-amino-3-(2,4-diamino-pyrimidin-5-ylmethyl)-6-ethoxy-biphenyl-2-yl ester or acid addition salts of this compound.

21. Propane-2-sulphonic acid 4'-amino-4-(2,4-diamino-pyrimidin-5-ylmethyl)-6-ethoxy-3'-methyl-biphenyl-2-yl ester or acid addition salts of this compound.

22. 5-(3'-Amino-6-cyclopropylmethoxy-2-ethoxy-biphenyl-4-ylmethyl)-pyrimidine-2,4-diamine or acid addition salts of this compound.

23. 5-(3-Amino-2,6-diethoxbiphenyl-4-ylmethyl)-pyrimidine-2,4-diamine or acid addition salts of this compound.

24. A compound of the formula:

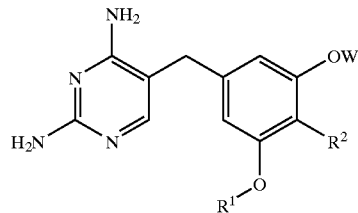

in which $R^1$ and $R^2$ have the meaning given in claim 1 and W represents hydrogen, benzyl or methoxymethyl.

25. The compound of claim 1 wherein the heterocyclic radicals are selected from the group consisting of pyridyl, pyrazinyl, pyridazinyl, pyrimidyl, piperidyl, piperazinyl, piperimidyl, pyrrolidinyl, pyrazolyl, pyrazolidinyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, 3H-1,2,3-oxadiazolyl, 1,2,3-oxadiazolyl, 1,2,5-oxadithiolyl, oxazolidinyl, tetrahydrofuranyl, tetrahydrothienyl, morpholino, thiomorphino, pyranyl, and dioxanyl, where the heterocyclic radicals are unsubstituted or substituted by halogen, hydroxyl, alkyl, alkoxy, hydroalkyl, alkoxyalkyl, cyano, cyanoalkyl or cyanoalkenyl.

26. A pharmaceutical composition comprising a compound of formula A in accordance with claim 1, and a carrier.

27. A pharmaceutical composition comprising a compound of formula A in accordance with claim 1, a sulphonamide compound, and a carrier, wherein the ratio in parts by weight of the compound of formula A to sulphonamide is between 1:40 and 1:1.

28. A pharmaceutical composition according to claim 27, wherein said ratio is from 1:10 to 1:2.

* * * * *